United States Patent
Wilkerson et al.

(10) Patent No.: US 10,428,342 B2
(45) Date of Patent: Oct. 1, 2019

(54) P-COUMAROYL-CoA:MONOLIGNOL TRANSFERASE

(71) Applicants: Wisconsin Alumni Research Foundation, Madison, WI (US); Board of Trustees of Michigan State University, East Lansing, MI (US); The Board of Trustees of Illinois State University, Normal, IL (US)

(72) Inventors: Curtis Wilkerson, Swartz Creek, MI (US); John Ralph, Madison, WI (US); Saunia Withers, Durham, NC (US); John Sedbrook, Bloomington, IL (US)

(73) Assignees: Board of Trustees of Michigan State University, East Lansing, MI (US); Wisconsin Alumni Research Foundation, Madison, WI (US); The Board of Trustees of Illinois State University, Normal, IL (US)

( * ) Notice: Subject to any disclaimer, the term of this patent is extended or adjusted under 35 U.S.C. 154(b) by 417 days.

(21) Appl. No.: 14/365,744

(22) PCT Filed: Dec. 14, 2012

(86) PCT No.: PCT/US2012/069902
§ 371 (c)(1),
(2) Date: Jun. 16, 2014

(87) PCT Pub. No.: WO2013/090814
PCT Pub. Date: Jun. 20, 2013

(65) Prior Publication Data
US 2016/0046955 A1   Feb. 18, 2016

Related U.S. Application Data

(60) Provisional application No. 61/576,515, filed on Dec. 16, 2011.

(51) Int. Cl.
*C12N 15/82* (2006.01)
*C12N 9/10* (2006.01)
*C12N 15/113* (2010.01)

(52) U.S. Cl.
CPC ....... *C12N 15/8255* (2013.01); *C12N 9/1029* (2013.01); *C12N 15/1137* (2013.01); *C12N 15/8218* (2013.01); *C12N 2310/14* (2013.01)

(58) Field of Classification Search
None
See application file for complete search history.

(56) References Cited

U.S. PATENT DOCUMENTS

| 4,107,111 A | 8/1978 | Lindberg et al. |
|---|---|---|
| 4,478,747 A | 10/1984 | Crawford et al. |
| 5,451,514 A | 9/1995 | Boudet et al. |
| 5,824,842 A | 10/1998 | MacKay et al. |
| 6,455,762 B1 | 9/2002 | Chiang et al. |
| 7,173,164 B2 | 2/2007 | Brugliera et al. |
| 7,317,136 B1 | 1/2008 | Forster et al. |
| 7,413,882 B2 | 8/2008 | Berka et al. |
| 7,435,556 B2 | 10/2008 | Vitanen et al. |
| 7,604,968 B2 | 10/2009 | Schmidt-Dannert et al. |
| 7,981,650 B2 | 7/2011 | Levasseur et al. |
| 8,569,465 B2 | 10/2013 | Ralph et al. |
| 9,441,235 B2 | 9/2016 | Wilkerson et al. |
| 9,487,794 B2 | 11/2016 | Wilkerson et al. |
| 10,047,113 B2 | 8/2018 | Wilkerson et al. |
| 2001/0007762 A1 | 7/2001 | Echigo et al. |
| 2003/0070192 A1 | 4/2003 | Keller et al. |
| 2003/0167511 A1 | 9/2003 | Narbad et al. |
| 2003/0216326 A1 | 11/2003 | Alimi |
| 2003/0226168 A1 | 12/2003 | Carlson |
| 2004/0049802 A1 | 3/2004 | Dixon et al. |
| 2004/0058983 A1 | 3/2004 | Vuorela et al. |
| 2004/0123343 A1* | 6/2004 | La Rosa ............. C07K 14/415 800/278 |
| 2006/0005270 A1 | 1/2006 | Dunn-Coleman et al. |
| 2006/0123505 A1* | 6/2006 | Kikuchi ............. C07K 14/415 800/278 |
| 2006/0183895 A1 | 8/2006 | Bloksberg et al. |
| 2008/0032344 A1 | 2/2008 | Fallavollita et al. |
| 2009/0044294 A1 | 2/2009 | Dixon et al. |

(Continued)

FOREIGN PATENT DOCUMENTS

| CA | 2806400 C | 9/2017 |
|---|---|---|
| EP | 2596104 B1 | 11/2016 |

(Continued)

OTHER PUBLICATIONS

Withers et al (The Journal of Biological Chemistry vol. 287, No. 11, pp. 8347-8355, Mar. 9, 2012).*
Friedberg (Brief. Bioinformatics (2006) 7: 225-242).*
Friedberg (Brief. Bioinformatics (2006) 7: 225-242) (Year: 2006).*
NCBI Reference Sequence: NP_001149738.2 (Year: 2017).*
Withers et al (The Journal of Biological Chemistry vol. 287, No. 11, pp. 8347-8355, Mar. 9, 2012) (Year: 2012).*
Friedberg (Brief. Bioinfornnatics (2006) 7: 225-242) (Year: 2006).*
U.S. Appl. No. 15/237,331, filed Aug. 15, 2016, Feruloyl-CoA:Monolignol Transferase.
"Canadian Application Serial No. 2,806,481, Office Action dated Nov. 21, 2016", 5 pgs.

(Continued)

*Primary Examiner* — Lee A Visone
(74) *Attorney, Agent, or Firm* — Schwegman Lundberg & Woessner, P.A.

(57) ABSTRACT

The invention relates to nucleic acids encoding a p-coumaroyl-CoA:monolignol transferase and to inhibitory nucleic acids adapted to inhibit the expression and/or translation of a p-coumaroyl-CoA:monolignol transferase RNA. Inhibition of p-coumaroyl-CoA:monolignol transferase in plants improves the incorporation of monolignol ferulates into the lignin of plants, giving rise to plant biomass that is more easily processed into useful products such as paper and biofuels.

11 Claims, 47 Drawing Sheets

Specification includes a Sequence Listing.

(56) References Cited

U.S. PATENT DOCUMENTS

| | | | |
|---|---|---|---|
| 2009/0062516 A1 | 3/2009 | Belanger et al. | |
| 2009/0087878 A9* | 4/2009 | La Rosa | C07H 21/04 435/69.1 |
| 2009/0209739 A1 | 8/2009 | Funaoka et al. | |
| 2010/0058498 A1 | 3/2010 | Apuya et al. | |
| 2010/0178670 A1 | 7/2010 | Smith et al. | |
| 2010/0287660 A1 | 11/2010 | Spangenberg et al. | |
| 2010/0305244 A1 | 12/2010 | Balakshin et al. | |
| 2012/0017338 A1* | 1/2012 | Wu | C07K 14/415 800/300 |
| 2013/0203973 A1 | 8/2013 | Wilkerson et al. | |
| 2013/0219547 A1 | 8/2013 | Wilkerson et al. | |
| 2013/0254930 A1 | 9/2013 | Han et al. | |
| 2014/0011984 A1 | 1/2014 | Ralph et al. | |

FOREIGN PATENT DOCUMENTS

| | | |
|---|---|---|
| EP | 2596103 B1 | 12/2016 |
| EP | 3138919 | 12/2018 |
| EP | 3138919 B1 | 12/2018 |
| WO | WO-2012012698 A1 | 1/2012 |
| WO | WO-2012012741 A1 | 1/2012 |
| WO | WO-2013090814 A2 | 6/2013 |
| WO | WO-2013090814 A3 | 6/2013 |

OTHER PUBLICATIONS

"Canadian Application Serial No. 2,859,564, Office Action dated Nov. 28, 2016", 4 pgs.

"European Application Serial No. 16193228.0, Extended European Search Report dated Dec. 9, 2016".

U.S. Appl. No. 13/811,823, filed May 8, 2013, Feruloyl-CoA:Monolignol Transferase.

U.S. Appl. No. 13/811,855, filed Apr. 26, 2013, Feruloyl-CoA:Monolignol Transferase.

"104_164_10434814_5_30003 Sorghum methylation filtered library (LibID: 104) Sorghum bicolor genomic clone 10434814, genomic survey sequence", Retrieved from EBI accession No. EM_GSS:CW024195, Database accession No. CW024195, (May 17, 2010), 1 pg.

"5261_H01_P01Z_001 Brachypodium distachyon callus EST library Brachypodium distachyon cDNA clone 5261_H01_P01, mRNA sequence", Retrieved from EBI accession No. EM_EST:DV471916, Database accession No. DV471916.1, (Oct. 21, 2005), 2 pgs.

"International Application Serial No. PCT/US2011/044981, International Preliminary Report on Patentability dated Jan. 31, 2013", 10 pgs.

"International Application Serial No. PCT/US2011/044981, International Search Report dated Nov. 3, 2011", 4 pgs.

"International Application Serial No. PCT/US2011/044981, Written Opinion dated Nov. 3, 2011", 10 pgs.

"International Application Serial No. PCT/US2011/045044, International Preliminary Report on Patentability dated Jan. 31, 2013", 9 pgs.

"International Application Serial No. PCT/US2011/045044, International Search Report dated Nov. 3, 2011", 4 pgs.

"International Application Serial No. PCT/US2011/045044, Written Opinion dated Nov. 3, 2011", 9 pgs.

"International Application Serial No. PCT/US2012/069902, International Search Report dated Aug. 22, 2013", 6 pgs.

"International Application Serial No. PCT/US2012/069902, Written Opinion dated Aug. 22, 2013", 9 pgs.

"NK 2012 Abstracts", (2012), 12 pgs.

Bedell, J. A, et al., "Sorghum Genome Sequencing by Methylation Filtration", PLoS Biol., 3(1): e13, (2005), 0103-0115.

Beurerle, Till, et al., "Enzymatic Synthesis and Purification of Aromatic Coenzyme A Esters", Analytical Biochemistry, vol. 302, doi:10.1006/abio.2001.5574, (Feb. 13, 2002), 305-312.

Grabber, John H, et al., "Coniferyl Ferulate Incorporation into Lignin Enhances the Alkaline Delignification and Enzymatic Degradation of Cell Walls", Biomacromolecules Sep. 2008 American Chemical Society US, vol. 9, No. 9, (Jan. 1, 2008), 2510-2516.

Hatfield, R. D, et al., "Enzymatic processes involved in the incorporation of hydroxycinnamates into grass cell walls", Phyochemistry Reviews, 9(1), (2010), 35-45.

Hatfield, R. D., et al., "Grass lignin acylation: p-coumaroyl transferase activity and cell wall characteristics of C3 and C4 grasses", Planta, 229(6), (2009), 1253-1267.

Ralph, J., et al., "Effects of Coumarate 3-Hydroxylase Down-regulation on Lignin Structure", The Journal of Biological Chemistry, 281(13), (2006), 8843-8853.

Ralph, John, "Hydroxycinnamates in lignification", Phytochemistry Reviews, vol. 9, No. 1, (Jan. 1, 2010), 65-83.

Simmons, Blake A, et al., "Advances in modifying lignin for enhanced biofuel production", Current Opinion in Plant Biology, Quadrant Subscription Services, vol. 13, No. 3, (Jun. 1, 2010), 312-319.

Vogel, John P, et al., "EST sequencing and phylogenetic analysis of the model grass *Brachypodium distachyon*", Theoretical and Applied Genetics, 113(2), (2006), 186-195.

Withers, S., et al., "Identification of Grass-specific Enzyme That Acylates Monolignols with p-Coumarate", Journal of Biological Chemistry, 287(11)), (2012), 8347-8355.

Xie, Jing-Jing, et al., "Optimization and Comparison of Five Methods for Extraction of Coniferyl Ferulate from Angelica sinensis", Molecules 2009 LNKD-PUBMED 19169202, vol. 14, No. 1, (2009), 555-565.

"U.S. Appl. No. 13/811,823, Advisory Action dated Mar. 22, 2016", 4 pgs.

"U.S. Appl. No. 13/811,823, Examiner Interview Summary dated Jan. 26, 2016", 3 pgs.

"U.S. Appl. No. 13/811,823, Examiner Interview Summary dated May 14, 2015", 3 pgs.

"U.S. Appl. No. 13/811,823, Final Office Action dated Nov. 19, 2015", 19 pgs.

"U.S. Appl. No. 13/811,823, Non Final Office Action dated Feb. 27, 2015", 31 pgs.

"U.S. Appl. No. 13/811,823, Notice of Allowance dated May 6, 2016", 10 pgs.

"U.S. Appl. No. 13/811,823, Preliminary Amendment filed Jan. 23, 2013", 9 pgs.

"U.S. Appl. No. 13/811,823, Response filed Jan. 18, 2016 to Final Office Action dated Nov. 19, 2015", 18 pgs.

"U.S. Appl. No. 13/811,823, Response filed Apr. 19, 2016 to Advisory Action dated Nov. 19, 2015", 16 pgs.

"U.S. Appl. No. 13/811,823, Response filed Jun. 24, 2015 to Non Final Office Action dated Feb. 27, 2015", 19 pgs.

"U.S. Appl. No. 13/811,823, Supplemental Preliminary Amendment filed Jan. 30, 2015", 3 pgs.

"U.S. Appl. No. 13/811,823, Supplemental Preliminary Amendment filed Apr. 3, 2013", 3 pgs.

"U.S. Appl. No. 13/811,823, Supplemental Preliminary Amendment filed Dec. 30, 2014", 9 pgs.

"U.S. Appl. No. 13/811,855, Corrected Notice of Allowance dated May 5, 2016", 6 pgs.

"U.S. Appl. No. 13/811,855, Corrected Notice of Allowance dated Sep. 22, 2016", 2 pgs.

"U.S. Appl. No. 13/811,855, Final Office Action dated Jun. 1, 2015", 7 pgs.

"U.S. Appl. No. 13/811,855, Non Final Office Action dated Jan. 30, 2015", 13 pgs.

"U.S. Appl. No. 13/811,855, Notice of Allowance dated Apr. 19, 2016", 10 pgs.

"U.S. Appl. No. 13/811,855, Notice of Allowance dated May 5, 2016", 6 pgs.

"U.S. Appl. No. 13/811,855, Notice of Allowance dated Jun. 20, 2016", 7 pgs.

"U.S. Appl. No. 13/811,855, Preliminary Amendment filed Jan. 23, 2013", 6 pgs.

"U.S. Appl. No. 13/811,855, Response filed Apr. 30, 2015 to Non Final Office Action dated Jan. 30, 2015", 6 pgs.

"U.S. Appl. No. 13/811,855, Response filed Sep. 1, 2015 to Final Office Action dated Jun. 1, 2015", 6 pgs.

(56) References Cited

OTHER PUBLICATIONS

"U.S. Appl. No. 13/811,855, Supplemental Preliminary Amendment filed Apr. 3, 2013", 3 pgs.
"U.S. Appl. No. 15/237,331, Supplemental Preliminary Amendment filed Aug. 24, 2016", 10 pgs.
"U.S. Appl. No. 15/237,331, Supplemental Preliminary Amendment Filed Sep. 22, 2016", 10 pgs.
"Canadian Application Serial No. 2,859,564 Office Action dated Jun. 30, 2015", 4 pgs.
"Canadian Application Serial No. 2,859,564, Response filed Dec. 30, 2015 to Office Action dated Jun. 30, 2015", 21 pgs.
"Chilean Application Serial No. 2013-00229, Office Action dated Jan. 7, 2015", (w/ English Translation), 4 pgs.
"Chilean Application Serial No. 2013-00229, Office Action dated Jul. 3, 2015", (w/ English Translation), 3 pgs.
"Chilean Application Serial No. 2013-00229, Response filed Feb. 24, 2015 to Office Action dated Jan. 7, 2015", (w/ English Translation of Claims), 9 pgs.
"Chilean Application Serial No. 2013-00229, Response filed Aug. 14, 2015 to Office Action dated Jul. 3, 2015", (w/ English Machine Translation), 6 pgs.
"European Application Serial No. 11746699.5, Office Action dated Jun. 8, 2015", 4 pgs.
"European Application Serial No. 11746699.5, Response filed Oct. 7, 2015 to Office Action dated Jun. 8, 2015", 17 pgs.
"European Application Serial No. 11746700.1, Office Action dated Jun. 12, 2015", 4 pgs.
"European Application Serial No. 11746700.1, Response filed Nov. 10, 2015 to Office Action dated Jun. 12, 2015", 17 pgs.
Kim, Hoon, et al., "Solution-state 2D NMR of Ball-milled Plant Cell Wall Gels in DMSO-$d_5$", BioEnergy Research, 1, (2008), 56-66.
Xie, Jing-Jing, et al., "Optimization and Comparison of Five Methods for Extraction of Coniferyl Ferulate from Angelica sinensis", *Molecules*, 14(1), (2009), 555-565.
"European Application Serial No. 16193228.0, Response filed Sep. 1, 2017 to Extended European Search Report dated Dec. 9, 2016", 9 pgs.
"Canadian Application Serial No. 2,806,481, Response Filed May 18, 2017 to Office Action dated Nov. 21, 2016", 18 pgs.
"Canadian Application Serial No. 2,859,564, Response Filed May 29, 2017 to Office Action dated Nov. 28, 2016", 15 pgs.
"U.S. Appl. No. 15/237,331, Non Final Office Action dated Nov. 24, 2017", 22 pgs.
"Canadian Application Serial No. 2,806,481, Office Action dated Jan. 18, 2018", 3 pgs.
"Canadian Application Serial No. 2,859,564, Office Action dated Dec. 14, 2017", 4 pgs.
"European Application Serial No. 16193228.0, Communication Pursuant to Article 94(3) EPC dated Nov. 28, 2017", 4 pgs.
Garcia-Cerdian, Jose G., et al., "The PsbW proteiin stabilizes the supramolecular organization of photosystem II in higher plants", The Plant Journal (2011) 65, 368-381, (2011), 368-381.
Nahid, Nazia, et al., "RNA interference-based resistance against a legume mastrevirus", Virology Journal 2011, 8:499, (2011), 8 pgs.
Radziejwoski, Amandine, et al., "Atypical E2F activity coordinates PHR1 photolyase gene transcription with endoreduplication onset", The EMBO Journal (2011) 30, 355-363, 2011 European Molecular Biology Organization, (2011), 355-363.
"U.S. Appl. No. 15/237,331, Notice of Allowance dated Apr. 11, 2018", 9 pgs.
"U.S. Appl. No. 15/237,331, Preliminary Amendment filed Aug. 15, 2016", 4 pgs.
"U.S. Appl. No. 15/237,331, Response filed Feb. 15, 2018 to Non-Final Office Action dated Nov. 24, 2017", 19 pgs.
"European Application Serial No. 16193228.0, Response filed Mar. 23, 2018 to Communication Pursuant to Article 94(3) EPC dated Nov. 28, 2017", 98 pgs.
"Canadian Application Serial No. 2,806,481, Response filed Jul. 18, 2018 to Office Action dated Jan. 18, 2018", 12 pgs.
"Canadian Application Serial No. 2,859,564, Response filed Apr. 19, 2018 to Office Action dated Dec. 14, 2017", 21 pgs.
"Chile Application Serial No. 2013-00229, Office Action dated Jul. 25, 2018", w/o English translation, 2 pgs.
"Canadian Application Serial No. 2,806,481, Examiner's Rule 30(2) Requisition dated Jan. 29, 2019", 5 pgs.
"Canadian Application Serial No. 2,859,564, Examiner's Rule 30(2) Requisition dated Nov. 1, 2018", 3 pgs.
"Canadian Application Serial No. 2,859,564, Response filed Apr. 10, 2019 to Examiner's Rule 30(2) Requisition dated Nov. 1, 2018", 18 pgs.
"Chile Application Serial No. 2013-00229, Response filed Oct. 17, 2018 to Office Action dated Jul. 25, 2018", (w/ English Translation of Claims), 13 pgs.
Hill, Margaret A, et al., "Functional Analysis of Conserved Histidines in ADP-Glucose Pyrophosphorylase from *Escherichia coli*", Biochem Biophys Res Commun., 244(2), (Mar. 17, 1998), 573-577.
Lazar, et al., "Transforming Growth Factor a: Mutation of Aspartic Acid 47 and Leucine 48 Results in Different Biological Activity", 1988, Mol. Cell. Biol. 8, (Mar. 1998), 1247-1252.
"Canadian Application Serial No. 2,859,564, Examiner's Rule 30(2) Requisition mailed Nov. 1, 2018", 3 pgs.
"Canadian Application Serial No. 2,806,481, Examiner's Rule 30(2) Requisition mailed Jan. 29, 2019", 5 pgs.
"Canadian Application Serial No. 2,859,564, Response filed Apr. 10, 2019 to Examiner's Rule 30(2) Requisition mailed Nov. 1, 2018", 18 pgs.
Hill, Margaret A, "Functional Analysis of Conserved Histidines in ADP-Glucose Pyrophosphorylase from *Escherichia coli*", Biochem Biophys Res Commun., 244(2), (Mar. 17, 1998), 573-577.
Lazar, "Transforming Growth Factor a: Mutation of Aspartic Acid 47 and Leucine 48 Results in Different Biological Activity", 1988, Mol. Cell. Biol. 8, (Mar. 1998), 1247-1252.
"U.S. Appl. No. 12/830,905, Non-Final Office Action dated Jun. 12, 2012", 8 pgs.
"U.S. Appl. No. 12/830,905, Non-Final Office Action dated Dec. 31, 2012", 10 pgs.
"U.S. Appl. No. 12/830,905, Notice of Allowance dated Jun. 13, 2013", 8 pgs.
"U.S. Appl. No. 12/830,905, Response filed Apr. 30, 2013 to Non-Final Office Action dated Dec. 31, 2012", 17 pgs.
"U.S. Appl. No. 12/830,905, Response filed Nov. 12, 2012 to Non-Final Office Action dated Jun. 12, 2012", 10 pgs.
"U.S. Appl. No. 13/811,823, Supplemental Preliminary Amendment filed Oct. 13, 2014", 8 pgs.
"Australian Serial No. 2011280960, First Examiner Report dated May 23, 2014", 2 pgs.
"Australian Serial No. 2011280960, Response filed Oct. 15, 2014 to First Examiner Report dated May 23, 2014", 4 pgs.
"Australian Serial No. 2011281001, First Examiner Report dated May 23, 2014", 3 pgs.
"Australian Serial No. 2011281001, Response filed Oct. 13, 2014 to First Examiner Report dated May 23, 2014", 22 pgs.
"Brazilian Application Serial No. BR1120130016710, Amendment filed Jul. 22, 2014", (w/English Translation of Claims), 8 pgs.
"European Application Serial No. 11746699.5, Office Action dated Mar. 7, 2013", 2 pgs.
"European Application Serial No. 11746699.5, Office Action dated May 22, 2014", 6 pgs.
"European Application Serial No. 11746699.5, Reply filed Sep. 11, 2013 to Office Action dated Mar. 7, 2013", 19 pgs.
"European Application Serial No. 11746699.5, Response filed Sep. 18, 2014 to Office Action dated May 22, 2014", 11 pgs.
"European Application Serial No. 11746699.5, Result of Consultation dated Oct. 22, 2014", 3 pgs.
"European Application Serial No. 11746700.1, Office Action dated May 26, 2014", 5 pgs.
"European Application Serial No. 11746700.1, Office Action dated Mar. 7, 2013", 2 pgs.
"European Application Serial No. 11746700.1, Reply filed Sep. 11, 2013 to Office Action dated Mar. 7, 2013", 12 pgs.
"European Application Serial No. 11746700.1, Response filed Sep. 18, 2014 to Office Action dated May 26, 2014", 43 pgs.

(56) References Cited

OTHER PUBLICATIONS

"International Application Serial No. PCT/US2012/069902, International Preliminary Report on Patentability dated Jun. 26, 2014", 10 pgs.
Bartel, David P., et al., "Isolation of New Ribozymes from a Large Pool of Random Sequence", Science, 261(5127), (1993), 1411-1418.
Baucher, Marie, et al., "Lignin: genetic engineering and impact on pulping", Crit. Rev. Biochem. Mol. Biol., 38(4), (2003), 305-350.
Beuerle, Till, et al., "Enzymatic Synthesis and Purification of Aromatic Coenzyme A Esters", Anal. Biochem., 302(2), (2002), 305-312.
Blumenkrantz, Nelly. et al., "New method for quantitative determination of uronic acids", Anal. Biochem., 54(2), (1973), 484-489.
Boerjan, Wout, et al., "Lignin Biosynthesis", Annu. Rev. Plant Biol., 54, (2003), 519-546.
Del Rio, Jose C., et al., "Highly Acylated (Acetylated and/or p-Coumaroylated) Native Lignins from Diverse Herbaceous Plants", J. Aqr. Food Chem., 56(20), (2008), 9525-9534.
Dien, Bruce S., et al., "Chapter 23. Converting Herbaceous Energy Crops to Bioethanol: A Review with Emphasis on Pretreatment Processes", In: Handbook of Industrial Biocatalysis, Hou. Ching T., CRC Press, LLC. Boca Raton, FL. (2005). 23-1-23-11.
Dien, Bruce S., et al., "Chemical composition and response to dilute-acid pretreatment and enzymatic saccharification of alfalfa, reed canarygrass, and switchgrass", Biomass and Bioenergy, 30(10), (2006), 880-891.
Donaldson, Lloyd A., et al., "Lignification and lignin topochemistry—an ultrastructural view", Phytochemistry, 57, (2001) 859-873.
Fukushima, Romualdo S., et al., "Comparison of the Acetyl Bromide Spectrophotometric Method with Other Analytical Lignin Methods for Determining Lignin Concentration in Forage Samples", J. Agric. Food Chem., 52, (2004), 3713-3720.
Grabber, J. H., et al., "p-Coumaroylated syringly units in maize lignin; implications for β-ether cleavage by thioacidolysis", Phytochem. 43(6), (1996), 1189-1194.
Grabber, John H., et al., "Apoplastic pH and Monolignol Addition Rate Effects on Lignin Formation and Cell Wall Degradability in Maize", J. Agric. Food Chem., 51, (2003), 4984-4989.
Grabber, John H., et al., "Coniferyl Ferulate Incorporation into Lignin Enhances the Alkaline Delignification and Enzymatic Degradation of Cell Walls", Biomacromolecules, 9, (2008), 2510-2516.
Grabber, Johh H., et al., "Cross-Linking of Maize Walls by Ferulate Dimerization and Incorporation into Lignin", J. Agric. Food Chem., 48, (2000), 6106-6113.
Grabber, John H., et al., "Dehydrogenation Polymer-Cell Wall Complexes as a Model for Lignified Grass Walls", J. Agric. Food Chem., 44, (1996), 1453-1459.
Grabber, John H., "Ferulate cross-linking in cell walls isolated from maize cell suspensions", Phytochemistry, (40)4, (1995), 1077-1082.
Grabber, John H., et al., "Ferulate Cross-Links Limit the Enzymatic Degradation of Synthetically Lignified Primary Walls of Maize", J. Agric. Food Chem., 46, (1998), 2609-2614.
Grabber, John H., et al., "Formation of syringyl-rich lignins in maize as influenced by feruloylated xylans and p-coumaroylated monolignols", Planta, 226(3), (2007), 741-751.
Grabber, John H., "How Do Lignin Composition, Structure, and Cross-Linking Affect Degradability? A Review of Cell Wall Model Studies", Crop. Sci., 45, (2005), 820-831.
Grabber, John H., et al., "Model Studies of Ferulate-Coniferyl Alcohol Cross-Product Formation in Primary Maize Walls: Implications for Lignification in Grasses", J. Agric. Food Chem., 50, (2002), 6008-6016.
Gratzl, Josef S., et al., "Chapter 20—Chemistry of Pulping: Lignin Reactions", In: Lignin: Historical, Biological, and Materials Perspectives, ACS Symposium Series, vol. 742, (2000), 392-421.
Hartley, R. D, "p-Coumaric and ferulic acid components of cell wals of ryegrass and their relationships with lignin and digestibility", J. Sci. Food. Agric., 23(11), (1972), 1347-1354.
Hartley, Roy D., "Monomeric and Dimeric Phenolic Acids Released from Cell Walls of Grasses by Sequential Treatment with Sodium Hydroxide", J. Sci. Food Agric., 55(3) (1991), 365-375.
Hatfield, R. D., et al., "Composition of cell walls isolated from cell types of grain sorghum stems", J. Sci. Food Agric., 79, (1999), 891-899.
Hatfield, R. D., et al., "Degradation Characteristics of Isolated and In Situ Cell Wall Lucerne Pectic Polysaccharides by Mixed Ruminal Microbes", J. Sci. Food Agric., 69, (1995), 185-196.
Hatfield, R. D., et al., "Using the Acetyl Bromide Assay to Determine Lignin Concentrations in Herbaceous Plants: Some Cautionary Notes", J. Agric. Food Chem., 47(2), (1999), 628-632.
Hatfield, Ronald D., et al., "A Comparison of the Insoluble Residues Produced by the Klason Lignin and Acid Detergent Lignin Procedures", J Sci Food Agric., 65, (1994), 51-58.
Hatfield, Ronald, et al., "A potential role for sinapyl p-coumarate as a radical transfer mechanism in grass lignin formation", Planta, 228, (2008), 919-928.
Helm, Richard F., et al., "Synthesis of feruloylated and p-coumaroylated methyl glycosides", Carbohydrate Research, 229(1), (1992), 183-194.
Howard, R. L., et al., "Lignocellulose biotechnology: issues of bioconversion and enzyme production", African Journal of Biotechnology, 2(12), (2003), 602-619.
Hsiao, Jeh-Jian, et al., "Lignans from the Wood of Aralia bipinnata", Phytochemistry, 39(4), (1995), 899-902.
Kim, Hoon, et al., "Solution-state 2D NMR of Ball-milled Plant Cell Wall Gels in DMSO-$d_6$", BioEnergy Research, 1, (2009), 56-66.
Kubes, G. J., et al., "Alkaline pulping with additivies. A review", Wood Sci. Technol., 14, (1980), 207-228.
Li, Song-Lin, et al., "Time-Course Accumulation of Main Bioactive Components in the Rhizome of Ligusticum chuanxiong", Planta Med., 72, (2006), 278-280.
Lu, Fachuang, et al., "Detection and Determination of p-Coumaroylated Units in Lignins", J. Agric. Food Chem., 47, (1999), 1988-1992.
Lu, Fachuang, et al., "Facile Synthesis of 4-Hydroxycinnamyl p-Coumarates", J. Agric. Food Chem., 46(8), (1998), 2911-2913.
Lu, Fachuang, et al., "Highly Selective Syntheses of Coniferyl and Sinapyl Alcohols", J. Agric. Food Chem., 46, (1998), 1794-1796.
Lu, Fachuang, et al., "Novel β-β-structures in lignins incorporating acylated monolignols", In: Proceedings, Thirteenth International Symposium on Wood, Fiber, and Pulping Chemistry, APPITA, vol. 3, Auckland, New Zealand, (2005), 233-237.
Lu, Fachuang, et al., "Novel tetrahydrofuran structures derived from β-β-coupling reactions involving sinapyl acetate in Kenaf lignins", Org. Biomol. Chem., 6(20), (2008), 3681-3694.
Lu, Fachuang, et al., "Preliminary evidence for sinapyl acetate as a lignin monomer in kenaf", Chemical Communications, Issue 1, (2002), 90-91.
Majcherczyk, Andrzej, et al., "Size-exclusion chromatography of lignin as ion-pair complex", Journal of Chromatography A, 764(2), (1997), 183-191.
Meyermans, Hugo, et al., "Modifications in Lignin and Accumulation of Phenolic Glucosides in Poplar Xylem upon Down-regulation of Caffeoyl-Coenzyme A O-Methyltransferase, an Enzyme Involved in Lignin Biosynthesis", The Journal of Biological Chemistry, 275(47), (2000), 36899-36909.
Mitchell, Rowan A, et al., "A Novel Bioinformatics Approach Identifies Candidate Genes for the Synthesis and Feruloylation of Arabinoxylan", Plant Physiology, 144(1), (2007), 43-53.
Murnen, H. K., et al., "Optimization of Ammonia Fiber Expansion (AFEX) Pretreatment and Enzymatic Hydrolysis of Miscanthus x Giganteus to Fermentable Sugars", Biotechnol. Prog., 23(4), (2007), 846-850.
Nakamura, Y., et al., "Ester linkage of p-coumaric acid in bamboo lignin. III. Dehydrogenative polymerization of coniferyl p-hydroxybenzoate and coniferyl p-coumarate", Cellulose Chem. Technol., 12(2), (1978), 209-221.
Nakano, J., et al., "Studies on lignin. XXXII. Ester groups of lignin", Tappi, 44(1), (1961), 30-32.

(56) References Cited

OTHER PUBLICATIONS

Oosterveld, Alexander, et al., "Formation of ferulic acid dehydrodimers through oxidative cross-linking of sugar beet pectin", *Carbohydrate Research*, 300, (1997), 179-181.

Paula, Vanderlucia F., et al., "Lignans from Ochroma lagopus Swartz", *Tetrahedron*, 51(45), (1995), 12453-12462.

Ralph, John, "An Unusual Lignin from Kenal", *Journal of Natural Products*, 59(4), (1996), 341-342.

Ralph, John, et al., "Lignin-ferulate cross-links in grasses: active incorporation of ferulate polysaccharide esters into ryegrass lignins", *Carbohydrate Research*, 275(1), (1995), 167-178.

Ralph, John, et al., "Lignin-Feruloyl Ester Cross-Links in Grasses. Part 1. Incorporation of Feruloyl Esters into Coniferyl Alcohol Dehydrogenation polymers", *Journal of the Chemical Society, Perkin Transactions 1*, Issue 21, (1992), 2961-2969.

Ralph, John, et al., "Lignins: Natural polymers from oxidative coupling of 4-hydroxyphenyl-propanoids", *Phytochemistry Reviews*, 3(1), (2004), 29-60.

Ralph, John, et al., "Methods of Modifying Lignin Structure", U.S. Appl. No. 61/213,706, filed Jul. 6, 2009, 92 pgs.

Ralph, John, et al., "Pathway of p-Coumaric Acid Incorporation into Maize Lignin as Revealed by NMR", *J. Am. Chem. Soc.*, 116, (1994,), 9448-9456.

Ralph, John, et al., "Peroxidase-dependant cross-linking reactions of p-hydroxycinnamates in plant cell walls", *Phytochemistry Reviews*, 3, (2004), 79-96.

Ralph, John, et al., "The DFRC Method for Lignin Analysis. 6. A Simple Modification for Identifying Natural Acetates on Lignins", *J. Agric. Food Chem.*, 46, (1998), 4616-4619.

Ralph, John, "What Makes a Good Monolignol Substitute?", *In: The Science and Lore of the Plant Cell Wall*, Hayashi, T., Editor, Brown Walker Press, Boca Raton, FL, (2006), 285-293.

Ralph, Sally A., et al., "NMR Database of Lignin and Cell Wall Model Compounds", [Online]. [archived on Feb. 24, 2013]. Retrieved from the Internet: <URL: https://web.archive.org/web/20130224043206/http://ars.usda.gov/Services/docs.htm?docid=10491>, (Nov. 2004), 2 pgs.

Santoro, Nicholas, et al., "A high-throughput screening assay for the carboxyltransferase subunit of acetyl-CoA carboxylase", *Anal. Biochem.*, 354(1), (2006), 70-77.

Sato, Yutaka, et al., "Field transcriptome revealed critical developmental and physiological transitions involved in the expression of growth potential in japonica rice", *BMC Plant Biology* 11(10), (2011), 1-15.

Sato, Yutaka, "RiceXPro: a platform grown for monitoring gene expression in japonica rice grown under natural field conditions", *Nucleic Acids Research*, 39(Sippl. 1), (2011), D1141-D1148.

Seca, Ana M. L., et al., "Phenolic constituents from the core of Kenaf (*Hibiscus cannabinus*)", *Phytochemistry*, 56, (2001), 759-767.

Selvendran, R. R., et al., "2. Developments in the Isolation and Analysis of Cell Walls From Edible Plants", *In: Biochemistry of Plant Cell Walls*, Brett, C. T., et al., Editors, Cambridge University Press, Cambridge, MA, (1985), 39-78.

Shatalov, A. A., et al., "*Arundo donax* L. reed: new perspectives for pulping and bleaching. Part 4. Peroxide bleaching of organosolv pulps.", *Bioresource Technology*, 96(8), (2005), 865-872.

Shea, Elaine M., et al., "Characterization of a Pectic Fraction from Smooth Bromegrass Cell Walls Using an Endopolygalacturonase", *J. Agric. Food Chem.*, 41, (1993), 380-307.

Shimada, Mikio, et al., "Ester Linkages of p-Coumaric Acide in Bamboo and Grass Lignins", *Tappi*, 54(1), (Jan. 1971), 72-78.

Smith, D. C. C., "p-Hydroxybenzoates groups in the lignin of Aspen (*Populus tremula*)", *J. Chem. Soc..*, (1955), 2347-2351.

Sun, R. C., et al., "Fractional Isolation and Structural Characterization of Lignins from Oil Palm Trunk and Empty Fruit Bunch Fibers", *Journal of Wood Chemistry and Technology*, 19(4), (1999), 335-356.

Vanholme, Ruben, et al., "Lignin engineering", *Current Opinion in Plant Biology*, 11, (2008), 278-285.

Wagner, Armin, et al., "CCoAOMT suppression modifies lignin composition in Pinus radiata", *The Plant Journal*, 67(1), (2011), 119-129.

Wilkerson, C. G., et al., "Monolignol Frerulate Transferase Introduces Chemically Labile Linkages in the Lignin Backbone", *Science*, 344(6179), and Supplementary Materials, (2014), 90-93, (34 pgs.).

Zhong, Ruiqin, et al., "A Battery of Transcription Factors Involved in the REgulation of Secondary Cell Wall Biosynthese in *Arabidopsis*", *The Plant Cell*, vol. 20, (2008), 2763-2782.

\* cited by examiner

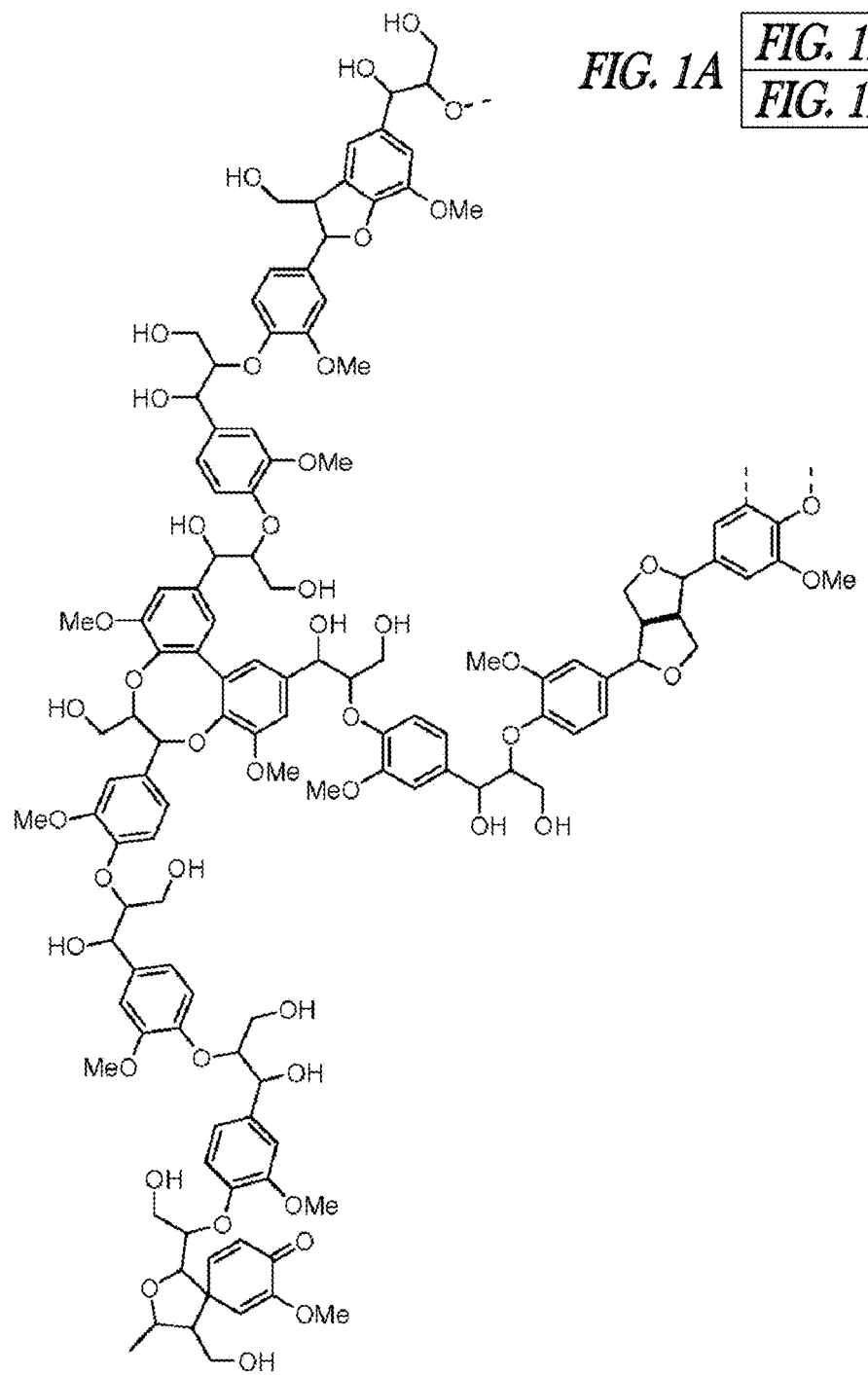
FIG. 1A1

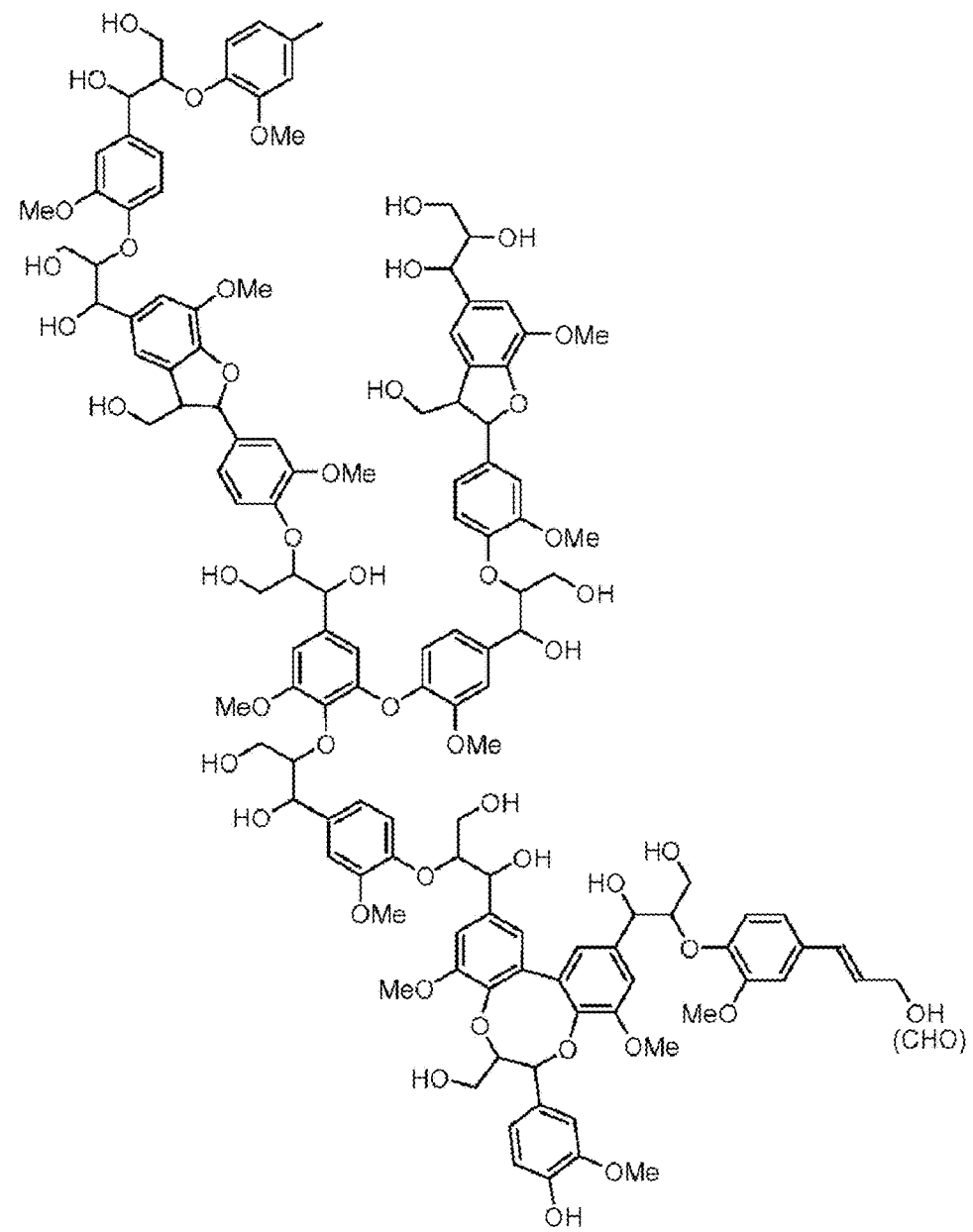
FIG. 1A2

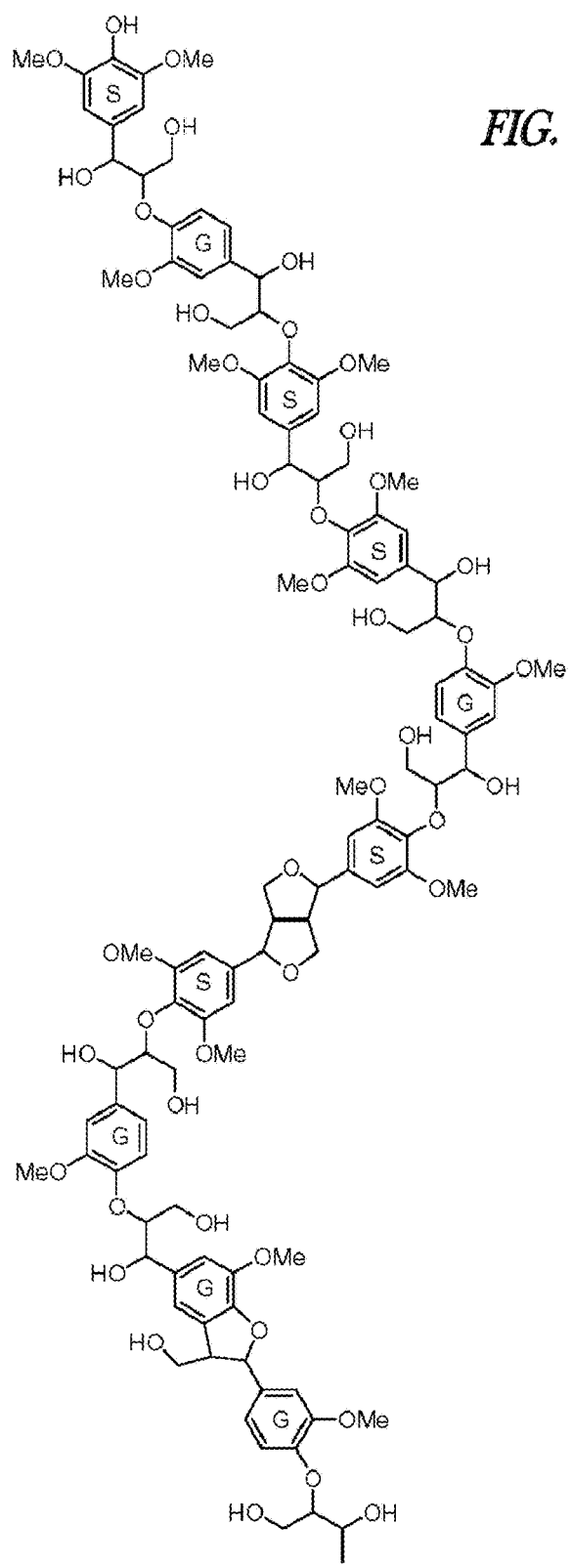
FIG. 1B1

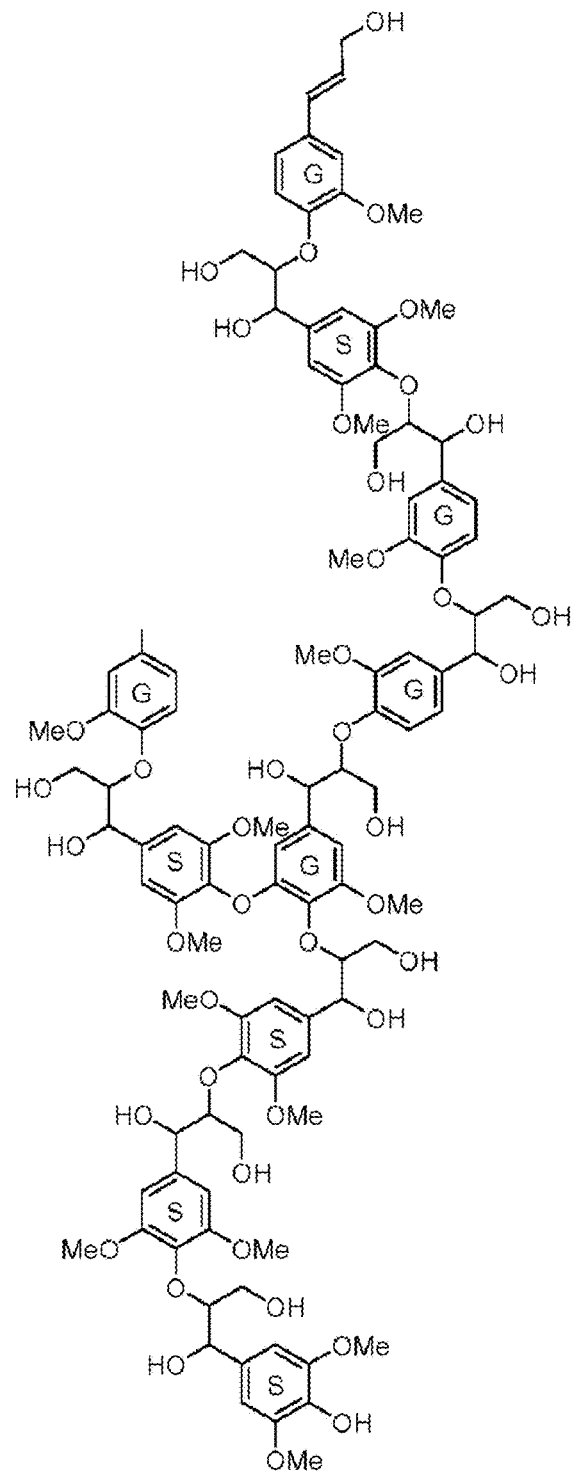
*FIG. 1B2*

Angelica sinensis and Hibiscus cannabinus protein sequence alignment

Score = 62.4 bits (150), Expect = 3e-14, Method: Compositional matrix adjust.
Identities = 88/389 (23%), Positives = 161/389 (41%), Gaps = 33/389 (8%)

```
Query  61   KSLSETLTKFYPLAGRFVQ--DG-FYVDCN-DEGVLYVEAEVNIPLNEFIGEKKNIQLI    116
            ++LS+ L +YPLAG+  + DG  +C  D+ V ++ A  + L+  + ++
Sbjct  70   EALSKLLVTYYPLAGRMK BETDGEKLRIACTADDSYFFLVATADCKLSSLMSLDGIDVHTG  129

Query  117  NDLVFKKNFKDINSTERPIVGLQMSYFKCGGLAICMYLSHVVADGYTAAAPTKEMSNTTN    176
                + +P+V +Q++ F CGG I + L+H V DG+ AA  +  +
Sbjct  130  KEFALDFASESDGGYTRPLV-MQVTKFICSSFTTALSLSHSVCDGFGAAQIFQALTME---  185

Query  177  GIIMGDHLVKSSPI-NEDLATLVFTKDL--STYIKFAVMPSKIKETKVYTRRFLEDEMA   233
             + +G   +V S P+    L    F +   + V K      T +V  F  E +
Sbjct  186  -LASGRNEFGVKPVNEBQLIVARPAEEIPRSIVDRDLSAASPYLPTTDIVSACFVVTEES  244

Query  234  ISAFFKDRVIKSESVMRFTBVENVTSVLNKALIMQSKL--BSSTLYFHLNERGKTCINTFFL  292
            I  K++IK       T ++V+++ +W+A     KL P +    + +  + +
Sbjct  245  IKTLKWNLIKRSKDESITSLEVLSAYIWRAFFRALRLSPDMTTHLGMAVGIRNTVKPRLP  304

Query  293  DNHFSLCGMFYTQVPTRFRGERNQTRQDLELRELVKLLKGMLRNTLKNCSEINTADGLFLE  352
            + ++       GM +  G        ++L+       L K ++       K SE N
Sbjct  305  EGTY----GNAFTSSARTANTG------KELDQGFLSKAVE-QIKESKKLASE-NDYIWNLMS  354

Query  353  AASNFNITGEDLEDEGVDVRIFFTILCKMPLFE-TELGN-GKFEWVTIFE---MHLEIVFL  407
                 +  E    +T R+ L E + GN G  +   +P   ++++V L
Sbjct  355  INEXLRELMSKFEAAAGSTMVITEMRKLGLLEDVDFGMKGSVMNIFLPWMFGYVDLVLL  414

Query  408  ------LDTKCGTNIEALVSMDEARNLQFE  431
                     LD    G    LVE    A  +F+
Sbjct  415  LPPCKLDQSMRGGEARVLVSFPTABIAKFK  443
```

FIG. 13

MGFAVVRTNREFVRPSAATPPSSGELLELSIIDRVVGLRHL
VRSLHIFSAAAPSGGDAKPSPARVIKEALGKALVDYYPFAG
RFVDGGGGPGSARVECTGEGAWFVEAAAGCSLDDVNGL
DHPLMIPEDDLLPDAAPGVHPLDLPLMMQVTEFSCGGFV
VGLISVHTMADGLGAGQFINAVGDYARGLDRPRVSPVW
AREAIPSPPKLPPGPPPELKMFQLRHVTADLSLDSINKAKS
AYFAATGHRCSTFDVAIAKTWQARTRALRLPEPTSRVNLCF
FANTRHLMAGAAAWPAPAAGGNGGNGFYGNCFYPVSV
VAESGAVEAADVAGVVGMIREAKARLPADFARWAVADFR
EDPYELSFTYDSLFVSDWTRLGFLEADYGWGPPSHVIPFAY
YPFMAVAIIGAPPVPKTGARIMTQCVEDDHLPAFKEEIKAF
DK

*FIG. 14A*

ATGGGGTTCGCGGTGGTGAGGACGAACCGGGAGTTCGTGCGGCCGAGCGCGGCGACGCCG
CCGTCGTCCGGCGAGCTGCTGGAGCTGTCCATCATCGACCGCGTGGTGGGGCTCCGCCAC
CTGGTGCGGTCGCTGCACATCTTCTCCGCCGCCGCCCCGAGCGGCGGCGACGCCAAGCCG
TCGCCGGCGCGGGTGATCAAGGAGGCGCTGGGGAAGGCGCTGGTGGACTACTACCCGTTC
GCGGGGAGGTTCGTGGACGGCGGCGGCGGGCCGGGGAGCGCCCGCGTGGAGTGCACCGGC
GAGGGCGCCTGGTTCGTGGAGGCCGCCGCCGGCTGCAGCCTCGACGACGTGAACGGCCTC
GACCACCCGCTCATGATCCCCGAGGACGACCTCCTCCCCGACGCCGCCCCCGGTGTCCAC
CCCCTCGACCTCCCCCTCATGATGCAGGTGACGGAGTTCAGTTGCGGAGGGTTCGTGGTG
GGCCTGATCTCGGTGCACACGATGGCGGACGGGCTAGGGGCCGGGCAGTTCATCAACGCG
GTGGGCGACTACGCCCGCGGGCTGGACAGGCCGAGGGTGAGCCCGGTCTGGGCCCGCGAG
GCCATCCCGAGCCCGCCGAAGCTGCCCCCGGGCCCGCCGCCGGAGCTGAAGATGTTCCAG
CTCCGCCACGTCACCGCCGACCTGAGCCTGGACAGCATCAACAAGGCCAAGTCCGCCTAC
TTCGCCGCCACCGGCCACCGCTGCTCCACCTTCGACGTCGCCATCGCCAAGACGTGGCAG
GCGCGCACCCGCGCGCTCCGCCTCCCGGAACCCACCTCCCGCGTCAACCTCTGCTTCTTC
GCCAACACCCGCCACCTCATGGCCGGCGCCGCCGCCTGGCCCGCACCCGCCGCCGGCGGC
AATGGCGGCAATGGGTTCTACGGCAACTGCTTCTACCCGGTGTCGGTGGTGGCGGAGAGC
GGGGCGGTGGAGGCGGCGGACGTGGCCGGGGTGGTGGGGATGATACGGGAGGCGAAGGCG
AGGCTGCCGGCGGACTTCGCGCGGTGGGCGGTGGCCGACTTCAGGGAGGATCCGTACGAG
CTGAGCTTCACGTACGATTCCCTGTTCGTCTCCGACTGGACGCGGCTGGGGTTCCTGGAG
GCGGACTACGGGTGGGGGCCGCCGTCGCACGTCATACCCTTCGCGTACTACCCGTTCATG
GCCGTCGCCATCATCGGCGCGCCGCCGGTGCCCAAGACCGGCGCCCGGATCATGACGCAG
TGCGTCGAGGACGACCACCTGCCGGCGTTCAAGGAGGAGATCAAGGCCTTCGACAAGTAA

*FIG. 14B*

```
ACCACCATCACCACCACCTCGAAGGTCTTGAGCTCCATCTCCGGCGACGGCGGCGACGAC
GACGACGACGGCGAGGAGGAGCTAGTAGCTAGCTGAGCCAGACAGCATGGGGTTCGCGGT
GGTGAGGACGAACCGGGAGTTCGTGCGGCCGAGCGCGGCGACGCCGCCGTCGTCCGGCGA
GCTGCTGGAGCTGTCCATCATCGACCGCGTGGTGGGGCTCCGCCACCTGGTGCGGTCGCT
GCACATCTTCTCCGCCGCCGCCCCGAGCGGCGGCGACGCCAAGCCGTCGCCGGCGCGGGT
GATCAAGGAGGCGCTGGGGAAGGCGCTGGTGGACTACTACCCGTTCGCGGGGAGGTTCGT
GGACGGCGGCGGCGGGCCGGGGAGCGCCCGCGTGGAGTGCACCGGCGAGGGCGCCTGGTT
CGTGGAGGCCGCCGCCGGCTGCAGCCTCGACGACGTGAACGGCCTCGACCACCCGCTCAT
GATCCCCGAGGACGACCTCCTCCCCGACGCCGCCCCGGTGTCCACCCCCTCGACCTCCC
CCTCATGATGCAGGTATAATACTACCCGTATACGTACGTTTCTACGTACGTAAGTACGTG
CTATACTTGCGAGCAGACAAAAACAAATAAAATCGGTAACAACAATTAACCATCCAGTTA
TGCTTACAACTAATTCAAATTATCTTAATTAATTAAAACTGTCCGGCTAATTAAGTGATT
ATTAAGGGTGTGTTTTTATCACATCTTCCCGACTGGTACTCCCTCATTTTCCACACGGAT
GTTTTACAACTGCTAAACGGTACGTATTATCAGAAAAAAGTTATATATATAAATTGTTTT
AAAATCATATTAATCTATTTTTAAGTTTATTTTAGCTAATAGTTAAATAAACACGCGCTA
ACGGATCATTATGTTTTGTGTGTGGGGAGATATAGTTTCTAACCTCCACCTCTAAACACA
GCATAATTGTTGGTACGTAGGGCCTATTCACTTTAACGCAAAAAAGAACCTTACCAAGT
TGCCAAAATTTTGGTAGGATTTCTTATATAGTTACTAAAATTTGATAGCAAACTAAATAT
AACCACTTTTTTATAACTTTACCAAAATTTGCTAAGATTGAAAATGGCATCAAAGTGAAC
AGGCCCGTATACGTACGGAGAATGCTGACCTCTCCGGATGATACCTTTAATTTTTCACTT
GTGTGGATGTGCACACATGTACGAGGACGAACACATTCAAACCCGTGAAGATTTTAATAT
GTGGACGAACTCGATCTATGGTATTGTTGCTGACGAATTAATTACAAAAGTGCTCAAGGA
GTTATGTAACTATAAGAACAAAACTATATATGTTTGCCCAAGTAGAAATATATACGAACA
AAAACACAGACATGAATAGAACCTACGCGTACGTACATATGTGCCATTACATGCATGTAC
ACAATCATTAGCTAGTGTCCTGGATTATATTCTAGTCAATTATAACTTTCTAGAAATTAG
GTACTAATATATGTATGACTCTCAAACTGTAGTCATGCTTGTGTCAAGTTATAATTAAGT
ACAATAATCACACCGATTTATTTTACATAAAGTACAGTAGGATTCAAGATAAGACTGAGC
TATATAGTACTAGGCAGGATGATGAGCTAGCTAGAGCTTAGTGCTCAACATAAACTAGTT
GGAGCGTGCACTGCAATTTTCAAAGTAAAATTAGTTAATTTGCACTAGGTGAAGTTGATC
CTGTCAGGTAGGTAAGCTCACCAACTCCAAAGATTGGACAGAATGAAGCATCTGTGGAAG
TGAAAGCAGTTGCGTTGGCGTAAGACCACACTAACCAGAGAACTCATAATACAAAATACA
TATACAGCACACAATTTATATTGTGTATATATATATATATATATATATATATGTATGT
ATGTATGTATGTATGTATTCTAACTGTGTTATCCAATTTTTAAGAAATTTCATCTTTTCA
AAAGTAGTAGTATTTGAGTGATGCATGTGCACGTTTTTAGATATGTACATATACCTCATC
TATCTTTAAAAATAAAATAAATTTTATACATGAGTCGGAACACTAAGCTTTAACACTGAT
ATCTGACGATAGCATGACGGGATGAGCTTGTCATCAATTGCAGCAGGGCAATTAGGCATG
TAAACTGGGGCCATTGATTTCTGTCGAGCACACTATGCTTTCCCTGTCTTATTCTGCCTA
```

*FIG. 14C1*

ACTTAACACTAATATTTGACACACTATCAATTGTTAGCTATTGATATGGCAGTTTGACAT
CGACCCTGCTCCATCATTATTACTGCATGCCCGCCCATTCGATGATTGACTTGACCAAAC
CCACAAGTGCAAATTGGAAAATTAATTAATTAATTAATTAGCAAGATAAATATATCCATC
AGGGATTCAGGATCAGGTCATGGATGTAATCACTCTCAAACATAGCTAATCATTGTGCTT
ATGGTCCAAGTGATCATTCCCCCTAATCAACAACTCGCTTGCTAGCAAGACGTCCCTTCG
AATGGATTATTTGATAGCTAGAGCATATCACCTTGCACTTCACCACTCCCCTTATGCAGA
GTGTACGTATGTCTAACCAGAATCTAGTGGTGAGCGTAAAAGATCAAAGTGCCCTTATCA
ATAACAAAATACTCCGTAATACATTTGGTGGATATATAGGTATATAAGTATTAAAGGAAT
AAAACTTTCAAATTTGTGGATTCTAATAAAAACTAATATTAATTTTGATAAACCTGAATT
GTAGATACTCTAACTTAGGGTAGTAGTTGAAGCATGCAAAGCTCTAAAAATATATATGAA
TTTCGGCGTGTTTATATATATTTCTCCGTGGATATAAAAGCTTAAAATTTATAATCATTT
TATGATGATCAGGTGACGGAGTTCAGTTGCGGAGGGTTCGTGGTGGGCCTGATCTCGGTG
CACACGATGGCGGACGGGCTAGGGGCCGGGCAGTTCATCAACGCGGTGGGCGACTACGCC
CGCGGGCTGGACAGGCCGAGGGTGAGCCCGGTCTGGGCCCGCGAGGCCATCCCGAGCCCG
CCGAAGCTGCCCCGGGCCCGCCGCCGGAGCTGAAGATGTTCCAGCTCCGCCACGTCACC
GCCGACCTGAGCCTGGACAGCATCAACAAGGCCAAGTCCGCCTACTTCGCCGCCACCGGC
CACCGCTGCTCCACCTTCGACGTCGCCATCGCCAAGACGTGGCAGGCGCGCACCCGCGCG
CTCCGCCTCCCGGAACCCACCTCCCGCGTCAACCTCTGCTTCTTCGCCAACACCCGCCAC
CTCATGGCCGGCGCCGCCGCCTGGCCCGCACCCGCCGCCGGCGGCAATGGCGGCAATGGG
TTCTACGGCAACTGCTTCTACCCGGTGTCGGTGGTGGCGGAGAGCGGGGCGGTGGAGGCG
GCGGACGTGGCCGGGGTGGTGGGGATGATACGGGAGGCGAAGGCGAGGCTGCCGGCGGAC
TTCGCGCGGTGGGCGGTGGCCGACTTCAGGGAGGATCCGTACGAGCTGAGCTTCACGTAC
GATTCCCTGTTCGTCTCCGACTGGACGCGGCTGGGGTTCCTGGAGGCGGACTACGGGTGG
GGGCCGCCGTCGCACGTCATACCCTTCGCGTACTACCCGTTCATGGCCGTCGCCATCATC
GGCGCGCCGCCGGTGCCCAAGACCGGCGCCCGGATCATGACGCAGTGCGTCGAGGACGAC
CACCTGCCGGCGTTCAAGGAGGAGATCAAGGCCTTCGACAAGTAAAATGCTTGTGAAATG
TGAACTTTGTTATTGTTACTACTTCTATGGGCTCGTTGCTCAATGGGCTTTTTTTTGCTT
TTGTTTTGTGTGTGTGGGCCGACACGATTGGTCAAAAGGGATTTGGTGGAGGCCCAGTTG
TAATAAGATGGTCCACGCATCATGGATTAATCGTTAATTGTAAGGTAGTACTACACGGAT
TTGTTAACAAGGAATAAGTTCACTTGGTGACCCAGTGA
```

*FIG. 14C2*

ATGGGATTTGCTGTTGTCCGCACAAACCGTGAATTTGTTCGCCCCTCGG
CAGCTACCCCACCATCATCCGGCGAATTATTGGAATTATCAATCATTGATC
GTGTAGTTGGTCTCCGTCATCTGGTTCGTTCTTTACATATTTTTCTGCAG
CTGCACCATCTGGCGGTGATGCAAAACCCTCCCCGGCTCGCGTTATTAA
AGAAGCATTGGGCAAAGCACTTGTAGACTACTATCCTTTCGCAGGTCGT
TTCGTTGACGGCGGCGGCGGTCCGGGCAGTGCGCGTGTAGAATGTACC
GGTGAAGGTGCTTGGTTTGTAGAAGCAGCTGCTGGATGTTCATTAGAC
GATGTCAATGGCTTAGATCATCCATTAATGATTCCTGAAGACGATCTCTTA
CCCGATGCAGCCCCTGGCGTTCACCCACTGGATTTACCGTTAATGATGCA
AGTTACTGAATTTTCATGCGGCGGTTTTGTTGTTGGCTTGATTAGCGTCC
ACACAATGGCTGACGGTTTAGGCGCAGGCCAATTTATCAATGCAGTAGG
CGATTATGCTCGTGGCCTCGACCGTCCGCGTGTTAGCCCGGTATGGGCA
CGCGAAGCCATTCCTAGCCCTCCGAAGTTACCACCCGGTCCACCTCCCG
AATTAAAAATGTTCCAACTTCGTCATGTGACAGCCGATTTGTCTCTCGATT
CTATCAACAAGGCGAAATCAGCGTATTTTGCAGCCACCGGTCATCGTTG
CTCCACATTCGACGTCGCTATTGCAAAAACATGGCAAGCCCGCACTCGT
GCCCTTCGTCTCCCAGAACCAACGTCACGTGTTAACCTGTGTTTTTTTGC
TAATACCCGCCATTTAATGGCAGGCGCAGCGGCCTGGCCCGCTCCAGCA
GCCGGAGGTAATGGTGGCAACGGCTTCTATGGCAATTGTTTCTACCCGG
TGTCTGTTGTGGCCGAATCAGGTGCAGTTGAAGCGGCAGATGTGGCAG
GTGTTGTTGGTATGATCCGTGAGGCCAAAGCCCGTCTCCCAGCCGATTT
TGCACGTTGGGCAGTTGCCGATTTTCGCGAAGACCCTTATGAACTTTCA
TTTACATATGATTCCTTGTTTGTCTCAGATTGGACTCGTTTAGGATTTCTC
GAAGCTGATTATGGTTGGGGCCCACCCTCTCATGTAATTCCTTTCGCATA
TTACCCGTTTATGGCGGTAGCTATCATCGGCGCTCCTCCAGTTCCAAAAA
CCGGCGCACGTATTATGACTCAGTGTGTAGAAGATGATCATTTACCAGCG
TTTAAAGAAGAAATTAAAGCCTTCGATAAGTGA

*FIG. 14D*

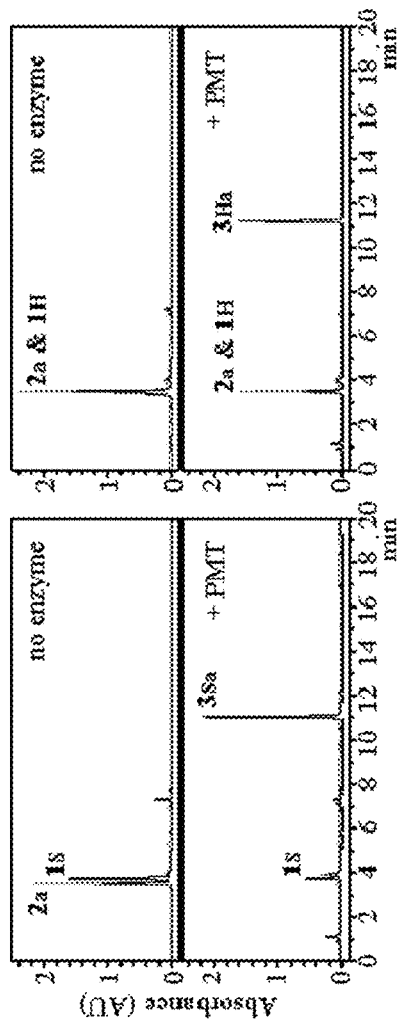
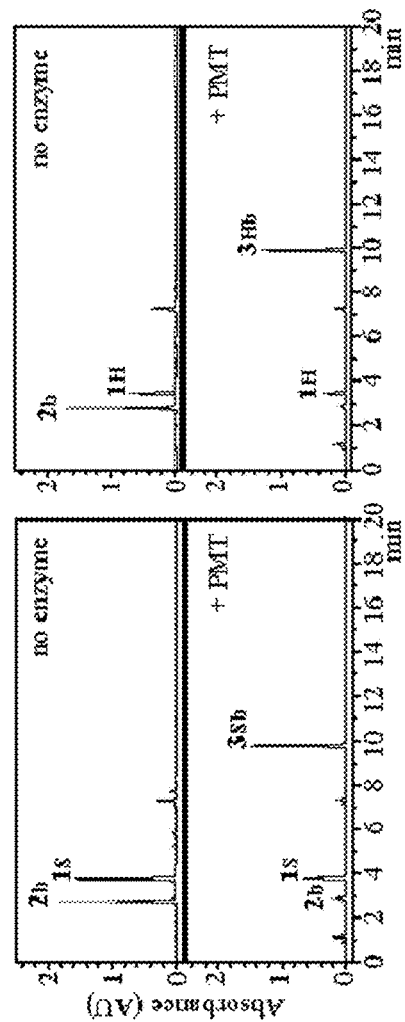
FIG. 19A  FIG. 19B  FIG. 19C  FIG. 19D

```
  1 TTAGCCTGCAGGCCGTGGATTTGATAGAGAGAGTGCTTTACAATGGAGAAGAAGTTCACG
    ..........................................ATGGAGAAGAAGTTCACG
    ..........................................~M~~E~~K~~K~~F~~T~

61 GTGACTAGGACTAGCAAGTCCCTGGTGCCCCCATCTTCGTCTTCCCCAACACCGGCGGCG
 19 GTGACTAGGACTAGCAAGTCCCTGGTGCCCCCATCTTCGTCTTCCCCAACACCGGCGGCG
  7 ~V~~T~~R~~T~~S~~K~~S~~L~~V~~P~~P~~S~~S~~S~~P~~T~~P~~A~~A~

121 ACAGAGGACGATGCACCAGTGCCGGTGATCATGCGCCTGTCGACGATCGACCGTGTTCCC
 79 ACAGAGGACGATGCACCAGTGCCGGTGATCATGCGCCTGTCGACGATCGACCGTGTTCCC
 27 ~T~~E~~D~~D~~A~~P~~V~~P~~V~~I~~M~~R~~L~~S~~T~~I~~D~~R~~V~~P~

181 GGGCTGCGCCACCTGGTGCTCTCCCTCCACGCCTTCGACGGCCATGGCGTCGTTGCCGGA
139 GGGCTGCGCCACCTGGTGCTCTCCCTCCACGCCTTCGACGGCCATGGCGTCGTTGCCGGA
 47 ~G~~L~~R~~H~~L~~V~~L~~S~~L~~H~~A~~F~~D~~G~~H~~G~~V~~V~~A~~G~

241 GAAGACGACGAAGAGCGAATTAGGTGGCCGGCGAGGGTGGTGAGGGAGGCGCTGGGGAAG
199 GAAGACGACGAAGAGCGAATTAGGTGGCCGGCGAGGGTGGTGAGGGAGGCGCTGGGGAAG
 67 ~E~~D~~D~~E~~E~~R~~I~~R~~W~~P~~A~~R~~V~~V~~R~~E~~A~~L~~G~~K~

301 GCGCTCGTGGACTACTACCCGTTTGCCGGGAGGTTCGTGGTGGACGAGGAAGGGGAGGTG
259 GCGCTCGTGGACTACTACCCGTTTGCCGGGAGGTTCGTGGTGGACGAGGAAGGGGAGGTG
 87 ~A~~L~~V~~D~~Y~~Y~~P~~F~~A~~G~~R~~F~~V~~V~~D~~E~~E~~G~~E~~V~

361 GGCGTGAAGTGCAGCGGCGAGGGGGCGTGGTTCGTGGAGGCCAAGGCGGAGTGCTCGTTG
319 GGCGTGAAGTGCAGCGGCGAGGGGGCGTGGTTCGTGGAGGCCAAGGCGGAGTGCTCGTTG
107 ~G~~V~~K~~C~~S~~G~~E~~G~~A~~W~~F~~V~~E~~A~~K~~A~~E~~C~~S~~L~

421 GAGGAGGCGAGGCACCTTGATGGGAACCCCATGGAGATGGTGATCCCCAAGGAGGACCTT
379 GAGGAGGCGAGGCACCTTGATGGGAACCCCATGGAGATGGTGATCCCCAAGGAGGACCTT
127 ~E~~E~~A~~R~~H~~L~~D~~G~~N~~P~~M~~E~~M~~V~~I~~P~~K~~E~~D~~L~

481 CTCCCGGAGCCCATTCCCGGGGTCGACCCCCTCGACATCCCCCTCATCATGCAGGTGACA
439 CTCCCGGAGCCCATTCCCGGGGTCGACCCCCTCGACATCCCCCTCATCATGCAGGTGACA
147 ~L~~P~~E~~P~~I~~P~~G~~V~~D~~P~~L~~D~~I~~P~~L~~I~~M~~Q~~V~~T~

541 GAATTCACATGCGGCGGCTTCGTGGTGGGCCTGATCTCGGTGCACACCATCGCCGACGGG
499 GAATTCACATGCGGCGGCTTCGTGGTGGGCCTGATCTCGGTGCACACCATCGCCGACGGG
167 ~E~~F~~T~~C~~G~~G~~F~~V~~V~~G~~L~~I~~S~~V~~H~~T~~I~~A~~D~~G~

601 CTAGGCGCCGGCCAGTTCATCAACGCGGTGGCGGACTACGCGCGGGGCCTCCCGAAGCCT
559 CTAGGCGCCGGCCAGTTCATCAACGCGGTGGCGGACTACGCGCGGGGCCTCCCGAAGCCT
187 ~L~~G~~A~~G~~Q~~F~~I~~N~~A~~V~~A~~D~~Y~~A~~R~~G~~L~~P~~K~~P~

661 CGTGTGTCTCCGGTGTGGGCCCGGGACCTCGTCCCGGACCCTCCGAAGATGCCGGCGCCA
619 CGTGTGTCTCCGGTGTGGGCCCGGGACCTCGTCCCGGACCCTCCGAAGATGCCGGCGCCA
207 ~R~~V~~S~~P~~V~~W~~A~~R~~D~~L~~V~~P~~D~~P~~P~~K~~M~~P~~A~~P~

721 CCGCCGAAGCTGGAGCTCCTGGACCTCCGCCACTTCACCGTGGACCTGAGCCCCGGACCAC
```

*FIG. 20B1*

```
 679 CCGCCGAAGCTGGAGCTCCTGGACCTCCGCCACTTCACCGTGGACCTGAGCCCGGACCAC
 227 -P---P---K---L---E---L---L---D---L---R---H---F---T---V---D---L---S---P---D---H-

781 ATCGCCAAGGTCAAGTCCCAGTACTTCGCCTCCACGGGCCACCGGCTGCTCCGCCTTCGAC
 739 ATCGCCAAGGTCAAGTCCCAGTACTTCGCCTCCACGGGCCACCGGCTGCTCCGCCTTCGAC
 247 -I---A---K---V---K---S---Q---Y---F---A---S---T---G---H---R---C---S---A---F---D-

841 GTCGTCGTCGCCGTCACCTGGCAGTCCCGCACCCGTGCCCTCCGCCTCGCCGGTGCCGGC
 799 GTCGTCGTCGCCGTCACCTGGCAGTCCCGCACCCGTGCCCTCCGCCTCGCCGGTGCCGGC
 267 -V---V---V---A---V---T---W---Q---S---R---T---R---A---L---R---L---A---G---A---G-

901 TACGACGACGTCCACGTCTGCTTCTTCGCCAACACCCGCCACCTCATGCTCCACGGTGGC
 859 TACGACGACGTCCACGTCTGCTTCTTCGCCAACACCCGCCACCTCATGCTCCACGGTGGC
 287 -Y---D---D---V---H---V---C---F---F---A---N---T---R---H---L---M---L---H---G---G-

961 GCCGGCGCGGCGGGGTTCTACGGCAACTGCTTCTACCCGGTGAGAGCCACGTGCGGGAGC
 919 GCCGGCGCGGCGGGGTTCTACGGCAACTGCTTCTACCCGGTGAGAGCCACGTGCGGGAGC
 307 -A---G---A---A---G---F---Y---G---N---C---F---Y---P---V---R---A---T---C---G---S-

1021 GCTGAGGTGGCGTCGGCTGACGTGGCGGGGGTGGTGAAGGTGGTGAGGGACGCCAAGGCC
 979 GCTGAGGTGGCGTCGGCTGACGTGGCGGGGGTGGTGAAGGTGGTGAGGGACGCCAAGGCC
 327 -A---E---V---A---S---A---D---V---A---G---V---V---K---V---V---R---D---A---K---A-

1081 AGGCTGGCGGGGGACGTGGCGAGGTGGGCCGTGGGCGGGTTCGAGCAGGACCCCTACGAG
1039 AGGCTGGCGGGGGACGTGGCGAGGTGGGCCGTGGGCGGGTTCGAGCAGGACCCCTACGAG
 347 -R---L---A---G---D---V---A---R---W---A---V---G---G---F---E---Q---D---P---Y---E-

1141 CTGACCTTCACCTACGACTCCCTCTTCGTGTCGGACTGGACCAGGCTGGGCTTTCTAGAG
1099 CTGACCTTCACCTACGACTCCCTCTTCGTGTCGGACTGGACCAGGCTGGGCTTTCTAGAG
 367 -L---T---F---T---Y---D---S---L---F---V---S---D---W---T---R---L---G---F---L---E-

1201 GCCGACTACGGGTGGGGGCCCCCGGCCCACGTGGTGCCCTTCTCGTATCACCCCTTCATG
1159 GCCGACTACGGGTGGGGGCCCCCGGCCCACGTGGTGCCCTTCTCGTATCACCCCTTCATG
 387 -A---D---Y---G---W---G---P---P---A---H---V---V---P---F---S---Y---H---P---F---M-

1261 GCTGTTGCCGTCATCGGCGCACCGCCCAAGCCCAAGCTCGGCTCCCGCGTCATGACCATG
1219 GCTGTTGCCGTCATCGGCGCACCGCCCAAGCCCAAGCTCGGCTCCCGCGTCATGACCATG
 407 -A---V---A---V---I---G---A---P---P---K---P---K---L---G---S---R---V---M---T---M-

1321 TGTGTGGAGGAAGACCACCTCCCGGAGTTCCGGGACCAGATGAACGCCTTCGCCTTCACC
1279 TGTGTGGAGGAAGACCACCTCCCGGAGTTCCGGGACCAGATGAACGCCTTCGCCTTCACC
 427 -C---V---E---E---D---H---L---P---E---F---R---D---Q---M---N---A---F---A---F---T-

1381 GCCGGGAAGTGAGTAAGCAACGATCCATAATCGTCCATGTATGAAGCCAATTGAGCGTG
1339 GCCGGGAAGTGA................................................
 447 -A---G---K---*-.............................................

1441 CAAGCGCTTAATTACTACACCTTTTTATAATCAGTAGCTCTTCTATGTCTGGTGTGTGTG
     ............................................................
     ............................................................
```

FIG. 20B2

1501 CGTGCAATGTATGTAATTTGCTTGTTTGATCGAACTGGCGCAATTAGGCGTTGTGCTTAA

1561 TTGTATCGTGGGTCCATCGAATGAACGATGATGAAGCAATAAATGACCATGATTTGTACT

1621 GCTTCCAAATGTATACTGGTAGTATATAGTACCATGTGTCATGTGCGTGTGTCATCTGGT

1681 AAAATTAAGACGGATTTTCTTCTGGCCT

*FIG. 20B3*

Citrus sinensis (orange1.1g014078m; peptide SEQ ID NO:29; nucleic acid sequence SEQ ID NO:47)

```
 991 gagctacctgttgaatttgctaagtacatgaatggagattttacc
      E  L  P  V  E  F  A  K  Y  M  N  G  D  F  T
1036 aggaacggtgaggacccattcgccccacctctggcttatacaaca
      R  N  G  E  D  P  F  A  P  P  L  A  Y  T  T
1081 ttgtttatatcagagtggggacgactgggattcaaccagattgac
      L  F  I  S  E  W  G  R  L  G  F  N  Q  I  D
1126 tatgggtggggccctcctgtccacgtggtaccaattcaaggctcg
      Y  G  W  G  P  P  V  H  V  V  P  I  Q  G  S
1171 agtattattccggttggcattgtgggttcgatgccgttgcccaaa
      S  I  I  P  V  G  I
```

Sorghum bicolor (Sb10g023160.1; peptide SEQ ID NO:30; nucleic acid sequence SEQ ID NO:48)

```
1036 gcgcggtggagcgcggggggacaccggcggcgtggacccgtaccgg
      A  R  W  S  A  G  D  T  G  G  V  D  P  Y  R
1081 atcacgtcggactaccggacgctgctggtgtcggactggtcgcgg
      I  T  S  D  Y  R  T  L  L  V  S  D  W  S  R
1126 ctcgggttcgcggaggtggactacgggtggggctgccccgtgcac
      L  G  F  A  E  V  D  Y  G  W  G  C  P  V  H
1171 gtcgtcccgctcaccaacctcgactacatcgcgacgtgcatcctg
      V  V  P  L  T  N  L  D  Y  I  A  T  C  I
```

Zea mays (GRMZM2G060210_T01; peptide SEQ ID NO:31; nucleic acid sequence SEQ ID NO:49)

```
1036 gaggacgccgaccccctaccagatcacctccgactaccggacgctg
      E  D  A  D  P  Y  Q  I  T  S  D  Y  R  T  L
1081 ctggtgtcggactggacgcggctgggcttcgcggaggtggactac
      L  V  S  D  W  T  R  L  G  F  A  E  V  D  Y
1126 ggctggggcccgcccgcccacgtggtgccgctgacgaacttggac
      G  W  G  P  P  A  H  V  V  P  L  T  N  L  D
1171 tacatcgccacgtgcatc
```

*FIG. 25A*

Bachypodium distachyon (Bradi4g06067.1; peptide SEQ ID NO:32; nucleic acid sequence SEQ ID NO:50)

```
1036 ttaggaggaggaggggctggggataagatgaagtttgtgcaggat
     L  G  G  G  A  G  D  K  M  K  F  V  Q  D
1081 gatccttatgagctgaggtttgagcataatgtgttgtttgtgtcg
     D  P  Y  E  L  R  F  E  H  N  V  L  F  V  S
1126 gattggacgaggcttgggttcttggaggtggactatggctggggc
     D  W  T  R  L  G  F  L  E  V  D  Y  G  W  G
1171 gtgcctagccatgttataccttcaattatgcggactacatggcg
     V  P  S  H  V  I  P  F  N  Y  A  D  Y  M  A
1216 gtcgcggtgctcggtgctccgccggcgccggtgaagggactcgg
     V  A  V
```

Oryza sativa (LOC_Os05g19910.1; peptide SEQ ID NO:33; nucleic acid sequence SEQ ID NO:51)

```
1036 ggggatgtgaaagttgatccctacgcattgacatttgaacacaat
     G  D  V  K  V  D  P  Y  A  L  T  F  E  H  N
1081 gtgcttttgtgtctgattggacgaggttaggattcttcgaggta
     V  L  F  V  S  D  W  T  R  L  G  F  F  E  V
1126 gactatggtggggtacacctaatcacatcataccattcacttat
     D  Y  G  W  G  T  P  N  H  I  I  P  F  T  Y
1171 gcagactacatggcagtcgcagtgcttggtgctccaccaatgcca
     A  D  Y  M  A  V  A  V
```

Panicum virgatum (Pavirv00015375m; peptide SEQ ID NO:34; nucleic acid sequence SEQ ID NO:52)

```
901  gggggattctatggcaactgcttctacccagtttctgtgacggcc
     G  G  F  Y  G  N  C  F  Y  P  V  S  V  T  A
946  actgctgaggatgttgtcactgcagggttgcttgatgtgatcagg
     T  A  E  D  V  V  T  A  G  L  L  D  V  I  R
991  atgataaggaatgggaaggccaggcttcccctggagttttccaag
     M  I  R  N  G  K  A  R  L  P  L  E  F  S  K
1036 tgggcagcaggggatgtgagtgtggatccataccagttgacattt
     W  A  A  G  D  V  S  V  D  P  Y  Q  L  T  F
1081 gagcacaacgtgttgtttgtgtctgattggacgagacttgggttc
     E  H  N  V  L  F  V  S  D  W  T  R  L  G  F
1126 tccgaggttgactatggtggggtgcaccggatcatatcgtgcca
     S  E  V  D  Y  G  W  G  A  P  D  H  I  V  P
1171 ttcacctatgcagactacatggcggtggcggttcttggggctccg
     F  T  Y  A  D  Y  M  A  V  A  V
```

*FIG. 25B*

Sorghum bicolor (Sb08g005680.1; peptide SEQ ID NO:35; nucleic acid sequence SEQ ID NO:53)

```
1036 tttgccaaatggtccatgggtgatgtgaaggtagacccatatcaa
      F  A  K  W  S  M  G  D  V  K  V  D  P  Y  Q
1081 ctgacattcaagcacaatgttctgtttgtgtctgattggacgagg
      L  T  F  K  H  N  V  L  F  V  S  D  W  T  R
1126 cttggattctttgaggttgactatgggtggggtgtaccaaaccat
      L  G  F  F  E  V  D  Y  G  W  G  V  P  N  H
1171 atcatacctttcacttatgcagactacatggctgtagcagttctt
      I  I  P  F  T  Y  A  D  Y  M  A  V  A  V
```

Zea mays (GRMZM2G130728_T01; peptide SEQ ID NO:36; nucleic acid sequence SEQ ID NO:54)

```
1036 acgggcaatgtgaaagtagacccatatcaactaacattcaagcac
      T  G  N  V  K  V  D  P  Y  Q  L  T  F  K  H
1081 aatgttctatttgtgtccgattggacacggcttggattctttgaa
      N  V  L  F  V  S  D  W  T  R  L  G  F  F  E
1126 gttgactatgggtggggtgtaccaaaccatatcctcccttccact
      V  D  Y  G  W  G  V  P  N  H  I  L  P  F  T
1171 tatgcagactacatggctgtagcagttcttggagctccaccgtct
      Y  A  D  Y  M  A  V  A  V
```

Bachypodium distachyon (Bradi2g36910.1; peptide SEQ ID NO:37; nucleic acid sequence SEQ ID NO:55)

```
1036 gccaggctggcgggggacgtggcgaggtgggccgtgggcgggttc
      A  R  L  A  G  D  V  A  R  W  A  V  G  G  F
1081 gagcaggacccctacgagctgaccttcacctacgactccctcttc
      E  Q  D  P  Y  E  L  T  F  T  Y  D  S  L  F
1126 gtgtcggactggaccaggctgggctttctagaggccgactacggg
      V  S  D  W  T  R  L  G  F  L  E  A  D  Y  G
1171 tgggggcccccggcccacgtggtgcccttctcgtatcaccccttc
      W  G  P  P  A  H  V  V  P  F  S  Y  H  P  F
1216 atggctgttgccgtcatcggcgcaccgcccaagcccaagctcggc
      M  A  V  A  V
```

*FIG. 25C*

Oryza sativa (LOC_Os05g04584.1; peptide SEQ ID NO:38; nucleic acid sequence SEQ ID NO:56)

```
1036 gtgggcgggttcgaggaggacccctacgagctgaccttcacctac
      V  G  G  F  E  E  D  P  Y  E  L  T  F  T  Y
1081 gactccctcttcgtctccgactggacgcggctcggcttcctagac
      D  S  L  F  V  S  D  W  T  R  L  G  F  L  D
1126 gccgactatggctggggcacgccgtcgcacgtcgtgccgttctcc
      A  D  Y  G  W  G  T  P  S  H  V  V  P  F  S
1171 taccacccgttcatggccgtcgccgtcatcggcgcgccgccggcg
      Y  H  P  F  M  A  V  A  V
```

Setaria italica (Si022109m; peptide SEQ ID NO:39; nucleic acid sequence SEQ ID NO:57)

```
 991 cggctggccgcggacttcgcgcggtgggcgggcggagggttcgag
      R  L  A  A  D  F  A  R  W  A  G  G  G  F  E
1036 cgcgacccctacgagctcaccttcacctacgactcgctcttcgtc
      R  D  P  Y  E  L  T  F  T  Y  D  S  L  F  V
1081 tccgactggacgcggctcgggttcctggaggcggactacgggtgg
      S  D  W  T  R  L  G  F  L  E  A  D  Y  G  W
1126 ggcacgccggcgcacgtcctgcccttctcgtaccaccccttcatg
      G  T  P  A  H  V  L  P  F  S  Y  H  P  F  M
1171 gccgtcgccgtcatcggagcgccgccggcgcccaagcccggagcg
      A  V  A  V
```

Panicum virgatum (Pavirv00037046m; peptide SEQ ID NO:40; nucleic acid sequence SEQ ID NO:58)

```
 991 gcgcggtgggcggcgggcgggttcgagcgcgacccctacgagctc
      A  R  W  A  A  G  G  F  E  R  D  P  Y  E  L
1036 accttcagctacgactcgctcttcgtctccgactggacgcggctg
      T  F  S  Y  D  S  L  F  V  S  D  W  T  R  L
1081 gggttcctggaggcggactacgggtggggcgcgccggcgcacgtc
      G  F  L  E  A  D  Y  G  W  G  A  P  A  H  V
1126 gtgcccttctcctaccacccettcatggccgtcgccgtcatcggc
      V  P  F  S  Y  H  P  F  M  A  V  A  V
```

*FIG. 25D*

Sorghum bicolor (Sb09g002910.1; peptide SEQ ID NO:41; nucleic acid sequence SEQ ID NO:59)

```
1036 tgggcggcgggcgggtttgatcgggaccccctacgagctcaccttc
      W  A  A  G  G  F  D  R  D  P  Y  E  L  T  F
1081 acctacgactccctcttcgtctccgactggacgaggctagggttc
      T  Y  D  S  L  F  V  S  D  W  T  R  L  G  F
1126 ctcgaggctgactatggctggggcacgccgacgcacgtcgtgccg
      L  E  A  D  Y  G  W  G  T  P  T  H  V  V  P
1171 ttctcgtaccacccgttcatggccgtcgccgtcatcggggcgccg
      F  S  Y  H  P  F  M  A  V  A  V
```

Zea mays (GRMZM2G028104_T01; peptide SEQ ID NO:42; nucleic acid sequence SEQ ID NO:60)

```
1036 gcgggcggcttcgaccgcgaccccctacgagctcaccttcacctac
      A  G  G  F  D  R  D  P  Y  E  L  T  F  T  Y
1081 gactcgctcttcgtctccgactggacgcgcctcggcttcctcgag
      D  S  L  F  V  S  D  W  T  R  L  G  F  L  E
1126 gcggactacggctggggcaccccgacacacgtcctgcccttctcc
      A  D  Y  G  W  G  T  P  T  H  V  L  P  F  S
1171 taccacccgttcatggccgtcgccgtcatcggcgccccgcctaag
      Y  H  P  F  M  A  V  A  V
```

Setaria italica (Si005037m; peptide SEQ ID NO:43; nucleic acid sequence SEQ ID NO:61)

```
1036 ccggcggagttcgcgcggtgggcggcggggggagctcgtcggggtc
      P  A  E  F  A  R  W  A  A  G  E  L  V  G  V
1081 gaggaccccctacgagctgccgttcgcgtacgaggcgctattcgtg
      E  D  P  Y  E  L  P  F  A  Y  E  A  L  F  V
1126 tcggactggacgcggcttgggttccaggaagcggactacgggtgg
      S  D  W  T  R  L  G  F  Q  E  A  D  Y  G  W
1171 ggtgggccttcccacgtgatacctttggcttatcacccgcacatg
      G  G  P  S  H  V  I  P  L  A  Y  H  P  H  M
1216 cccatcgccatcgtcggtgcaccgccggcgccacggatgggggtc
      P  I  A  I
```

*FIG. 25E*

Oryza sativa (LOC_Os01g18744.1; peptide SEQ ID NO:44; nucleic acid sequence SEQ ID NO:62)

```
1036 ttcgcgcggtgggcggtggccgacttcagggaggatccgtacgag
      F  A  R  W  A  V  A  D  F  R  E  D  P  Y  E
1081 ctgagcttcacgtacgattccctgttcgtctccgactggacgcgg
      L  S  F  T  Y  D  S  L  F  V  S  D  W  T  R
1126 ctggggttcctggaggcggactacgggtgggggccgccgtcgcac
      L  G  F  L  E  A  D  Y  G  W  G  P  P  S  H
1171 gtcataccttcgcgtactacccgttcatggccgtcgccatcatc
      V  I  P  F  A  Y  Y  P  F  M  A  V  A  I
```

Setaria italica (Si004231m; peptide SEQ ID NO:45; nucleic acid sequence SEQ ID NO:63)

```
1036 ctcgtggagaaggaccccctacgagctgaccttttcgtacgagtcg
      L  V  E  K  D  P  Y  E  L  T  F  S  Y  E  S
1081 ctgttcgtgtcggactggacccggctggggttcctggacgctgac
      L  F  V  S  D  W  T  R  L  G  F  L  D  A  D
1126 tacggctgggggacgccgttgcaggtgatacccttacgtaccac
      Y  G  W  G  T  P  L  Q  V  I  P  F  T  Y  H
1171 ccggccatgcccatcgccatcatcagcgcgccgccggcgcccaag
      P  A  M  P  I  A  I
```

Panicum virgatum (Pavirv00066580m; peptide SEQ ID NO:46; nucleic acid sequence SEQ ID NO:64)

```
829  gcgcggctccccgccgagttcgcgcggtgggcggcgggcgagctc
      A  R  L  P  A  E  F  A  R  W  A  A  G  E  L
874  gtggcgcaggaccccctacgagctgagcttcacgtacgagtcgctg
      V  A  Q  D  P  Y  E  L  S  F  T  Y  E  S  L
919  ttcgtgtcggactggacgcggctggggttcctggaggcggactac
      F  V  S  D  W  T  R  L  G  F  L  E  A  D  Y
964  ggctgggggcacgccggagcaggtgatacccttcgcgtaccaccccg
      G  W  G  T  P  E  Q  V  I  P  F  A  Y  H  P
1009 tgcatgcccatcgcggtcatcggcccgccgccggcgcccaagacg
      C  M  P  I  A  V  I
```

*FIG. 25F*

… # P-COUMAROYL-COA:MONOLIGNOL TRANSFERASE

This application is a U.S. National Stage Application under 35 U.S.C. § 371 of PCT/US2012/069902, filed on Dec. 14, 2012, and published on Jun. 20, 2013 as WO 2013/090814, which claims benefit of the filing date of U.S. Provisional Application Ser. No. 61/576,515, filed Dec. 16, 2011, the contents of which are specifically incorporated herein by reference in their entirety.

This application is related to U.S. Patent Application Ser. No. 61/366,977, filed Jul. 23, 2010, and PCT/US2011/044981, filed Jul. 22, 2011, the contents of both of which are specifically incorporated herein by reference in their entireties. This application is also related to published U.S. patent application Ser. No. 12/830,905, filed Jul. 6, 2010 and to U.S. Patent Application Ser. No. 61/213,706, filed Jul. 6, 2009, the contents of both of which are specifically incorporated herein by reference in their entireties.

This invention was made with government support under DE-FC02-07ER64494 awarded by the U.S. Department of Energy. The government has certain rights in the invention.

BACKGROUND OF THE INVENTION

Lignin is an important cell wall component that provides structural support to plants and is needed for plant vascular tissue function. It is one of the most abundant organic polymers on Earth, constituting about 30% of non-fossil organic carbon and from a quarter to a third of the dry mass of wood. Because the chemical structure of lignin is difficult to degrade by chemical and enzymatic means, lignin makes the task of producing paper and biofuels from plant cell walls difficult.

Therefore, researchers continue to search for products and processes that will enable humans to effectively control insects or modify their behavior without negative effects.

SUMMARY OF THE INVENTION

The invention relates to increasing the amount of monolignol ferulates in plant lignins, to generate biomass that contains readily cleavable lignin. Lignins that contain monolignol ferulates are more readily cleaved than lignins that contain other types of monolignols such as p-coumarate conjugates. According to the invention, inhibition or reduction of the activity of a newly isolated acyltransferase, called the p-coumaroyl-CoA:monolignol transferase (also called PMT, or a monolignol coumarate transferase) can improve the incorporation of monolignol ferulates into lignins, yielding a plant with lignin that is even more readily processed into useful products such as paper and biofuels.

The p-coumaroyl-CoA:monolignol transferase gene is newly isolated and produces monolignol p-coumarate conjugates, which are a part of plant lignins. Applicants copending U.S. Patent Application Ser. Nos. 61/366,977, 61/213,706, 12/830,905, PCT/US2011/044981, describe isolation and use of the feruloyl-CoA:monolignol transferase (FMT, also called a monolignol ferulate transferase) nucleic acids and enzymes that incorporate ferulates (not p-coumarates) into plant lignin, to yield a lignin has an altered structure/content and is more easily and economically processed into useful products such as biofuels and paper. When p-coumaroyl-CoA:monolignol transferase expression or activity is inhibited in a plant that expresses feruloyl-CoA:monolignol transferase, greater amounts of monolignol ferulates are incorporated into the plant's lignins, generating a plant with lignin that is even more readily cleavable than a plant that expresses feruloyl-CoA:monolignol transferase without inhibition of p-coumaroyl-CoA:monolignol transferase.

One aspect of the invention is a transgenic plant with a knockdown or knockout of the plant's endogenous p-coumaroyl-CoA:monolignol transferase gene. The plant can also have a feruloyl-CoA:monolignol transferase nucleic acid operably linked to a promoter functional in cells of the transgenic plant. For example, the feruloyl-CoA:monolignol transferase nucleic acid can be a transgene or recombinant nucleic acid introduced into the plant. Hence, the plant with the knockdown or knockout of the plant's endogenous p-coumaroyl-CoA:monolignol transferase gene can express feruloyl-CoA:monolignol transferase. Such an endogenous p-coumaroyl-CoA:monolignol transferase gene can hybridize to a nucleic acid with a sequence selected from the group consisting of SEQ ID NO:16, 18, 19, 22, 23, 25, 26, 27, 28, 47-63 and 64. Such an endogenous p-coumaroyl-CoA: monolignol transferase gene can have at least 50% sequence identity with a nucleic acid sequence selected from the group consisting of SEQ ID NO:16, 18, 19, 22, 23, 25, 26, 27, 28, 47-63 and 64.

The knockdown or knockout of the plant's endogenous p-coumaroyl-CoA:monolignol transferase gene can be a mutation selected from the group consisting of a point mutation, a deletion, a missense mutation, insertion or a nonsense mutation in the endogenous p-coumaroyl-CoA: monolignol transferase gene. Such a knockdown or knockout mutation can, for example, be a point mutation, a deletion, a missense mutation, insertion or a nonsense mutation in the endogenous p-coumaroyl-CoA:monolignol transferase gene, where the gene encodes a polypeptide with at least 60% sequence identity to an amino acid sequence selected from the group consisting of SEQ ID NO: 17, 24, 29-45 and 46.

The knockdown or knockout of the plant's endogenous p-coumaroyl-CoA:monolignol transferase gene can also be mediated by expression of at least one inhibitory nucleic acid comprising a nucleic acid sequence with at least 90% sequence identity to either strand of a nucleic acid comprising a sequence selected from the group consisting of SEQ ID NO:16, 18, 19, 22, 23, 25, 26, 27, 28, 47-63 and 64.

Such knockdown or knockout of the plant's endogenous p-coumaroyl-CoA:monolignol transferase gene reduces acylation of monolignols with p-coumarate. For example, the knockdown or knockout can reduce acylation of monolignols with p-coumarate, where the monolignols are selected from the group consisting of p-coumaryl alcohol, coniferyl alcohol and sinapyl alcohol. The knockdown or knockout can reduce acylation of monolignols with p-coumarate by at least by 10%, or by at least by 20%, or by at least by 30%, or by at least by 40%, or by at least by 50%, or by at least by 60%, or by at least by 70%, or by at least by 80%, or by at least by 90%.

Such transgenic plants can have a feruloyl-CoA:monolignol transferase nucleic acid encoding an amino acid sequence selected from the group consisting of SEQ ID NO:2, 9, 20 and 21. The feruloyl-CoA:monolignol transferase nucleic acid can be operably linked to a promoter selected from the group consisting of a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene, or anactin promoter from rice.

The transgenic plant can be plant from a variety of species. For example, the transgenic plant can be a grass species. The transgenic plant species can be selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (sorghum) and *Bachypodium distachyon* (purple false brome).

Such transgenic plants can be fertile. One or more seeds can be collected from such transgenic plants. Hence, the invention provides transgenic seeds, plant cells and plants.

Another aspect of the invention is an inhibitory nucleic acid that includes a DNA or RNA comprising a nucleic acid sequence with at least 90% sequence identity to either strand of a nucleic acid comprising a sequence selected from the group consisting of SEQ ID NO:16, 18, 19, 22, 23, 25, 26, 27, 28, 47-63 and 64. Another aspect of the invention is an expression cassette that includes a nucleic acid segment encoding the inhibitory nucleic acid operably linked to a promoter functional in a host cell. Another aspect of the invention is an isolated cell includes such an inhibitory nucleic acid or such an expression cassette. The isolated cell can be a microorganism or a plant cell. For example, the isolated cell can be a grass plant cell. Other examples of species include plant cells selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (sorghum), and *Bachypodium distachyon* (purple false brome). A transgenic plant can be generated from or include such isolated cells.

Another aspect of the invention is a method of incorporating monolignol ferulates into lignin of a plant comprising:
a) obtaining one or more plant cells having a knockout or knockdown of the plant cells' endogenous p-coumaroyl-CoA:monolignol transferase gene;
b) regenerating one or more of the plant cells into at least one transgenic plant.

The method can include stably transforming the one or more plant cells with an expression cassette comprising a feruloyl-CoA:monolignol transferase nucleic acid operably linked to a promoter to generate one or more transformed plant cells with the endogenous p-coumaroyl-CoA:monolignol transferase knockout or knockdown mutation, before regenerating the cells into at least one transgenic plant.

Another aspect of the invention is a method of incorporating monolignol ferulates into lignin of a plant comprising:
a) obtaining one or more plant cells stably transformed with a feruloyl-CoA:monolignol transferase nucleic acid operably linked to a promoter to generate at least one transformed plant cell;
b) mutating the at least transformed plant cell to generate at least one transformed mutant plant cell with a knockout or knockdown mutation of the plant cell's endogenous p-coumaroyl-CoA:monolignol transferase gene;
c) regenerating one or more of the transformed mutant plant cells into at least one transgenic plant.

The endogenous p-coumaroyl-CoA:monolignol transferase genes can hybridize to a nucleic acid with a sequence selected from the group consisting of SEQ ID NO:16, 18, 19, 22, 23, 25, 26, 27, 28, 47-63 and 64. For example, the endogenous p-coumaroyl-CoA:monolignol transferase gene has at least 50% sequence identity, with a nucleic acid sequence selected from the group consisting of SEQ ID NO:16, 18, 19, 22, 23, 25, 26, 27, 28, 47-63 and 64.

A method of inhibiting expression and/or translation of p-coumaroyl-CoA:monolignol transferase RNA in a plant cell comprising:
a) contacting or transforming plant cells with an expression cassette to generate transformed plant cells, wherein the expression cassette comprises a segment encoding at least one inhibitory nucleic acid with nucleic acid sequence with at least 90% sequence identity to either strand of a nucleic acid comprising a sequence selected from the group consisting of SEQ ID NO:16, 18, 19, 22, 23, 25, 26, 27, 28, 47-63 and 64; and
b) regenerating the transformed plant cells into at least one transgenic plant, wherein an inhibitory nucleic acid is adapted to inhibit the expression and/or translation of a p-coumaroyl-CoA:monolignol transferase mRNA is expressed in at least one transgenic plant in an amount sufficient to incorporate monolignol ferulates into the lignin of the transgenic plant.

The plant cells in such a method can be stably transformed with a feruloyl-CoA:monolignol transferase nucleic acid operably linked to a promoter.

Another aspect of the invention is an isolated nucleic acid encoding a p-coumaroyl-CoA:monolignol transferase, wherein the nucleic acid can selectively hybridize to a DNA or RNA with any of the SEQ ID NO:16, 18, 19, 22, 23, 25, 26, 27, 28, 47-63 and 64 sequences. For example, in some embodiments, the nucleic acid can selectively hybridize to a DNA or RNA with any of the SEQ ID NO:16, 18, 19, 22, 23, 25, 26, 27, 28, 47-63 and 64 sequences under physiological conditions. In other embodiments, the nucleic acid can selectively hybridize to a DNA or RNA with any of the SEQ ID NO:16, 18, 19, 22, 23, 25, 26, 27, 28, 47-63 and 64 sequences under stringent hybridization conditions. In some embodiments, the stringent hybridization conditions comprise a wash in 0.1×SSC, 0.1% SDS at 65° C. Such an isolated nucleic acid can have at least about 90% sequence identity with any of the SEQ ID NO:16, 18, 19, 22, 23, 25, 26, 27, 28, 47-63 and 64 sequences. In some embodiments, the isolated nucleic acid with any of the SEQ ID NO:16, 18, 19, 22, 23, 25, 26, 27, 28, 47-63 and 64 sequences encodes a rice p-coumaroyl-CoA:monolignol transferase, for example, an *Oryza sativa* p-coumaroyl-CoA:monolignol transferase.

In some embodiments, the p-coumaroyl-CoA:monolignol transferase nucleic acid encodes a p-coumaroyl-CoA:monolignol transferase polypeptide that includes a SEQ ID NO:17, 24, 29-45 or 26 sequence. In other embodiments, the nucleic acids can, for example, encode a p-coumaroyl-CoA:monolignol transferase that can catalyze the synthesis of monolignol p-coumarate(s) from a monolignol(s) and p-coumaroyl-CoA with at least about 50%, of the activity of a p-coumaroyl-CoA:monolignol transferase with the SEQ ID NO:17, 24, 29-45 or 26.

Such p-coumaroyl-CoA:monolignol transferases can catalyze the synthesis of monolignol p-coumarates from monolignol(s) and p-coumaroyl-CoA. For example, the monolignol can be coniferyl alcohol, p-coumaryl alcohol, sinapyl alcohol or a combination thereof, and the p-coumaroyl-CoA:monolignol transferase can, for example, synthesize coniferyl p-coumarate, p-coumaryl p-coumarate, sinapyl p-coumarate or a combination thereof.

As described in more detail herein, the p-coumaroyl-CoA: monolignol transferase nucleic acids and polypeptides produce monolignol p-coumarates that can compete with monolignol ferulates for incorporation into lignin. However, lignin that contains monolignol ferulates is more readily cleavable than lignin that contains little or no monolignol ferulates. As described herein, plants with increased percentages of monolignol ferulates can be generated by inhibiting the expression or activity of p-coumaroyl-CoA:monolignol transferase.

One aspect of the invention is a transgenic plant cell, plant or seed comprising a p-coumaroyl-CoA:monolignol transferase knockdown mutation. For example, such a knockdown mutation can be generated by recessive gene disruption and dominant gene silencing.

Another aspect of the invention is a transgenic plant cell comprising a mutating or an inhibitory nucleic acid capable of hybridizing to a p-coumaroyl-CoA:monolignol transferase nucleic acid under plant physiological conditions. The nucleic acid can include a sequence that is homologous or complementary to the p-coumaroyl-CoA:monolignol transferase nucleic acid sequences described herein. For example, the mutating or the inhibitory nucleic acid can selectively hybridize to a DNA or RNA with any of the SEQ ID NO:16, 18, 19, 22, 23, 25, 26, 27, 28, 47-63 and 64 sequences (or a sequence complementary to any of the SEQ ID NO:16, 18, 19, 22, 23, 25, 26, 27, 28, 47-63 and 64 sequences) under physiological conditions present in a plant in vivo.

Another aspect of the invention is a transgenic plant cell comprising a mutating or an inhibitory nucleic acid adapted to hybridize to a p-coumaroyl-CoA:monolignol transferase nucleic acid. The nucleic acid can include a sequence that is homologous or complementary to the p-coumaroyl-CoA: monolignol transferase nucleic acid sequences described herein. For example, the mutating or inhibitory nucleic acid selectively hybridizes to a DNA or RNA with any of the SEQ ID NO:16, 18, 19, 22, 23, 25, 26, 27, 28, 47-63 and 64 sequences (or any complement thereof) under physiological conditions present in a plant in vivo.

Another aspect of the invention is an expression cassette comprising one of the mutating or inhibitory nucleic acids described herein, where the mutating or inhibitory nucleic acid is operably linked to a promoter functional in a host cell. Such a nucleic acid can be a nucleic acid that can selectively hybridize to a DNA or RNA with any of the SEQ ID NO:16, 18, 19, 22, 23, 25, 26, 27, 28, 47-63 and 64 sequences, or any complement thereof, under physiological conditions present in a plant in vivo. The expression cassette can further comprise a selectable marker gene. In some embodiments, the expression cassette further comprises plasmid DNA. For example, the expression cassette can be within an expression vector. Promoters that can be used within such expression cassettes include promoters functional during plant development or growth.

Another aspect of the invention is a plant cell that includes an expression cassette comprising one of the feruloyl-CoA: monolignol transferase nucleic acids described herein that is operably linked to a promoter functional in a host cell, such as a plant cell. Such a nucleic acid can be a nucleic acid that can selectively hybridize to a DNA with either or both of the SEQ ID NO:1 and 8 sequences. In some embodiments, the plant cell can also include an expression cassette comprising any of the mutating or inhibitory nucleic acids described herein, wherein the mutating or inhibitory nucleic acid(s) is operably linked to a promoter functional in a host cell. The plant cell can have an endogenous p-coumaroyl-CoA:monolignol transferase gene knockdown or knockout, so that little or no functional PMT enzyme is synthesized by the plant cell. The plant cell can be a monocot cell. The plant cell can also be a gymnosperm cell. For example, the plant cell can be a maize, grass or softwood cell. In some embodiments, the plant cell is a dicot cell. For example, the plant cell can be a hardwood cell.

Another aspect of the invention is a plant that includes an expression cassette comprising one of the feruloyl-CoA: monolignol transferase nucleic acids described herein that is operably linked to a promoter functional in a host cell, such as a plant cell. The plant can have an endogenous p-coumaroyl-CoA:monolignol transferase gene knockdown or knockout, so that little or no functional PMT enzyme is synthesized by the plant cell. Such a feruloyl-CoA:monolignol transferase nucleic acid can be a nucleic acid that can selectively hybridize to a DNA with either or both of the SEQ ID NO:1 and 8 sequences. In some embodiments, the plant can also include an expression cassette comprising any of the inhibitory nucleic acids described herein, wherein the inhibitory nucleic acid(s) is operably linked to a promoter functional in a host cell. Such a plant can be a monocot. The plant can also be a gymnosperm. For example, the plant can be a maize, grass or softwood plant. In some embodiments, the plant is a dicot plant. For example, the plant can be a hardwood plant.

Another aspect of the invention is a plant seed that includes an expression cassette comprising one of the feruloyl-CoA:monolignol transferase nucleic acids described herein that is operably linked to a promoter functional in a host cell, such as a plant cell. The plant seed can have an endogenous p-coumaroyl-CoA:monolignol transferase gene knockdown or knockout, so that little or no functional PMT enzyme is synthesized by a plant grown from the seed. Such a feruloyl-CoA:monolignol transferase nucleic acid can be a nucleic acid that can selectively hybridize to a DNA with either or both of the SEQ ID NO:1 and 8 sequences. In some embodiments, the plant seed can include an expression cassette comprising any of the inhibitory nucleic acids described herein, wherein the inhibitory nucleic acid(s) is operably linked to a promoter functional in a host cell. Such a plant seed can be a monocot. The plant seed can also be a gymnosperm. For example, the plant seed can be a maize, grass or softwood plant seed. In some embodiments, the plant seed is a dicot plant. For example, the plant seed can be a hardwood plant seed.

Another aspect of the invention is a method for incorporating monolignol ferulates into lignin of a plant that includes:
  a) obtaining one or more plant cells each having a knockout or knockdown of the plant cells' endogenous p-coumaroyl-CoA:monolignol transferase gene;
  b) stably transforming the one or more plant cells with an expression cassette comprising feruloyl-CoA:monolignol transferase nucleic acid to generate one or more transformed plant cells;

c) regenerating one or more of the transformed plant cells into at least one transgenic plant,
  wherein the knockout or knockdown of the plant cells' endogenous p-coumaroyl-CoA:monolignol transferase gene increases incorporation of monolignol ferulates into the lignin of at least one of the transgenic plants compared to a control plant that does not have such a knockout or knockdown but is stably transformed with the expression cassette comprising feruloyl-CoA:monolignol transferase nucleic acid.

The knockout or knockdown of the plant or plant cells' endogenous p-coumaroyl-CoA:monolignol transferase gene can increase incorporation of monolignol ferulates into the lignin of a plant, for example, by at least by 1%, or by at least 2%, or by at least 3%, or by at least 5% relative to the control plant. The endogenous p-coumaroyl-CoA:monolignol transferase gene can, for example, selectively hybridize to a nucleic acid with any of the SEQ ID NO:16, 18, 19, 22, 23, 25, 26, 27, 28, 47-63 and 64 sequences. The endogenous p-coumaroyl-CoA:monolignol transferase gene can, for example, have a percentage of sequence identity with a nucleic acid having any of the SEQ ID NO:16, 18, 19, 22, 23, 25, 26, 27, 28, 47-63 and 64 sequences, such as at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, or at least 97% sequence identity with a nucleic acid having any of the SEQ ID NO:16, 18, 19, 22, 23, 25, 26, 27, 28, 47-63 and 64 sequence.

Another aspect of the invention is a method for incorporating monolignol ferulates into lignin of a plant that includes:
  a) stably transforming one or more plant cells with any of the mutating nucleic acids described herein or with an expression cassette comprising any of the inhibitory nucleic acids described herein (e.g., a mutating or an inhibitory nucleic acid adapted to hybridize to a p-coumaroyl-CoA:monolignol transferase nucleic acid) to generate transformed plant cells;
  b) regenerating the transformed plant cells into at least one transgenic plant,
  wherein the mutating nucleic acid or the inhibitory nucleic acid inhibits expression of a p-coumaroyl-CoA:monolignol transferase nucleic in at least one transgenic plant in an amount sufficient to incorporate monolignol ferulates into the lignin of the transgenic plant.

Such stable transformation can increase incorporation of monolignol ferulates into the lignin of the transgenic plant, for example, by at least by 1%, or by at least 2%, or by at least 3%, or by at least 5% relative to the control plant that has not been stably transformed with the mutating or inhibitory nucleic acid. Such an inhibitory nucleic acid can, for example, be a nucleic acid that can selectively hybridize to any of the SEQ ID NO:16, 18, 19, 22, 23, 25, 26, 27, 28, 47-63 and 64 sequences. In some embodiments, the method can also include stably transforming the plant cells with an expression cassette comprising any of the feruloyl-CoA:monolignol transferase nucleic acids described herein that are operably linked to a promoter functional in a host cell.

Such methods can be used to generate transgenic plants that are fertile. The method can further include recovering transgenic seeds from the transgenic plants, wherein the transgenic seeds include the mutating or inhibitory nucleic acid, and/or the nucleic acid encoding a feruloyl-CoA:monolignol transferase. The plant so generated can contain monolignol ferulates within its lignin.

Another aspect of the invention is a method for incorporating monolignol ferulates into lignin of a plant that includes:
  a) stably transforming plant cells with the expression cassette comprising one of the feruloyl-CoA:monolignol transferase nucleic acids described herein to generate transformed plant cells;
  b) regenerating the transformed plant cells into at least one transgenic plant, wherein feruloyl-CoA:monolignol transferase is expressed in at least one transgenic plant in an amount sufficient to incorporate monolignol ferulates into the lignin of the transgenic plant.

For example, such a nucleic acid can be a nucleic acid that can selectively hybridize to a DNA with either or both of the SEQ ID NO:1 and 8 sequences. The plant cells can have a knockout or knockdown of the plant cells' endogenous p-coumaroyl-CoA:monolignol transferase gene. In some embodiments, the method can also include stably transforming the plant cells with an expression cassette comprising any of the inhibitory nucleic acids described herein, wherein the inhibitory nucleic acid(s) is operably linked to a promoter functional in a host cell. Such a method can be used to generate a transgenic plant that is fertile. The method can further include recovering transgenic seeds from the transgenic plant, wherein the transgenic seeds include the nucleic acid encoding a feruloyl-CoA:monolignol transferase.

The method for incorporating monolignol ferulates into lignin of a plant can also include breeding the fertile transgenic plant to yield a progeny plant, where the progeny plant has an increase in the percentage of monolignol ferulates in the lignin of the progeny plant relative to the corresponding untransformed plant.

Another aspect of the invention is a lignin isolated from the transgenic plant that has a knockout or knockdown of the plant's endogenous p-coumaroyl-CoA:monolignol transferase gene and/or any of the feruloyl-CoA:monolignol transferase isolated nucleic acids described herein. The plant from which the lignin is obtained can have any of the inhibitory of mutating nucleic acids described herein. Lignin in such a plant can include at least 1% monolignol ferulate. In other embodiments, the lignin in the plant can include at least 2% monolignol ferulate, or at least 5% monolignol ferulate, or at least 10% monolignol ferulate, or at least 10% monolignol ferulate, or at least 20% monolignol ferulate, or at least 25% monolignol ferulate. In further embodiments, the lignin in the plant includes about 1-30% monolignol ferulate, or about 2-30% monolignol ferulate.

Another aspect of the invention is a method of making a product from a transgenic plant comprising: (a) providing a transgenic plant that has a knockout or knockdown of the plant's endogenous p-coumaroyl-CoA:monolignol transferase gene and/or that includes an isolated nucleic acid that encodes a feruloyl-CoA:monolignol transferase; and (b) processing the transgenic plant's tissues under conditions sufficient to digest to the lignin; to thereby generate the product from the transgenic plant, wherein the transgenic plant's tissues comprise lignin having an increased percent of monolignol ferulates relative to a corresponding untransformed plant. The transgenic plant can have a mutating and/or an inhibitory nucleic acid to knockout or knockdown of the plant's endogenous p-coumaroyl-CoA:monolignol transferase gene. The corresponding untransformed plant can be a plant of the same species, strain and/or accession as the transformed plant. The conditions sufficient to digest to the lignin can include conditions sufficient to cleave ester bonds within monolignol ferulate-containing lignin. In some embodiments, the conditions sufficient to digest to the lignin include mildly alkaline conditions. In some embodiments, the conditions sufficient to digest to the lignin include contacting the transgenic plant's tissues with ammonia for a time and a temperature sufficient to cleave ester bonds within monolignol ferulate-containing lignin. In some embodiments, the conditions sufficient to digest to the lignin would not cleave substantially any of the ether and carbon-carbon bonds in lignin from a corresponding plant that does not contain the isolated nucleic acid encoding the feruloyl-CoA:monolignol transferase.

Therefore, the invention embraces mutating nucleic acids and nucleic acids encoding an inhibitory nucleic acid adapted to inhibit the expression and/or translation of p-coumaroyl-CoA:monolignol transferase nucleic acids, as well as expression cassettes, plant cells and plants that have such inhibitory nucleic acids, and methods of making and using such nucleic acids. The mutating nucleic acids and/or the inhibitory nucleic acids can be made and/or used in conjunction with feruloyl-CoA:monolignol transferase nucleic acids to improve the incorporation of monolignol ferulates into plant lignins. Alternatively, the plant cells having a knockout or knockdown of the plant cells' endogenous p-coumaroyl-CoA:monolignol transferase gene can be stably transformed with feruloyl-CoA:monolignol transferase nucleic acids to improve the incorporation of monolignol ferulates into plant lignins.

In some embodiments, the plant, plant cell or seed produced or used in the methods described herein is a grass species such as a *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (sorghum), *Bachypodium distachyon* (purple false brome), and the like. For example, the plant, plant cell or seed can also be any of the grass species or strains recited in FIG. 20 or Table 2.

DESCRIPTION OF THE DRAWINGS

FIGS. 1A1, 1A2, 1B1 and 1B2 illustrate structural models for some types of lignin polymers. FIGS. 1A1 and 1A2 show examples of lignin structures with 25 units that may be found in a softwood (spruce). FIGS. 1B1 and 1B2 show examples of lignin structures with 20 units that may be present in a hardwood (poplar). [Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK]. The softwood lignin is generally more branched and contains a lower proportion of β-ether units. Note that each of these structures represents only one of billions of possible isomers [Ralph, J., Lundquist, K., Brunow, G., Lu, F., Kim, H., Schatz, P. F., Marita, J. M., Hatfield, R. D., Ralph, S. A., Christensen, J. H., and Boerjan, W. Lignins: natural polymers from oxidative coupling of 4-hydroxyphenylpropanoids. (2004) *Phytochem. Revs.* 3(1), 29-60]. Thus, these structures are merely illustrative of some of the linkage types that may be present different lignins. An "S" within a ring indicates a syringyl unit while a "G" within a unit indicates a guaiacyl unit.

FIG. 2A is a no enzyme control assay while FIG. 2B shows the HPLC-separated assay results when the feruloyl-CoA:monolignol transferase enzyme from *Angelica sinensis* is present in the assay mixture. The peaks are numbered to distinguish the separated components of the assay as follows: 1) coniferyl alcohol (at about 4.4 min); 2) feruloyl-CoA (at about 5.4 min); 3) ferulic acid (about about 6.0 min); and 4) coniferyl ferulate (at about 9.8 min)

FIG. 3A shows the assigned proton NMR spectrum of the product isolated from a reaction of coniferyl alcohol and feruloyl-CoA using the feruloyl-CoA:monolignol transferase from *Angelica sinensis*. FIG. 3B is a 2D $^1H$-$^{13}C$ correlation (HSQC) spectrum of the same produced coniferyl ferulate, further authenticating the product; the tabulated $^{13}C$ NMR data are from the 1D $^{13}C$ NMR spectrum with the quaternary (non-protonated) carbons assigned by long-range $^1H$-$^{13}C$ correlation (HMBC) spectra (not shown). These spectra (and proton and carbon data) match those from authentic (synthesized) coniferyl ferulate.

FIG. 4A shows the results of a no-enzyme control assay while FIG. 4B shows the results of the assay with the feruloyl-CoA:monolignol transferase from *Angelica sinensis*. The peaks are numbered to distinguish the separated components of the assay as follows: 1) p-coumaryl alcohol (at about 3.5 min), 2) feruloyl-CoA (at about 5.5 min), and 3) p-coumaryl ferulate (at about 9.0 min).

FIG. 5A shows the results of a no-enzyme control assay while FIG. 5B shows the results of the assay with the feruloyl-CoA:monolignol transferase from *Angelica sinensis*. The peaks are numbered to distinguish the separated components of the assay as follows: 1) sinapyl alcohol (at about 4.4 min); 2) feruloyl-CoA (at about 5.5 min); and 3) sinapyl ferulate (at about 9.4 min).

FIG. 6A shows the results of a no-enzyme control assay while FIG. 6B shows the results of the assay with the feruloyl-CoA:monolignol transferase from *Angelica sinensis*. The peaks are numbered to distinguish the separated components of the assay as follows: 1) coniferyl alcohol and p-coumaroyl-CoA (at about 4.4 min), the overlapping peaks cause a slight UV 280 asymmetry due to the coniferyl alcohol elution only slightly before the p-coumaroyl-CoA; and 3) coniferyl p-coumarate (at about 9.4 min).

FIG. 7A shows the results of a no-enzyme control assay while FIG. 7B shows the results of the assay with the feruloyl-CoA:monolignol transferase from *Angelica sinensis*. The peaks are numbered to distinguish the separated components of the assay as follows: 1) coniferyl alcohol (at about 4.4 min); and 2) caffeoyl-CoA (at about 2.4 min).

FIG. 10A illustrates GFP-trap Mag enrichment and detection of FMT expression in the leaves of transgenic poplar trees that express FMT that has been N-terminally tagged with Yellow Fluorescent Protein (YFP-FMT). A western blot is shown of electrophoretically separated fractions obtained after GFPtrap (Chromotek) enrichment of YFP-FMT from the leaves of the transgenic poplar trees that express YFP-FMT. The FMT9 and FMT13 lanes contain extracts from two different genetically modified Poplar trees. FMT expression was detected using anti-GFP antibodies (Abcam). FIG. 10B illustrates the results obtained from a poplar leaf extract FMT enzyme assay. UPLC traces are of control and transgenic Poplar leaf extracts, where the transgenic Poplar trees express the YFP-FMT from *Angelica sinensis*. The absorbance of the substrates coniferyl alcohol (1) and feruloyl-CoA (2) are shown along with the FMT product, coniferyl ferulate (3), was detected at 280 nm (solid line) and 340 nm (dotted line). The top panel shows results obtained for wild-type Poplar leaf extracts (containing no *Angelica sinensis* FMT nucleic acids) while the bottom panel shows results obtained from extracts of transgenic poplar leaves that express the *Angelica sinensis* FMT. Coniferyl ferulate (3) was detected only with the leaf extract from YFP-FMT Poplar.

FIG. 11A illustrates the products of Reverse Transcriptase PCR that were amplified from *Arabidopsis* leaves transformed with empty vector or with a vector expressing the FMT transcript, when reverse transcriptase is added (+RT) or not added (−RT) to the PCR reaction mixture. A PCR product of the expected size for FMT (1326 base pairs) is visible only in the reaction containing total RNA from *Arabidopsis* transformed with the *Angelica sinensis* FMT when the reverse transcriptase is present. FIG. 11B provides representative UPLC traces showing FMT activity in ground stems from *Arabidopsis* transformed with the FMT from *Angelica sinensis*, when the FMT enzyme assay is employed (bottom panel). The absorbance for each of the substrates, coniferyl alcohol (1) and feruloyl-CoA (2) and for the product, coniferyl ferulate (3), was measured at 280 nm (solid line) and 340 nm (dotted line). Control reactions were conducted with stems expressing empty vector (top panel). Coniferyl ferulate (3) is detected only when protein from the transformed *Arabidopsis*-FMT stems was added.

FIG. 12A illustrates *Hibiscus cannabinus* FMT expression in *E. coli* BL21 cells (Invitrogen). The *Hibiscus cannabinus* FMT was expressed with an N-terminal 6×His tag in the pDEST17 vector (Invitrogen) and the soluble protein (~50 kDa) was purified over a $Ni^{2+}$ column using an AKTA purifier (GE Healthcare). Fractions containing purified protein (fractions 29 and 30) were assayed for FMT activity. FIG. 12B shows the products of an FMT enzyme assay after UPLC separation and detection by absorbance at 280 nm (solid line) and 340 nm (dotted line) for the substrates coniferyl alcohol (1) and feruloyl-CoA (2). A control reaction with no enzyme is shown at the top. The reaction containing the *Hibiscus cannabinus* FMT enzyme is shown in the bottom panel. The production of coniferyl ferulate (3) is visible only when the *Hibiscus cannabinus* FMT enzyme is present in the assay (bottom panel). The product and substrate peaks were identified by comparison to synthetic standards.

FIG. 13 shows an alignment of the *Hibiscus cannabinus* (lower sequence, SEQ ID NO:20) and *Angelica sinensis* (upper sequence, SEQ ID NO:21) feruloyl-CoA:monolignol transferase sequences. As illustrated, the *Hibiscus cannabinus* and *Angelica sinensis* feruloyl-CoA:monolignol transferases share only about 23% sequence identity. When similar amino acid substitutions are considered, the *Hibiscus cannabinus* and *Angelica sinensis* feruloyl-CoA:monolignol transferases share only about 41% sequence similarity.

FIGS. 14A-D provide examples of p-coumaroyl-CoA: monolignol transferase (PMT, also called a monolignol coumarate transferase) sequences. FIG. 14A shows an example of an amino acid sequence (SEQ ID NO:17) of an *Oryza sativa* p-coumaroyl-CoA:monolignol transferase. FIG. 14B shows an example of a nucleic acid sequence (SEQ ID NO:16) for a coding region of the SEQ ID NO:17 *Oryza sativa* p-coumaroyl-CoA:monolignol transferase. FIG. 14C1 and FIG. 14C2 show an example of a genomic nucleic acid sequence (SEQ ID NO:18) for a coding region of the SEQ ID NO:17 *Oryza sativa* p-coumaroyl-CoA: monolignol transferase. The SEQ ID NO:18 genomic sequence continues from FIG. 14C1 to FIG. 14C2. FIG. 14D shows an example of a nucleic acid sequence (SEQ ID NO:19) for the SEQ ID NO:17 *Oryza sativa* p-coumaroyl-CoA:monolignol transferase that has been codon-optimized for expression.

FIG. 17A shows a chromatogram obtained by fast protein liquid chromatography (FPLC) showing immobilized metal ion affinity chromatography (IMAC) purification of expressed soluble PMT from *E. coli* represented in black, with the buffer gradient represented in gray, and the collected fractions below. FIG. 17B shows proteins electrophoretically separated by SDS-Polyacrylamide gels electrophoresis. In the panel to the left, soluble and insoluble protein fractions from *E. coli* are visible upon induction of PMT at time zero (T0), and after 18 h of induction (T18). The middle panel shows IMAC-purified fractions 18-20 (f18, f19 and f20). The right panel shows Superdex 75 gel filtration fractions assayed for PMT enzyme activity, where lanes labeled with one or more plus (+) indicate fractions with PMT activity, and the lane labeled with a minus sign (−) indicates no activity measured.

FIG. 18A shows that the crude product generated by PMT contains sinapyl p-coumarate 3Sa as a major product, as determined by comparison of its proton and 2D COSY NMR spectra (solid black lines) with the spectra of authentic (synthetic) sinapyl p-coumarate 3Sa shown in FIG. 18B.

FIG. 19A-D illustrate HPLC chromatographs from analyses of PMT enzyme assay mixtures with no enzyme and with purified rice OsPMT (+PMT) enzyme added. The UV absorbance was monitored at 280 nM (black) and at 340 nM (blue) for the following reactions. FIG. 19A shows the chromatographs for a reaction mixture of p-coumaroyl-CoA 2a with sinapyl alcohol 1S to evaluate whether sinapyl p-coumarate 3Sa is made. FIG. 19B shows the chromatographs for a reaction mixture of p-coumaroyl-CoA 2a with p-coumaryl alcohol 1H to evaluate whether p-coumaryl p-coumarate 3Ha is made. FIG. 19C shows the chromatographs for a reaction of caffeoyl-CoA 2b with sinapyl alcohol 1S to evaluate whether sinapyl caffeate 3Sb is made. FIG. 19D shows the chromatographs for a reaction mixture of caffeoyl-CoA 2b with p-coumaryl alcohol 1H to evaluate whether p-coumaryl caffeate 3Hb is made.

FIG. 20A-B shows identification of a *Brachypodium distachyon* p-coumaroyl-CoA: monolignol transferase gene, its relationship to the rice p-coumaroyl-CoA: monolignol transferase gene, and the sequence of the *Brachypodium distachyon* p-coumaroyl-CoA: monolignol transferase cDNA and protein. FIG. 20A is a schematic diagram listing and illustrating the relationship of grass genes related to the rice p-coumaroyl-CoA: monolignol transferase (OsPMT1) gene. Methods for generating this relationship tree are those described above for FIG. 16. FIG. 20B1-20B3 shows sequences for the *Brachypodium distachyon* p-coumaroyl-CoA: monolignol transferase cDNA with untranslated 5' and 3' sequences (top sequence, SEQ ID NO:22), the cDNA coding region (middle sequence, SEQ ID NO:23) and the amino acid sequence (bottom sequence, SEQ ID NO:24). Note that the sequences extend from FIG. 20B1 to FIG. 20B3.

FIG. 22A graphically illustrates reduction of p-coumaroyl-CoA: monolignol transferase expression by RNAi knockdown in two transgenic *Brachypodium distachyon* plants independently transformed with RNAi construct 61. p-Coumaroyl-CoA: monolignol transferase expression was detected by quantitative reverse transcription-polymerase chain reaction (real-time PCR). FIG. 22B shows that transgenic RNAi knockdown plants (PMT RNAi 4B) have comparable growth to wild type.

FIG. 23A graphically illustrates reduced p-coumarate levels in RNAi knockdown plant transformants 4B and 7A, but fairly normal levels of ferulate compared to wild type cell walls. The plant tissues were treated with base and then analyzed by use of gas chromatography-flame ionization detector. FIG. 23B graphically illustrates reduced levels of syringyl and guaiacil in the RNAi knockdown plants, especially plant 7A, compared to wild type *Brachypodium distachyon*. Plant tissues were subjected to thioacidolysis to cleave ether linkages in lignin.

FIG. 24 shows the 2D-NMR spectrum of wild type *Brachypodium distachyon* plant cell wall extracts. FIG. 24 shows the 2D-NMR spectrum of RNAi knockdown *Brachypodium distachyon* plant cell wall extracts. FIG. 24 is a knockdown versus wild type difference spectrum showing reduced levels of the darker-highlighted moieties (syringyl and p-coumarate; red in the original) and the increased levels of the lighter-highlighted moieties (pyridine; gray in the original) compared to wild type.

FIG. 25A-25F show amino acid and nucleotide sequences with potential p-coumaroyl-CoA: monolignol transferase function. These sequences can be used as targets for knockout and knockdown of endogenous p-coumaroyl-CoA: monolignol transferase genes.

Figure 2A:
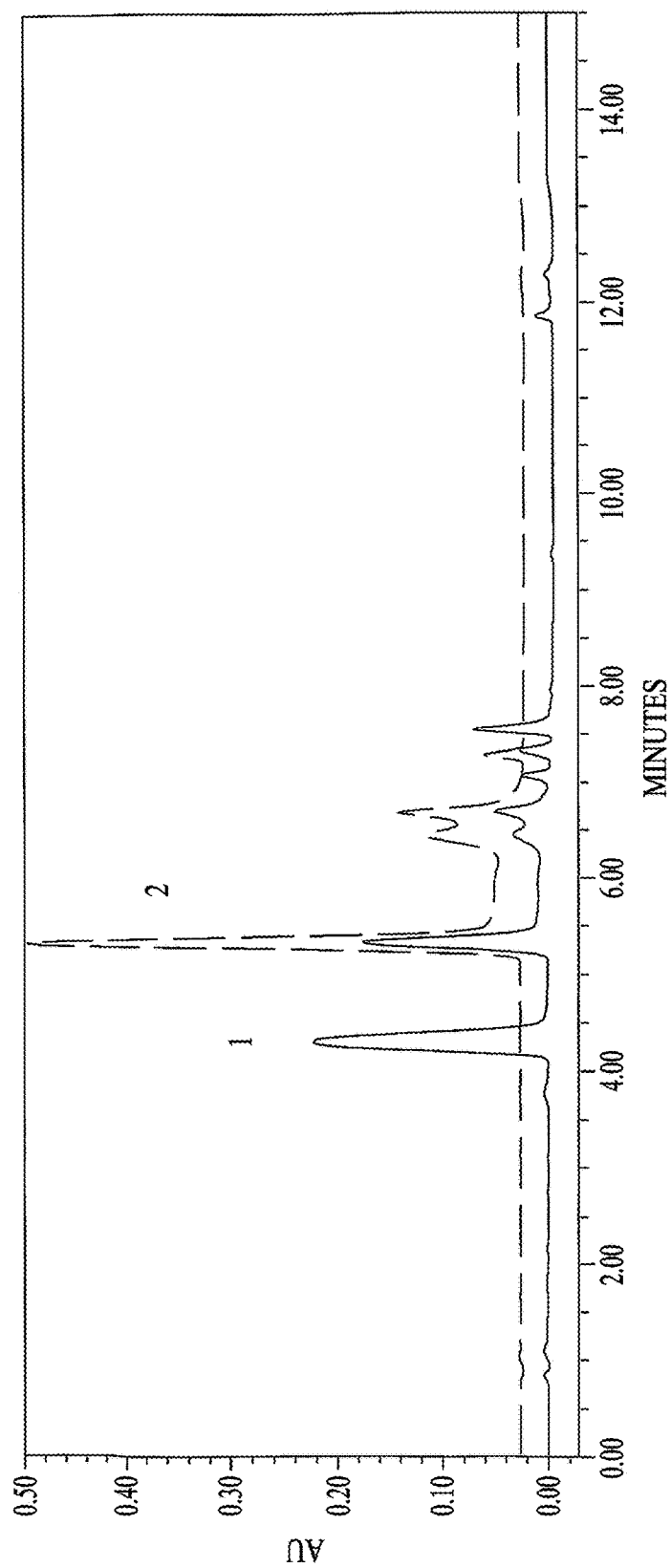
FIG. 2A-2B show HPLC traces of assay mixtures generated to test for feruloyl-CoA:monolignol transferase activity using coniferyl alcohol and feruloyl-CoA as substrates. The UV 340 trace is the dashed line while the UV 280 trace is the solid line.

Unless defined otherwise, all technical and scientific terms used herein have the same meaning as commonly understood by one of ordinary skill in the art to which this

DETAILED DESCRIPTION OF THE INVENTION

The invention provides nucleic acids and methods useful for altering lignin structure, lignin attachment to plant components and/or the lignin content in plants. Plants with such altered lignin structure/attachment/content are more easily and economically processed into useful products such as biofuels and paper.

Acyl-CoA Dependent Acyltransferases

Plant acyl-CoA dependent acyltransferases constitute a large but specific protein superfamily, named BAHD. Members of this family take an activated carboxylic acid (i.e., a CoA thioester form of the acid) as an acyl donor and either an alcohol or, more rarely, a primary amine, as an acyl acceptor and catalyze the formation of an ester or an amide bond, respectively. The acyl donors and acyl acceptors that act as substrates for BAHD acyltransferases are quite diverse, and different BAHD family members exhibit a range of substrate specificities.

The invention relates to BAHD acyltransferase nucleic acids and enzymes that enable the production of transgenic plants with altered lignin. As described herein, some acyltransferases actively generate easily cleaved ferulate-containing lignin, whereas other acyltransferases can compete with and inhibit the production of ferulate-containing lignin. By stimulating the expression or activity of ferulate-incorporation acyltransferases, and inhibiting the expression or activity of acyltransferases that reduce the incorporation of monolignol ferulates into lignin, plants with optimal amounts of readily cleavable lignin can be generated.

Acyltransferases that Increase Monolignol Ferulate Incorporation

Feruloyl-CoA:monolignol transferases improve the incorporation of monolignol ferulates into lignin by synthesizing monolignol ferulates from any of three monolignols (p-coumaryl, coniferyl and sinapyl alcohols). For example, the feruloyl-CoA:monolignol transferases described herein can synthesize coniferyl ferulate from coniferyl alcohol and feruloyl-CoA, as shown below.

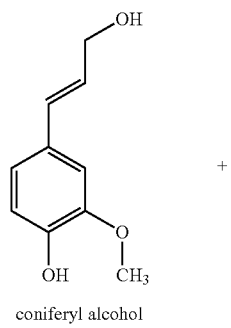
coniferyl alcohol

+

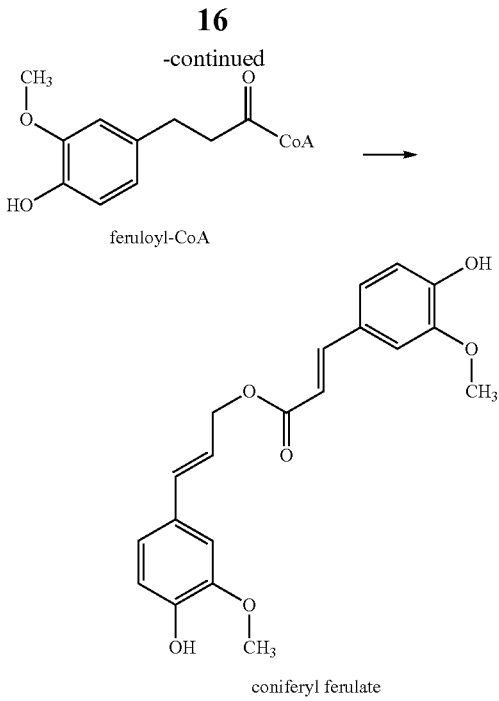

The feruloyl-CoA:monolignol transferases enable production of plants with lignin that is readily cleaved and/or removed, for example, because the lignin in these plants contains monolignol ferulates such as coniferyl ferulate (CAFA) that have ester linkages (rather than ether or carbon-carbon linkages).

The terms "feruloyl-CoA:monolignol transferase(s)" and "monolignol ferulate transferase(s)" and the abbreviation "FMT" are used interchangeably herein.

Nucleic acids encoding the feruloyl-CoA:monolignol transferases that are useful for making coniferyl ferulate (and other monolignol ferulates) were isolated from the roots of *Angelica sinensis* as clone Dq155 pdest17. The coding region of the *Angelica sinensis* clone Dq155 pdest17 has the following nucleic acid sequence (SEQ ID NO:1).

```
  1  ATGACGATCA TGGAGGTTCA AGTTGTATCT AAGAAGATGG
 41  TAAAGCCATC AGTTCCGACT CCTGACCACC ACAAGACTTG
 81  CAAATTGACG GCATTCGATC AGATTGCTCC TCCGGATCAA
121  GTTCCCATTA TTTACTTCTA CAACAGCAGC AACATCCACA
161  ATATTCGCGA GCAATTGGTA AAATCCTTGT CCGAAACTCT
201  AACCAAGTTT TATCCATTAG CTGGAAGATT TGTTCAAGAT
241  GGTTTCTATG TCGATTGTAA TGATGAAGGG GTCTTGTACG
281  TAGAAGCTGA AGTTAACATT CCGCTAAACG AATTCATCGG
321  ACAAGCAAAG AAAAATATAC AACTTATCAA TGATCTTGTT
361  CCGAAAAAAA ACTTCAAGGA TATTCATTCA TATGAAAATC
401  CAATAGTGGG ATTACAGATG AGTTATTTCA AGTGTGGTGG
441  ACTTGCTATT TGCATGTATC TTTCGCATGT TGTAGCTGAT
481  GGATATACAG CAGCAGCATT CACTAAAGAG TGGTCTAACA
521  CAACCAATGG CATCATCAAT GGCGATCAAC TAGTTTCTTC
```

```
561  TTCTCCGATT AACTTCGAAT TGGCAACTCT AGTCCCAGCT
601  AGAGATTTAT CGACGGTGAT CAAGCCAGCC GTGATGCCAC
641  CATCAAAGAT CAAGGAAACC AAGGTTGTCA CAAGGAGGTT
681  TCTGTTCGAT GAAAATGCGA TATCAGCTTT CAAAGACCAT
721  GTCATCAAAT CCGAAAGCGT TAACCGGCCT ACACGGGTGG
761  AAGTTGTGAC ATCTGTGTTA TGGAAGGCTC TGATCAACCA
801  GTCTAAGCTT CCAAGTTCTA CACTATATTT TCACCTCAAC
841  TTTAGAGGGA AAACAGGCAT CAACACCCCA CCGCTAGATA
881  ATCATTTTTC GCTTTGCGGA AACTTTTACA CTCAGGTTCC
921  TACAAGGTTC AGGGGGGGAA ATCAAACAAA ACAGGATTTG
961  GAATTGCATG AATTGGTCAA GTTGTTGAGA GGAAAGTTGC
1001 GTAACACTCT GAAGAATTGC TCCGAAATTA ACACTGCCGA
1041 TGGGCTGTTC CTGGAAGCAG CTAGTAATTT CAATATTATA
1081 CAGGAAGATT TGGAGGACGA ACAAGTGGAT GTTCGGATTT
1121 TTACAACGTT GTGTAGGATG CCTTTGTATG AAACTGAGTT
1161 TGGGTGGGGA AAACCAGAAT GGGTTACCAT TCCAGAGATG
1201 CATTTGGAGA TAGTGTTTCT TTTGGACACT AAATGTGGGA
1241 CTGGTATTGA GGCATTAGTG AGCATGGATG AAGCAGATAT
1281 GCTTCAGTTT GAACTTGATC CCACCATCTC TGCTTTCGCT
1321 TCCTAG
```

The SEQ ID NO:1 nucleic acid encodes an *Angelica sinensis* clone Dq155 pdest17 feruloyl-CoA:monolignol transferase enzyme with the following amino acid sequence (SEQ ID NO:2).

```
  1  MTIMEVQVVS KKMVKPSVPT PDHHKTCKLT AFDQIAPPDQ
 41  VPIIYFYNSS NIHNIREQLV KSLSETLTKF YPLAGRFVQD
 81  GFYVDCNDEG VLYVEAEVNI PLNEFIGQAK KNIQLINDLV
121  PKKNFKDIHS YENPIVGLQM SYFKCGGLAI CMYLSHVVAD
161  GYTAAAFTKE WSNTTNGIIN GDQLVSSSPI NFELATLVPA
201  RDLSTVIKPA VMPPSKIKET KVVTRRFLFD ENAISAFKDH
241  VIKSESVNRP TRVEVVTSVL WKALINQSKL PSSTLYFHLN
281  FRGKTGINTP PLDNHFSLCG NFYTQVPTRF RGGNQTKQDL
321  ELHELVKLLR GKLRNTLKNC SEINTADGLF LEAASNFNII
361  QEDLEDEQVD VRIFTTLCRM PLYETEFGWG KPEWVTIPEM
401  HLEIVFLLDT KCGTGIEALV SMDEADMLQF ELDPTISAFA
441  S
```

Other nucleic acids encoding the feruloyl-CoA:monolignol transferases that are useful for making coniferyl ferulate (and other monolignol ferulates) were isolated from the stem of *Hibiscus cannabinus* (Kenaf). The coding region of the *Hibiscus cannabinus* (Kenaf) has the following nucleic acid sequence (SEQ ID NO:8).

```
   1  ATGGCAACCC ACAGCACTAT CATGTTCTCA GTCGATAGAA
  41  ACGATGTCGT GTTTGTCAAA CCCTTCAAAC CTACACCCTC
  81  ACAGGTTCTA TCTCTCTCCA CCATCGACAA TGATCCCAAC
 121  CTTGAGATCA TGTGCCATAC TGTTTTTGTG TATCAAGCCA
 161  ATGCCGATTT CGATGTTAAG CCCAAGGATC CAGCTTCCAT
 201  AATCCAGGAA GCACTCTCCA AGCTCTTGGT TTATTACTAT
 241  CCCTTAGCGG GGAAGATGAA GAGGGAGACC GATGGAAAAC
 281  TTCGAATCGC TTGCACTGCC GACGATAGCG TGCCCTTCTT
 321  AGTAGCCACC GCCGATTGCA AGCTCTCGTC GTTGAACCAC
 361  TTGGATGGCA TAGATGTTCA TACCGGGAAA GAATTCGCCT
 401  TGGATTTTGC ATCCGAATCC GACGGTGGCT ATTATCACCC
 441  TCTGGTCATG CAGGTGACGA AGTTCATATG CGGAGGGTTC
 481  ACCATCGCTT TGAGTTTATC GCACTCGGTT TGTGATGGCT
 521  TCGGTGCAGC TCAGATCTTT CAAGCATTGA CCGAGCTCGC
 561  AAGTGGCAGG AACGAGCCCT CGGTTAAACC CGTGTGGGAG
 601  AGGCAACTAT TAGTGGCGAA ACCGGCCGAG GAAATCCCTC
 641  GGTCGATTGT CGATAAGGAC TTGTCGGCAG CTTCACCGTA
 681  TCTGCCGACA ACCGACATAG TCCATGCCTG CTTTTATGTA
 721  ACCGAGGAGA GTATAAAAAC ACTGAAAATG AATCTGATCA
 761  AAGAAAGCAA AGATGAGAGT ATAACCAGTC TCGAGGTCCT
 801  TTCAGCCTAT ATATGGAGAG CAAGGTTTAG AGCATTGAAA
 841  TTGAGTCCAG ATAAAACCAC AATGCTCGGC ATGGCCGTAG
 881  GCATACGACG CACCGTGAAA CCACGGTTGC CGAAGGATA
 921  CTACGGGAAT GCTTTCACCT CGGCAAATAC GGCCATGACC
 961  GGGAAGGAAC TCGACCAAGG ACCGCTCTCG AAAGCTGTGA
1001  AACAAATCAA GGAGAGCAAA AAGCTTGCTT CGGAGAATGA
1041  CTATATCTGG AACTTGATGA GCATTAACGA GAAGCTGAGA
1081  GAACTGAATT CGAAGTTCGA AGCGGCCGCC GGTTCAACCA
1121  TGGTCATAAC AGATTGGAGG CGGTTGGGAC TATTGGAAGA
1161  TGTGGATTTT GGATGGAAAG GTAGCGTAAA CATGATACCA
1201  CTGCCGTGGA ACATGTTCGG GTACGTGGAT TTGGTTCTTT
1241  TATTGCCTCC TTGTAAACTG GACCAATCGA TGAAAGGCGG
1281  TGCTAGAGTG TTGGTTTCCT TTCCCACGGC TGCTATTGCC
1321  AAATTCAAGG AAGAAATGGA TGCTCTCAAA CATGATAACA
1361  AGGTTGCCGG CGATGCTCTA GTGATCTAG
```

The SEQ ID NO:8 nucleic acid encodes a *Hibiscus cannabinus* (Kenaf). feruloyl-CoA:monolignol transferase enzyme with the following amino acid sequence (SEQ ID NO:9).

```
  1  MATHSTIMFS VDRNDVVFVK PFKPTPSQVL SLSTIDNDPN
 41  LEIMCHTVFV YQANADFDVK PKDPASIIQE ALSKLLVYYY
```

```
 81  PLAGKMKRET DGKLRIACTA DDSVPFLVAT ADCKLSSLNH

121  LDGIDVHTGK EFALDFASES DGGYYHPLVM QVTKFICGGF

161  TIALSLSHSV CDGFGAAQIF QALTELASGR NEPSVKPVWE

201  RQLLVAKPAE EIPRSIVDKD LSAASPYLPT TDIVHACFYV

241  TEESIKTLKM NLIKESKDES ITSLEVLSAY IWRARFRALK

281  LSPDKTTMLG MAVGIRRTVK PRLPEGYYGN AFTSANTAMT

321  GKELDQGPLS KAVKQIKESK KLASENDYIW NLMSINEKLR

361  ELNSKFEAAA GSTMVITDWR RLGLLEDVDF GWKGSVNMIP

401  LPWNMFGYVD LVLLLPPCKL DQSMKGGARV LVSFPTAAIA

441  KFKEEMDALK HDNKVAGDAL VI
```

Acyltransferases that Decrease Monolignol Ferulate Incorporation

Nucleic acids encoding a p-coumaroyl-CoA:monolignol transferase (PMT, also called a monolignol coumarate transferase) that can inhibit the incorporation of coniferyl ferulate (and other monolignol ferulates) into lignin. One example of a p-coumaroyl-CoA:monolignol transferase gene was isolated from rice (*Oryza sativa*). This PMT gene expresses a BAHD acyltransferase that catalyzes the acylation of monolignols (e.g., p-coumaryl alcohol, coniferyl alcohol and/or sinapyl alcohol) with p-coumarate, for example, as illustrated below.

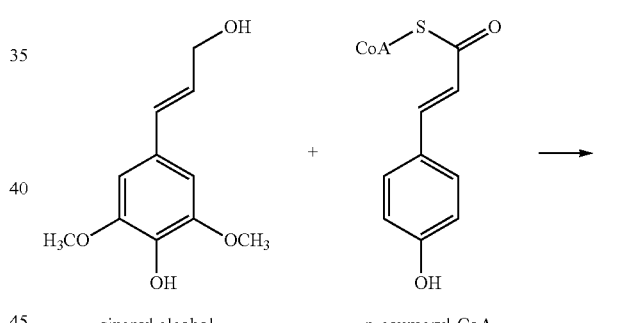

p-coumaryl alcohol       p-coumaryl-CoA p-coumaryl p-coumarate

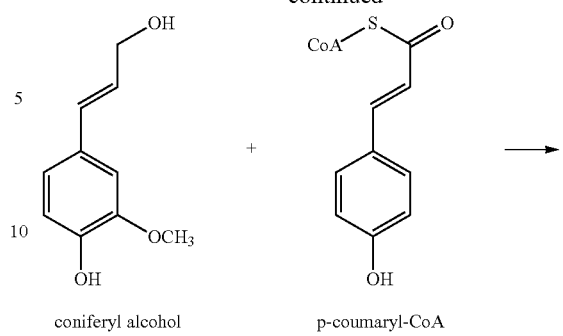

coniferyl alcohol        p-coumaryl-CoA

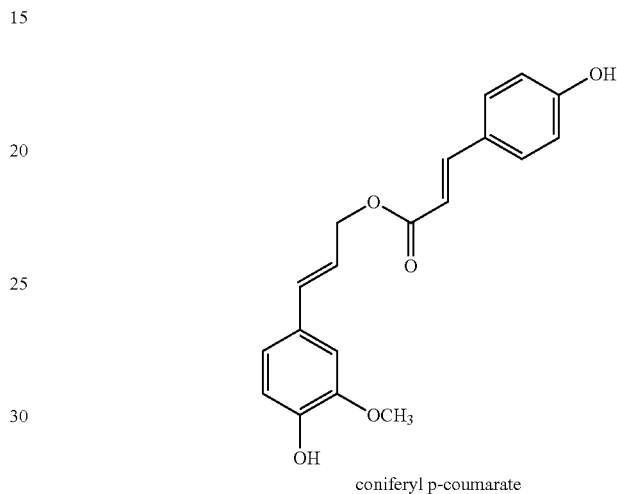

coniferyl p-coumarate

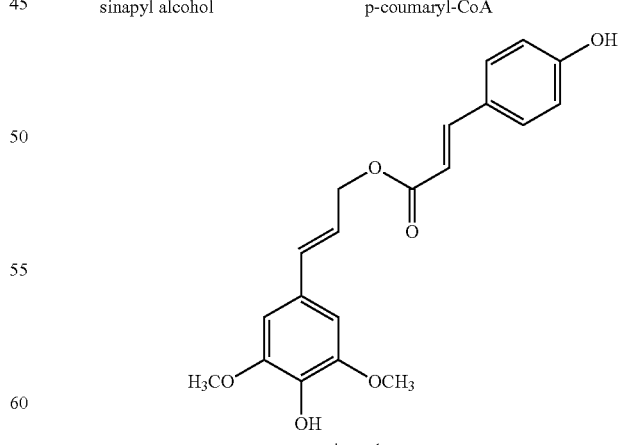

sinapyl alcohol          p-coumaryl-CoA sinapyl p-coumarate

The coding region of the *Oryza sativa* p-coumaroyl-CoA:monolignol transferase has the following nucleic acid sequence (SEQ ID NO:16).

```
   1 ATGGGGTTCG CGGTGGTGAG GACGAACCGG GAGTTCGTGC
  41 GGCCGAGCGC GGCGACGCCG CCGTCGTCCG GCGAGCTGCT
  81 GGAGCTGTCC ATCATCGACC GCGTGGTGGG GCTCCGCCAC
 121 CTGGTGCGGT CGCTGCACAT CTTCTCCGCC GCCGCCCCGA
 161 GCGGCGGCGA CGCCAAGCCG TCGCCGGCGC GGGTGATCAA
 201 GGAGGCGCTG GGAAGGCGC TGGTGGACTA CTACCCGTTC
 241 GCGGGGAGGT TCGTGGACGG CGGCGGCGGG CCGGGGAGCG
 281 CCCGCGTGGA GTGCACCGGC GAGGGCGCCT GGTTCGTGGA
 321 GGCCGCCGCC GGCTGCAGCC TCGACGACGT GAACGGCCTC
 361 GACCACCCGC TCATGATCCC CGAGGACGAC CTCCTCCCCG
 401 ACGCCGCCCC CGGTGTCCAC CCCCTCGACC TCCCCCTCAT
 441 GATGCAGGTG ACGGAGTTCA GTTGCGGAGG GTTCGTGGTG
 481 GGCCTGATCT CGGTGCACAC GATGGCGGAC GGGCTAGGGG
 521 CCGGGCAGTT CATCAACGCG GTGGGCGACT ACGCCCGCGG
 561 GCTGGACAGG CCGAGGGTGA GCCCGGTCTG GGCCCGCGAG
 601 GCCATCCCGA GCCCGCCGAA GCTGCCCCCG GGCCCGCCGC
 641 CGGAGCTGAA GATGTTCCAG CTCCGCCACG TCACCGCCGA
 681 CCTGAGCCTG GACAGCATCA ACAAGGCCAA GTCCGCCTAC
 721 TTCGCCGCCA CCGGCCACCG CTGCTCCACC TTCGACGTCG
 761 CCATCGCCAA GACGTGGCAG GCGCGCACCC GCGCGCTCCG
 801 CCTCCCGAA CCCACCTCC GCGTCAACCT CTGCTTCTTC
 841 GCCAACACCC GCCACCTCAT GGCCGGCGCC GCCGCCTGGC
 881 CCGCACCCGC CGCCGGCGGC AATGGCGGCA ATGGGTTCTA
 921 CGGCAACTGC TTCTACCCGG TGTCGGTGGT GGCGGAGAGC
 961 GGGGCGGTGG AGGCGGCGGA CGTGGCCGGG GTGGTGGGGA
1001 TGATACGGGA GGCGAAGGCG AGGCTGCCGG CGGACTTCGC
1041 GCGGTGGGCG GTGGCCGACT TCAGGGAGGA TCCGTACGAG
1081 CTGAGCTTCA CGTACGATTC CCTGTTCGTC TCCGACTGGA
1121 CGCGGCTGGG GTTCCTGGAG GCGGACTACG GGTGGGGGCC
1161 GCCGTCGCAC GTCATACCCT TCGCGTACTA CCCGTTCATG
1201 GCCGTCGCCA TCATCGGCGC GCCGCCGGTG CCCAAGACCG
1241 GCGCCCGGAT CATGACGCAG TGCGTCGAGG ACGACCACCT
1281 GCCGGCGTTC AAGGAGGAGA TCAAGGCCTT CGACAAGTAA
```

This *Oryza sativa* p-coumaroyl-CoA:monolignol transferase nucleic acid encodes the following amino acid sequence (SEQ ID NO:17).

```
   1 MGFAVVRTNR EFVRPSAATP PSSGELLELS IIDRVVGLRH
  41 LVRSLHIFSA AAPSGGDAKP SPARVIKEAL GKALVDYYPF
  81 AGRFVDGGGG PGSARVECTG EGAWFVEAAA GCSLDDVNGL
 121 DHPLMIPEDD LLPDAAPGVH PLDLPLMMQV TEFSCGGFVV
 161 GLISVHTMAD GLGAGQFINA VGDYARGLDR PRVSPVWARE
 201 AIPSPPKLPP GPPPELKMFQ LRHVTADLSL DSINKAKSAY
 241 FAATGHRCST FDVAIAKTWQ ARTRALRLPE PTSRVNLCFF
 281 ANTRHLMAGA AAWPAPAAGG NGGNGFYGNC FYPVSVVAES
 321 GAVEAADVAG VVGMIREAKA RLPADFARWA VADFREDPYE
 361 LSFTYDSLFV SDWTRLGFLE ADYGWGPPSH VIPFAYYPFM
 401 AVAIIGAPPV PKTGARIMTQ CVEDDHLPAF KEEIKAFDK
```

A genomic DNA sequence for the SEQ ID NO:17 *Oryza sativa* p-coumaroyl-CoA:monolignol transferase has the following nucleic acid sequence (SEQ ID NO:18).

```
   1 ACCACCATCA CCACCACCTC GAAGGTCTTG AGCTCCATCT
  41 CCGGCGACGG CGGCGACGAC GACGACGACG GCGAGGAGGA
  81 GCTAGTAGCT AGCTGAGCCA GACAGCATGG GGTTCGCGGT
 121 GGTGAGGACG AACCGGGAGT TCGTGCGGCC GAGCGCGGCG
 161 ACGCCGCCGT CGTCCGGCGA GCTGCTGGAG CTGTCCATCA
 201 TCGACCGCGT GGTGGGGCTC CGCCACCTGG TGCGGTCGCT
 241 GCACATCTTC TCCGCCGCCG CCCCGAGCGG CGGCGACGCC
 281 AAGCCGTCGC CGGCGCGGGT GATCAAGGAG GCGCTGGGGA
 321 AGGCGCTGGT GGACTACTAC CCGTTCGCGG GGAGGTTCGT
 361 GGACGGCGGC GGCGGGCCGG GGAGCGCCCG CGTGGAGTGC
 401 ACCGGCGAGG GCGCCTGGTT CGTGGAGGCC GCCGCCGGCT
 441 GCAGCCTCGA CGACGTGAAC GGCCTCGACC ACCCGCTCAT
 481 GATCCCCGAG GACGACCTCC TCCCCGACGC CGCCCCCGGT
 521 GTCCACCCCC TCGACCTCCC CCTCATGATG CAGGTATAAT
 561 ACTACCCGTA TACGTACGTT TCTACGTACG TAAGTACGTG
 601 CTATACTTGC GAGCAGACAA AAACAAATAA AATCGGTAAC
 641 AACAATTAAC CATCCAGTTA TGCTTACAAC TAATTCAAAT
 681 TATCTTAATT AATTAAAACT GTCCGGCTAA TTAAGTGATT
 721 ATTAAGGGTG TGTTTTTATC ACATCTTCCC GACTGGTACT
 761 CCCTCATTTT CCACACGGAT GTTTTACAAC TGCTAAACGG
 801 TACGTATTAT CAGAAAAAAG TTATATATAT AAATTGTTTT
 841 AAAATCATAT TAATCTATTT TTAAGTTTAT TTTAGCTAAT
 881 AGTTAAATAA ACACGCGCTA ACGGATCATT ATGTTTTGTG
 921 TGTGGGGAGA TATAGTTTCT AACCTCCACC TCTAAACACA
 961 GCATAATTGT TGGTACGTAG GGCCTATTCA CTTTAACGCA
1001 AAAAAGAAC CTTACCAAGT TGCCAAAATT TTGGTAGGAT
1041 TTCTTATATA GTTACTAAAA TTTGATAGCA AACTAAATAT
1081 AACCACTTTT TTATAACTTT ACCAAAATTT GCTAAGATTG
1121 AAAATGGCAT CAAAGTGAAC AGGCCCGTAT ACGTACGGAG
1161 AATGCTGACC TCTCCGGATG ATACCTTTAA TTTTTCACTT
1201 GTGTGGATGT GCACACATGT ACGAGGACGA ACACATTCAA
```

```
1241 ACCCGTGAAG ATTTTAATAT GTGGACGAAC TCGATCTATG
1281 GTATTGTTGC TGACGAATTA ATTACAAAAG TGCTCAAGGA
1321 GTTATGTAAC TATAAGAACA AAACTATATA TGTTTGCCCA
1361 AGTAGAAATA TATACGAACA AAAACACAGA CATGAATAGA
1401 ACCTACGCGT ACGTACATAT GTGCCATTAC ATGCATGTAC
1441 ACAATCATTA GCTAGTGTCC TGGATTATAT TCTAGTCAAT
1481 TATAACTTTC TAGAAATTAG GTACTAATAT ATGTATGACT
1521 CTCAAACTGT AGTCATGCTT GTGTCAAGTT ATAATTAAGT
1561 ACAATAATCA CACCGATTTA TTTTACATAA AGTACAGTAG
1601 GATTCAAGAT AAGACTGAGC TATATAGTAC TAGGCAGGAT
1641 GATGAGCTAG CTAGAGCTTA GTGCTCAACA TAAACTAGTT
1681 GGAGCGTGCA CTGCAATTTT CAAAGTAAAA TTAGTTAATT
1721 TGCACTAGGT GAAGTTGATC CTGTCAGGTA GGTAAGCTCA
1761 CCAACTCCAA AGATTGGACA GAATGAAGCA TCTGTGGAAG
1801 TGAAAGCAGT TGCGTTGGCG TAAGACCACA CTAACCAGAG
1841 AACTCATAAT ACAAAATACA TATACAGCAC ACAATTTATA
1881 TTGTGTATAT ATATATATAT ATATATATAT ATATGTATGT
1921 ATGTATGTAT GTATGTATTC TAACTGTGTT ATCCAATTTT
1961 TAAGAAATTT CATCTTTTCA AAAGTAGTAG TATTTGAGTG
2001 ATGCATGTGC ACGTTTTTAG ATATGTACAT ATACCTCATC
2041 TATCTTTAAA AATAAAATAA ATTTTATACA TGAGTCGGAA
2081 CACTAAGCTT TAACACTGAT ATCTGACGAT AGCATGACGG
2121 GATGAGCTTG TCATCAATTG CAGCAGGGCA ATTAGGCATG
2161 TAAACTGGGG CCATTGATTT CTGTCGAGCA CACTATGCTT
2201 TCCCTGTCTT ATTCTGCCTA ACTTAACACT AATATTTGAC
2241 ACACTATCAA TTGTTAGCTA TTGATATGGC AGTTTGACAT
2281 CGACCCTGCT CCATCATTAT TACTGCATGC CCGCCCATTC
2321 GATGATTGAC TTGACCAAAC CCACAAGTGC AAATTGGAAA
2361 ATTAATTAAT TAATTAATTA GCAAGATAAA TATATCCATC
2401 AGGGATTCAG GATCAGGTCA TGGATGTAAT CACTCTCAAA
2441 CATAGCTAAT CATTGTGCTT ATGGTCCAAG TGATCATTCC
2481 CCCTAATCAA CAACTCGCTT GCTAGCAAGA CGTCCCTTCG
2521 AATGGATTAT TTGATAGCTA GAGCATATCA CCTTGCACTT
2561 CACCACTCCC CTTATGCAGA GTGTACGTAT GTCTAACCAG
2601 AATCTAGTGG TGAGCGTAAA AGATCAAAGT GCCCTTATCA
2641 ATAACAAAAT ACTCCGTAAT ACATTTGGTG GATATATAGG
2681 TATATAAGTA TTAAAGGAAT AAAACTTTCA AATTTGTGGA
2721 TTCTAATAAA AACTAATATT AATTTTGATA AACCTGAATT
2761 GTAGATACTC TAACTTAGGG TAGTAGTTGA AGCATGCAAA
2801 GCTCTAAAAA TATATATGAA TTTCGGCGTG TTTATATATA
2841 TTTCTCCGTG GATATAAAAG CTTAAAATTT ATAATCATTT
2881 TATGATGATC AGGTGACGGA GTTCAGTTGC GGAGGGTTCG
2921 TGGTGGGCCT GATCTCGGTG CACACGATGG CGGACGGGCT
2961 AGGGGCCGGG CAGTTCATCA ACGCGGTGGG CGACTACGCC
3001 CGCGGGCTGG ACAGGCCGAG GGTGAGCCCG GTCTGGGCCC
3041 GCGAGGCCAT CCCGAGCCCG CCGAAGCTGC CCCCGGGCCC
3081 GCCGCCGGAG CTGAAGATGT TCCAGCTCCG CCACGTCACC
3121 GCCGACCTGA GCCTGGACAG CATCAACAAG GCCAAGTCCG
3161 CCTACTTCGC CGCCACCGGC CACCGCTGCT CCACCTTCGA
3201 CGTCGCCATC GCCAAGACGT GGCAGGCGCG CACCCGCGCG
3241 CTCCGCCTCC CGGAACCCAC CTCCCGCGTC AACCTCTGCT
3281 TCTTCGCCAA CACCCGCCAC CTCATGGCCG GCGCCGCCGC
3321 CTGGCCCGCA CCCGCCGCCG GCGGCAATGG CGGCAATGGG
3361 TTCTACGGCA ACTGCTTCTA CCCGGTGTCG GTGGTGGCGG
3401 AGAGCGGGGC GGTGGAGGCG GCGGACGTGG CCGGGGTGGT
3441 GGGGATGATA CGGGAGGCGA AGGCGAGGCT GCCGGCGGAC
3481 TTCGCGCGGT GGGCGGTGGC CGACTTCAGG GAGGATCCGT
3521 ACGAGCTGAG CTTCACGTAC GATTCCCTGT TCGTCTCCGA
3561 CTGGACGCGG CTGGGGTTCC TGGAGGCGGA CTACGGGTGG
3601 GGGCCGCCGT CGCACGTCAT ACCCTTCGCG TACTACCCGT
3641 TCATGGCCGT CGCCATCATC GGCGCGCCGC CGGTGCCCAA
3681 GACCGGCGCC CGGATCATGA CGCAGTGCGT CGAGGACGAC
3721 CACCTGCCGG CGTTCAAGGA GGAGATCAAG GCCTTCGACA
3761 AGTAAAATGC TTGTGAAATG TGAACTTTGT TATTGTTACT
3801 ACTTCTATGG GCTCGTTGCT CAATGGGCTT TTTTTTGCTT
3841 TTGTTTTGTG TGTGTGGGCC GACACGATTG GTCAAAAGGG
3881 ATTTGGTGGA GGCCCAGTTG TAATAAGATG GTCCACGCAT
3921 CATGGATTAA TCGTTAATTG TAAGGTAGTA CTACACGGAT
3961 TTGTTAACAA GGAATAAGTT CACTTGGTGA CCCAGTGA
```

A nucleic acid sequence for the SEQ ID NO:17 *Oryza sativa* p-coumaroyl-CoA:monolignol transferase that has been optimized for expression has the following nucleic acid sequence (SEQ ID NO:19).

```
  1 ATGGGATTTG CTGTTGTCCG CACAAACCGT GAATTTGTTC
 41 GCCCCTCGGC AGCTACCCCA CCATCATCCG GCGAATTATT
 81 GGAATTATCA ATCATTGATC GTGTAGTTGG TCTCCGTCAT
121 CTGGTTCGTT CTTTACATAT TTTTTCTGCA GCTGCACCAT
161 CTGGCGGTGA TGCAAAACCC TCCCCGGCTC GCGTTATTAA
201 AGAAGCATTG GCAAAGCAC TTGTAGACTA CTATCCTTTC
241 GCAGGTCGTT TCGTTGACGG CGGCGGCGGT CCGGGCAGTG
281 CGCGTGTAGA ATGTACCGGT GAAGGTGCTT GGTTTGTAGA
321 AGCAGCTGCT GGATGTTCAT TAGACGATGT CAATGGCTTA
```

```
361  GATCATCCAT TAATGATTCC TGAAGACGAT CTCTTACCCG
401  ATGCAGCCCC TGGCGTTCAC CCACTGGATT TACCGTTAAT
441  GATGCAAGTT ACTGAATTTT CATGCGGCGG TTTTGTTGTT
481  GGCTTGATTA GCGTCCACAC AATGGCTGAC GGTTTAGGCG
521  CAGGCCAATT TATCAATGCA GTAGGCGATT ATGCTCGTGG
561  CCTCGACCGT CCGCGTGTTA GCCCGGTATG GGCACGCGAA
601  GCCATTCCTA GCCCTCCGAA GTTACCACCC GGTCCACCTC
641  CCGAATTAAA AATGTTCCAA CTTCGTCATG TGACAGCCGA
681  TTTGTCTCTC GATTCTATCA ACAAGGCGAA ATCAGCGTAT
721  TTTGCAGCCA CCGGTCATCG TTGCTCCACA TTCGACGTCG
761  CTATTGCAAA AACATGGCAA GCCCGCACTC GTGCCCTTCG
801  TCTCCCAGAA CCAACGTCAC GTGTTAACCT GTGTTTTTTT
841  GCTAATACCC GCCATTTAAT GGCAGGCGCA GCGGCCTGGC
881  CCGCTCCAGC AGCCGGAGGT AATGGTGGCA ACGGCTTCTA
921  TGGCAATTGT TTCTACCCGG TGTCTGTTGT GGCCGAATCA
961  GGTGCAGTTG AAGCGGCAGA TGTGGCAGGT GTTGTTGGTA
1001 TGATCCGTGA GGCCAAAGCC CGTCTCCCAG CCGATTTTGC
1041 ACGTTGGGCA GTTGCCGATT TTCGCGAAGA CCCTTATGAA
1081 CTTTCATTTA CATATGATTC CTTGTTTGTC TCAGATTGGA
1121 CTCGTTTAGG ATTTCTCGAA GCTGATTATG GTTGGGGCCC
1161 ACCCTCTCAT GTAATTCCTT TCGCATATTA CCCGTTTATG
1201 GCGGTAGCTA TCATCGGCGC TCCTCCAGTT CCAAAAACCG
1241 GCGCACGTAT TATGACTCAG TGTGTAGAAG ATGATCATTT
1281 ACCAGCGTTT AAAGAAGAAA TTAAAGCCTT CGATAAGTGA
```

As described in more detail herein, nucleic acids encoding p-coumaroyl-CoA:monolignol transferase can be targeted for inhibition, knockdown or knockout. For example, p-coumaroyl-CoA:monolignol transferase nucleic acids that are endogenous within various species of plant cells, seeds and plants can be targeted for knockout by mutation using mutagens or recombinant technology. Endogenous p-coumaroyl-CoA:monolignol transferase gene that can be targeted for inhibition, knockdown or knockout include, for example, nucleic acids that include any of the SEQ ID NO:16, 18, 19, 22, 23, 25, 26, 27, 28, 47-63 and 64 p-coumaroyl-CoA:monolignol transferase sequences. In addition, inhibitory nucleic acids that are homologous, identical and/or complementary to any of the SEQ ID NO:16, 18, 19, 22, 23, 25, 26, 27, 28, 47-63 and 64 p-coumaroyl-CoA:monolignol transferase nucleic acids can be used to inhibit the expression of p-coumaroyl-CoA:monolignol transferase.

Knockout of Endogenous p-Coumaroyl-CoA:Monolignol Transferase Nucleic Acids

Also provided herein are partial or full PMT knockout mutant plants and partial or full PMT knockout plant cells. "Knockout" means that a plant has a mutation in an endogenous gene (a PMT gene) that substantially reduces or deletes the expression of function of the protein encoded by the gene compared to a wild-type plant that has no such mutation. For example, a knockout mutation can reduce PMT expression by about 80%, or by 90%, or by 95%, or by 98%, or by 99%, or by 100%.

"Knockdown" means that the expression or function of an endogenous gene is partially reduced. Knockdown can be accomplished by mutation of the endogenous gene so that a protein with reduced function is expressed, or by introduction of an inhibitory RNA that reduces production of the active protein. For example, a knockdown can reduce PMT expression by at least 10%, or by 20%, or by 30%, or by 40%, or 50%, or by 60%, or by 70%. While knockdown is generally understood to only partially reduce the function of a gene, as illustrated herein PMT expression can be reduced by introduction of an inhibitory nucleic acid by about 95%.

Plants, plant cells and seeds can have the knockout and/or knockdown mutation. Plants, plant cells and seeds also can have an inhibitory nucleic acid that reduces PMT expression. PMT inhibitory nucleic acids can lead to, complete or partial reduction expression of PMT. Nucleic acid sequences that can facilitate partial and full knockout of PMT in plant cells and plants are also provided herein, and are referred to as PMT mutating nucleic acids.

The endogenous mutant knockout or knockdown PMT nucleic acid molecules can include one or more mutations, such as one or more missense mutations, nonsense mutations, STOP codon mutations, insertion mutations, deletion mutation, frameshift mutations and/or splice site mutations. Basically, an endogenous knockout or knockdown PMT nucleic acid can include any mutation that results in little or no expression of the PMT protein, or in expression of a PMT protein that has at least one amino acid insertion, deletion and/or substitution relative to the wild type protein resulting in a non-functional PMT protein or no PMT protein at all. Such mutations result in a partial or full knockout PMT allele. It is, however, understood that mutations in certain parts of the protein are more likely to result in a non-functional PMT protein, such as mutations leading to truncated proteins. Such truncated proteins can have one or more of the functional amino acid residues or significant portions of the functional domains deleted or replaced.

Thus in one embodiment, nucleic acid sequences comprising one or more of the mutations described above are provided (in isolated form), as well as plants, plant cells, plant parts and plant seeds endogenously comprising such sequences. Mutant PMT alleles may be generated (for example, induced by chemical or recombinant mutagenesis) and/or identified using a range of methods available in the art (for example using PCR based methods to amplify part or all of the mutant PMT genomic DNA or cDNA).

Mutant PMT alleles may be generated and/or identified using a range of available methods. For example, partial or full knockout of PMT function can be induced by chemical or insertional mutagenesis, recombinant technology, and other available techniques. Mutagens such as ethyl methanesulfonate, radiation, *Agrobacterium tumefaciens*-mediated T-DNA transformation, transposon mutagenesis, zinc finger nuclease (ZFN)-mediated targeting of natural genes by homologous recombination, and variations thereof can be used. In some embodiments, the Rapid Trait Development System (RTDS™) developed by Cibus can be employed (see, website at cibus.com/pdfs/Cibus_Brochure.pdf).

Plant seeds or plant cells comprising one or more mutant PMT alleles can be generated and identified using other methods, such as the "Delete-a-gene™" method that employs PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method that identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wild type DNA heteroduplexes and detection using a sequencing gel system). The use of TILLING to identify plants or plant parts comprising one or more mutant PMT alleles and methods for generating and identifying such plants, plant organs, tissues and seeds is encompassed herein.

The methods provided herein can also include one or more of the following steps: mutagenizing plant cells or seeds (e.g. EMS mutagenesis, T-DNA insertion, mutation via recombinant insertion or replacement of defective sequences), pooling of plant individuals or plant DNA, PCR amplification of a region of interest, heteroduplex formation and high-throughput detection, identification of a mutant plant or DNA, and/or sequencing of mutant nucleic acid products. It is understood that other mutagenesis and selection methods may also be used to generate such mutant plants.

Instead of inducing mutations in PMT alleles, natural (spontaneous) mutant alleles may be identified by methods available in the art. For example, ECOTILLING may be used (Henikoff et al. 2004, Plant Physiology 135(2):630-6) to screen a plurality of plants or plant parts for the presence of natural mutant PMT alleles. As for the mutagenesis techniques above, preferably Poaceae species are screened, so that the identified PMT allele can subsequently be introduced into other Poaceae species, such as any of those listed above, by crossing (inter- or intraspecific crosses) and selection. In ECOTILLING natural polymorphisms in breeding lines or related species are screened for by the TILLING methodology described above, in which individual or pools of plants are used for PCR amplification of the PMT target, heteroduplex formation and high-throughput analysis. This can be followed by selecting individual plants having a required mutation that can be used subsequently in a breeding program to incorporate the desired mutant allele.

The identified mutant alleles can be sequenced and the sequence can be compared to the wild type allele to identify the mutation(s). Optionally, whether a mutant allele functions as a partial or full knockout PMT mutant allele can be tested as described herein. Using this approach a plurality of mutant PMT alleles (and Poaceae plants comprising one or more of these) can be identified. The desired mutant alleles can then be combined with the desired wild type alleles by crossing and selection methods. A single plant comprising the desired number of mutant PMT and the desired number of wild type and or knockout PMT alleles is generated.

Mutant PMT alleles or plants comprising mutant PMT alleles can be identified or detected by methods available in the art, such as direct sequencing, PCR based assays or hybridization based assays. Alternatively, methods can also be developed using the specific mutant PMT allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

Full or partial knockout mutant PMT nucleic acid sequences can, for example, be generated in various species of the Poaceae family of grasses (also called Gramineae or true grasses). Poaceae are a large and nearly ubiquitous family of monocotyledonous flowering plants. See the list of genera within the Poaceae family at the website theplantlist.org/browse/A/Poaceae/. Grass species with PMT knockout mutations can include species such as *Miscanthus giganteus Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), (thatch), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (*sorghum*), *Bachypodium distachyon* (purple false brome), and the like. Poaceae nucleic acids can be isolated, mutated and reintroduced or used to knockout the endogenous PMT gene in various plant species. Loss of PMT function can augment biofuel production from such species.

Following mutagenesis, plants are grown from the treated seeds, or regenerated from the treated cells using available techniques. For instance, mutagenized seeds may be planted in accordance with conventional growing procedures and, following self-pollination, seed is formed on the plants. Alternatively, doubled haploid plantlets may be extracted from treated microspore or pollen cells to immediately form homozygous plants. Seeds formed as a result of such self-pollination or seeds from subsequent generations may be harvested and screened for the presence of mutant PMT alleles, using techniques that are available in the art, for example polymerase chain reaction (PCR) based techniques (amplification of the PMT alleles) or hybridization based techniques, e.g. Southern blot analysis, BAC library screening, and the like, and/or direct sequencing of PMT alleles. To screen for the presence of point mutations (e.g., Single Nucleotide Polymorphisms or SNPs) in mutant PMT alleles, available SNP detection methods can be used, for example oligo-ligation-based techniques, single base extension-based techniques, such as pyrosequencing, or techniques based on differences in restriction sites, such as TILLING.

Inhibitory and Mutating Nucleic Acids

In another embodiment, the invention relates to an inhibitory nucleic acid that can reduce the expression and/or translation of p-coumaroyl-CoA:monolignol transferase in a plant or plant cell. In other embodiments, the invention relates to mutating nucleic acids that can knockout the expression of a p-coumaroyl-CoA:monolignol transferase in a plant or plant cell. For example, the inhibitory nucleic acid that can reduce the expression and/or translation of a p-coumaroyl-CoA:monolignol transferase having any of the SEQ ID NO:16, 18, 19, 22, 23, 25, 26, 27, 28, 47-63 and 64 sequences. The inhibitory nucleic acid can, for example, reduce the expression of a p-coumaroyl-CoA:monolignol transferase by any amount such as, for example, by 2%, 5%, 10%, 20%, 40% or more than 40%. Mutating nucleic acid can knockout or knockdown the expression or function of a p-coumaroyl-CoA:monolignol transferase having 50% or more sequence identity to any of the SEQ ID NO:16, 18, 19, 22, 23, 25, 26, 27, 28, 47-63 and 64 sequences. For example, a mutating nucleic acid can mutate or replace an endogenous p-coumaroyl-CoA:monolignol transferase gene having 50% or more sequence identity to any of the SEQ ID NO:16, 18, 19, 22, 23, 25, 26, 27, 28, 47-63 and 64 sequences.

In one embodiment, an inhibitory nucleic acid may be an oligonucleotide that will hybridize to a p-coumaroyl-CoA:monolignol transferase nucleic acid under intracellular, physiological or stringent conditions. The oligonucleotide is capable of reducing expression of a nucleic acid encoding the p-coumaroyl-CoA:monolignol transferase. A nucleic acid encoding a p-coumaroyl-CoA:monolignol transferase may be genomic DNA as well as messenger RNA. For example, in some embodiments, the inhibitory nucleic acid can hybridize to any of the SEQ ID NO:16, 18, 19, 22, 23, 25, 26, 27, 28, 47-63 and 64 sequences, or to a complementary strand of any of the SEQ ID NO:16, 18, 19, 22, 23, 25, 26, 27, 28, 47-63 and 64 sequences. The inhibitory nucleic acid may, for example, be incorporated into a plasmid vector or viral DNA. The inhibitory nucleic acid may be single stranded or double stranded, circular or linear. The inhibitory nucleic acid may also have a stem-loop structure.

A mutating nucleic acid can, for example, have two segments that are complementary to a targeted p-coumaroyl-CoA:monolignol transferase gene. For example, the segments of a mutating nucleic acid can hybridize to any of the SEQ ID NO:16, 18, 19, 22, 23, 25, 26, 27, 28, 47-63 and 64 sequences, or to a complementary strand of any of the SEQ ID NO:16, 18, 19, 22, 23, 25, 26, 27, 28, 47-63 and 64 sequences. Such a mutating nucleic acid can hybridize via those two segments to an endogenous p-coumaroyl-CoA:monolignol transferase gene within a plant cell and replace or mutate segments of the endogenous p-coumaroyl-CoA:monolignol transferase gene. For example, a mutating nucleic acid can include two segments, referred to segment A and segment B, that are separately selected from any of the PMT nucleic acid sequences described herein, with a non-PMT nucleic acid segment between segments A and B. The non-PMT nucleic acid sequence has at least one nucleotide that can replace at least one nucleotide in vivo within an endogenous plant PMT. Segment B is selected from a region that is downstream (3') to the segment A sequence. The structure of mutating nucleic acid, for example, can be as follows:

(Segment A)-(non-PMT segment)-(Segment B)
wherein:
Segment A is a nucleic acid that can hybridize to an endogenous PMT gene in vivo at a position 3' to the region where Segment B hybridizes;
non-PMT segment is a nucleic acid that can replace part of an endogenous PMT gene in vivo when segments A and B are hybridized to the endogenous PMT gene; and Segment B is a nucleic acid that can hybridize to an endogenous PMT gene in vivo at a position 5' to the region where Segment A hybridizes.

Segments A and B are each separately about 15-50 nucleotides in length, or about 16-40 nucleotides in length, or about 17-30 nucleotides in length, or about 18-25 nucleotides in length, or any number of nucleotides in length between 15-50 nucleotides.

The non-PMT segment is at least one nucleotide in length. However, the non-PMT segment can also be 1-10,000 nucleotides in length, or 1-1000 nucleotides in length, or 1-100 nucleotides in length, or 1-50 nucleotides in length, or 1-20 nucleotides in length, or 5-50 nucleotides in length, or any numerical value or range within 1-10000 nucleotides in length.

Such a mutating nucleic acid can introduce point mutations into the endogenous PMT gene, or it can replace whole parts of the endogenous PMT gene.

The inhibitory or mutating nucleic acids can be polymers of ribose nucleotides or deoxyribose nucleotides. For example, inhibitory and/or mutating nucleic acids may include naturally-occurring nucleotides as well as synthetic, modified, or pseudo-nucleotides. The inhibitory and/or mutating nucleic acids can include modified nucleotides such as phosphorothiolates; 2'-O alkyl-containing nucleotides, and nucleotides having a detectable label such as $P^{32}$, biotin or digoxigenin. The inhibitory and mutating nucleic acids can include peptide nucleic acid (PNA), locked nucleic acid (LNA) and morpholino nucleotide sequences.

Such inhibitory or mutating nucleic acids can be of varying lengths. For example, an inhibitory oligonucleotide can be more than 13 nucleotides, or more than 14 nucleotides, or more than 15 nucleotides, or more than 16 nucleotides, or more than 17 nucleotides in length. Mutating nucleic acids be of similar length but are often longer than inhibitory nucleic acids. For example, a mutating nucleic acid can be more than 30 nucleotides in length.

An inhibitory or mutating nucleic acid that can reduce the expression and/or activity of a p-coumaroyl-CoA:monolignol transferase nucleic acid, may include segments that are completely complementary and/or completely identical to the p-coumaroyl-CoA:monolignol transferase nucleic acid (e.g., a DNA or RNA). Alternatively, some variability between the sequences may be permitted. An inhibitory or mutating nucleic acid that can inhibit or knockout a p-coumaroyl-CoA:monolignol transferase nucleic acid can hybridize to the p-coumaroyl-CoA:monolignol transferase nucleic acid under intracellular conditions or under stringent hybridization conditions. For example, an inhibitory or mutating nucleic acid can be sufficiently complementary to inhibit expression of, or to recombine and replace, an endogenous p-coumaroyl-CoA:monolignol transferase nucleic acid. Intracellular conditions refer to conditions such as temperature, pH and salt concentrations typically found inside a cell, for example, a living plant cell.

Inhibitory nucleic acids (e.g., oligonucleotides) and/or mutating nucleic acids can include, for example, 2, 3, 4, or 5 or more stretches of contiguous nucleotides that are precisely complementary to a p-coumaroyl-CoA:monolignol transferase nucleic acid coding sequence, each separated by a stretch of contiguous nucleotides that are not complementary to adjacent coding sequences, may inhibit the function of a p-coumaroyl-CoA:monolignol transferase nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an oligonucleotide or nucleic acid hybridized to a nucleic acid target to estimate the degree of mismatching that will be tolerated for inhibiting or mutating expression of a particular target nucleic acid.

Inhibitory nucleic acids include, for example, ribozymes, antisense nucleic acids, interfering RNA, microRNA, small interfering RNA (siRNA), and combinations thereof.

An antisense nucleic acid molecule is typically single-stranded that is complementary to the target nucleic acid (a nucleic acid encoding a p-coumaroyl-CoA:monolignol transferase). The antisense nucleic acid may function in an enzyme-dependent manner or, more frequently, by steric blocking. Steric blocking antisense, which are RNase-H independent, interferes with gene expression or other mRNA-dependent cellular processes by binding to a target mRNA and getting in the way of other processes.

An antisense oligonucleotide can be complementary to a sense nucleic acid encoding a p-coumaroyl-CoA:monolignol transferase protein. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding a p-coumaroyl-CoA:monolignol transferase protein. The noncoding region includes the 5' and 3' regions that flank the coding region, for example, the 5' and 3' untranslated sequences. An antisense oligonucleotide is generally at least six nucleotides in length, but may be about 8, 12, 15, 20, 25, 30, 35, 40, 45, or 50 nucleotides long. Longer oligonucleotides may also be used.

An antisense oligonucleotide may be prepared using methods known in the art, for example, by expression from an expression vector encoding the antisense oligonucleotide or from an expression cassette. For example, an antisense nucleic acid can be generated simply by flipping over the coding region of an mRNA, thereby allowing a regulatory sequence (e.g., a promoter) to transcribe the "wrong" DNA strand. The transcript so-produced is an antisense RNA, which will bind and inactivate the RNA produced by the normal gene.

RNA interference (also referred to as "RNA-mediated interference") (RNAi) is an effective mechanism by which gene expression can be reduced or eliminated. Double stranded RNA (dsRNA) or single stranded RNA has been observed to mediate the reduction, which is a multi-step process (for details of single stranded RNA methods and compositions see Martinez et al., *Cell*, 110(5):563 (2002)). dsRNA activates post-transcriptional gene expression surveillance mechanisms that appear to function to defend cells from virus infection and transposon activity (Fire et al., *Nature*, 391:806-811 (1998); Grishok et al., *Cell*, 106: 23-34 (2001); Ketting et al., *Cell*, 99:133-141 (1999); Lin and Avery, *Nature*, 402:128-129 (1999); Montgomery et al., *Proc. Natl. Acad. Sci. USA*, 95:15502-07 (1998); Sharp and Zamore, *Science*, 287:2431-2433 (2000); Tabara et al., *Cell*, 99:123-132 (1999)). Activation of these mechanisms targets mature, dsRNA-complementary mRNA for destruction. The double stranded RNA reduces the expression of the gene to which the dsRNA corresponds.

For example, RNAi can be made from two oligonucleotides consisting of partially complementary sequences. The oligonucleotides can be made recombinantly, for example, from one or two expression cassettes and/or expression vectors.

RNAi has some advantages including high specificity, ease of movement across cell membranes, and prolonged down-regulation of the targeted gene. (Fire et al., 1998; Grishok et al., 2000; Ketting et al., 1999; Lin et al., 1999; Montgomery et al., 1998; Sharp et al., 2000; Tabara et al., 1999). Moreover, dsRNA has been shown to silence genes in a wide range of systems, including plants, protozoans, fungi, *C. elegans, Trypanasoma, Drosophila,* and mammals (Grishok et al., 2000; Sharp, *Genes Dev.*, 13:139-141 (1999); Sharp et al., 2000; Elbashir et al., *Nature,* 411:494-498 (2001)).

Small interfering RNAs (siRNAs) or short hairpin RNAs (shRNAs) can also be used to specifically reduce p-coumaroyl-CoA:monolignol transferase expression such that the level of p-coumaroyl-CoA:monolignol transferase polypeptides is reduced. siRNAs are double-stranded RNA molecules that mediate post-transcriptional gene silencing in a sequence-specific manner. See, for example, Hamilton & Baulcombe, Science 286 (5441): 950-2 (1999); see also, the website at www.ambion.com/techlib/hottopics/rnai/rnai_may2002_print.html (last retrieved May 10, 2006). Once incorporated into an RNA-induced silencing complex, siRNA mediate cleavage of the homologous endogenous mRNA transcript by guiding the complex to the homologous mRNA transcript, which is then cleaved by the complex.

For example, siRNA can be made from two partially or fully complementary oligonucleotides. Alternatively, short hairpin RNA (shRNA) can be employed that is a one oligonucleotide that forms a double-stranded region by folding back onto itself via a tight hairpin turn. The siRNA and/or shRNA may have sequence identity, sequence complementarity and/or be homologous to any region of the p-coumaroyl-CoA:monolignol transferase mRNA transcript. The region of sequence homology or complementarity may be 50 nucleotides or less in length, less than 45 nucleotides, less than 40 nucleotides, less than 35 nucleotides, less than 30 nucleotides, or less than 25 nucleotides in length. In some embodiments, the region of sequence homology or complementarity of a siRNA or shRNA may be about 21 to 23 nucleotides in length.

SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411: 494-498 (2001); Harborth et al. *Antisense Nucleic Acid Drug Dev.* 13: 83-106 (2003). Typically, a target site that begins with AA, has 3' UU overhangs for both the sense and antisense siRNA strands, and has an approximate 50% G/C content is selected. SiRNAs may be chemically synthesized, created by in vitro transcription, or expressed from an siRNA expression vector or a PCR expression cassette. See, e.g., the website at www.ambion-.com/techlib/tb/tb_506html (last retrieved May. 10, 2006).

When a shRNA is expressed from an expression vector or a PCR expression cassette, the insert encoding the shRNA may be expressed as an RNA transcript that folds into an shRNA hairpin. Thus, the shRNA transcript may include a sense siRNA sequence that is linked to its reverse complementary antisense siRNA sequence by a spacer sequence that forms the loop of the hairpin as well as a string of U's at the 3' end. The loop of the hairpin may be of various lengths. For example, the loop can be 3 to 30 nucleotides in length, or 3 to 23 nucleotides in length. Examples of nucleotide sequences for the loop include AUG, CCC, UUCG, CCACC, CTCGAG, AAGCUU, CCACACC and UUCAAGAGA (SEQ ID NO: 65).

SiRNAs also may be produced in vivo by cleavage of double-stranded RNA introduced directly or via a transgene or virus. Further information on selection and properties of inhibitory nucleic acids is provided in the next section.

The inhibitory nucleic acid may also be a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996). A ribozyme may be used to catalytically cleave a PMT mRNA transcript and thereby inhibit translation of the mRNA. See, for example, Haseloff et al., U.S. Pat. No. 5,641,673. A ribozyme having specificity for a PMT nucleic acid may be designed based on the nucleotide sequence of any of the SEQ ID NO:16, 18, 19, 22, 23, 25, 26, 27, 28, 47-63 and 64 sequences. Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from a nucleic acid having any of the SEQ ID NO:16, 18, 19, 22, 23, 25, 26, 27, 28, 47-63 and 64 sequences. Longer complementary sequences may be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target. Thus, an existing ribozyme may be modified to target a PMT mRNA by modifying the hybridization region of the ribozyme to include a sequence that is complementary to the target PMT. Alternatively, an mRNA encoding a PMT may be used to select a catalytic RNA having a specific ribonuclease activity from a pool of RNA molecules. See, for example, Bartel & Szostak, Science 261:1411-1418 (1993).

Inhibitory and mutating nucleic acids can be generated by recombinant means, for example, by expression from an expression cassette or expression vector. Alternatively, the inhibitory or mutating nucleic acids can also be prepared by chemical synthesis using naturally-occurring nucleotides, modified nucleotides or any combinations thereof. In some embodiments, these nucleic acids are made from modified nucleotides or non-phosphodiester bonds, for example, that are designed to increase biological stability of the nucleic acid or to increase intracellular stability of the duplex formed between the inhibitory or mutating nucleic acids and endogenous nucleic acids. Naturally-occurring nucleotides include the ribose or deoxyribose nucleotides adenosine, guanine, cytosine, thymine and uracil. Examples of modified nucleotides include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine. Thus, inhibitory or mutating nucleic acids may include modified nucleotides, as well as natural nucleotides such as combinations of ribose and deoxyribose nucleotides, and inhibitory or mutating nucleic acids of the invention may be of any length sufficient to inhibit or mutate an endogenous nucleic acid.

Such inhibitory or mutating nucleic acids can be homologous and/or complementary to any of the SEQ ID NO:16, 18, 19, 22, 23, 25, 26, 27, 28, 47-63 and 64 sequences. Such inhibitory or mutating nucleic acids can also have at least 50%, or at least 55%, or at least 60%, or at least 65%, or at least 70%, or at least 75%, or at least 80%, or at least 85%, or at least 90%, or at least 95%, or at least 98% sequence identity or sequence complementarity to any of the SEQ ID NO:16, 18, 19, 22, 23, 25, 26, 27, 28, 47-63 and 64 sequences.

Related Acyltransferases

The nucleic acids described herein also allow identification and isolation of related nucleic acids and their encoded enzymes that can facilitate production of altered lignins in plants. Such nucleic acids can encode or hybridize to BAHD acyltransferases and fragments thereof. In addition, as described herein, inhibitory or mutating nucleic acids can be used to inhibit or destroy the expression of a p-coumaroyl-CoA:monolignol transferase nucleic acid, reduce the amount of p-coumaroyl-CoA:monolignol transferase enzyme translated, and/or mutate an endogenous of p-coumaroyl-CoA:monolignol transferase gene so that an encoded enzyme is not produced or has substantially no activity. The procedures described below can be employed to make an inhibitory or mutating nucleic acid.

For example, related nucleic acids can be isolated and identified by use of the SEQ ID NO:1, 8, 16, 18, 19, 22, 23, 25, 26, 27, 28, 47-63 and 64 nucleic acid sequences and/or by hybridization to DNA and/or RNA isolated from other plant species using the SEQ ID NO:1, 8, 16, 18, 19, 22, 23, 25, 26, 27, 28, 47-63 and 64 nucleic acids as probes. The sequence of the acyltransferase enzyme (e.g., SEQ ID NO:2, 9, 17, 20, 21, 24, 29-45 and/or 46) can also be examined and used a basis for designing alternative acyltransferase nucleic acids.

For example, the sequence of a p-coumaroyl-CoA:monolignol transferase nucleic acid (e.g., SEQ ID NO:16, 18, 19, 22, 23, 25, 26, 27, 28, 47-63 and/or 64) can be examined and used a basis for designing inhibitory or mutating nucleic acids for reducing the expression of p-coumaroyl-CoA:monolignol transferase.

The p-coumaroyl-CoA:monolignol transferase nucleic acids of the invention include any nucleic acid that can selectively hybridize to a nucleic acid with any of SEQ ID NO:16, 18, 19, 22, 23, 25, 26, 27, 28, 47-63 and 64 sequences. In another embodiment, the inhibitory or mutating nucleic acids can also include any nucleic acid that can selectively hybridize to either strand of a nucleic acid with any of the SEQ ID NO:16, 18, 19, 22, 23, 25, 26, 27, 28, 47-63 and 64 sequences. As described herein, the nucleic acid is adapted to encode a feruloyl-CoA:monolignol transferase and/or inhibit a p-coumaroyl-CoA:monolignol transferase nucleic acid.

The feruloyl-CoA:monolignol transferase nucleic acids of the invention include any nucleic acid that can selectively hybridize to a nucleic acid with any of SEQ ID NO:1 or 8.

The term "selectively hybridize" includes hybridization, under stringent hybridization conditions, of a nucleic acid sequence to a specified nucleic acid target sequence (e.g., SEQ ID NO:1, SEQ ID NO:8, SEQ ID NO:16, SEQ ID NO:18, SEQ ID NO:19, SEQ ID NO:22, SEQ ID NO:23, SEQ ID NO:25, SEQ ID NO:26, SEQ ID NO:27, SEQ ID NO:28, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and/or SEQ ID NO:64) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with each other. In some embodiments, a selectively hybridizing sequence has about at least about 50% sequence identity or complementarity with any of SEQ ID NO:1, SEQ ID NO:8, SEQ ID NO:16, SEQ ID NO:18 and/or SEQ ID NO:19.

Thus, for example, the nucleic acids of the invention include those with about 500 of the same nucleotides as any of the SEQ ID NO:16, 18, 19, 22, or 23 sequences, or include about 600 of the same nucleotides as any of the SEQ ID NO:16, 18, 19, 22, or 23 sequences, or about 700 of the same nucleotides as any of the SEQ ID NO:16, 18, 19, 22, or 23 sequences, or about 800 of the same nucleotides as any of the SEQ ID NO:16, 18, 19, 22, or 23 sequences, or about 900 of the same nucleotides as any of the SEQ ID NO:16, 18, 19, 22, or 23 sequences, or about 1000 of the same nucleotides as any of the SEQ ID NO:16, 18, 19, 22, or 23 sequences, or about 1100 of the same nucleotides as any of the SEQ ID NO:16, 18, 19, 22, or 23 sequences, or about 1200 of the same nucleotides as any of the SEQ ID NO:16, 18, 19, 22, or 23 sequences, or about 1300 of the same nucleotides as any of the SEQ ID NO:16, 18, 19, 22, or 23 sequences, or about 500-1325 of the same nucleotides as any of the SEQ ID NO:16, 18, 19, 22, 23, 25, 26, 27, 28, 47-63 and 64 sequences. The identical nucleotides can be distributed throughout the nucleic acid or the encoded protein, and need not be contiguous.

The nucleic acids of the invention include those with about 70 of the same nucleotides as any of the SEQ ID NO:25, 26, 27, 28, 47-63 and 64 sequences, or any with about 60 of the same nucleotides as any of the SEQ ID NO:25, 26, 27, 28, 47-63 and 64 sequences, or any with about 50 of the same nucleotides as any of the SEQ ID NO:25, 26, 27, 28, 47-63 and 64 sequences, or any with about 40 of the same nucleotides as any of the SEQ ID NO:25, 26, 27, 28, 47-63 and 64 sequences, or any with about 30 of the same nucleotides as any of the SEQ ID NO:25, 26, 27, 28, 47-63 and 64 sequences. The identical nucleotides can be distributed throughout the nucleic acid or the encoded protein, and need not be contiguous.

In some embodiments, an inhibitory or mutating the nucleic acid of the invention can include a sequence that is substantially identical or complementary to a nucleic acid with any of the SEQ ID NO:16, 18, 19, 22, 23, 25, 26, 27, 28, 47-63 and 64 sequences. For example, an inhibitory or mutating the nucleic acid of the invention can include those with about 15 of the same (or complementary) nucleotides as any of the SEQ ID NO:16, 18, 19, 22, 23, 25, 26, 27, 28, 47-63 and 64 sequences, or about 16 of the same (or complementary) nucleotides as any of the SEQ ID NO:16, 18, 19, 22, 23, 25, 26, 27, 28, 47-63 and 64 sequences, or about 17 of the same (or complementary) nucleotides as any of the SEQ ID NO:16, 18, 19, 22, 23, 25, 26, 27, 28, 47-63 and 64 sequences, or about 18 of the same (or complementary) nucleotides as any of the SEQ ID NO:16, 18, 19, 22, 23, 25, 26, 27, 28, 47-63 and 64 sequences, or about 19 of the same (or complementary) nucleotides as any of the SEQ ID NO:16, 18, 19, 22, 23, 25, 26, 27, 28, 47-63 and 64 sequences, or about 20 of the same (or complementary) nucleotides as any of the SEQ ID NO:16, 18, 19, 22, 23, 25, 26, 27, 28, 47-63 and 64 sequences, or about 21 of the same (or complementary) nucleotides as any of the SEQ ID NO:16, 18, 19, 22, 23, 25, 26, 27, 28, 47-63 and 64 sequences, or about 22 of the same (or complementary) nucleotides as any of the SEQ ID NO:16, 18, 19, 22, 23, 25, 26, 27, 28, 47-63 and 64 sequences, or about 23 of the same (or complementary) nucleotides as any of the SEQ ID NO:16, 18, 19, 22, 23, 25, 26, 27, 28, 47-63 and 64 sequences, or about 24 of the same (or complementary) nucleotides as any of the SEQ ID NO:16, 18, 19, 22, 23, 25, 26, 27, 28, 47-63 and 64 sequences, or about 25 of the same (or complementary) nucleotides as any of the SEQ ID NO:16, 18, 19, 22, 23, 25, 26, 27, 28, 47-63 and 64 sequences, or about 26 of the same (or complementary) nucleotides as any of the SEQ ID NO:16, 18, 19, 22, 23, 25, 26, 27, 28, 47-63 and 64 sequences, or about 27 of the same (or complementary) nucleotides as any of the SEQ ID NO:16, 18, 19, 22, 23, 25, 26, 27, 28, 47-63 and 64 sequences, or about 28 of the same (or complementary) nucleotides as any of the SEQ ID NO:16, 18, 19, 22, 23, 25, 26, 27, 28, 47-63 and 64 sequences, or about 29 of the same (or complementary) nucleotides as any of the SEQ ID NO:16, 18, 19, 22, 23, 25, 26, 27, 28, 47-63 and 64 sequences, or about 30 of the same (or complementary) nucleotides as any of the SEQ ID NO:16, 18, 19, 22, 23, 25, 26, 27, 28, 47-63 and 64 sequences, or about 31 of the same (or complementary) nucleotides as any of the SEQ ID NO:16, 18, 19, 22, 23, 25, 26, 27, 28, 47-63 and 64 sequences, or about 32 of the same (or complementary) nucleotides as any of the SEQ ID NO:16, 18, 19, 22, 23, 25, 26, 27, 28, 47-63 and 64 sequences, or about 33 of the same (or complementary) nucleotides as any of the SEQ ID NO:16, 18, 19, 22, 23, 25, 26, 27, 28, 47-63 and 64 sequences, or about 34 of the same (or complementary) nucleotides as any of the SEQ ID NO:16, 18, 19, 22, 23, 25, 26, 27, 28, 47-63 and 64 sequences, or about 35 of the same (or complementary) nucleotides as any of the SEQ ID NO:16, 18, 19, 22, 23, 25, 26, 27, 28, 47-63 and 64 sequences, or about 36 of the same (or complementary) nucleotides as any of the SEQ ID NO:16, 18, 19, 22, 23, 25, 26, 27, 28, 47-63 and 64 sequences, or about 37 of the same (or complementary) nucleotides as any of the SEQ ID NO:16, 18, 19, 22, 23, 25, 26, 27, 28, 47-63 and 64 sequences, or about 38 of the same (or complementary) nucleotides as any of the SEQ ID NO:16, 18, 19, 22, 23, 25, 26, 27, 28, 47-63 and 64 sequences, or about 39 of the same (or complementary) nucleotides as any of the SEQ ID NO:16, 18, 19, 22, 23, 25, 26, 27, 28, 47-63 and 64 sequences, or about 40 of the same (or complementary) nucleotides as any of the SEQ ID NO:16, 18, 19, 22, 23, 25, 26, 27, 28, 47-63 and 64 sequences, or about 41 of the same (or complementary) nucleotides as any of the SEQ ID NO:16, 18, 19, 22, 23, 25, 26, 27, 28, 47-63 and 64 sequences, or about 42 of the same (or complementary) nucleotides as any of the SEQ ID NO:16, 18, 19, 22, 23, 25, 26, 27, 28, 47-63 and 64 sequences, or about 43 of the same (or complementary) nucleotides as any of the SEQ ID NO:16, 18, 19, 22, 23, 25, 26, 27, 28, 47-63 and 64 sequences, or about 44 of the same (or complementary) nucleotides as any of the SEQ ID NO:16, 18, 19, 22, 23, 25, 26, 27, 28, 47-63 and 64 sequences, or about 45 of the same (or complementary) nucleotides as any of the SEQ ID NO:16, 18, 19, 22, 23, 25, 26, 27, 28, 47-63 and 64 sequences, or about 15-50 of the same (or complementary) nucleotides as any of the SEQ ID NO:16, 18, 19, 22, 23, 25, 26, 27, 28, 47-63 and 64 sequences.

Note that if a value of a variable that is necessarily an integer, e.g., the number of nucleotides or amino acids in a nucleic acid or protein, is described as a range, e.g., 90-99% sequence identity what is meant is that the value can be any integer between 90 and 99 inclusive, i.e., 90, 91, 92, 93, 94, 95, 96, 97, 98 or 99, or any range between 90 and 99 inclusive, e.g., 91-99%, 91-98%, 92-99%, etc.

In some embodiments, related nucleic acid hybridize to the nucleic acids described herein under "stringent conditions" or "stringent hybridization conditions." In other embodiments, an inhibitory or mutating nucleic acid can hybridize to the nucleic acids described herein under "physiological conditions," "stringent conditions" or "stringent hybridization conditions."

The term "physiological conditions" refers to salt and temperature conditions that are commonly present in a live plant in vivo, for example, in a growing plant or seedling. Inhibitory or mutating nucleic acids can, for example, hybridize to an endogenous nucleic acid (e.g., an mRNA arising from a nucleic acid with any of the SEQ ID NO:16, 18, 19, 22, 23, 25, 26, 27, 28, 47-63 and 64 sequences or a genomic DNA with any of SEQ ID NO:16, 18 or 19 sequences) under plant physiological conditions. In some embodiments, under such plant physiological conditions, the inhibitory or mutating nucleic acids selectively hybridize to a mRNA with any of the SEQ ID NO:16, 18, 19, 22, 23, 25, 26, 27, 28, 47-63 and 64 sequences, but do not significantly hybridize to a SEQ ID NO:1 or a SEQ ID NO:8 mRNA.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences that have up to 100% complementarity to an inhibitory or mutating nucleic acid can hybridize (homologous probing) to a probe for identifying a new inhibitory or mutating nucleic acid. Alternatively, stringency conditions can be adjusted to allow some mismatching in sequences so that lower degrees of sequence similarity are detected (heterologous probing). The probe can be approximately 15-500 nucleotides in length, but can vary greatly in length from about 18 nucleotides to equal to the entire length of the target sequence. In some embodiments, the probe is about 10-50 nucleotides in length, or about 15-50 nucleotides in length, or about 16-45 nucleotides in length, or about 18-25 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984)):

$$T_m = 81.5°\ C. + 16.6(\log M) + 0.41(\%\ GC) - 0.61(\%\ formamide) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$, is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of the SEQ ID NO:16, 18, 19, 22, 23, 25, 26, 27, 28, 47-63 and 64 sequences. Similarly, those of ordinary skill can identify and isolate inhibitory or mutating nucleic acids with sequences that effectively inhibit the expression of a nucleic acid that includes any of the SEQ ID NO:16, 18, 19, 22, 23, 25, 26, 27, 28, 47-63 and 64 sequences.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECU- LAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison (e.g., any of the SEQ ID NO:1, 8, 16, 18, 19, 22, 23, 25, 26, 27, 28, 47-63 and 64 sequences). The reference sequence can be a nucleic acid sequence (e.g., any of the SEQ ID NO:1, 8, 16, 18, 19, 22, 23, 25, 26, 27, 28, 47-63 and 64 sequences) or an amino acid sequence (e.g., any of the SEQ ID NO:2, 9, 17, 20, 21, 24, 29-45 and 46 sequences). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 16 contiguous nucleotides in length, and optionally can be 18, 20, 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63)

and XNU (C.sub.1-ayerie and States, (1993) Comput. Chem. 17:191-201) low-complexity filters can be employed alone or in combination.

The terms "substantial identity" indicates that an inhibitory or mutating nucleic acid, a polypeptide, or a related nucleic acid comprises a sequence with between 55-100% sequence identity to a reference sequence, with at least 55% sequence identity, or at least 60%, or at least 70%, or at least 80%, or at least 90% or at least 95% sequence identity or any percentage of range between 55-100% sequence identity relative to the reference sequence over a specified comparison window. Optimal alignment may be ascertained or conducted using the homology alignment algorithm of Needleman and Wunsch, supra.

An indication that two polypeptide sequences are substantially identical is that both polypeptides have p-coumaroyl-CoA:monolignol transferase activity, meaning that both polypeptides can synthesize monolignol p-coumarates from a monolignol and p-coumaroyl-CoA. The polypeptide that is substantially identical to a p-coumaroyl-CoA:monolignol transferase including one or more of the SEQ ID NO:17, 24, 29-45 or 46 sequences may not have exactly the same level of activity as the p-coumaroyl-CoA:monolignol transferase that includes the SEQ ID NO:17, 24, 29-45 or 46 sequence. Instead, the substantially identical polypeptide may exhibit greater or lesser levels of p-coumaroyl-CoA:monolignol transferase activity than the p-coumaroyl-CoA:monolignol transferase that includes the SEQ ID NO:17, 24, 29-45 or 46 sequence, as measured by assays available in the art or described herein (see, e.g., Examples). For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the p-coumaroyl-CoA:monolignol transferase that includes the SEQ ID NO:17, 24, 29-45 or 46 sequence when measured by similar assay procedures.

Alternatively, substantial identity is present when second polypeptide is immunologically reactive with antibodies raised against the first polypeptide (e.g., a polypeptide with the SEQ ID NO:17, 24, 29-45 or 46 sequence). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The p-coumaroyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of the SEQ ID NO:17, 24, 29-45 or 46 sequence sequence. Alternatively, the p-coumaroyl-CoA:monolignol transferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of the SEQ ID NO:17, 24, 29-45 or 46 sequence. Thep-coumaroyl-CoA:monolignol transferase polypeptides of the present invention may include 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, and 125 amino acid residues flanking the SEQ ID NO:29-45 or 46 sequence.

Lignin

Lignin broadly refers to a biopolymer that is typically part of secondary cell walls in plants. Lignin is a complex moderately cross-linked aromatic polymer (see, e.g., FIG. 1). Lignin may also be covalently linked to hemicelluloses. Hemicellulose broadly refers to a class of branched sugar polymers composed of pentoses and hexoses. Hemicelluloses typically have an amorphous structure with up to hundreds or thousands of pentose units and they are generally at least partially soluble in dilute alkali. Cellulose broadly refers to an organic compound with the formula $(C_6H_{10}O_5)_z$ where z is an integer. Cellulose is a linear polysaccharide that can include linear chains of beta-1-4-linked glucose residues of several hundred to over ten thousand units.

Lignocellulosic biomass represents an abundant, inexpensive, and locally available feedstock for conversion to carbonaceous fuel (e.g., ethanol, biodiesel, biofuel and the like). However, the complex structure of lignin, which includes ether and carbon-carbon bonds that bind together the various subunits of lignin, and the crosslinking of lignin to other plant cell wall polymers, make it the most recalcitrant of plant polymers. Thus, significant quantities of lignin in a biomass can inhibit the efficient usage of plants as a source of fuels and other commercial products. Gaining access to the carbohydrate and polysaccharide polymers of plant cells for use as carbon and energy sources therefore requires significant energy input and often harsh chemical treatments, especially when significant amounts of lignin are present. For example, papermaking procedures in which lignin is removed from plant fibers by delignification reactions are typically expensive, can be polluting and generally require use of high temperatures and harsh chemicals largely because the structure of lignin is impervious to mild conditions. Plants with altered lignin structures that could be more readily cleaved under milder conditions would reduce the costs of papermaking and make the production of biofuels more competitive with currently existing procedures for producing oil and gas fuels.

Plants make lignin from a variety of subunits or monomers that are generally termed monolignols. Such primary monolignols include p-coumaryl alcohol, coniferyl alcohol, and sinapyl alcohol.

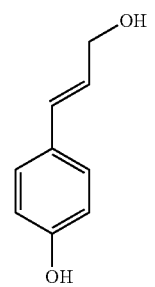

p-coumaryl alcohol

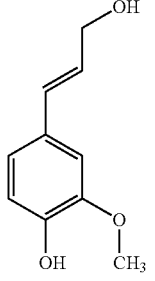

coniferyl alcohol

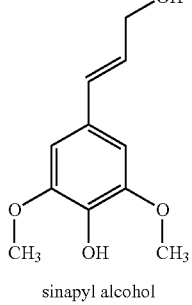

sinapyl alcohol

Monolignols destined for lignin polymerization in normal plants can be preacylated with acetate, p-hydroxybenzoate, or p-coumarate (Ralph et al., *Phytochem. Rev.* 3:29-60 (2004)). p-Coumarates acylate the γ-position of phenylpropanoid side chains mainly found in the syringyl units of lignin. Studies indicate that monolignols, primarily sinapyl alcohol, are enzymatically pre-acylated with p-coumarate prior to their incorporation into lignin, indicating that the monolignol p-coumarate conjugates, coniferyl p-coumarate and sinapyl p-coumarate, can also be 'monomer' precursors of lignin.

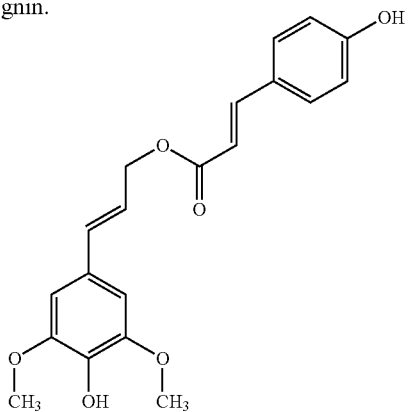

sinapyl p-coumarate

While monolignol p-coumarate-derived units may comprise up to 40% of the lignin in some grass tissues, the p-coumarate moiety from such conjugates does not enter into the radical coupling (polymerization) reactions occurring during lignifications. Instead, the p-coumarate moieties substantially remain as terminal units with an unsaturated side chain and a free phenolic group (Ralph et al., *J. Am. Chem. Soc.* 116: 9448-9456 (1994); Hatfield et al., *J. Sci. Food Agric.* 79: 891-899 (1999)). Thus, the presence of sinapyl p-coumarate conjugates produces a lignin 'core' with terminal p-coumarate groups and no new bonds in the backbone of the lignin polymer, resulting in a lignin that is not significantly more easily cleaved.

In contrast to p-coumarate, ferulate esters do undergo radical coupling reactions under lignification conditions. Model ferulates, such as the ferulate shown below (where R is $CH_3$—, $CH_3$—$CH_2$—, a sugar, a polysaccharide, pectin, cell-wall (arabino)xylan or other plant component), readily undergo radical coupling reactions with each other and with lignin monomers and oligomers to form cross-linked networks.

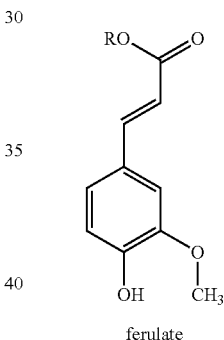

ferulate

If present during lignification, ferulates can become bound into the lignin by ether, ester and C—C bonds. Although such ferulate moieties are no more extractable or cleavable from the lignin structure than other lignin units, the ester itself can be readily cleaved. Upon cleavage of such ester bonds, other plant cell wall components can be released. For example, an arabinoxylan (hemicellulose) chain can be released from a ferulate-mediated lignin attachment by cleaving the ester.

Ferulate-monolignol ester conjugates (unlike their p-coumarate analogs), such as coniferyl ferulate or sinapyl ferulate have not been identified in natural plant lignins, but some types of plants make them as secondary metabolites during, among other things, lignin biosynthesis. [Paula et al, *Tetrahedron* 51: 12453-12462 (1994); Seca et al., *Phytochemistry* 56: 759-767 (2001); Hsiao & Chiang, *Phytochemistry* 39: 899-902 (1995); Li et al., *Planta Med.* 72: 278-280 (2005)]. The structures of coniferyl ferulate and sinapyl ferulate are shown below.

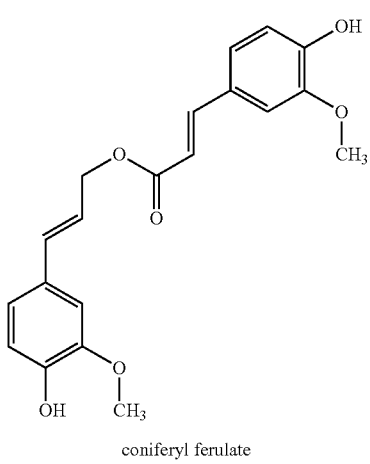

coniferyl ferulate

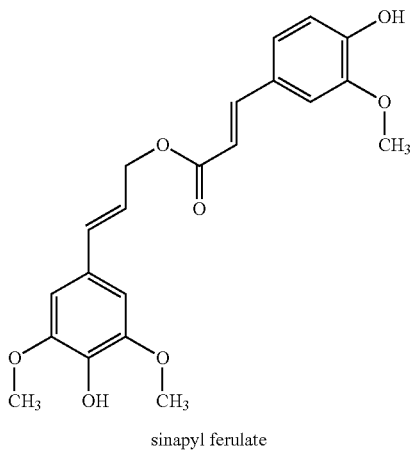

sinapyl ferulate

For example, the feruloyl-CoA:monolignol transferases described herein biosynthesize coniferyl ferulate from coniferyl alcohol and feruloyl-CoA as shown below.

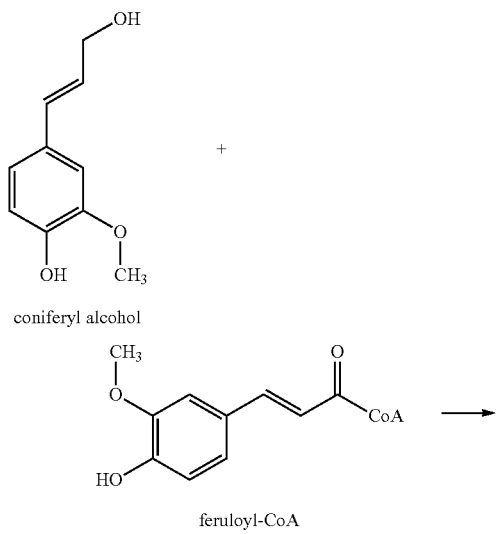

coniferyl alcohol feruloyl-CoA

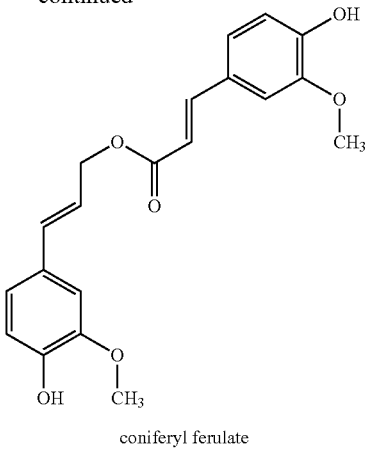

coniferyl ferulate

The incorporation of monolignol ferulates into the lignin of plants allows the cell wall materials and lignin to be readily cleaved or processed into useful products. See also, U.S. Patent Application No. 61/213,706, the contents of which are specifically incorporated herein by reference in their entirety.

The monolignol ferulates made by the methods and feruloyl-CoA:monolignol transferases described herein can be incorporated by radical coupling into plant lignins. Both the monolignol and the ferulate moieties can undergo such coupling, resulting in a lignin that can be complex. However, such 'double-ended-incorporation' still yields readily cleavable ester linkages that have been engineered into the backbone of the lignin polymer network. Esters are readily cleaved under much less stringent conditions by the same chemical processes used to cleave lignin, but the lignin resulting from the methods described herein is significantly easier to cleave, and provides more facile and less costly access to the plant cell wall polysaccharides. See also, "Method for modifying lignin structure using monolignol ferulate conjugates", U.S. Patent Application No. 61/213,706.

Lignins can be degraded by chemical or enzymatic means to yield a variety of smaller monomers and oligomers. While enzymatic processes are generally preferred because they do not require high temperatures and harsh chemicals, such enzymatic processes have previously not been as effective at solubilizing lignin moieties away from valuable plant cell constituents (e.g., polysaccharides and carbohydrates).

According to the invention, plants with the feruloyl-CoA: monolignol transferase nucleic acids and/or enzymes described herein supply monolignol ferulates for facile lignification in plants, thereby yielding plants with lignins that are more readily cleaved or processed to release cellulose, hemicelluloses and lignin breakdown products.

Conditions for releasing the cellulose, hemicelluloses and lignin breakdown products from plants containing the feruloyl-CoA:monolignol transferase nucleic acids and/or enzymes described herein include conditions typically employed for cleaving ester bonds. Thus, the ester bonds within monolignol ferulate-rich lignins can be cleaved by milder alkaline and/or acidic conditions than the conditions typically used to break down the lignin of plants that are not rich in monolignol ferulates. For example, mildly alkaline conditions involving use of ammonia may be used to cleave the ester bonds within monolignol ferulate-rich lignins, whereas such conditions would not cleave substantially any of the ether and carbon-carbon bonds in normal lignins. See also, U.S. patent application Ser. No. 12/830,905, filed Jul. 6, 2010 and to U.S. Patent Application Ser. No. 61/213,706, filed Jul. 6, 2009, the contents of both of which are specifically incorporated herein by reference in their entireties.

Transgenic Plants

In order to engineer plants with lignins that contain significant levels of monolignol ferulates, one of skill in the art can introduce inhibitory or mutating nucleic acids that reduce the expression and/or translation of p-coumaroyl-CoA:monolignol transferase. Those of skill in the art can also introduce feruloyl-CoA:monolignol transferases or nucleic acids encoding such feruloyl-CoA:monolignol transferases into the plants.

For example, one of skill in the art can inject PMT inhibitory or mutating nucleic acids, and/or inject feruloyl-CoA:monolignol transferase enzymes into young plants or into plants cells.

Alternatively, one of skill in the art can generate genetically-modified plants that contain mutant (knockout) PMT or inhibitory PMT nucleic acids, as well as nucleic acids encoding feruloyl-CoA:monolignol transferases within their somatic and/or germ cells. Such genetic modification can be accomplished by procedures available in the art. For example, one of skill in the art can prepare an expression cassette or expression vector that can express one or more PMT inhibitory/mutating nucleic acids and/or one or more encoded feruloyl-CoA:monolignol transferase enzymes. Plant cells can be transformed by the expression cassette or expression vector, and whole plants (and their seeds) can be generated from the plant cells that were successfully transformed with the PMT inhibitory/mutating nucleic acids and/or with the feruloyl-CoA:monolignol transferase nucleic acids. Some procedures for making such genetically modified plants and their seeds are described below.

Promoters: The PMT inhibitory/mutating nucleic acids and/or the feruloyl-CoA:monolignol transferase nucleic acids can be operably linked to a promoter, which provides for expression of an inhibitory PMT RNA, a mutant PMT RNA and/or a functional mRNA from the feruloyl-CoA:monolignol transferase nucleic acids. The promoter is typically a promoter functional in plants and/or seeds, and can be a promoter functional during plant growth and development. A PMT inhibitory/mutating nucleic acid and/or a feruloyl-CoA:monolignol transferase nucleic acid is operably linked to the promoter when it is located downstream from the promoter, to thereby form an expression cassette. The PMT inhibitory/mutating nucleic acids can be separately regulated from the feruloyl-CoA:monolignol transferase nucleic acids by use of separate promoters and/or separate expression cassettes.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but are not limited to, a plant promoter such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Other promoters useful in the practice of the invention are known to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A PMT inhibitory/mutating nucleic acid and/or a feruloyl-CoA:monolignol transferase nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed, for example, as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The PMT inhibitory/mutating nucleic acid and/or feruloyl-CoA:monolignol transferase nucleic acids can be subcloned downstream from the promoter using restriction enzymes and positioned to ensure that the DNA is inserted in proper orientation with respect to the promoter so that the DNA can be expressed as sense or antisense RNA. Once the PMT inhibitory/mutating nucleic acid and/or feruloyl-CoA:monolignol transferase nucleic acid is operably linked to a promoter, the expression cassette so formed can be subcloned into a plasmid or other vector (e.g., an expression vector).

In some embodiments, a cDNA clone encoding a feruloyl-CoA:monolignol transferase protein is employed that has been isolated from *Angelica sinensis* root tissue or from *Hibiscus cannabinus* (Kenaf) stem sections. In other embodiments, cDNA clones from other species that encode a feruloyl-CoA:monolignol transferase protein are isolated from selected plant tissues, or a nucleic acid encoding a mutant or modified feruloyl-CoA:monolignol transferase protein is prepared by available methods or as described herein. For example, the nucleic acid encoding a mutant or modified feruloyl-CoA:monolignol transferase protein can be any nucleic acid with a coding region that hybridizes, for example, to SEQ ID NO: 1 or SEQ ID NO:8 and that has feruloyl-CoA:monolignol transferase activity.

Using restriction endonucleases, the PMT inhibitory/mutating nucleic acid and/or the entire coding sequence for the feruloyl-CoA:monolignol transferase can be subcloned downstream of the promoter in a 5' to 3' sense orientation.

Targeting Sequences: Additionally, expression cassettes can be constructed and employed to target the PMT inhibitory nucleic acids and/or feruloyl-CoA:monolignol transferase nucleic acids to an intracellular compartment within plant cells or to direct an encoded protein to the extracellular environment. This can generally be achieved by joining a DNA sequence encoding a transit or signal peptide sequence to the coding sequence of the PMT inhibitory nucleic acid and/or feruloyl-CoA:monolignol transferase nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

In general, PMT mutating nucleic acids are directed to the nucleus of a plant cell.

3' Sequences: When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the PMT inhibitory nucleic acids and/or feruloyl-CoA:monolignol transferase nucleic acids by standard methods.

Selectable and Screenable Marker Sequences: In order to improve identification of transformants, a selectable or screenable marker gene can be employed with the PMT inhibitory/mutating nucleic acids and/or the feruloyl-CoA:monolignol transferase nucleic acids. For example, a mutating nucleic acid can include the coding region of a marker gene as its non-PMT segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, P1. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. In some embodiments, any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)). This binary Ti vector can be replicated in prokaryotic bacteria such as *E. coli* and *Agrobacterium.* The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes: Once the expression cassette is constructed and subcloned into a suitable plasmid, it can be screened for the ability to express the encoded feruloyl-CoA:monolignol transferases and/or to substantially reduce or inhibit the expression or translation of a mRNA coding the p-coumaroyl-CoA:monolignol transferase by standard methods. For example, for hybrid selection or arrested translation of p-coumaroyl-CoA:monolignol transferase mRNA, a preselected inhibitory nucleic acid sequence can be subcloned into a selected expression cassette or vector (e.g., a SP6/T7 containing plasmid, which is supplied by ProMega Corp.). For transformation of plants cells, suitable vectors include plasmids such as described herein. Typically, hybrid arrest translation is an in vitro assay that measures the inhibition of translation of an mRNA encoding the p-coumaroyl-CoA:monolignol transferase. This screening method can also be used to select and identify more effective PMT inhibitory nucleic acid. A nonsense nucleic acid can be expressed from an expression cassette that is introduced into plants or plants cells as a control. The phenotypes of the control and test cells or plants can also be assessed.

DNA Delivery of the DNA Molecules into Host Cells: The present invention generally includes steps directed to introducing a PMT inhibitory/mutating nucleic acid and/or feruloyl-CoA:monolignol transferase nucleic acids into a recipient cell to create a transformed cell. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant species with lignin containing monolignol ferulates (e.g., coniferyl ferulate), wherein the plant has an endogenous PMT knockout and/or has an introduced PMT inhibitory nucleic acid and/or an introduced feruloyl-CoA:monolignol transferase nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include wheat, rice, *Arabidopsis*, tobacco, maize, soybean, and the like. In some embodiments, the plant or cell is a monocotyledon plant or cell. For example, the plant or cell can be a grass (e.g., maize) plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium.* Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as grasses can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the PMT mutating or inhibitory nucleic acid(s), and/or the feruloyl-CoA:monolignol transferase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic Black Mexican Sweet (BMS) cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize: After effecting delivery of the PMT mutating nucleic acids, PMT inhibitory nucleic acid(s) and/or the feruloyl-CoA:monolignol transferase nucleic acid(s) to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the PMT mutating/inhibitory nucleic acid(s) and/or the feruloyl-CoA:monolignol transferase nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the feruloyl-CoA:monolignol transferase nucleic acids and/or the mutant (e.g. knockout) endogenous PMT gene into the genome of inbred plants. In some embodiments, regenerated plants can also be crossed with inbred plants to introgress the PMT knockout or PMT inhibitory nucleic acid(s) into the genome of the plants. This process is referred to as backcross conversion. When a sufficient number of crosses to the recurrent inbred parent have been completed in order to produce a product of the backcross conversion process that is substantially isogenic with the recurrent inbred parent except for the presence of the introduced PMT knockout or PMT inhibitory nucleic acid(s) and/or feruloyl-CoA:monolignol transferase nucleic acids, the plant is self-pollinated at least once in order to produce a homozygous backcross converted inbred containing the PMT knockout or PMT inhibitory nucleic acid(s) and/or feruloyl-CoA:monolignol transferase nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the feruloyl-CoA: monolignol transferase nucleic acids (or the feruloyl-CoA: monolignol transferase enzyme). Seed from the fertile transgenic plants can then be evaluated for the presence and/or expression of the PMT knockout mutation or the PMT inhibitory nucleic acid(s). Transgenic plant and/or seed tissue can be analyzed for the PMT knockout mutation or the PMT inhibitory nucleic acid(s) and/or feruloyl-CoA:monolignol transferase expression using standard methods such as SDS polyacrylamide gel electrophoresis, liquid chromatography (e.g., HPLC) or other means of detecting a product of feruloyl-CoA:monolignol transferase activity (e.g., coniferyl ferulate).

Once a transgenic seed containing the PMT knockout mutation or the PMT inhibitory nucleic acid(s) and/or feruloyl-CoA:monolignol transferase nucleic acid(s), and having an increase in monolignol ferulates in the lignin of the plant is identified, the seed can be used to develop true breeding plants. The true breeding plants are used to develop a line of plants with an increase in the percent of monolignol ferulates in the lignin of the plant while still maintaining other desirable functional agronomic traits. Adding the trait of increased monolignol ferulate production in the lignin of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of monolignol ferulates in the lignin of the plant. The resulting progeny are then crossed back to the parent that expresses the increased monolignol ferulate trait. The progeny from this cross will also segregate so that some of the progeny carry the trait and some do not. This back-crossing is repeated until an inbred line with the desirable functional agronomic traits, and with expression of the trait involving an increase in monolignol ferulates (e.g., coniferyl ferulate) within the lignin of the plant. Such expression of the increased percentage of monolignol ferulates in plant lignin can be expressed in a dominant fashion.

Subsequent to back-crossing, the new transgenic plants can be evaluated for an increase in the weight percent of monolignol ferulates incorporated into the lignin of the plant. This can be done, for example, by NMR analysis of whole plant cell walls (Kim, H., and Ralph, J. Solution-state 2D NMR of ball-milled plant cell wall gels in DMSO-$d_6$/pyridine-$d_5$. (2010) *Org. Biomol. Chem.* 8(3), 576-591; Yelle, D. J., Ralph, J., and Frihart, C. R. Characterization of non-derivatized plant cell walls using high-resolution solution-state NMR spectroscopy. (2008) *Magn. Reson. Chem.* 46(6), 508-517; Kim, H., Ralph, J., and Akiyama, T. Solution-state 2D NMR of Ball-milled Plant Cell Wall Gels in DMSO-$d_6$. (2008) *BioEnergy Research* 1(1), 56-66; Lu, F., and Ralph, J. Non-degradative dissolution and acetylation of ball-milled plant cell walls; high-resolution solution-state NMR. (2003) *Plant J.* 35(4), 535-544). The new transgenic plants can also be evaluated for a battery of functional agronomic characteristics such as lodging, kernel hardness, yield, resistance to disease, resistance to insect pests, drought resistance, and/or herbicide resistance.

Plants that may be improved by these methods include but are not limited to grass species, oil and/or starch plants (canola, potatoes, lupins, sunflower and cottonseed), forage plants (alfalfa, clover and fescue), grains (maize, wheat, barley, oats, rice, *sorghum*, millet and rye), grasses (switchgrass, prairie grass, wheat grass, sudangrass, *sorghum*, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues: To confirm the presence of the PMT knockout mutation or the PMT inhibitory nucleic acid(s) and/or the feruloyl-CoA:monolignol transferase nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from the PMT knockout mutant gene or the introduced PMT inhibitory nucleic acid(s) and/or the introduced feruloyl-CoA:monolignol transferase nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the PMT knockout mutation or the PMT inhibitory nucleic acid(s) and/or the feruloyl-CoA:monolignol transferase nucleic acid in question, they do not provide information as to whether the preselected DNA segment is being expressed. Expression may be evaluated by specifically identifying the protein products of the introduced feruloyl-CoA:monolignol transferase nucleic acids, by assessing the level of p-coumaroyl-CoA:monolignol transferase mRNA and/or enzyme expressed, or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the feruloyl-CoA:monolignol transferase such as evaluation by amino acid sequencing following purification. The Examples of this application also provide assay procedures for detecting and quantifying the PMT inhibitory nucleic acid, the mutant p-coumaroyl-CoA:monolignol transferase and/or feruloyl-CoA:monolignol transferase activity.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Kits

Any of the nucleic acids or polypeptides described herein may be comprised in a kit. In some embodiments, the kits can include a container that includes a nucleic acid, or a mixture of nucleic acids. Such a nucleic acid or mixture of nucleic acids can be used, for example, to transform plant cells and/or generate transgenic plants. In some embodiments, the nucleic acid(s) can encode a feruloyl-CoA:monolignol transferase. In another example, the kits can include a container that includes an PMT mutating nucleic acid for introducing one or more mutations into an endogenous PMT gene. In another example, the kits can include a container that includes an inhibitory nucleic acid, or a mixture of inhibitory nucleic acids. Such inhibitory nucleic acids can be used, for example, to inhibit the expression of p-coumaroyl-CoA:monolignol transferases.

The kits can also include more than one container. For example, the kits can include two or more containers, where one container includes a feruloyl-CoA:monolignol transferase nucleic acid, and another container includes an inhibitory nucleic acid that inhibits the expression of p-coumaroyl-CoA:monolignol transferases.

In some embodiments, reagents for generating or assembling an inhibitory nucleic acid (e.g., siRNA) cocktail or candidate siRNA molecules can be included in a kit. The kit may further include individual siRNAs that can be mixed to create a siRNA cocktail or individual DNA constructs that can be mixed and transfected or transduced into cells wherein they express a cocktail of siRNAs. The kit may also include multiple DNA templates encoding siRNAs to multiple sites on one or more genes that when transcribed create an siRNA cocktail. The kit may also comprise reagents for creating or synthesizing the dsRNA and a polypeptide with RNAse III activity that can be used in combination to create siRNA cocktails.

The kits can also include one or more buffers, such as a nuclease buffer, transcription buffer, or a hybridization buffer, compounds for preparing the DNA template or the dsRNA, and components for isolating the resultant template, dsRNA, or siRNA.

The components of the kits may be packaged either in aqueous media or in lyophilized form. The containers can be vials, test tubes, flasks, bottles, syringes or other container means, into which a component may be placed, and preferably, suitably aliquoted.

Where there is more than one component in the kit, the kit also will generally contain a second, third or other additional container into which the additional components may be separately placed. However, various combinations of components may also be included in one container. The kits of the present invention also will typically include a means for containing the nucleic acids, and any other reagent containers in close confinement for commercial sale. Such containers may include injection or blow-molded plastic packages into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

In some embodiments, nucleic acids are provided in dried form or suspended in an appropriate buffer or solvent. It is contemplated that 0.1, 1, 5, 10, 20, 30, 40, 50, 60, 70, 80, 90, 100, 120, 120, 130, 140, 150, 160, 170, 180, 190, 200, 300, 400, 500, 600, 700, 800, 900, 1000 mg or nucleic acid can be provided in kits of the invention. The PMT mutating nucleic acids and/or PMT inhibitory nucleic acids are typically provided in a separate container from the FMT encoding nucleic acids.

The kits of the present invention will also typically include a means for containing the vials in close confinement for commercial sale, such as, e.g., injection and/or blow-molded plastic containers into which the desired vials are retained.

Such kits may also include components that preserve or maintain the nucleic acids or that protect against their degradation. Such components may be RNAse-free or protect against RNAses, such as RNase inhibitors. Such kits generally will comprise, in suitable means, distinct containers for each individual reagent or solution.

A kit will also include instructions for employing the kit components as well the use of any other reagent not included in the kit. Instructions may include variations that can be implemented.

Definitions

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, a "native" nucleic acid or polypeptide means a DNA, RNA or amino acid sequence or segment that has not been manipulated in vitro, i.e., has not been isolated, purified, and/or amplified.

As used herein, "recessive gene disruption" refers to mutating an endogenous target p-coumarate monolignol transferase (PMT) gene sequence to eliminate either expression or function. Methods for mutating a target sequence are known in the art, and include, without limitation, the generation of mutations via chemical or radiation damage followed by isolation of the mutant. In addition, available molecular biology approaches for decreasing the expression of a functional phenotype may be used, and include without limitation, various knockout or knockdown methods. These methods capitalize upon knowledge of sequence either in the gene of interest or in the DNA sequence flanking the gene. Such sequences are then examined to find suitable sequences that can be targeted to accomplish either excision of the target gene or fragments of the gene. Thus, an endogenous p-coumarate monolignol transferase (PMT) expression in tissue of any of the disclosed transgenic plants is inhibited by a recessive gene disruption selected from a mutant p-coumarate monolignol transferase (PMT) gene that eliminates endogenous p-coumarate monolignol transferase (PMT) expression, an endogenous p-coumarate monolignol transferase (PMT) knockout mutant, and an endogenous p-coumarate monolignol transferase (PMT) knockdown mutant.

As used herein, "dominant gene silencing" refers to inducing or destroying/inhibiting the mRNA transcript of the gene, a means which provides the benefit of being done in a spatial or temporal manner by the selection of specific promoters. Of the dominant gene silencing approaches, dsRNA-triggered RNAi is one of the most powerful and the most efficient at gene silencing, and allows one to enhance or capitalize upon a natural regulatory mechanism which destroys intact mRNA by providing an antisense oligonucleotide that is specific for an endogenous p-coumarate monolignol transferase (PMT) gene (For review, see, Behlke, 2006, Molecular Therapy 13(4): 644-670; see also, Tang and Galili, 2004, Trends Biotechnology 22:463-; Rajewsky and Socci, 2004, Developmental Biology 267:529-535; Hamilton et al., 2002, EMBO J. 21:4671-4679J). In one embodiment, a construct comprising a suitable RNAi sequence under the control of a promoter is introduced into the plant in order to silence p-coumarate monolignol transferase (PMT) protein expression. Accordingly, in certain embodiments, the endogenous p-coumarate monolignol transferase (PMT) expression of any of the disclosed transgenic plants is inhibited by an RNAi antisense oligonucleotide that is specific for an endogenous p-coumarate monolignol transferase (PMT) gene.

The following non-limiting Examples illustrate how aspects of the invention have been developed and can be made and used.

EXAMPLE 1

Materials and Methods

This Example illustrates some methods that can be employed to make and use the invention.

*Angelica sinensis* Tissue Collection and Total RNA Extraction

One- and two-year-old field grown *Angelica sinensis* plants (Mountain Gardens Herbs), were transplanted into Readi-Earth and grown for two months in a greenhouse to recover. The single root of a two-year plant was harvested, cut into small pieces, and ground in liquid nitrogen to a fine powder. Total RNA was extracted by adding 100 mg of powdered *Angelica sinensis* root tissue to 1 ml Trizol buffer (Invitrogen) and incubating for 15 minutes while vortexing at room temperature. One-fifth volume of chloroform was added and incubated for an additional 15 minutes. After centrifugation at 15000×g for 35 minutes at 4° C., the aqueous phase was extracted with ⅕volume of chloroform. Total RNA was precipitated from the aqueous phase by adding ⅕volume of a solution containing 1 M sodium chloride and 0.8 M sodium citrate and ⅕volume of isopropyl alcohol. The RNA was collected by centrifugation at 12,000×g and the pellet was washed in 70% ethanol, dried and dissolved in RNase-free water. Residual DNA was removed by DNase digestion using the RNase-free DNase Kit (Qiagen), following manufacturer's guidelines. RNA quality was assessed using an Agilent 2100 Bioanalyzer.
Library Quality cDNA Synthesis and 454 Sequencing A cDNA library was constructed from *Angelica sinensis* root RNA using the Creator SMART cDNA Library Construction Kit (Clontech). First-strand cDNA was synthesized by combining 1 μg of RNA with 10 pM SMART IV Oligo, 10 pM of modified CDS III/3' cDNA synthesis primer 5'-TAG AGG CCG AGG CGG CCG ACA TGT TTT GTT TTT TTT TCT TTT TTT TTT VN-3' (SEQ ID NO:3) with PAGE purification (Integrated DNA Technologies), and deionized water to a final volume of 5 μL and incubated at 72° C. for 2 minutes. Samples were cooled on ice for 2 minutes and a solution of 2 μL 5× First Strand Buffer, 20 nM dithiothreitol (Creator SMART cDNA Library Construction Kit, Clontech), 10 nM dNTP mix and 200 units SuperScript II Reverse Transcriptase (Invitrogen) was added to each reaction tube. Samples were incubated at 42° C. for 1 hour, and then placed on ice to terminate first strand cDNA synthesis.

Double stranded cDNA was amplified from first strand cDNA synthesis reactions by combining 2 μL of first strand cDNA, 10 μL 10× Advantage 2 PCR Buffer (Advantage 2 Polymerase Mix, Clontech), 20 nM dNTP mix (Invitrogen), 20 pM 5' PCR Primer (Creater SMART cDNA Library Construction Kit, Clontech), 20 pM Modified CDS III/3' PCR Primer (IDT, see sequence above), 2 μL 50× Advantage 2 Polymerase Mix (Clontech), and deionized water to a final volume of 100 μL. This reaction was placed in a thermal cycler, preheated to 95° C., and cycled 24 times (95° C. for 1.25 minutes and 68° C. for 6 minutes). A 5 μL aliquot of each double stranded cDNA reaction was analyzed by gel electrophoresis. The cDNA was subjected to Proteinase K digestion by adding 40 μg of Proteinase K with incubation at 45° C. for 20 minutes. A solution of 50% phenol and 50% chloroform was used to extract proteins from each cDNA sample followed by two chloroform extraction. The double stranded cDNA was pooled from all reactions and precipitated by adding 1/10 volume of 3 M sodium acetate pH 4.8, 20 μg glycogen, and 2.5 volumes ethanol at room temperature. After centrifugation at 15000×g, the cDNA pellet was washed with 80% ethanol, dried and dissolved in 79 μL deionized water. The double stranded cDNA was digested with SfiI to remove concatenated primers and size fractionated using Chroma Spin+TE-1000 Columns (Clontech) to remove short fragments. Fractions were analyzed by agarose gel electrophoresis and the fractions with sizes above 500 base pairs were pooled. cDNA was submitted to the Genomics Core at Michigan State University for Roche 454 sequencing using the 454 GSFLX Titanium Sequencer.
Amplification and Cloning of Feruloyl-CoA:Monolignol Transferase (FMT)

cDNA was synthesized from the *Angelica sinensis* root total RNA, using Superscript III Reverse Transcriptase (Invitrogen). After DNase digestion, 5 μg of total RNA was added to 0.5 μg Oligo d(T)$_{12-18}$, 10 nM dNTP mix (Invitrogen) and DEPC water to a volume of 13 μL. The reaction mixture was incubated at 65° C. for 5 minutes. After cooling the sample on ice for 2 minutes, 4 μL of 5× First-strand Buffer, 100 nM DTT, 40 units RNase OUT and 200 units Superscript III Reverse Transcriptase (Invitrogen) were added and incubated at 50° C. for 60 minutes. The reaction was inactivated by heating to 70° C. for 15 minutes and stored on ice. The FMT coding sequence was amplified using 5'-AAA AAA GCA GGC TTC ATG ACG ATC ATG GAG GTT CAA GTT-3' (SEQ ID NO:4) and 5'-GTA CAA GAA AGC TGG GTT CTA GGA AGC GAA AGC AGA GAT-3' (SEQ ID NO:5) oligonucleotides (Integrated DNA Technologies) as forward and reverse gene specific primers with partial Gateway attB1 and attB2 attachment sites. Using the Platinum Pfx DNA Polymerase kit (Invitrogen), 2 μL 10× Pfx Amplification Buffer, 7.5 nM dNTP mix, 25 nM magnesium sulfate, 10 mM of each primer, 2.5 units of Plantinum Pfx DNA Polymerase and deionized water to a final volume of 20 μL was added to 200 ng cDNA. The sample was denatured at 94° C. for 4 minutes, followed by 25 cycles of 94° C. for 30 seconds, 55° C. for 30 seconds, and 68° C. for 1 minute 45 seconds. After a cooling the sample to 4° C., a second PCR reaction was completed, as described above, using 5'-GGGG ACA AGT TTG TAC AAA AAA GCA GGC T-3' (SEQ ID NO:6) and 5'-GGG AC CAC TTT GTA CAA GAA AGC TGG GT-3' (SEQ ID NO:7) oligonucleotides (Integrated DNA Technologies) as forward and reverse primers and 2.5 µL of the first PCR reaction to add full length Gateway attB1 and attB2 attachment sites to the coding sequence. After amplification, the reaction was analyzed by electrophoresis on a 0.8% agarose gel and the PCR product was purified using the QIAquick Gel Extraction Kit (Qiagen), following manufacturer's guidelines.

The amplified FMT coding sequence was cloned into the Gateway entry vector pDONR221 (Invitrogen) using the BP Clonase II Enzyme Mix (Invitrogen). After purification, 150 ng of PCR product was added to 150 ng of pDONR221 entry vector, to a final volume of 4 µL with TE buffer, and 1 µL BP Clonase II Enzyme Mix. The reaction was incubated overnight at room temperature, inactivated by adding 1 µg Proteinase K and incubating at 37° C. for 10 minutes. After cooling on ice, 2.5 µL of the reaction was used to transform One Shot Top 10 Chemically Competent E. coli Cells (Invitrogen) according to manufacturer's guidelines. The transformants were grown at 37° C. overnight on LB agar plates containing and 50 µg/ml Kanamycin. Single colonies were picked and grown in LB media containing 50 µg/ml Kanamycin overnight at 37° C. Plasmid DNA was purified from these cultures using the QIAprep Spin Miniprep Kit (Qiagen), according to manufacturer's guidelines. Samples were submitted for high throughput sequencing, using the M13 forward and M13 reverse primers (Invitrogen) at the Michigan State University Genomics Core, and compared to the 454 sequencing data to verify coding sequence using DNASTAR Lasergene 8 software.

Sequences in entry vectors were inserted into pDEST17 vector using 150 ng of plasmid DNA from the entry clone, 150 ng of pDEST17 vector and 1 µL LR Clonase II Enzyme Mix. The reaction was incubated overnight at room temperature. Transformation of competent cells was completed as described above. Transformants were selected on LB agar plates containing 100 µg/ml Ampicillin. Clones were screened by PCR using Gotaq Hot Start Green Master Mix (Promega) by adding 10 µL of the 2× master mix to 10 mM of each gene specific primer, deionized water to final volume of 20 µL. This PCR reaction was denatured at 94° C. for 3 minutes then cycled 25 times through 94° C. for 30 seconds, 55° C. for 30 seconds, 72° C. for 1 minute 45 seconds, with a final elongation step at 72° C. for 5 minutes before cooling to 4° C. Each reaction was analyzed by gel electrophoresis. Clones were then transformed into One Shot BL21 Chemically Competent E. coli Cells (Invitrogen), according to manufacturer's guidelines, for expression.

Expression of Feruloyl-CoA:Monolignol Transferase (FMT) in E. coli

Cultures of BL21 E. coli containing FMT nucleic acids in the expression vector were grown at 37° C. overnight in 5 ml LB media containing 100 µg/ml ampicillin. The cultures were then added to 1 L of LB media containing 100 µg/ml ampicillin and grown to an OD600 of 0.4 to 0.5. Protein expression in the cells was induced by adding 1 mM of isopropyl β-D-1-thiogalactopyranoside (IPTG) and the cells were incubated for 6 hours at 22° C. Cells were harvested by centrifugation at 4° C. and pellets were stored at −80° C. The pellets were suspended in 10 ml of binding buffer, a solution containing 20 mM Tris-hydrochloride pH 8, 0.5 M sodium chloride, 1 mM 2-mercaptoethanol and cells were lysed using a French press. The extract was then centrifuged at 50,000×g for 30 minutes at 4° C. to separate soluble and insoluble protein fractions. The soluble protein fraction in the supernatant was collected and the insoluble protein fraction was suspended in 10 ml of suspension buffer. Both fractions were analyzed for expression on an SDS-PAGE gel.

Purification of E. coli Expressed Feruloyl-CoA:Monolignol Transferase (FMT)

HIS-tagged FMT was purified using an AKTA purifier (GE Healthcare) operated with UNICORN 5.11—workstation version (GE Healthcare) and a protocol modified from the manufacturer's guidelines. Four 5 ml HiTrap desalting columns (GE Healthcare) were equilibrated with binding buffer. A 5 ml aliquot of the soluble protein was injected onto the desalting column and eluted with binding buffer at a flow rate of 1 ml/minute. Fractions with the highest protein concentrations, as indicated by higher UV absorbance, were collected in 1 ml fractions. These fractions were applied to a 1 ml HisTrap HP column (GE Healthcare), conditioned and charged with 0.1 M $NiSO_4$, according to manufacturer's guidelines, at a flow rate of 0.1 ml/minute. The column was washed with 5 ml of buffer A (20 mM Tris-hydrochloride pH 8, 0.5 M sodium chloride, 1 mM 2-mercaptoethanol, and 20 mM imidazole) then bound protein was eluted at 1 ml/minute with a 20 ml linear gradient from buffer A to buffer B (20 mM Tris-hydrochloride pH 8, 0.5 M sodium chloride, 1 mM 2-mercaptoethanol, and 500 mM imidazole). Fractions containing protein were collected and analyzed by SDS-PAGE. Fractions with the highest concentration of FMT were combined and desalted using an Amicon Ultracel 10K membrane filter (Millipore).

Feruloyl-CoA:Monolignol Transferase (FMT) Enzymatic Assay

The feruloyl-CoA, p-coumaroyl-CoA, and caffeoyl-CoA substrates used in the FMT assay were enzymatically synthesized using the tobacco 4-coumarate-CoA-ligase (4CL) with a c-terminal HIS tag in pCRT7/CT TOPO, provided by Eran Pichersky. Following a method modified from Beuerle and Pichersky (Anal. Biochem. 302(2): 305-12 (2001)) 3.3 mg of ferulic acid, coumaric acid or caffeic acid, 2 mg coenzyme A, and 6.9 mg ATP were added to 50 mM Tris-hydrochloride pH 8 and 2.5 mM magnesium chloride in a final volume of 10 ml. The reaction was started by adding 0.25 mg 4CL, protein purified as described by the method of Beurerle and Pichershy. After a five-hour incubation at room temperature, additional 6.9 mg ATP, 2 mg coenzyme A, and 0.25 mg purified 4CL were added and the reaction was incubated overnight. The CoA esters were purified on an SPE cartridge as described in Beuerle and Pichersky (2001).

The FMT activity assay contained 100 mM MOPS pH 6.8, 1 mM dithiothreitol (DTT), 1 mM feruloyl-CoA, 1 mM coniferyl alcohol, 3.9 µg of purified FMT protein and deionized water to a volume of 50 µL. After a 30-minute incubation, 1 µL of 10 M hydrochloric acid was added to stop the reaction. Because the product synthesized in the reaction, coniferyl ferulate (CAFA), is insoluble, 50 µL of methanol was added to solubilize the CAFA. Prior to UPLC, protein and insoluble material were removed by filtering through an Amicon Ultracel 10K membrane filter (Millipore). The flow-through was analyzed using an Acquity Ultra Performance LC with an Acquity UPLC BEH C18 1.7 µm 2.1×100 mm column and the Acquity Console and Empower 2 Software, all from Waters Corporation. The solvents used in this method were solvent A, 0.1% trifluoroacetic acid, and solvent B, 100% acetonitrile. Samples were analyzed using the following gradient conditions, 13% B, for 5 minutes, 1 minute linear gradient to 42% B, held for 4 minutes, 1 minute linear gradient to 100% B, held for 1 minutes and 3 minutes at 13% B with a flow rate of 0.3 ml/minute. This method was then used to analyze a 10 µL injection of each assay reaction; standards for each of the substrates along with chemically synthesized CAFA were used to determine retention times for each compound.

Size Exclusion Chromatography of FMT

A 100 µL sample of protein purified by immobilized metal ion affinity chromatography (IMAC) was loaded onto a Superdex 75 10/300 GL gel filtration column (GE Healthcare), equilibrated with 100 mM MOPS pH 6.8. The protein was eluted with the same buffer at a constant flow rate of 0.1 ml/minute and collected in 0.5 ml fractions. Aliquots of the protein sample prior to gel filtration, and each of the fractions near the elution peak were analyzed for protein content by SDS-PAGE gel electrophoresis. Protein containing fractions were analyzed to determine the amount of FMT activity, as described above.

NMR

Figure 3A:
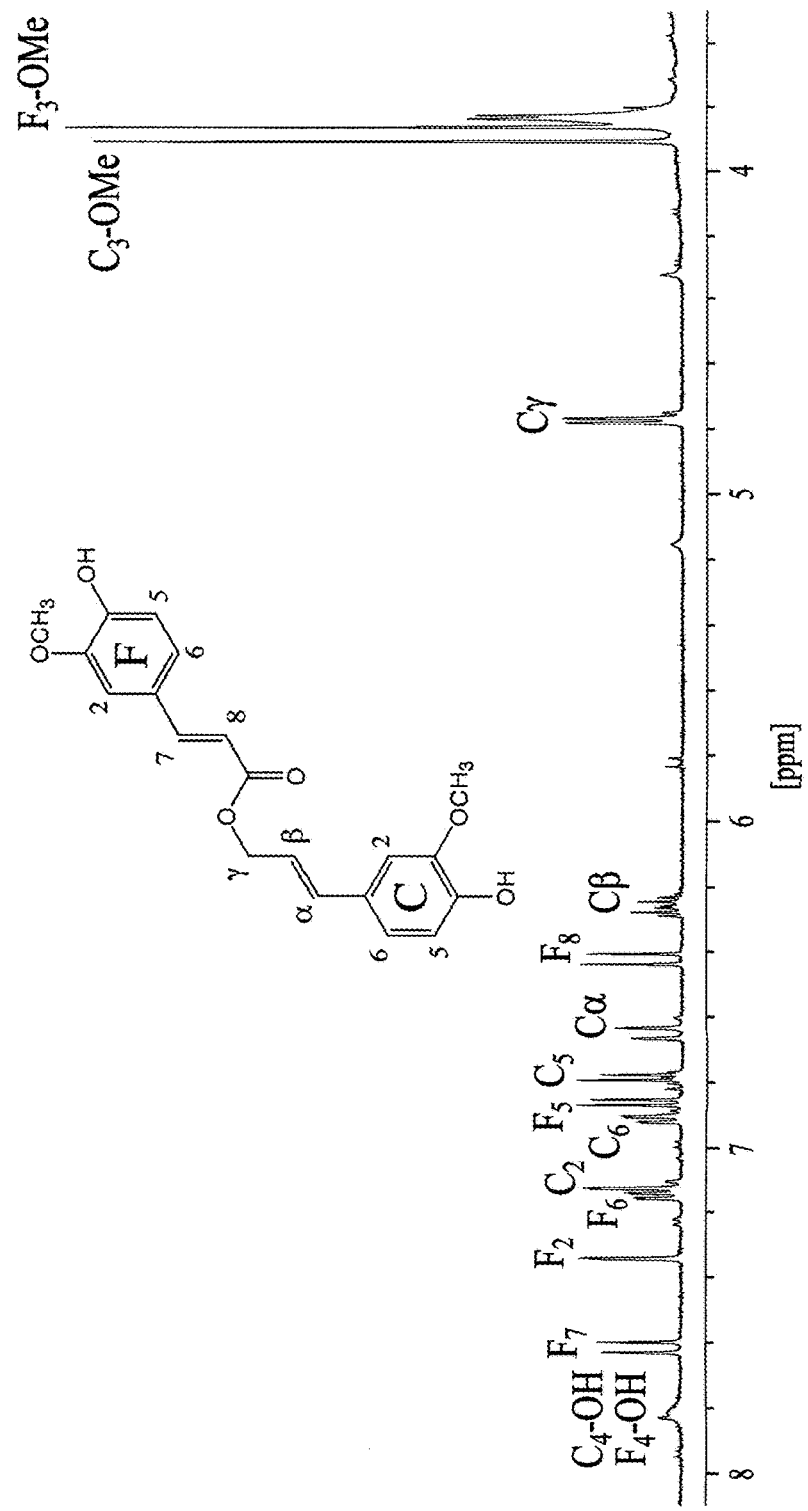
FIG. 3A-3B illustrate the NMR identification of coniferyl ferulate (CAFA).
Figure 3B:
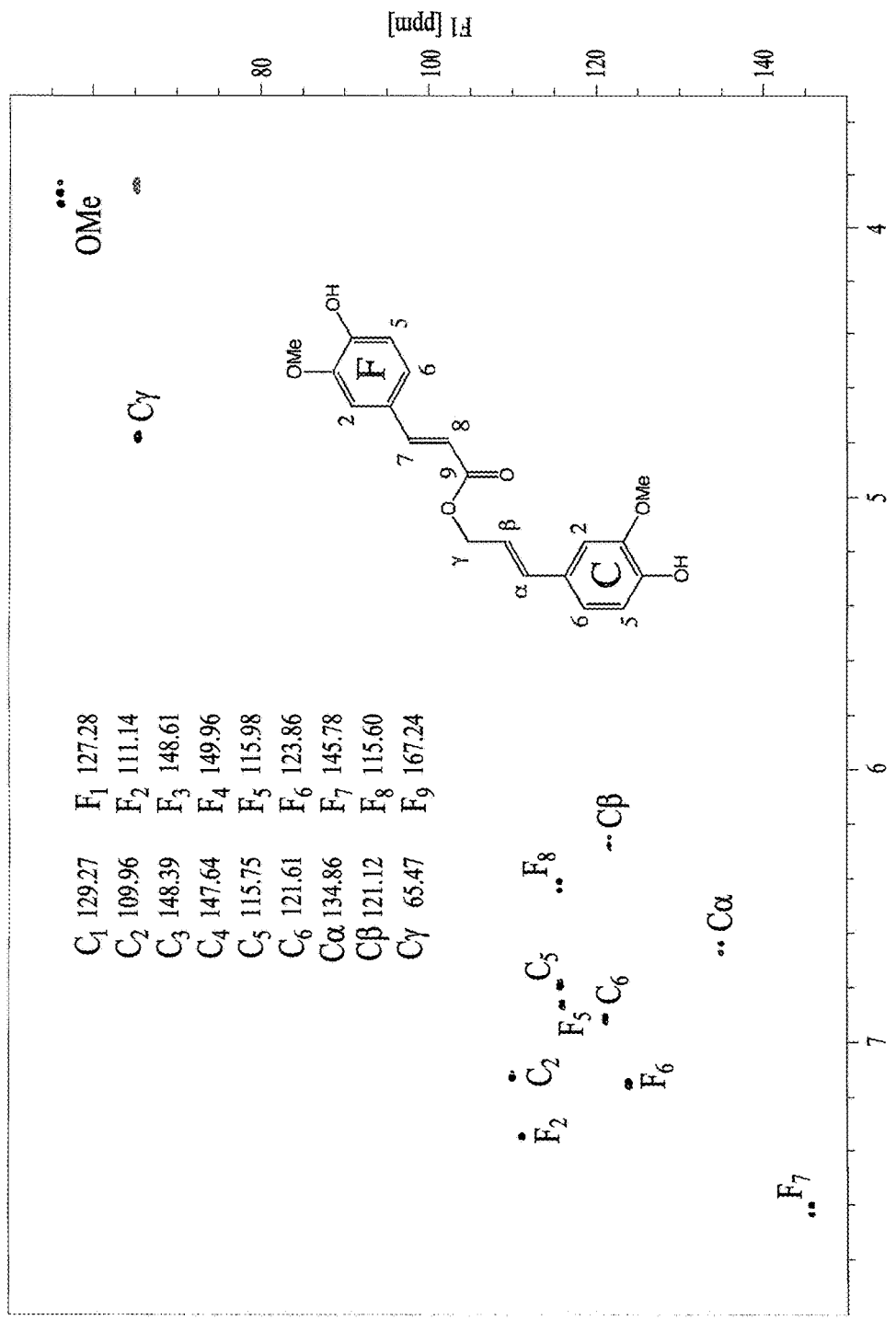

To confirm the identification based on the chromatogram peak comparisons, the reaction product, which was insoluble before addition of methanol, was centrifuged to pellet the coniferyl ferulate, which was dissolved in perdeuteroacetone and analyzed by NMR. The proton NMR spectrum, FIG. 3A, unambiguously confirmed the authenticity of the coniferyl ferulate product, particularly when compared with the spectrum from the independently synthesized coniferyl ferulate (described below). For absolute confirmation, $^{13}$C NMR data was also obtained via a 2D $^{1}$H—$^{13}$C correlation (HSQC) spectrum (for the protonated carbons, FIG. 3B) and a 2D $^{1}$H—$^{13}$C long-range correlation (HMBC) spectrum (not shown, but data for all carbons is given on FIG. 3B).

Synthesis of Authentic Coniferyl Ferulate

Figure 9:
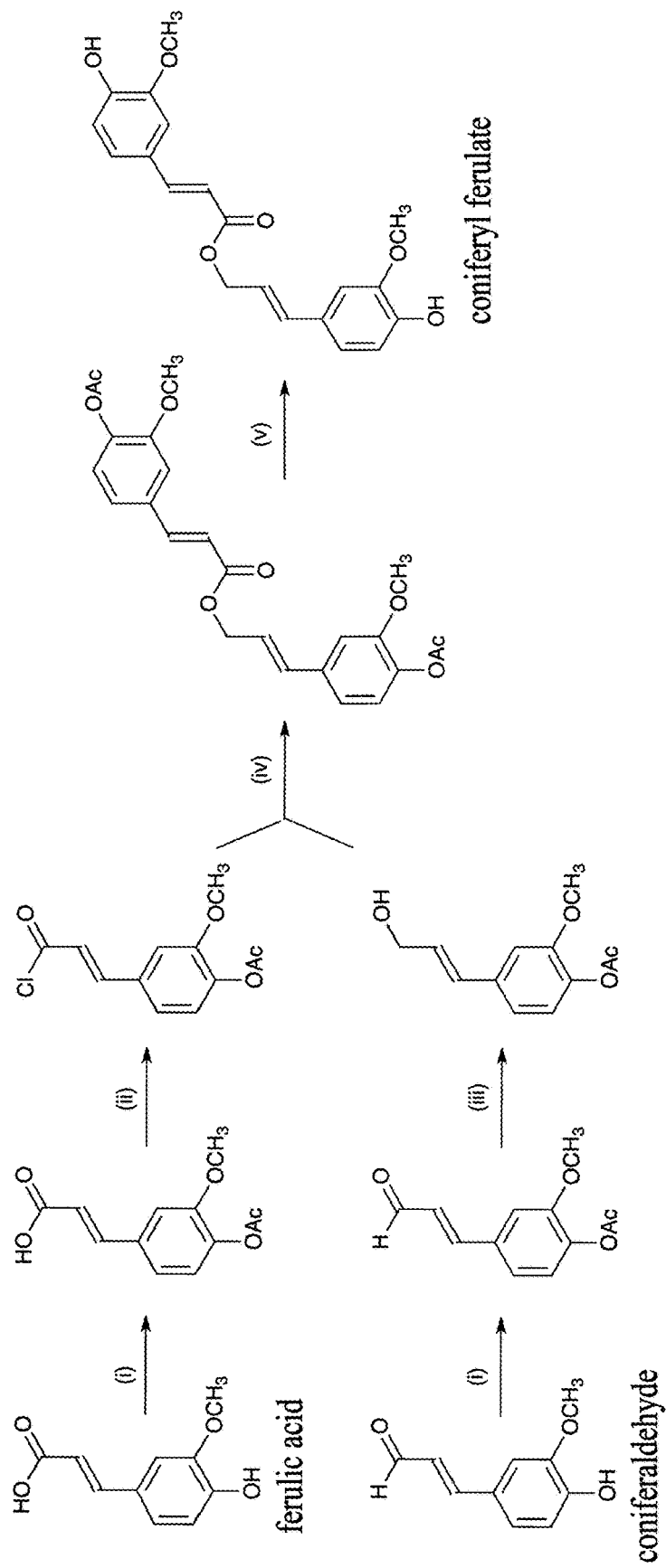
FIG. 9 illustrates the synthetic scheme used to prepare authentic coniferyl ferulate, employing (i) acetic anhydride, pyridine; (ii) thionyl chloride; (iii) borane/tert-butylamine; (iv) triethylamine, dimethylaminopyridine; and (v) pyrrolidine.

The synthesis was similar to that described for the related compound, coniferyl p-coumarate (Lu, F., and Ralph, J. Facile synthesis of 4-hydroxycinnamyl p-coumarates. (1998) *J. Agr. Food Chem.* 46(8), 2911-2913). Thus, as shown in FIG. 9, 4-acetoxyferuloyl chloride was prepared from ferulic acid by acetylation followed by chlorination using $SOCl_2$ according to a previous method (Helm, R. F., Ralph, J., and Hatfield, R. D. Synthesis of feruloylated and p-coumaroylated methyl glycosides. (1992) *Carbohydr. Res.* 229(1), 183-194).

4-Acetoxyconiferaldaldehyde was prepared in 94-96% yield by acetylation of coniferaldehyde with acetic anhydride/pyridine and then reduced with borane/tert-butylamine complex to give the corresponding alcohol, as follows. The 4-acetoxyconiferaldehyde was dissolved in methylene chloride to which borane/tert-butylamine complex (1.5 equiv) was added. The mixture was stirred at room temperature for 2 h, when TLC showed that the starting material had disappeared completely. The solvent was evaporated at 40° C. under reduced pressure. The residue was hydrolyzed with 0.5 M $H_2SO_4$ in ethanol/water (1:1) for 1.5 h. Most of the ethanol was removed by evaporation, and the product was extracted with ethyl acetate. The ethyl acetate solution was washed with saturated $NH_4Cl$ and dried over $MgSO_4$. Evaporation of the ethyl acetate gave the product, 4-acetoxyconiferyl alcohol as a pale yellow oil (96% yield); $^1$H NMR (acetone-$d_6$) δ 2.31 (3H, s, OAc), 3.83 (3H, s, OAc), 3.90 (1H, t, J) 5.5 Hz, γ-OH), 4.22 (2H, dt, J) 5.5, 1.7 Hz, γ), 6.38 (1H, dt, J) 15.9, 5.2 Hz, β), 6.58 (1H, dt, J=15.9, 1.7 Hz, α), 6.97 (2H, m, A5/6), 7.15 (s, 1H, A2); 13C NMR δ 20.5 (OAc), 56.2 (OMe), 63.1 (γ), 110.9 (A2), 119.5 (A6), 123.6 (A5), 129.3 (α), 131.4 (β), 137.2 (A1), 140.2 (A4), 152.3 (A3), 169.0 (OAc).

4-Acetoxyconiferylferulate. Coupling of 4-acetoxyferuloyloyl chloride with 4-acetoxyconiferyl alcohol was efficiently carried out using 4-(dimethylamino)-pyridine (DMAP). Thus, 4-acetoxyconiferyl alcohol and 4-acetoxyferuloyl chloride were dissolved in dry $CH_2Cl_2$ (120 mL) to which DMAP (0.25 equiv) and $Et_3N$ (0.85 equiv) were added. The mixture was stirred for 2 h, when TLC [$CHCl_3$/EtOAc (5:1)] showed the starting material was converted into a faster moving compound. The solution was diluted with $CH_2Cl_2$ and washed successively with aqueous 3% HCl and saturated $NH_4Cl$. Drying over $MgSO_4$, evaporation, and purification by flash chromatography [$CHCl_3$/EtOAc (19:1)] gave the diacetate of coniferyl ferulate (94%) as a pale yellow oil.

Coniferyl ferulate. The above diacetate (0.195 mmol) was dissolved in pyrrolidine (1 mL). Once dissolution was complete, the pyrrolidine solution was diluted with 50 mL of ethyl acetate and washed with 1 M $H_2SO_4$ (3×20 mL) and saturated $NH_4Cl$ (2×20 mL). After drying over $MgSO_4$ and evaporation, the resulting syrup was submitted to solid phase extraction [$CHCl_3$/EtOAc (19:1)] to afford coniferyl ferulate (93%) as a white solid. NMR spectra are the same as those for the FMT-enzyme generated product, as shown in FIG. 3.

EXAMPLE 2

Identification and Cloning of a feruloyl-CoA:monolignol transferase

Mature *A. sinensis* plants were purchased from Mountains, Gardens and Herbs (North Carolina) and RNA was extracted from the roots of these plants. This RNA was used to synthesize double-stranded cDNA. The cDNA was sequenced using a Roche GSFLX Titanium Sequencer and 736,017 sequences were obtained. The sequences were assembled into 62425 contigs using CAP3 (Huang, X., A contig assembly program based on sensitive detection of fragment overlaps. (1992) *Genomics* 14: 18-25). The consensus sequence for each contig was searched against all proteins from *Arabidopsis* and the NCBI non-redundant protein databases using the BLASTX software program (Altschul S, Gish W, Miller W, Myers E, Lipman D. Basic local alignment search tool. (1990) *J Mol Biol* 215(3), 403-410). The sequences were sorted by abundance and filtered to show only sequences annotated as being within a "transferase family," which is the annotation in the TAIR9 database assigned to members of the BAHD class of acyltransferases.

Two very abundant BAHD acyltransferases were identified as well as a number of such enzymes with lower EST counts. These two sequences were cloned by PCR from an *A. sinensis* cDNA pool using oligonucleotides designed to amplify their coding regions. The coding region of the *A. sinensis* sequences was transferred to the expression vector pDEST17 using Gateway technology. This vector adds an amino-terminal 6×HIS-tag to the protein, which allows for affinity purification by immobilized metal affinity chromatography (IMAC). *E. coli* clones containing the recombinant protein where grown and induced to produce recombinant protein. The enzyme was purified from the *E. coli* protein extract using IMAC.

Figure 2B:
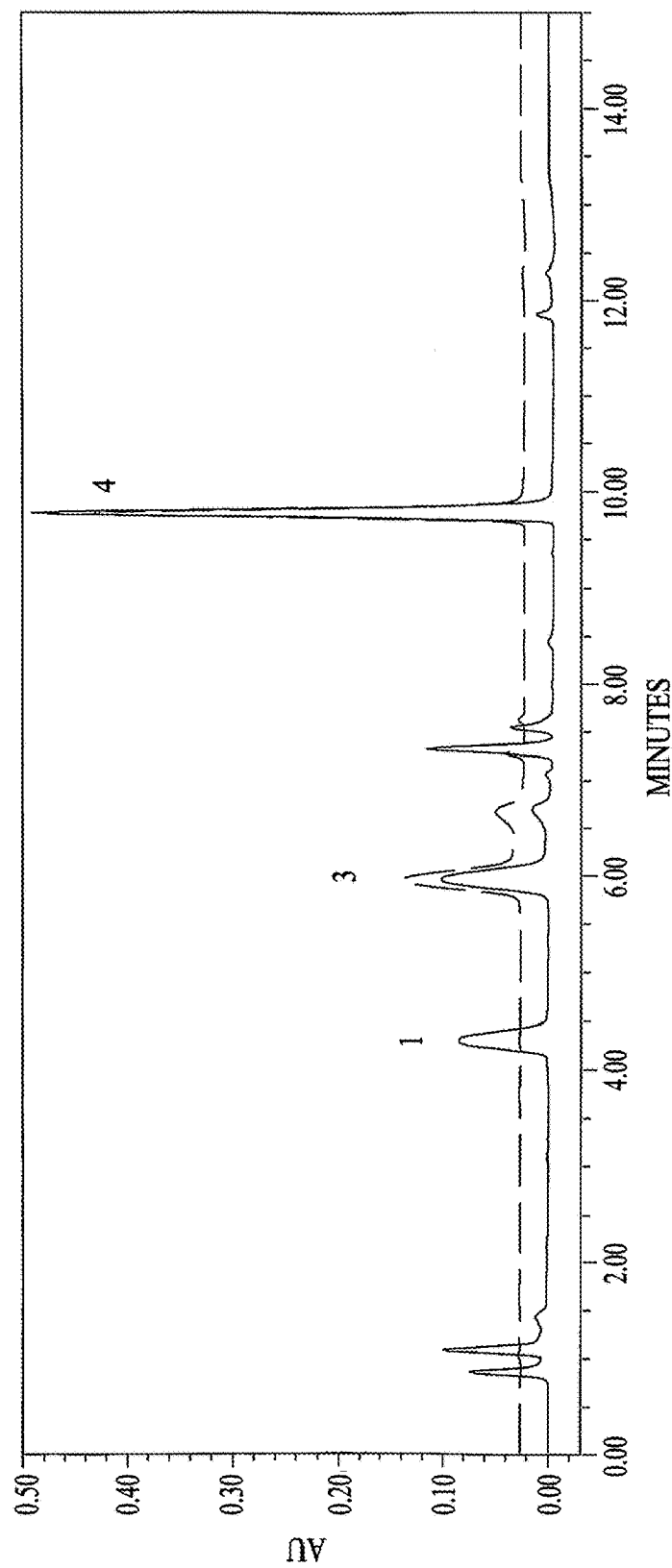

Purified recombinant enzyme was assayed for FMT activity using a reaction mixture containing 2 mM coniferyl alcohol, 0.5 feruloyl-CoA, 100 mM HEPES pH 7.4 and 1 mM DTT. The second most abundant BAHD acyltransferase gene when incubated with Coniferyl alcohol and feruloyl-CoA produced a compound with the retention time of authentic coniferyl ferulate (CAFA) (FIG. 2). The product produced was mostly insoluble in water. The addition of methanol to 50% after stopping the enzyme with acid was required to analyze the product by UPLC. The insolubility of the product made partial purification easy as the product was separated from the substrates by centrifugation.

Figure 4A:
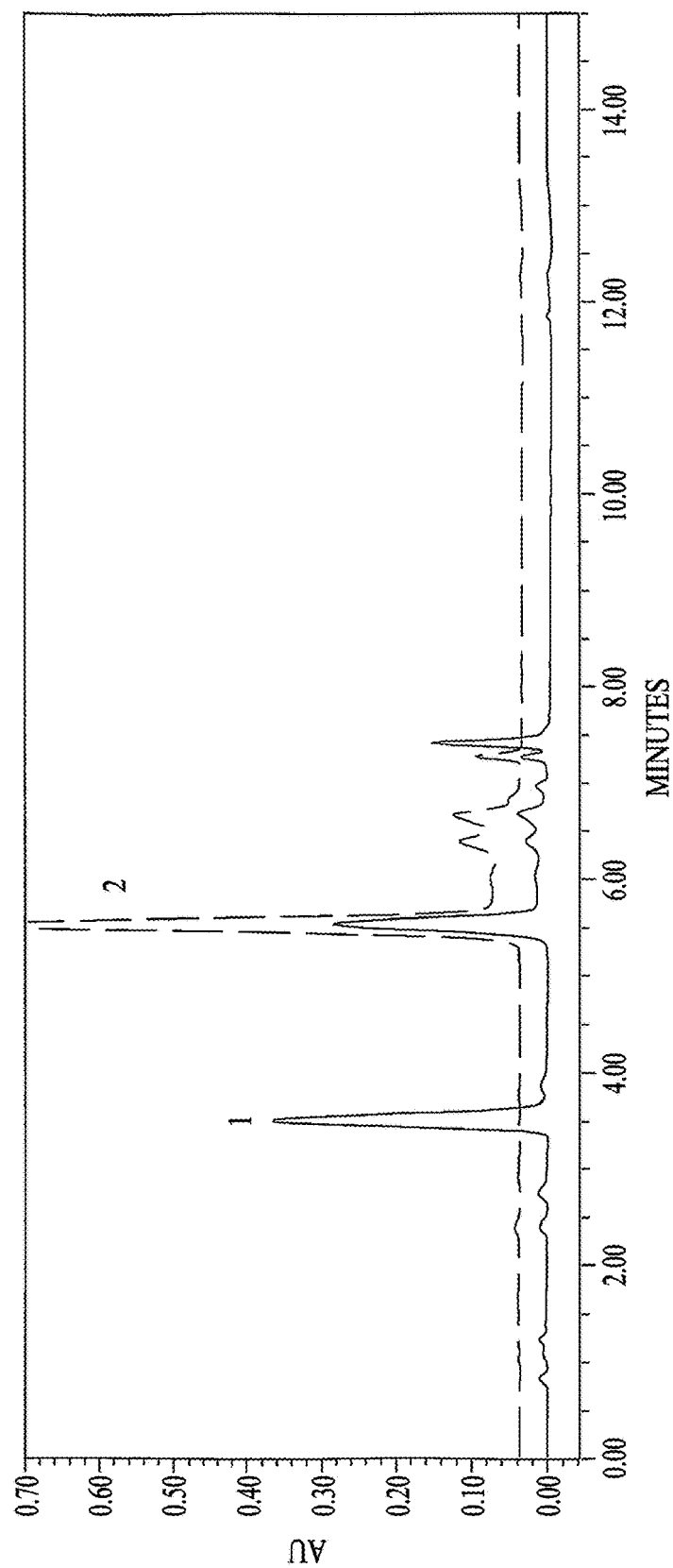
FIG. 4A-4B shows HPLC separation of assay components where the assay was for feruloyl-CoA:monolignol transferase (FMT) activity using feruloyl-CoA and p-coumaryl alcohol as substrates. The UV 340 trace is the dashed line while the UV 280 trace is the solid line.
Figure 4B:
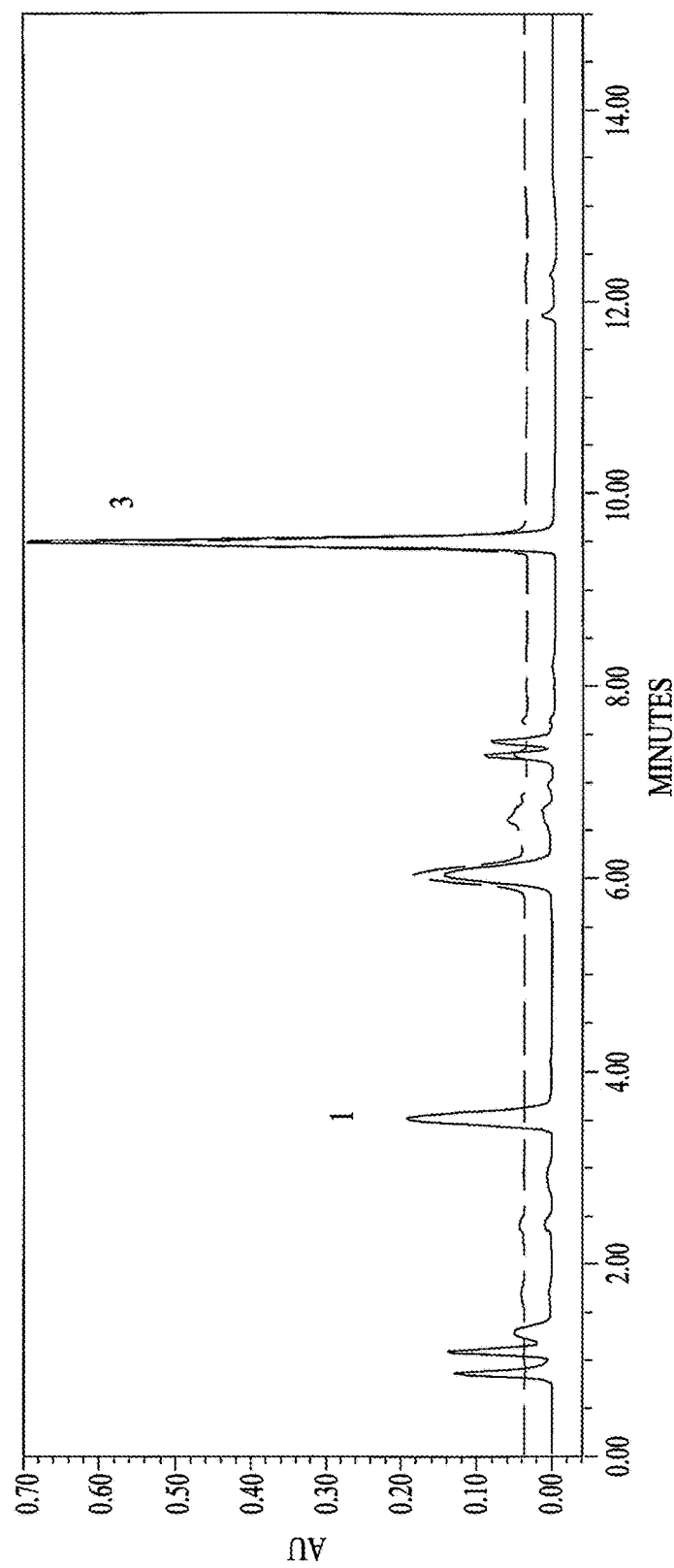
Figure 5A:
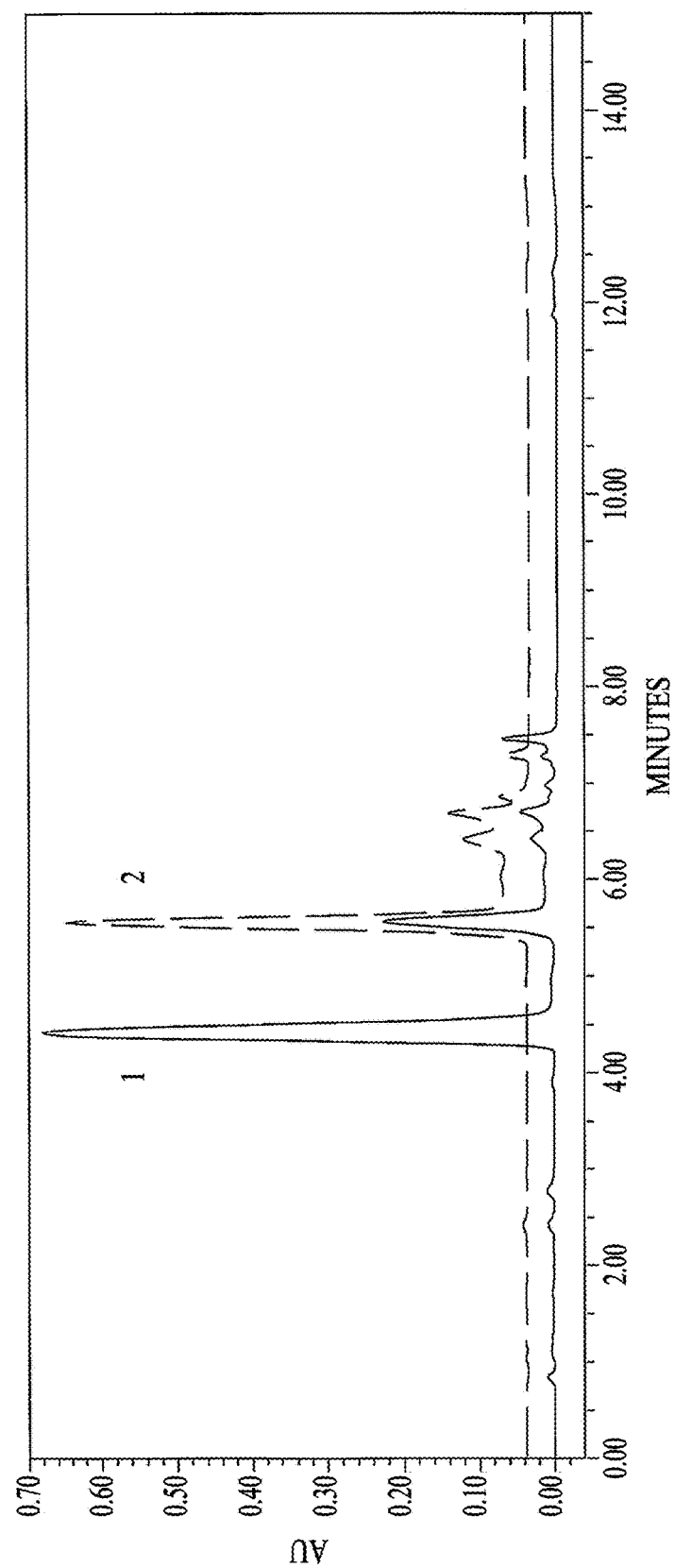
FIG. 5A-5B shows HPLC separation of assay components where the assay was for feruloyl-CoA:monolignol transferase (FMT) activity using sinapyl alcohol and feruloyl-CoA as substrates. The UV 340 trace is the dashed line while the UV 280 trace is the solid line.
Figure 5B:
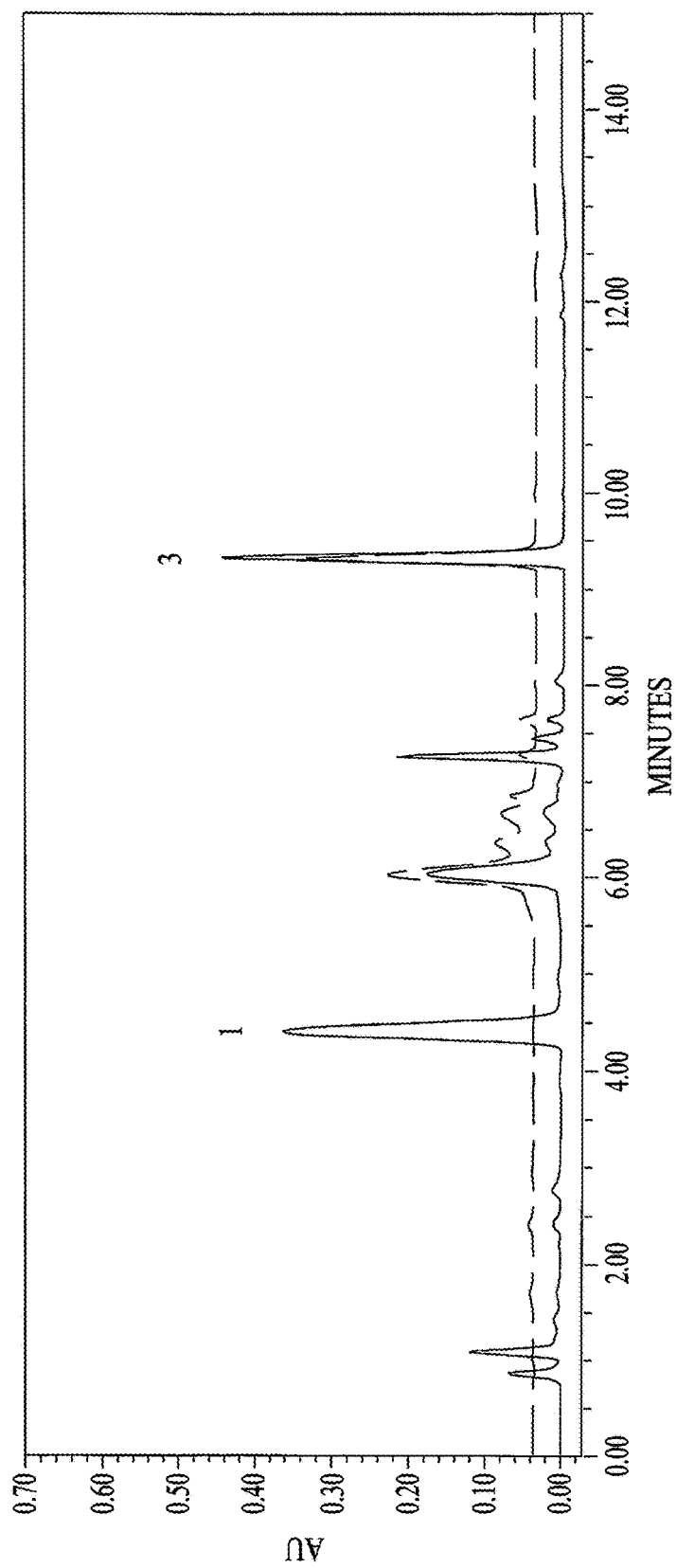
Figure 6A:
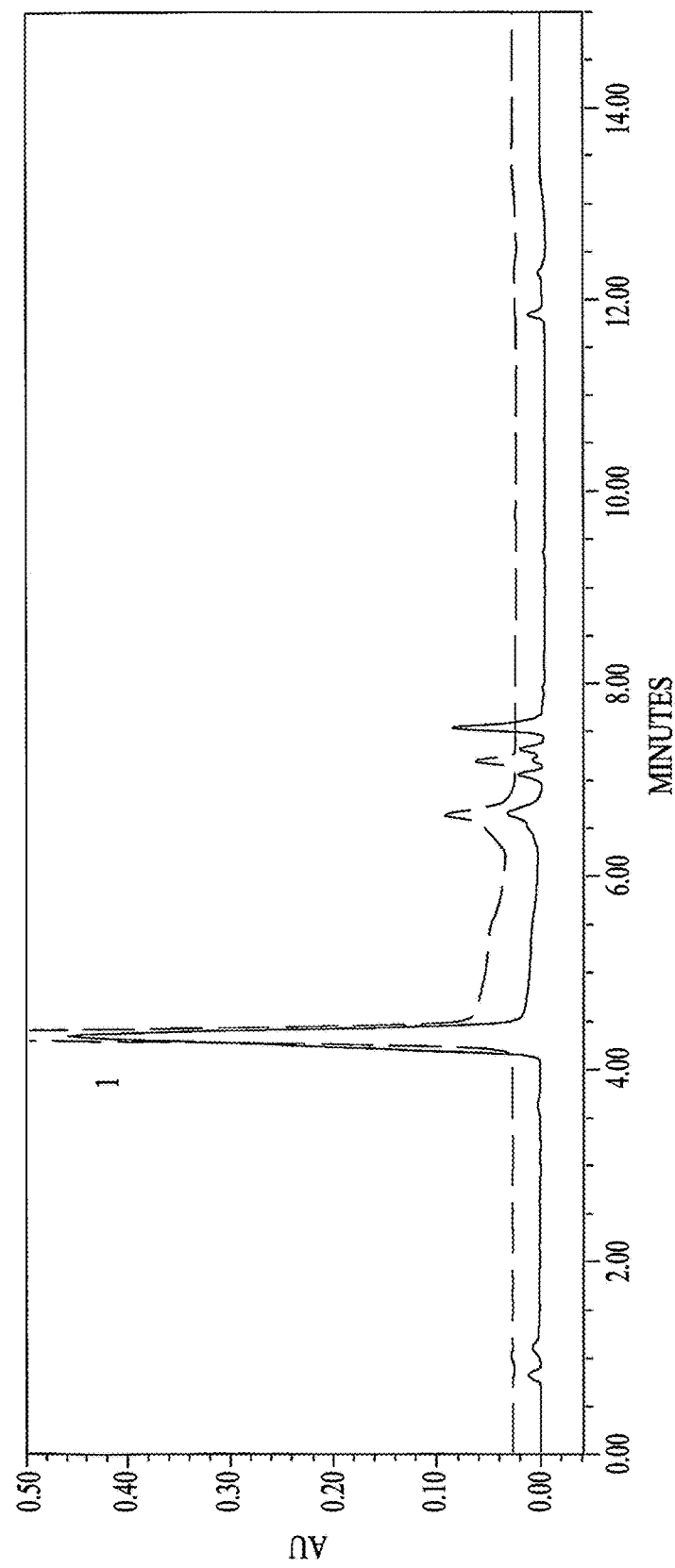
FIG. 6A-6B shows HPLC separation of assay components where the assay was for feruloyl-CoA:monolignol transferase (FMT) activity using coniferyl alcohol and p-coumaroyl-CoA as substrates. The UV 340 trace is the dashed line while the UV 280 trace is the solid line.
Figure 6B:
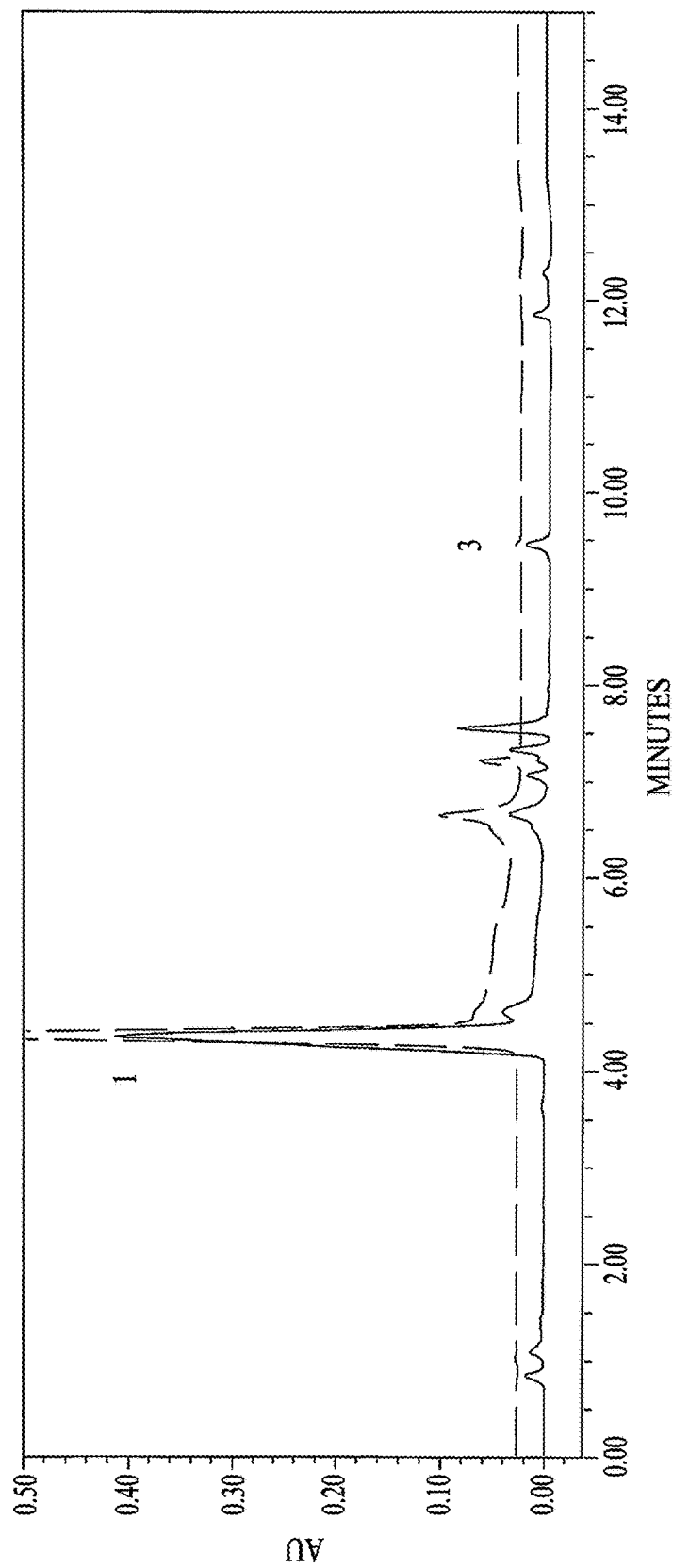
Figure 7A:
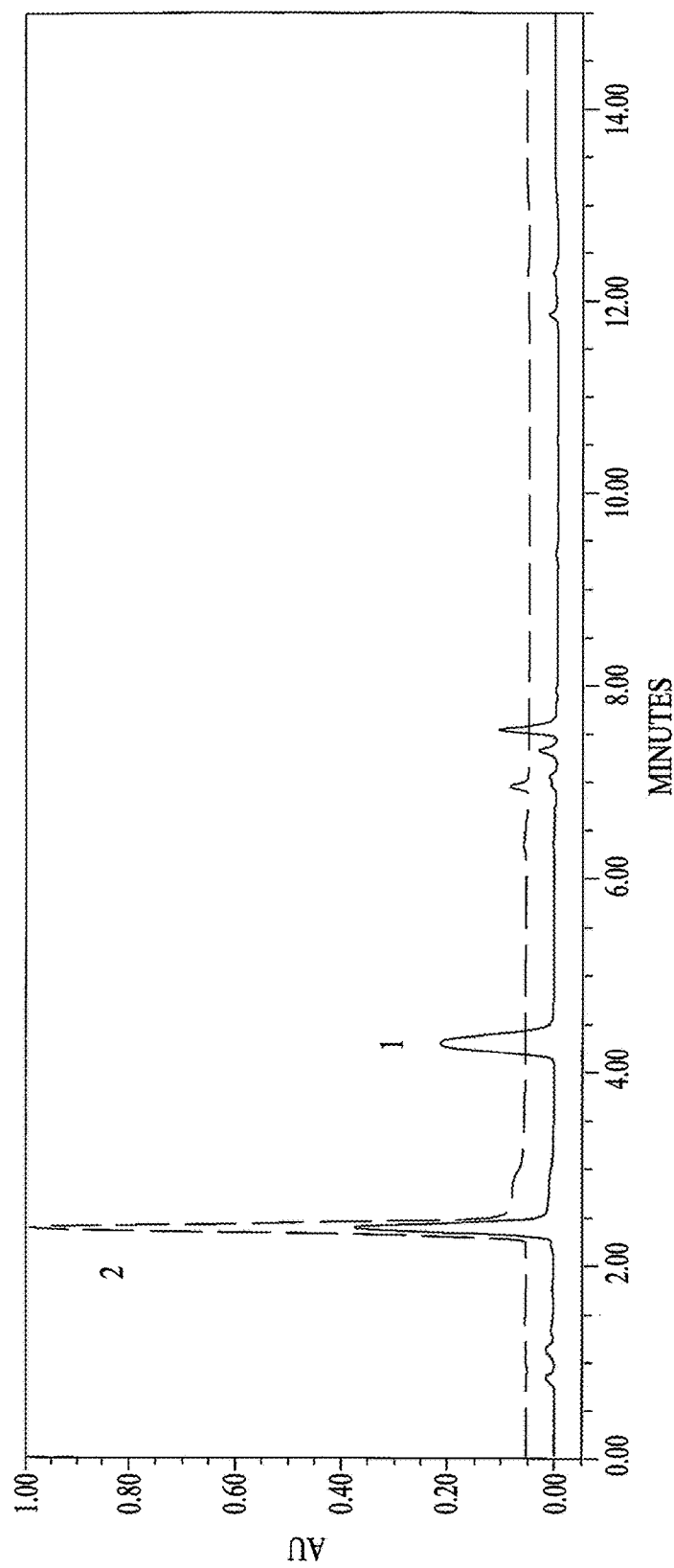
FIG. 7A-7B shows HPLC separation of assay components where the assay was for feruloyl-CoA:monolignol transferase (FMT) activity using caffeoyl-CoA and coniferyl alcohol as substrates. The UV 340 trace is the dashed line while the UV 280 trace is the solid line.
Figure 7B:
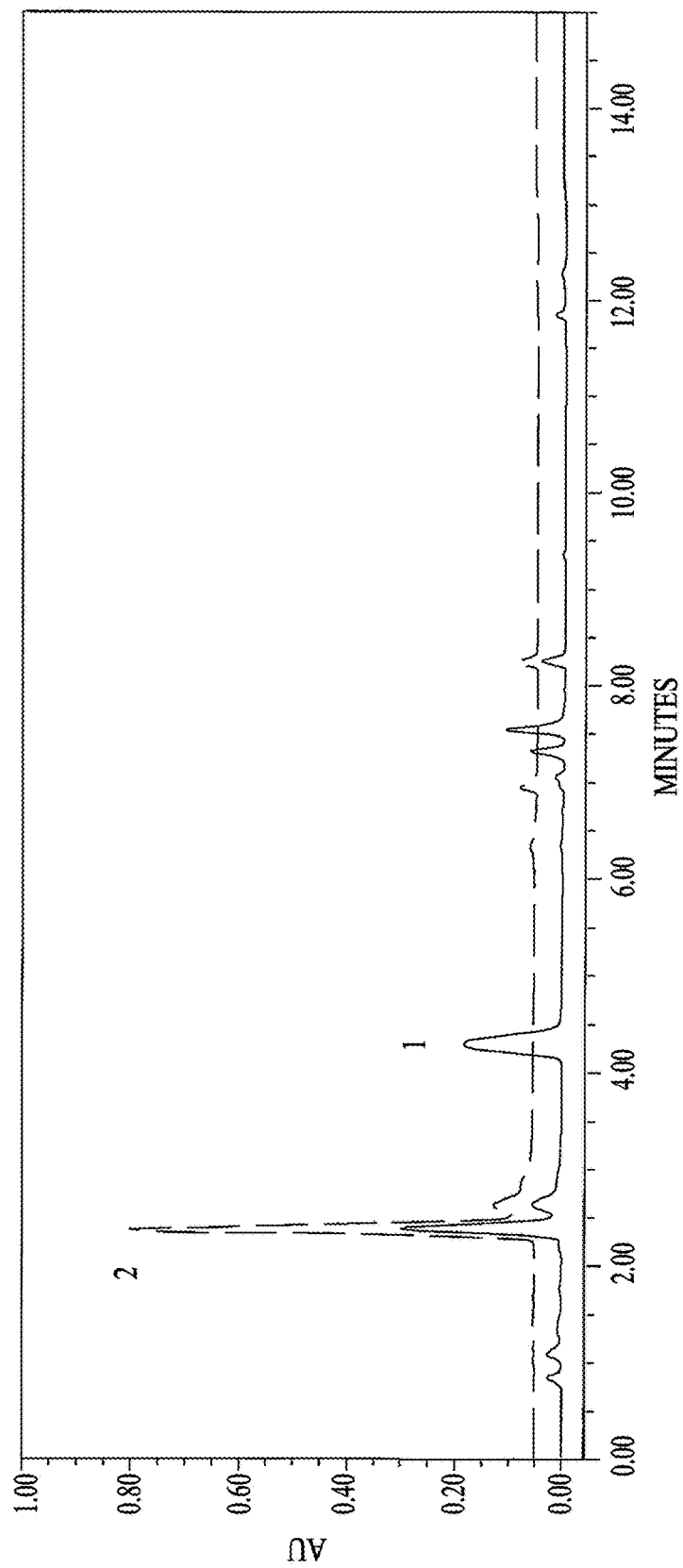

This partial purified product was analyzed by NMR. The identity of the product as CAFA was confirmed by $^1$H-NMR (FIG. 3). The enzyme was tested with p-coumaryl alcohol (FIG. 4) and sinapyl alcohol (FIG. 5) in addition to coniferyl alcohol (FIG. 2). The enzyme is active with all three monolignols, i.e., p-coumaryl alcohol, coniferyl alcohol and sinapyl alcohol. The enzyme was tested with p-coumaroyl-CoA (FIG. 6) and caffeoyl-CoA (FIG. 7) as well as feruloyl-CoA (FIG. 2). The enzyme has a strong preference for feruloyl-CoA as can be seen by comparison of FIGS. 2, 6 and 7. In FIGS. 6 and 7, very little product is produced from p-coumaroyl-CoA and caffeoyl-CoA substrates. However, substantial product is formed when feruloyl-CoA is used instead (FIG. 2).

Figure 8:
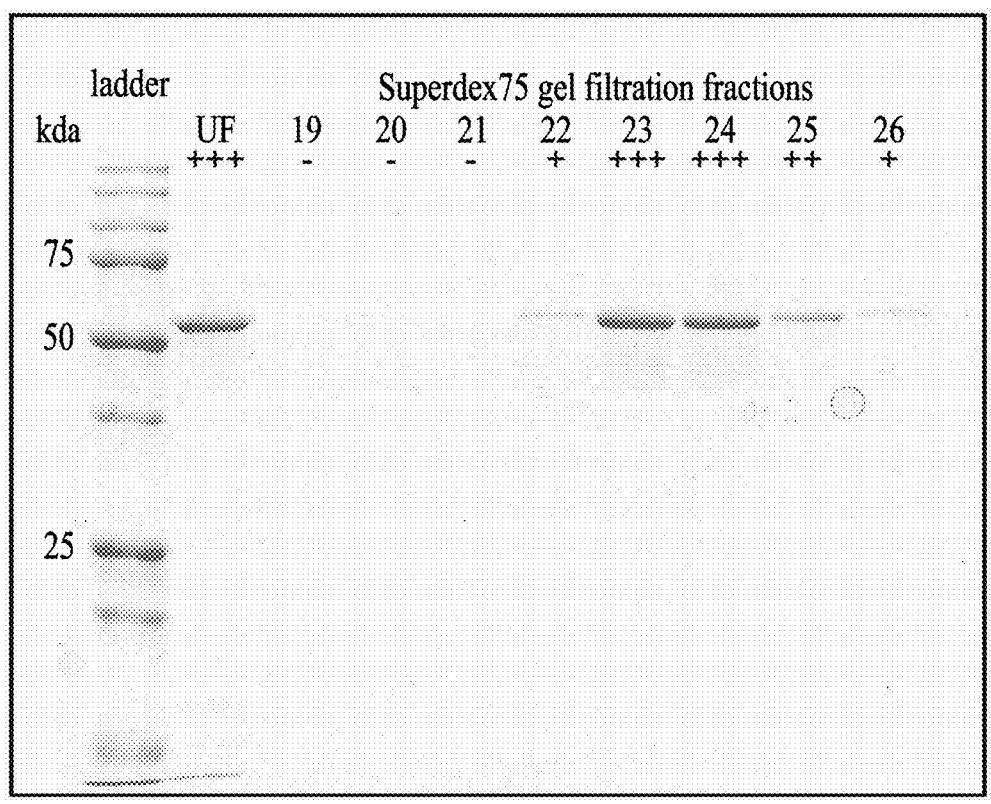
FIG. 8 illustrates SDS-PAGE analysis of size exclusion chromatography fractions from immobilized metal ion affinity chromatography (IMAC) purified feruloyl-CoA:monolignol transferase. The term UF is an abbreviations for unfractionated purified feruloyl-CoA:monolignol transferase. The numbers 19 through 26 represent Superdex75 gel filtration fractions. The symbol (−) identifies fractions with no feruloyl-CoA:monolignol transferase activity while the symbols (+), (++) and (+++) mark fractions with progressively increased activity.

The IMAC purified FMT had a few lower molecular weight proteins as shown in FIG. 8. These lower molecular proteins are likely proteolytic fragments of FMT as determined by analysis of tryptic digests of these bands by mass spectrometry. To ensure that the major band was responsible for the activity, FMT was further purified using size-exclusion chromatography. The FMT activity elutes coincident with the major protein band (FIG. 8).

EXAMPLE 3

Analysis of Transgenic Poplar Containing the FMT Sequence

This Example illustrates the expression and enzymatic activity observed in poplar trees that were genetically modified to express the *Angelica sinensis* feruloyl-CoA:monolignol transferase nucleic acids described herein.

Methods

Hybrid poplar (*Populus alba×grandidentata*) was transformed using *Agrobacterium tumefaciens* EHA105 employing a common leaf disk inoculation. Two constructs were created to drive the expression of FMT in poplar: 1) 35S:: YFP-FMT (cauliflower mosaic virus ubiquitous 35S promoter with an N-terminal tagged Yellow Fluorescent Protein), and 2) CesA8::YFP-FMT (poplar xylem-specific secondary cell wall specific cellulose synthase 8 promoter with an N-terminal tagged Yellow Fluorescent Protein). The binary plasmids were inserted into EHA105 using the freeze-thaw technique, and incubated overnight in liquid Woody Plant Media (WPM) supplemented with 100 µM acetosyringone. Leaf disks were cut and co-cultured with EHA105 for one hour at room temperature, blotted dry and plated abaxailly onto WPM supplemented with 0.1 µM each α-naphthalene acetic acid (NAA), 6-benzylaminopurine (BA), and thiadiazuron (TDZ) and solidified with 3% (w/v) agar and 1.1% (w/v) phytagel (WPM 0.1/0.1/0.1). After three days the discs were transferred to WPM 0.1/0.1/0.1 supplemented with carbenicillin disodium (500 mg L$^{-1}$) and cefotaxime sodium salt (250 mg L$^{-1}$). Following three additional days, the discs were transferred to WPM 0.1/0.1/ 0.1 containing carbenicillin, cefotaxime and hygromycin (25 mg L$^{-1}$). After five weeks, shoots and callus material were transferred to WPM with agar and phytagel, 0.01 µM BA, carbenicillin, cefotaxime and hygromycin. Once individual shoots were visible, plantlets were transferred to solidified WPM with 0.01 µM NAA and carbenicillin, cefotaxime and hygromycin to induce rooting. After two consecutive five-week periods on this media, shoot tips were isolated to solidified antibiotic-free WPM with 0.01 µM NAA.

Plants were confirmed as transgenic by PCR screening of genomic DNA employing gene specific oligonucleotides. All shoot cultures, including transgenic and non-transformed wild-type lines, were maintained on solid WPM with 0.01 µM NAA in GA-7 vessels at 22° C. under a 16-hour photoperiod with an average photon flux of 50 µmol m$^{-2}$ s$^{-1}$ until out-planting to the greenhouse. Plants were then transferred to soil and grown under supplemental lights (@300 W m$^2$) on flood tables and watered with fertigated water daily in a greenhouse.

Purification of YFP-FMT was via GFPtrap_A (Chromotek) following the manufactures guidelines. Briefly, leaves from transgenic 1-year poplar trees were ground to a powder in liquid nitrogen and 250 mg powder of each ground leaf sample was separately suspended in 300 µl 100 mM sodium phosphate pH 6. An aliquot of 5 ul was added to the FMT enzyme assay described in the foregoing Examples. After 45 minutes of incubation, the reaction was stopped with 100 mM hydrochloric acid, and the products were solubilized with the addition of methanol to a concentration of 50%. The protein and insoluble materials were removed by filtration through an Amicon Ultracel 10K membrane filter (Millipore). Control reactions were also completed using a protein extract from wild type hybrid poplar, as well as the standard no enzyme control. These samples were analyzed by western blot and the UPLC method described in the Examples above. Formation of coniferyl ferulate was also detected by comparison of the UPLC traces of leaf extracts with authentic coniferyl ferulate.

Results

Figure 10A:
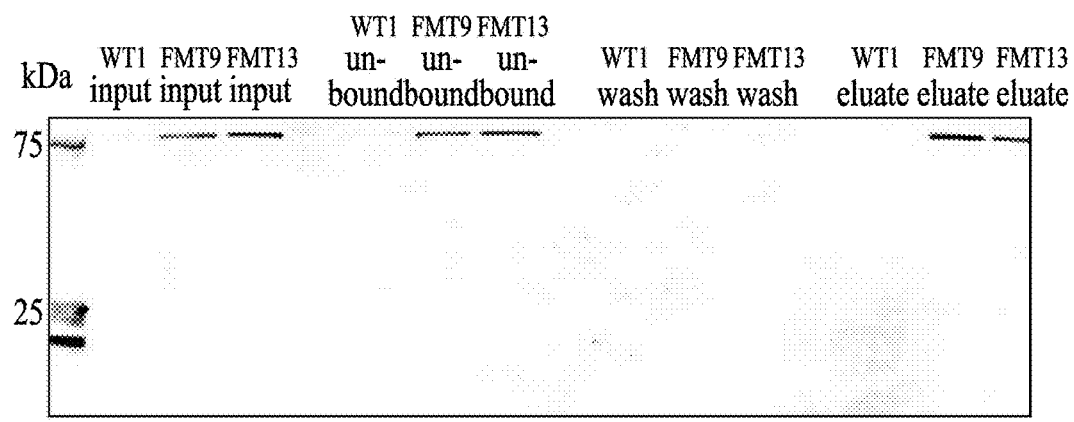
FIG. 10A-10B illustrates that transgenic Poplar tree leaves express an enzymatically active *Angelica sinensis* feruloyl-CoA:monolignol transferase. The Poplar trees were genetically modified using standard procedures to incorporate the *Angelica sinensis* FMT nucleic acids described herein.
Figure 10B:
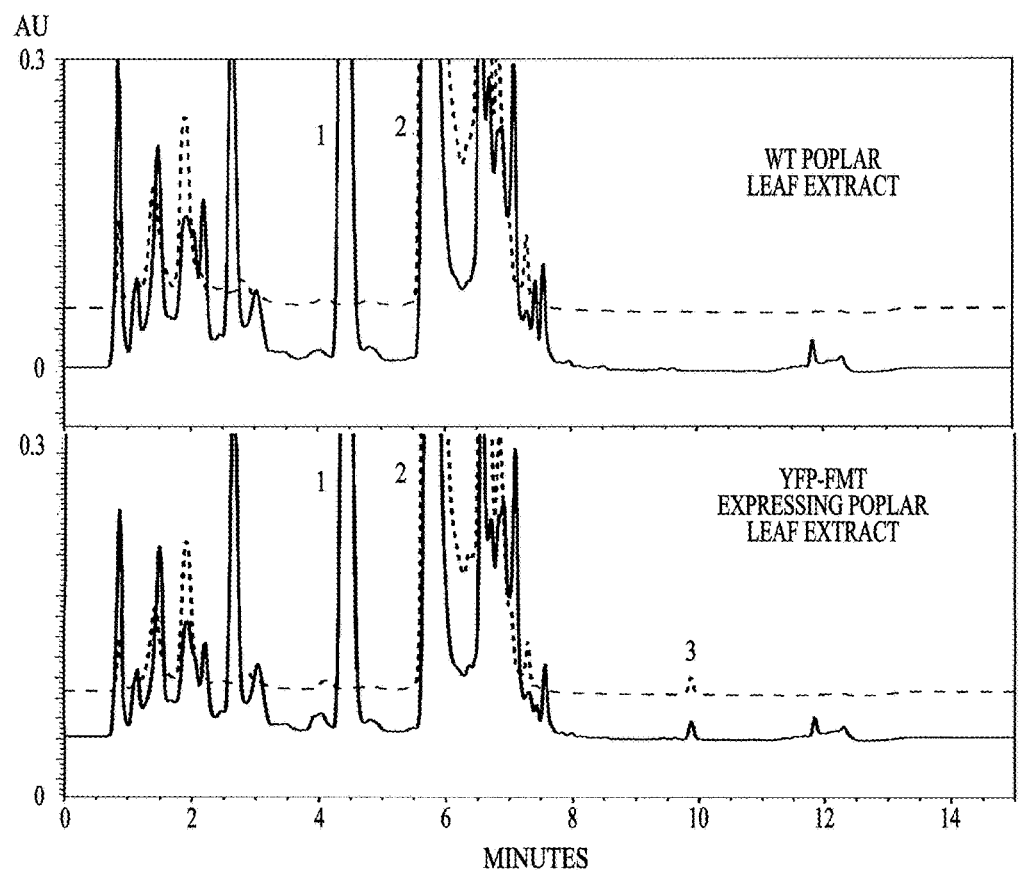

As shown in FIG. 10, FMT activity was identified in extracts from transgenic poplar lines containing the *Angelica sinensis* FMT by observing a product peak at the same retention time as the authentic standard (FIG. 10B). No such peak was observed for wild type popular leaf extracts or in the no enzyme control. Similarly, FMT protein expression was detected by western blot analysis only in leaves from poplar trees that had been genetically modified to express the *Angelica sinensis* FMT (FIG. 10A).

EXAMPLE 4

Transgenic *Arabidopsis* with the *Angelica sinensis* FMT

This Example illustrates that other plant species can readily be transformed with the *Angelica sinensis* feruloyl-CoA:monolignol transferase nucleic acids described herein to express an enzymatically active FMT.

Methods:

*Arabidopsis* were transformed by standard procedures with the *Angelica sinensis* feruloyl-CoA:monolignol transferase nucleic acids described herein. As a control some samples of *Arabidopsis* were transformed with an empty vector that did not contain the *Angelica sinensis* FMT. FMT expression was detected by Reverse Transcriptase PCR of protein isolated from the transgenic *Arabidopsis* leaves. Enzymatic activity by the expressed FMT was detected using the assay described in Example 1.

Results

Figure 11A:
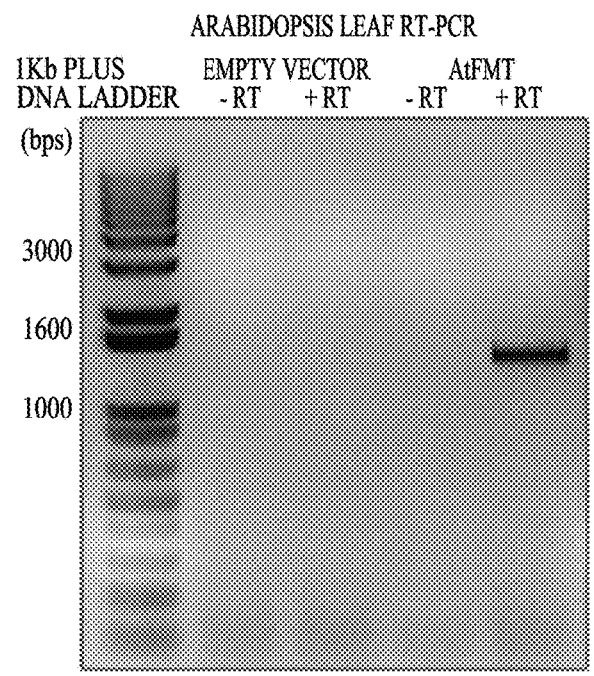
FIG. 11A-11B illustrates that transgenic *Arabidopsis* express an enzymatically active *Angelica sinensis* feruloyl-CoA:monolignol transferase. FMT expression is demonstrated by Reverse Transcriptase PCR in *Arabidopsis* leaf. FMT enzymatic activity is demonstrated within the *Arabidopsis* stem.

As illustrated in FIG. 11, the transgenic *Arabidopsis* plants express an enzymatically active *Angelica sinensis* feruloyl-CoA:monolignol transferase. FIG. 11A shows the products of Reverse Transcriptase PCR amplification of transcripts from *Arabidopsis* leaves transformed with empty vector or with a vector expressing the FMT transcript. As shown, FMT transcripts were detected only when reverse transcriptase was added (+ RT) to the PCR reaction mixture, and not when reverse transcriptase was absent (− RT) from the PCR reaction mixture. A PCR product of the expected size for the FMT enzyme (1326 base pairs) was visible only in the reaction containing total RNA from *Arabidopsis* transformed with the *Angelica sinensis* FMT when the reverse transcriptase is present.

Figure 11B:
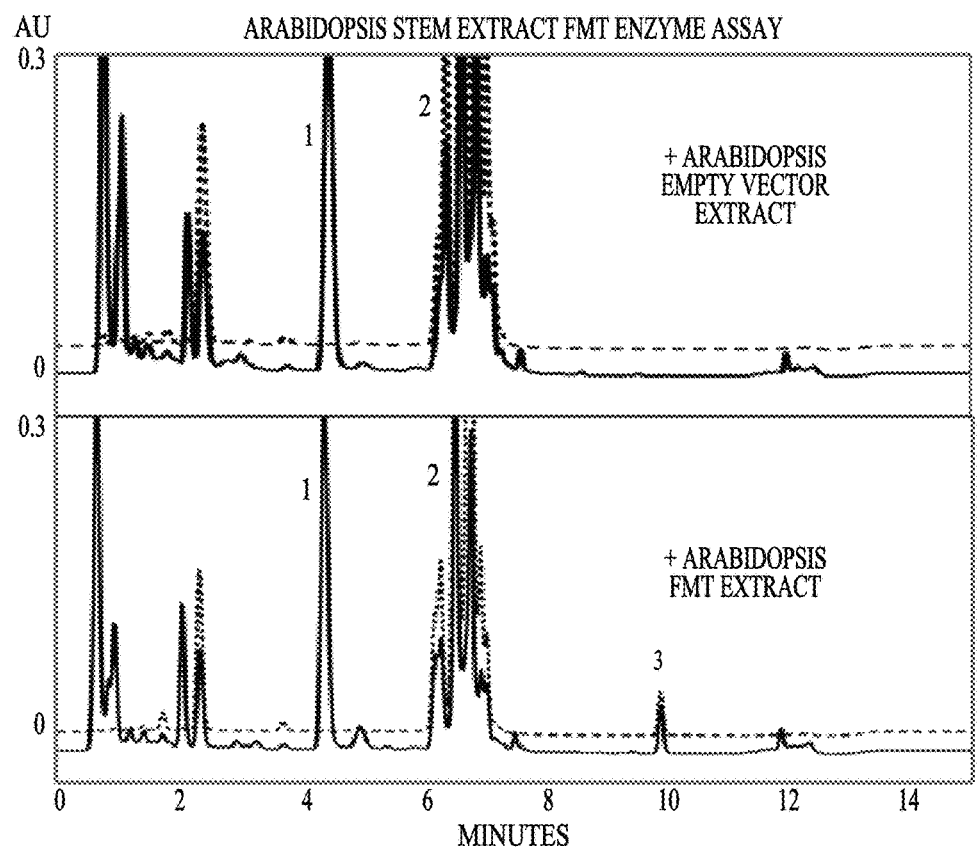

FIG. 11B shows representative UPLC traces illustrating FMT activity in ground stems from *Arabidopsis* transformed with the FMT from *Angelica sinensis* (see, bottom panel). The absorbance for each of the substrates, coniferyl alcohol (1) and feruloyl-CoA (2) and for the product, coniferyl ferulate (3), was detected at 280 nm (solid line) and at 340 nm (dotted line). The top panel of FIG. 11B shows the results of control reactions of stems transformed with empty vector (top panel). Coniferyl ferulate (3) is detected only when protein from the transformed *Arabidopsis*-FMT stems was added.

These data indicate that plants can readily be transformed with the *Angelica sinensis* nucleic acids described herein and such transformed plants can readily express an enzymatically active feruloyl-CoA:monolignol transferase that incorporates monolignol ferulates such as coniferyl ferulate into plant tissues.

EXAMPLE 5

Isolation of *Hibiscus cannabinus* (Kenaf) FMT

This Example illustrates isolation of the *Hibiscus cannabinus* (Kenaf) feruloyl-CoA:monolignol transferase nucleic acids and expression of an enzymatically active FMT.

Materials and Methods

*Hibiscus cannabinus* (Kenaf) stem sections were collected and stored in RNAlater (Qiagen) until processing. The tissue was then removed from the RNAlater solution and ground to a powder in liquid nitrogen. Total RNA was extracted by adding 100 mg of powdered *Hibiscus cannabinus* stem sections to 1 ml Trizol buffer (Invitrogen) and incubating for 15 minutes while vortexing at room temperature. One-fifth volume of chloroform was added and the mixture was incubated for an additional 15 minutes. After centrifugation at 15000×g for 35 minutes at 4° C., the aqueous phase was extracted with ⅕ volume of chloroform. Total RNA was precipitated from the aqueous phase by adding ⅕ volume of a solution containing 1 M sodium chloride and 0.8 M sodium citrate and ⅕ volumes of isopropyl alcohol. The RNA was collected by centrifugation at 12,000×g and the pellet was washed in 70% ethanol, dried and dissolved in RNase-free water. Residual DNA was removed by DNase digestion using the RNase-free DNase Kit (Qiagen), following manufacturer's guidelines. RNA quality was assessed using an Agilent 2100 Bioanalyzer. Total RNA from *Hibiscus cannabinus* was submitted to the Genomics Core at Michigan State University for Roche 454 sequencing using the 454 GSFLX Titanium Sequencer.

Candidate Selection

Ferulate monolignol transferase (FMT) candidates were chosen from the Kenaf_CLC 454 sequencing database by searching for "transferase family proteins" that have no close homologs in *Arabidopsis thaliana*. The two candidates with the largest number of EST sequences were amplified and cloned.

Cloning of *Hibiscus cannabinus* FMT cDNA was synthesized from the *Hibiscus cannabinus* stem sections total RNA, using Superscript III Reverse Transcriptase (Invitrogen). After DNase digestion, 5 μg of total RNA was added to 0.5 μg Oligo d(T)$_{12\text{-}18}$, 10 nM dNTP mix (Invitrogen) and DEPC water to a volume of 13 μL. The reaction mixture was incubated at 65° C. for 5 minutes. After cooling the sample on ice for 2 minutes, 4 μL of 5× First-strand Buffer, 100 nM DTT, 40 units RNase OUT and 200 units Superscript III Reverse Transcriptase (Invitrogen) were added and incubated at 50° C. for 60 minutes. The reaction was inactivated by heating to 70° C. for 15 minutes and stored on ice. The *Hibiscus cannabinus* FMT coding sequence was amplified using 5′-AAAAAAGCAGGCT-TCATGGCAACCCACAGCACTATCAT-3′ (SEQ ID NO:10) and 5′-GTACAAGAAAGCTGGGTTCTAGAT-CACTAGAGCATCGCCGG-3′ (SEQ ID NO:11) oligonucleotides (Integrated DNA Technologies) as forward and reverse gene specific primers with partial Gateway attB1 and attB2 attachment sites. Using the Platinum Pfx DNA Polymerase kit (Invitrogen), 2 μL 10× Pfx Amplification Buffer, 7.5 nM dNTP mix, 25 nM magnesium sulfate, 10 mM of each primer, 2.5 units of Plantinum Pfx DNA Polymerase and deionized water to a final volume of 20 μL was added to 200 ng cDNA. The sample was denatured at 94° C. for 4 minutes, followed by 25 cycles of 94° C. for 30 seconds, 52° C. for 30 seconds, and 68° C. for 2 minutes. After a cooling the sample to 4° C., a second PCR reaction was completed, as described above with a 55° C. annealing temperature, using 5′-GGGG ACA AGT TTG TAC AAA AAA GCA GGC T-3′ (SEQ ID NO:12) and 5′-GGG AC CAC TTT GTA CAA GAA AGC TGG GT-3′ (SEQ ID NO:13) oligonucleotides (Integrated DNA Technologies) as forward and reverse primers and 2.5 μL of the first PCR reaction to add full length Gateway attB1 and attB2 attachment sites to the coding sequence. After amplification, the reaction was analyzed by electrophoresis on a 0.8% agarose gel and the PCR product was purified using the QIAquick Gel Extraction Kit (Qiagen), following manufacturer's guidelines.

The amplified FMT coding sequence was cloned into the Gateway entry vector pDONR221 (Invitrogen) using the BP Clonase II Enzyme Mix (Invitrogen). After purification, 150 ng of PCR product was added to 150 ng of pDONR221 entry vector, to a final volume of 4 μL with Tris-EDTA (TE) buffer, and 1 μL BP Clonase II Enzyme Mix. The reaction was incubated overnight at room temperature, inactivated by adding 1 μg Proteinase K and incubating at 37° C. for 10 minutes. After cooling on ice, 2.5 μL of the reaction was used to transform One Shot Top 10 Chemically Competent *E. coli* Cells (Invitrogen) according to manufacturer's guidelines. The transformants were grown at 37° C. overnight on LB agar plates containing and 50 μg/ml Kanamycin. Single colonies were picked and grown in LB media containing 50 μg/ml Kanamycin overnight at 37° C. Plasmid DNA was purified from these cultures using the QIAprep Spin Miniprep Kit (Qiagen), according to manufacturer's guidelines. Samples were submitted for high throughput sequencing, using the M13 forward and M13 reverse primers (Invitrogen), along with 5′-CGCACTCGGTTTGTGATGGC-3′ (SEQ ID NO:14) and 5′-TTCACAGCTTTCGAGAGCG-GTC-3′ (SEQ ID NO:15) as two gene specific primers, at the Michigan State University Genomics Core. This sequence data was compared to the 454 sequencing data to verify coding sequence using DNASTAR Lasergene 8 Sequence Manager software.

The following were the *Hibiscus cannabinus* (Kenaf) nucleotide and protein sequences chosen for expression. Nucleotide sequence SEQ ID NO:8:

```
   1 ATGGCAACCC ACAGCACTAT CATGTTCTCA GTCGATAGAA
  41 ACGATGTCGT GTTTGTCAAA CCCTTCAAAC CTACACCCTC
  81 ACAGGTTCTA TCTCTCTCCA CCATCGACAA TGATCCCAAC
 121 CTTGAGATCA TGTGCCATAC TGTTTTTGTG TATCAAGCCA
 161 ATGCCGATTT CGATGTTAAG CCCAAGGATC CAGCTTCCAT
 201 AATCCAGGAA GCACTCTCCA AGCTCTTGGT TTATTACTAT
 241 CCCTTAGCGG GGAAGATGAA GAGGGAGACC GATGGAAAAC
 281 TTCGAATCGC TTGCACTGCC GACGATAGCG TGCCCTTCTT
 321 AGTAGCCACC GCCGATTGCA AGCTCTCGTC GTTGAACCAC
 361 TTGGATGGCA TAGATGTTCA TACCGGGAAA GAATTCGCCT
 401 TGGATTTTGC ATCCGAATCC GACGGTGGCT ATTATCACCC
 441 TCTGGTCATG CAGGTGACGA AGTTCATATG CGGAGGGTTC
 481 ACCATCGCTT TGAGTTTATC GCACTCGGTT TGTGATGGCT
 521 TCGGTGCAGC TCAGATCTTT CAAGCATTGA CCGAGCTCGC
 561 AAGTGGCAGG AACGAGCCCT CGGTTAAACC CGTGTGGGAG
 601 AGGCAACTAT TAGTGGCGAA ACCGGCCGAG GAAATCCCTC
 641 GGTCGATTGT CGATAAGGAC TTGTCGGCAG CTTCACCGTA
 681 TCTGCCGACA ACCGACATAG TCCATGCCTG CTTTTATGTA
 721 ACCGAGGAGA GTATAAAAAC ACTGAAAATG AATCTGATCA
 761 AAGAAAGCAA AGATGAGAGT ATAACCAGTC TCGAGGTCCT
 801 TTCAGCCTAT ATATGGAGAG CAAGGTTTAG AGCATTGAAA
 841 TTGAGTCCAG ATAAAACCAC AATGCTCGGC ATGGCCGTAG
 881 GCATACGACG CACCGTGAAA CCACGGTTGC CCGAAGGATA
 921 CTACGGGAAT GCTTTCACCT CGGCAAATAC GGCCATGACC
 961 GGGAAGGAAC TCGACCAAGG ACCGCTCTCG AAAGCTGTGA
1001 AACAAATCAA GGAGAGCAAA AAGCTTGCTT CGGAGAATGA
1041 CTATATCTGG AACTTGATGA GCATTAACGA GAAGCTGAGA
1081 GAACTGAATT CGAAGTTCGA AGCGGCCGCC GGTTCAACCA
1121 TGGTCATAAC AGATTGGAGG CGGTTGGGAC TATTGGAAGA
1161 TGTGGATTTT GGATGGAAAG GTAGCGTAAA CATGATACCA
1201 CTGCCGTGGA ACATGTTCGG GTACGTGGAT TTGGTTCTTT
1241 TATTGCCTCC TTGTAAACTG GACCAATCGA TGAAAGGCGG
1281 TGCTAGAGTG TTGGTTTCCT TTCCCACGGC TGCTATTGCC
1321 AAATTCAAGG AAGAAATGGA TGCTCTCAAA CATGATAACA
1361 AGGTTGCCGG CGATGCTCTA GTGATCTAG
```

The SEQ ID NO:8 nucleic acid encodes a *Hibiscus cannabinus* (Kenaf) feruloyl-CoA:monolignol transferase enzyme with the following amino acid sequence (SEQ ID NO:9).

```
  1 MATHSTIMFS VDRNDVVFVK PFKPTPSQVL SLSTIDNDPN
 41 LEIMCHTVFV YQANADFDVK PKDPASIIQE ALSKLLVYYY
 81 PLAGKMKRET DGKLRIACTA DDSVPFLVAT ADCKLSSLNH
121 LDGIDVHTGK EFALDFASES DGGYYHPLVM QVTKFICGGF
161 TIALSLSHSV CDGFGAAQIF QALTELASGR NEPSVKPVWE
201 RQLLVAKPAE EIPRSIVDKD LSAASPYLPT TDIVHACFYV
241 TEESIKTLKM NLIKESKDES ITSLEVLSAY IWRARFRALK
281 LSPDKTTMLG MAVGIRRTVK PRLPEGYYGN AFTSANTAMT
321 GKELDQGPLS KAVKQIKESK KLASENDYIW NLMSINEKLR
361 ELNSKFEAAA GSTMVITDWR RLGLLEDVDF GWKGSVNMIP
401 LPWNMFGYVD LVLLLPPCKL DQSMKGGARV LVSFPTAAIA
441 KFKEEMDALK HDNKVAGDAL VI
```

Sequences in entry vectors were inserted into pDEST17 vector using 150 ng of plasmid DNA from the Kenaf FMT entry clone, 150 ng of pDEST17 vector and 1 μL LR Clonase II Enzyme Mix. The reaction was incubated overnight at room temperature. Transformation of competent cells was completed as described above. Transformants were selected on LB agar plates containing 100 μg/ml Ampicillin. Clones were screened by PCR using Gotaq Hot Start Green Master Mix (Promega) by adding 10 μL of the 2× master mix to 10 mM of each gene specific primer with partial Gateway attB1 and attB2 attachment sites as described above, deionized water to final volume of 20 μL. This PCR reaction was denatured at 94° C. for 3 minutes then cycled 25 times through 94° C. for 30 seconds, 52° C. for 30 seconds, 72° C. for 2 minutes, with a final elongation step at 72° C. for 5 minutes before cooling to 4° C. Each reaction was analyzed by gel electrophoresis. Clones were then transformed into One Shot BL21 Chemically Competent *E. coli* Cells (Invitrogen), according to manufacturer's guidelines, for expression.

Expression of FMT in *E. coli*

Cultures of BL21 *E. coli* containing the Kenaf FMT in the expression vector, were grown at 37° C. overnight in 5 ml LB media containing 100 μg/ml ampicillin, then added to 500 ml of LB media containing 100 μg/ml ampicillin and grown to an OD600 of 0.3 to 0.4. The culture was then induced by adding 1 mM of Isopropyl β-$_D$-1-thiogalactopyranoside, IPTG, and incubated overnight at 18° C. Cells were harvested by centrifugation at 4° C. and pellets were stored at −80° C. The pellets were suspended in 10 ml of binding buffer, a solution containing 20 mM Tris-hydrochloride pH 8, 0.5 M sodium chloride, 1 mM 2-mercaptoethanol and cells were lysed using a French press. The extract was then centrifuged at 50,000×g for 30 minutes at 4° C. to separate soluble and insoluble protein fractions. The soluble protein fraction, supernatant, was collected and the insoluble protein fraction was suspended in 10 ml of suspension buffer. Both fractions were analyzed for expression on an SDS-PAGE gel.

Purification of *E. coli* Expressed FMT

HIS-tagged Kenaf FMT was purified using an AKTA purifier (GE Healthcare) operated with UNICORN 5.11—workstation version (GE Healthcare) and a protocol modified from the manufacturer's guidelines. Four 5 ml HiTrap Desalting columns (GE Healthcare) were equilibrated with binding buffer. A 5 ml aliquot of the soluble protein was injected onto the desalting column and eluted with binding buffer at a flow rate of 1 ml/minute. Fractions with the highest protein concentrations, as indicated by higher UV absorbance, were collected in 1 ml fractions. These fractions were applied to a 1 ml HisTrap HP column (GE Healthcare), conditioned and charged with 0.1 M $NiSO_4$ according to manufacturer's guidelines, at a flow rate of 0.1 ml/minute. The column was washed with 5 ml of buffer A (20 mM Tris-hydrochloride pH 8, 0.5 M sodium chloride, 1 mM 2-mercaptoethanol, and 20 mM imidazole) then bound protein was eluted at 1 ml/minute with a 20 ml linear gradient from buffer A to buffer B (20 mM Tris-hydrochloride pH 8, 0.5 M sodium chloride, 1 mM 2-mercaptoethanol, and 500 mM imidazole). Fractions containing protein were collected and analyzed by SDS-PAGE. Fractions with the highest concentration of Kenaf FMT were combined and desalted using an Amicon Ultracel 10K membrane filter (Millipore).

FMT Enzymatic Assay

The feruloyl CoA, p-coumaroyl CoA, and caffeoyl CoA substrates used in the FMT assay were enzymatically synthesized using the tobacco 4-coumarate CoA-ligase (4CL) with a c-terminal HIS tag in pCRT7/CT TOPO. Following a method modified from Beuerle and Pichersky (2001) 3.3 mg of ferulic acid, coumaric acid or caffeic acid, 2 mg coenzyme A, and 6.9 mg ATP were 50 mM Tris-hydrochloride pH 8, 2.5 mM magnesium chloride in a final volume of 10 ml. The reaction was started by adding 0.25 mg 4CL protein, purified as described by the method of Beurerle and Pichershy. After a five-hour incubation at room temperature, an additional 6.9 mg ATP, 2 mg coenzyme A, and 0.25 mg purified 4CL were added and the reaction was incubated overnight. The CoA esters were purified on an SPE cartridge as described in Beuerle and Pichersky (2001).

The FMT activity assay contained 100 mM sodium phosphate buffer pH 6, 1 mM dithiothreitol (DTT), 1 mM feruloyl CoA, 1 mM coniferyl alcohol, 0.5 µg of purified Kenaf FMT protein and deionized water to a volume of 50 µL. After a 45-minute incubation, 100 mM hydrochloric acid was added to stop the reaction. Because the product synthesized in the reaction, coniferyl ferulate (CAFA), is partially insoluble, 50 µL of methanol was added to solubilize the CAFA. Prior to UPLC, protein and insoluble material were removed by filtering through an Amicon Ultracel 10K membrane filter (Millipore). The flow-through was analyzed using an Acquity Ultra Performance LC with an Acquity UPLC BEH C18 1.7 µm 2.1×100 mm column and the Acquity Console and Empower 2 Software, all from Waters Corporation. The solvents used in this method were solvent A, 0.1% trifluoroacetic acid, and solvent B, 100% acetonitrile. Samples were analyzed using the following gradient conditions, 13% B, for 5 minutes, 1 minute linear gradient to 42% B, held for 4 minutes, 1 minute linear gradient to 100% B, held for 1 minute and 3 minutes at 13% B with a flow rate of 0.3 ml/minute. This method was then used to analyze a 10 µL injection of each assay reaction; standards for each of the substrates along with chemically synthesized CAFA were used to determine retention times for each compound.

Figure 12A:
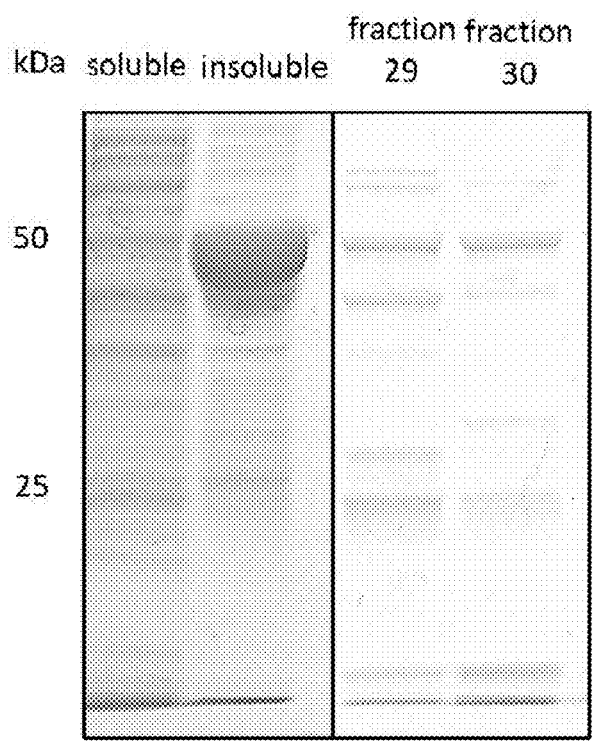
FIG. 12A-12B illustrate the expression, purification and enzyme activity for FMT from *Hibiscus cannabinus*.
Figure 12B:
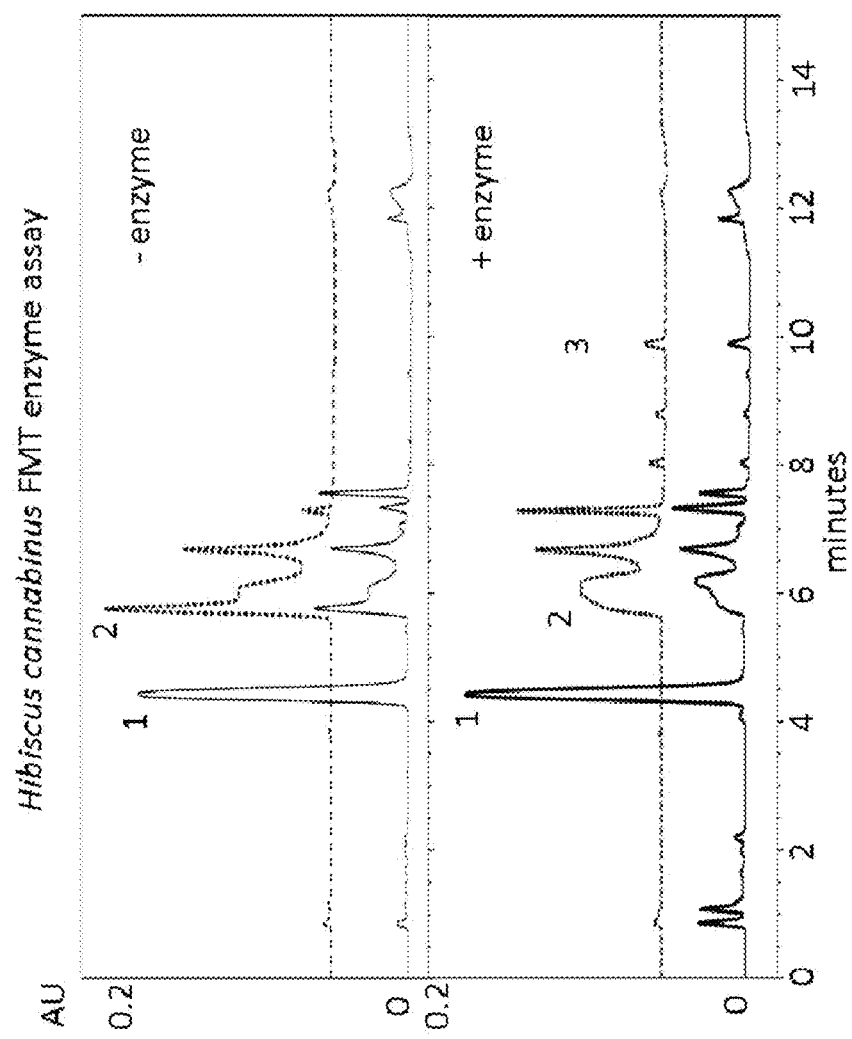

FIGS. 12A and 12B illustrate the expression, purification and enzyme activity for FMT from *Hibiscus cannabinus*. FIG. 12A shows that the *Hibiscus cannabinus* FMT is expressed in *E. coli* BL21 cells. The *Hibiscus cannabinus* FMT was expressed with an N-terminal 6×His tag in the pDEST17 vector (Invitrogen) and the soluble protein (~50 kDa) was purified over a $Ni^{2+}$ column using an AKTA purifier (GE Healthcare).

Fractions 29 and 30 from the $Ni^{2+}$ column that contained purified protein were assayed for FMT activity. FIG. 12B shows the products of an FMT enzyme assay of fractions 29 and 30 after UPLC separation. The products of the FMT enzyme assay were detected by absorbance at 280 nm (solid line) and 340 nm (dotted line) for the substrates coniferyl alcohol (1) and feruloyl-CoA (2). A control reaction with no enzyme is shown at the top of FIG. 12B. The products of the assay containing the *Hibiscus cannabinus* FMT enzyme are shown in the bottom panel of FIG. 12B. The production of coniferyl ferulate (3) is visible only when the *Hibiscus cannabinus* FMT enzyme was present in the assay (bottom panel). The product and substrate peaks were identified by comparison to synthetic standards.

FIG. 13 shows an alignment of the *Hibiscus cannabinus* and *Angelica sinensis* feruloyl-CoA:monolignol transferase sequences. As illustrated, the *Hibiscus cannabinus* and *Angelica sinensis* feruloyl-CoA:monolignol transferases share only about 23% sequence identity. When similar amino acid substitutions are considered, the *Hibiscus cannabinus* and *Angelica sinensis* feruloyl-CoA:monolignol transferases share only about 41% sequence similarity.

EXAMPLE 6

Isolation of p-Coumarate Monolignol Transferase from Rice

This Example illustrates isolation of the *Oryza sativa* (rice) p-coumarate monolignol transferase (PMT) nucleic acids and expression of an enzymatically active PMT enzyme.

Materials and Methods

Gene Synthesis—A PMT nucleic segment from *Oryza sativa* was synthesized and cloned into the entry vector pENTR221 (Invitrogen). The coding region of the *Oryza sativa* p-coumaroyl-CoA:monolignol transferase has the following nucleic acid sequence (SEQ ID NO:16).

```
  1  ATGGGGTTCG CGGTGGTGAG GACGAACCGG GAGTTCGTGC
 41  GGCCGAGCGC GGCGACGCCG CCGTCGTCCG GCGAGCTGCT
 81  GGAGCTGTCC ATCATCGACC GCGTGGTGGG GCTCCGCCAC
121  CTGGTGCGGT CGCTGCACAT CTTCTCCGCC GCCGCCCCGA
161  GCGGCGGCGA CGCCAAGCCG TCGCCGGCGC GGGTGATCAA
201  GGAGGCGCTG GGGAAGGCGC TGGTGGACTA CTACCCGTTC
241  GCGGGGAGGT TCGTGGACGG CGGCGGCGGG CCGGGGAGCG
281  CCCGCGTGGA GTGCACCGGC GAGGGCGCCT GGTTCGTGGA
321  GGCCGCCGCC GGCTGCAGCC TCGACGACGT GAACGGCCTC
361  GACCACCCGC TCATGATCCC CGAGGACGAC CTCCTCCCCG
401  ACGCCGCCCC CGGTGTCCAC CCCCTCGACC TCCCCCTCAT
441  GATGCAGGTG ACGGAGTTCA GTTGCGGAGG GTTCGTGGTG
481  GGCCTGATCT CGGTGCACAC GATGGCGGAC GGGCTAGGGG
521  CCGGGCAGTT CATCAACGCG GTGGGCGACT ACGCCCGCGG
561  GCTGGACAGG CCGAGGGTGA GCCCGGTCTG GGCCCGCGAG
601  GCCATCCCGA GCCCGCCGAA GCTGCCCCCG GGCCCGCCGC
```

```
-continued
 641  CGGAGCTGAA GATGTTCCAG CTCCGCCACG TCACCGCCGA

681  CCTGAGCCTG GACAGCATCA ACAAGGCCAA GTCCGCCTAC

721  TTCGCCGCCA CCGGCCACCG CTGCTCCACC TTCGACGTCG

761  CCATCGCCAA GACGTGGCAG GCGCGCACCC GCGCGCTCCG

801  CCTCCCGGAA CCCACCTCCC GCGTCAACCT CTGCTTCTTC

841  GCCAACACCC GCCACCTCAT GGCCGGCGCC GCCGCCTGGC

881  CCGCACCCGC CGCCGGCGGC AATGGCGGCA ATGGGTTCTA

921  CGGCAACTGC TTCTACCCGG TGTCGGTGGT GGCGGAGAGC

961  GGGGCGGTGG AGGCGGCGGA CGTGGCCGGG GTGGTGGGGA

1001  TGATACGGGA GGCGAAGGCG AGGCTGCCGG CGGACTTCGC

1041  GCGGTGGGCG GTGGCCGACT TCAGGGAGGA TCCGTACGAG

1081  CTGAGCTTCA CGTACGATTC CCTGTTCGTC TCCGACTGGA

1121  CGCGGCTGGG GTTCCTGGAG GCGGACTACG GGTGGGGGCC

1161  GCCGTCGCAC GTCATACCCT TCGCGTACTA CCCGTTCATG

1201  GCCGTCGCCA TCATCGGCGC GCCGCCGGTG CCCAAGACCG

1241  GCGCCCGGAT CATGACGCAG TGCGTCGAGG ACGACCACCT

1281  GCCGGCGTTC AAGGAGGAGA TCAAGGCCTT CGACAAGTAA
```

This Oryza sativa p-coumaroyl-CoA:monolignol transferase nucleic acid encodes the following amino acid sequence (SEQ ID NO:17).

```
  1  MGFAVVRTNR EFVRPSAATP PSSGELLELS IIDRVVGLRH

41  LVRSLHIFSA AAPSGGDAKP SPARVIKEAL GKALVDYYPF

81  AGRFVDGGGG PGSARVECTG EGAWFVEAAA GCSLDDVNGL

121  DHPLMIPEDD LLPDAAPGVH PLDLPLMMQV TEFSCGGFVV

161  GLISVHTMAD GLGAGQFINA VGDYARGLDR PRVSPVWARE

201  AIPSPPKLPP GPPPELKMFQ LRHVTADLSL DSINKAKSAY

241  FAATGHRCST FDVAIAKTWQ ARTRALRLPE PTSRVNLCFF

281  ANTRHLMAGA AAWPAPAAGG NGGNGFYGNC FYPVSVVAES

321  GAVEAADVAG VVGMIREAKA RLPADFARWA VADFREDPYE

361  LSFTYDSLFV SDWTRLGFLE ADYGWGPPSH VIPFAYYPFM

401  AVAIIGAPPV PKTGARIMTQ CVEDDHLPAF KEEIKAFDK
```

An expression vector containing an N-terminal 6×His tag was made by incorporating OsPMT (SEQ ID NO:16) into pDEST17 (Invitrogen) using Invitrogen's Gateway cloning technology, according to manufacturer's guidelines.

Expression of OsPMT in *E. coli*, and Purification—Cultures of BL21 cells (Invitrogen) containing the OsPMT expression vector were grown to an $OD_{600}$ between 0.4 and 0.5, cooled to 18° C., and expression was induced by adding isopropyl β-D-1-thiogalactopyranoside (IPTG; Roche). After 18-h (overnight) incubation at 18° C., cells were harvested by centrifugation and frozen at −80° C. The pellets from a 1 L culture were suspended in 20 ml of binding buffer (20 mM Tris-hydrochloride pH 8, 0.5 M sodium chloride, 1 mM 2-mercaptoethanol), and cells were lysed using a French pressure cell press. The extract was then centrifuged at 50,000×g for 30 min at 4° C. to separate soluble and insoluble protein fractions. Soluble protein was collected and the pellet was suspended in 10 ml of 20 mM pH 8 Tris-hydrochloride. Both fractions were analyzed for expression on an SDS-PAGE gel by comparing bands of the expected molecular weight from an uninduced culture to the induced culture.

His-tagged OsPMT was purified by IMAC using an AKTA purifier (GE Healthcare) operated with UNICORN 5.11 workstation (GE Healthcare) and a protocol modified from the manufacturer's guidelines. Four stacked 5 ml HiTrap desalting columns (GE Healthcare) were equilibrated with binding buffer. A 5 ml aliquot of the soluble protein was injected onto the desalting column and eluted with binding buffer at a flow rate of 1 ml/min. Fractions with the highest protein concentrations, as indicated by UV absorbance, were collected in 1 ml fractions. These combined fractions were applied to a 1 ml HisTrap HP column (GE Healthcare), charged with $Ni^{2+}$ and conditioned with binding buffer, at a flow rate of 0.2 ml/min. The column was washed with 5 ml of buffer A (20 mM Tris-hydrochloride pH 8, 0.5 M sodium chloride, 1 mM 2-mercaptoethanol, and 20 mM imidazole) then bound protein was eluted at 1 ml/min over a 20 ml linear gradient from buffer A to buffer B (20 mM Tris-hydrochloride pH 8, 0.5 M sodium chloride, 1 mM 2-mercaptoethanol, and 500 mM imidazole). Fractions containing protein were collected and analyzed by SDS-PAGE; bands of the expected size were extracted from the SDS-PAGE gel and sent to the MSU Proteomics Core for in-gel trypsin digestion followed by LCMS/MS. Peptides were searched against the *Oryza sativa* genome database (NCBI), and identified by Mascot. IMAC fractions with the highest concentration of OsPMT were combined and further purified by size-exclusion chromatography using a Superdex 75 10/300 GL gel filtration column (GE Healthcare) and exchanged into a pH 6 buffer containing 100 mM sodium phosphate. Protein samples were concentrated to 1 µg/µl in 100 mM sodium phosphate pH 6 containing 100 ng/µl BSA (NEB) and a complete mini EDTA-free protease inhibitor tablet (Roche) using an Amicon Ultracel 10K membrane filter (Millipore).

Enzyme Activity Assay—The CoA thioesters, p-coumaroyl-CoA 2a, caffeoyl-CoA 2b, and feruloyl-CoA 2c, for use as substrates in the OsPMT enzyme assay, were synthesized using the tobacco 4-coumarate CoA-ligase (4CL) with a C-terminal His tag in the vector pCRT7/CT TOPO via the following reaction.

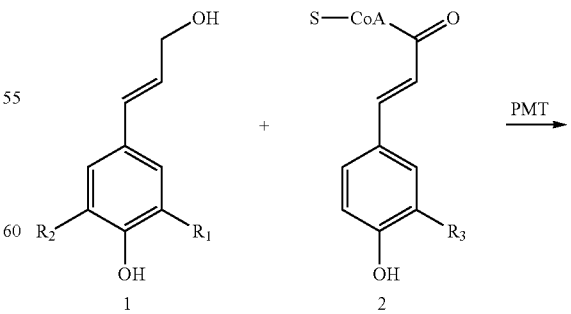

-continued

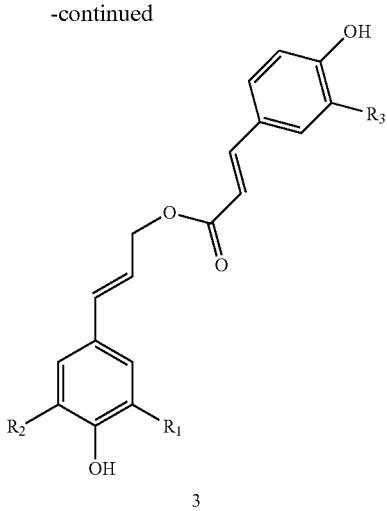

3 wherein $R_1$ and $R_2$ are separately hydrogen, hydroxy, or alkoxy (e.g., O—$CH_3$).

The different compounds are identified by number as relating to compound 1, 2 or 3 with the following symbols for substituents:

H means that $R_1$ and $R_2$ are hydrogen;
C means that $R_1$ is OH and $R_2$ is hydrogen;
G means that $R_1$ is O—$CH_3$ and $R_2$ is hydrogen;
S means that $R_1$ and $R_2$ are O—$CH_3$;
a means that $R_3$ is hydrogen;
b means that $R_3$ is hydroxy; and
c means that $R_3$ is O—$CH_3$.

Compounds relating to compound 1 include:
$1_H$ is p-coumaryl alcohol;
$1_C$ is caffeyl alcohol;
$1_G$ is coniferyl alcohol; and
$1_S$ is sinapyl alcohol.

Compounds relating to compound 2 include:
$2_a$ is p-coumaroyl-CoA;
$2_b$ is caffeoyl-CoA; and
$2_c$ is feruloyl-CoA;

Compounds relating to compound 3 include:
$3_{Hc}$ is p-coumaryl ferulate;
$3_{Hb}$ is p-coumaryl caffeate;
$3_{Ha}$ is p-coumaryl p-coumarate;
$3_{Ca}$ is caffeyl p-coumarate;
$3_{Cb}$ is caffeyl caffeate;
$3_{Cc}$ is caffeyl ferulate;
$3_{Ga}$ is coniferyl p-coumarate;
$3_{Gb}$ is coniferyl caffeate;
$3_{Gc}$ is coniferyl ferulate;
$3_{Sa}$ is sinapyl p-coumarate;
$3_{Sb}$ is sinapyl caffeate; and
$3_{Sc}$ is sinapyl ferulate.

The CoA thioesters, p-coumaroyl-CoA 2a, caffeoyl-CoA 2b, and feruloyl-CoA 2c were purified using Sep-pak cartridges (Waters) following a method modified from Beuerle & Pichersky (*Anal. Biochem.* 302:305-312 (2002)). The concentration for each CoA thioester was calculated based on its absorbance maximum and extinction coefficient. Ferulic acid, caffeic acid and p-coumaric acid were purchased from Sigma-Aldrich. Purified CoA thioesters were analyzed for purity using an Acquity Ultra Performance LC with an Acquity UPLC BEH C18 (1.7 µm 2.1×100 mm) column and the Acquity Console and Empower 2 Software (Waters Corporation).

Authentic coniferyl p-coumarate 3Ga and sinapyl p-coumarate 3Sa were synthesized as described by Lu & Ralph (J. Agr. Food Chem. 46: 2911-2913 (1998)). p-Coumaryl p-coumarate 3Ha was made by an analogous route (see, id.).

The OsPMT enzyme activity assay, in 50 mM pH 6 sodium phosphate buffer containing 1 mM dithiothreitol (DTT), 1 mM CoA thioester, 1 mM monolignol, and deionized water to produce a final volume of 50 µL, was initiated by adding of 1 µg of purified PMT protein in 1×BSA (NEB). After a 30-min. incubation, the reaction was stopped by the addition of 100 mM hydrochloric acid.

Reaction products were solubilized by adjusting the solution to 50% methanol. An identical assay with no enzyme added was performed for every reaction. Protein was removed by filtering through an Amicon Ultracel 10K membrane filter (Millipore) and the flow-through was analyzed by ultraperformance liquid chromatography (UPLC). The solvents used in this method were: solvent A, 0.1% trifluoroacetic acid, and solvent B, 100% acetonitrile. Samples were analyzed using a method with an initial concentration of 10% B, followed by a 15 minute linear gradient to 60% B, held for 1 minute, then a 1 minute linear gradient to 100% B, held for 1 minute, and a 1 minute linear gradient to the initial 10% B, held for 2 minutes, with a constant flow rate of 0.3 ml/minute. Eluting compounds were detected at 280 nm and 340 nm. Enzyme activity was also determined for the reverse reaction, using authentic sinapyl p-coumarate 3Sa or p-coumaryl p-coumarate 3Ha and coenzyme-A as substrates, with all other assay conditions as mentioned above. Standards for each of the substrates along with chemically synthesized standards of each monolignol conjugate 3 were used to determine retention times for each compound and identify HPLC chromatogram peaks. Crude reaction products isolated from the enzymatic reaction of sinapyl alcohol 1S and p-coumaroyl-CoA 2a, catalyzed by PMT, were identified by comparison with the synthetic standard peaks in proton NMR spectra and matching correlations in 2D COSY NMR spectra.

1D Proton & 2D COSY NMR—NMR spectra of synthesized compounds and the crude reaction products from PMT reactions, dissolved in acetone-$d_6$, were acquired using standard pulse experiments and conditions on a Bruker Biospin (Billerica, Mass.) AVANCE 500 (500 MHz) spectrometer fitted with a cryogenically cooled 5-mm TCI gradient probe with inverse geometry (proton coils closest to the sample). Spectral processing used Bruker's Topspin 2.1 software. The central solvent peaks were used as internal reference [δH/δC 2.04/29.8]. Standard Bruker implementations were used for one- and two-dimensional [gradient-selected multiple-quantum-filtered correlation spectroscopy (COSY), Bruker pulse program 'cosygpmfqf' with gradients strengths (ratio 16:12:40) selected for a double quantum filter] spectra. HSQC and HMBC experiments were also used as usual for routine structural assignments of synthesized compounds. The COSY experiments shown in FIG. 18 used the following parameters: acquired from 10 to 0 ppm in both dimensions, in F2 (1H) with 2 k data points (acquisition time 205 ms), and in F1 (1H) with 256 increments (F1 acquisition time 25.6 ms) of 1 scan (for standards) or 4 scans for the crude PMT product, with a 1 second inter-scan delay. Processing used simple unshifted sine-bell apodization in both dimensions and benefited from one level of linear prediction (32 coefficients) in F1.

Kinetics—Kinetic analyses were performed using an assay modified from Santoro et al. (Anal. Biochem. 354: 70-77 (2006)). The standard 100 µL reaction mixture contained 50 mM sodium phosphate pH 6, 2 mM 5,5'-dithiobis- (2-nitrobenzoic acid) (DTNB), 0.01-1 mM CoA thioester substrate, and 0.005-1.0 mM monolignol alcohol substrate and initiated by adding 100 ng of purified OsPMT protein in 1×BSA (NEB). The CoA thioester substrates included p-coumaroyl-CoA 2a and caffeoyl-CoA 2b, and the monolignol substrates included sinapyl alcohol 1S and p-coumaryl alcohol 1H. Enzyme activity was measured as an increase in CoASH, detected with DTNB at $A_{412}$, which is released as a result of monolignol conjugate synthesis (id.). The absorbance was measured every three min. for 40 min on a Spectramax Plus microplate reader using Softmax Pro 5.3 (Molecular Devices). The reactions were stopped by adding hydrochloric acid to a concentration of 100 mM, and then solubilized by adding methanol to 50%. Aliquots of 10 µL from each assay were analyzed via UPLC to verify product production. A standard curve was created for each CoA thioester from triplicate assays of five concentrations from 50 nM to 1 mM of coenzyme-A. Each reaction contained the same buffer and DTNB concentrations as the kinetic assays, along with 0.5 mM of a CoA thioester (p-coumaroyl-CoA 2a, caffeoyl-CoA 2b, or feruloyl-CoA 2c). The equation derived from fitting this standard curve was used to calculate the quantity (moles) of product synthesized in the assay. Kinetic parameters, Vmax and Km, were calculated using a nonlinear regression by entering the reaction rate and substrate concentration into the program R64, version 2.12.0 (Team, R. D. C., *R: A language and environment for statistical computing*, R Foundation for Statistical Computing, Vienna, Austria (2010).

Results

Figure 16:
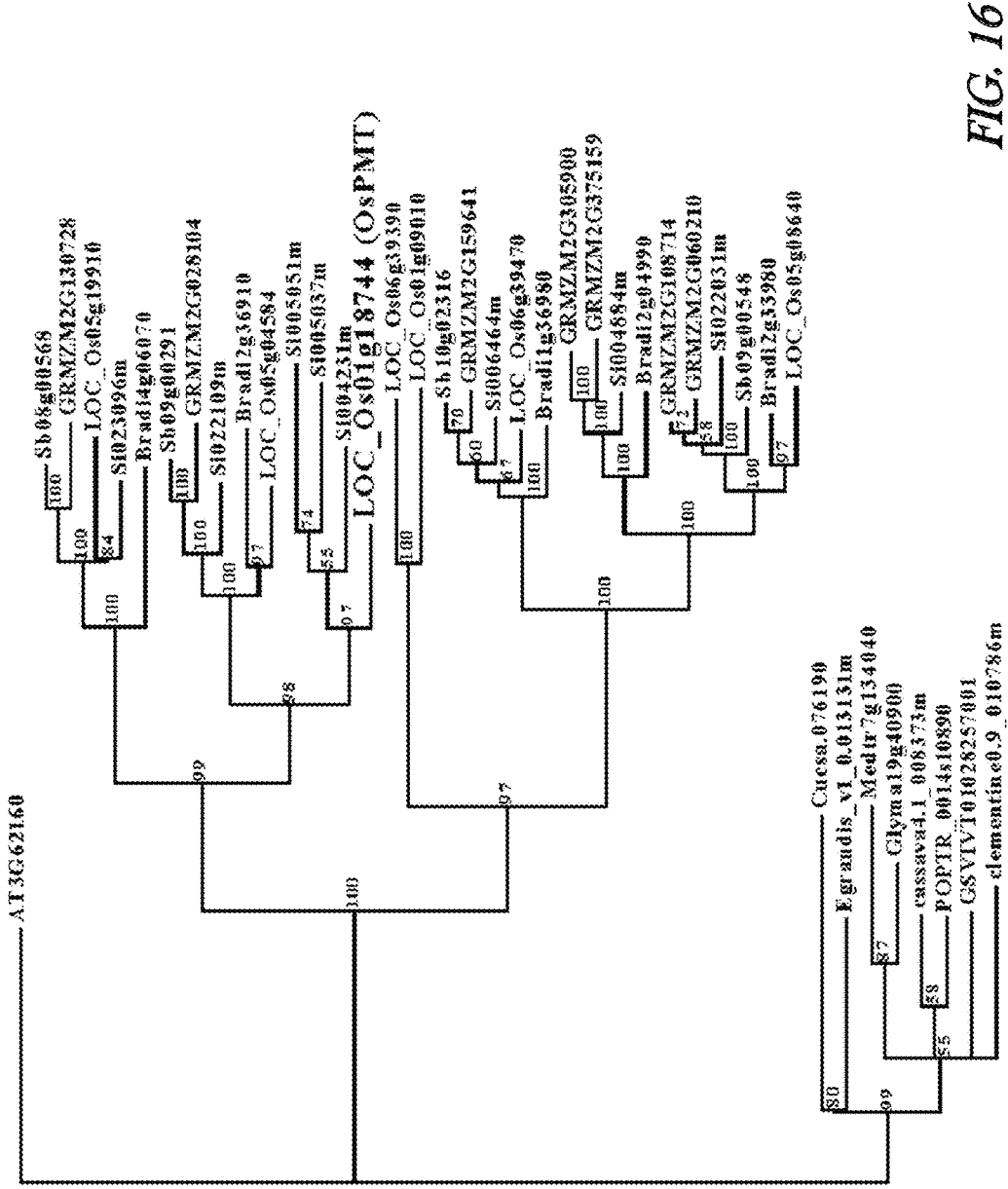
FIG. 16 shows a phylogenetic tree of HxxxD acyltransferases related to the rice p-coumaroyl-CoA: monolignol transferase (OsPMT1) gene. Angiosperm sequences related to OsPMT (bold) were obtained using Phytozome 7 and aligned using the multiple sequence alignment program MUSCLE 3.8.31. The resulting alignment was input into the program TREEPUZZLE 5.2 with default settings to produce a phylogenetic tree. A dendrogram was produced using the program Dendroscope (Ouyang et al., Nucleic Acids Research 35, D883-D887 (2007); Edgar, BMC Bioinformatics 5: 113 (2004); Schmidt et al., Bioinformatics 18(3): 502-504 (2002); Huson et al., Bioinformatics 8: 460 (2007); Mitchell et al., Plant Physiol. 144(1): 43-53 (2007).

Identification of a Candidate Gene—The most likely class of enzymes to catalyze acylation of monolignols with p-coumarate belong to the BAHD-acyltransferases, currently referred to as HxxxD-acyltransferases, as they catalyze many similar reactions. As p-coumaroylation is a distinctive feature of grass lignins, the inventors reasoned that a grass specific HxxxDacyltransferase that is co-expressed with genes involved in monolignol biosynthesis would be a good candidate for the enzyme responsible for acylation of monolignols. The RiceXPro database version 1.5 co-expression tool (ricexpro.dna.affrc.go.jp) at the National Institute of Agrobiological Sciences Genome Resource Center (Ibaraki, Japan) was used to identify HxxxD acyltransferases co-expressed with each of the three 4CL genes in rice (Sato et al., BMC Plant Biology 11:10 (2011); Sato et al., Nuc. Acids Res. 39: D1141-D1148 (2011)). The 4CL enzyme is required for the synthesis of lignin monomers, and the most highly correlated gene with 4CL (Os08g0245200) is Os01g18744, an HxxxDacyltransferase hereafter referred to as OsPMT (or simply as PMT). Closely related sequences were obtained from plant species having sequenced genomes using the Phytozome 7 locus keyword search feature (Ouyang et al., Nucleic Acids Research 35, D883-D887 (2007). These sequences were aligned using the program MUSCLE and generated a phylogenetic tree with the program TREEPUZZLE (Edgar, *BMC Bioinformatics* 5: 113 (2004); Schmidt et al., *Bioinformatics* 18(3): 502-504 (2002)). Trees were displayed using the program Dendroscope (Huson et al., *Bioinformatics* 8: 460 (2007)). The tree shown in FIG. 16 indicates that OsPMT is in a grass specific group (Mitchell et al., Plant Physiol. 144(1): 43-53 (2007)). As OsPMT is a grass-specific HxxxD-acyltransferase co-expressed with 4CL, this gene was chosen for further study.

Figure 17A:
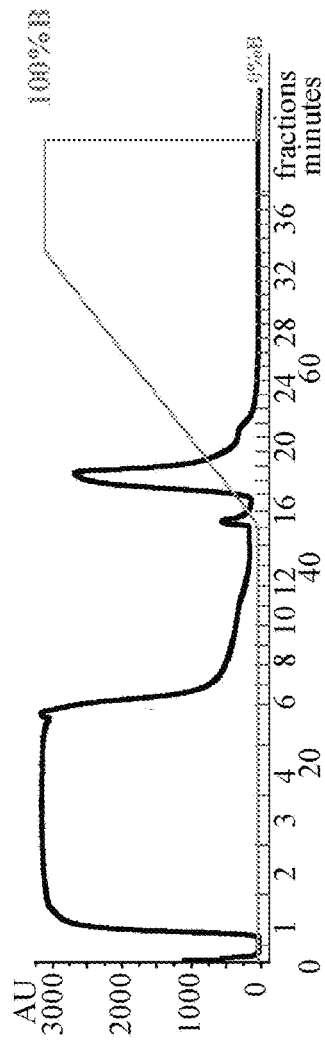
FIG. 17A-B illustrate heterologous expression of the rice p-coumaroyl-CoA: monolignol transferase in *E. coli*.

Expression of OsPMT in *E. coli*—A synthetic gene having the amino acid sequence for OsPMT but optimized for expression in *Escherichia coli* was synthesized and cloned into the Gateway entry vector pENTR221 (Invitrogen) by Blue Heron Bio (Bothell, Wash.). This OsPMT construct was used to create a plasmid that expressed a N-terminal His-tagged version of OsPMT in *E. coli* BL21 cells. Protein expression was induced by addition of IPTG for 18 h at 18° C. (FIG. 17). Soluble protein was purified using immobilized metal affinity chromatography (IMAC) followed by size exclusion chromatography (FIG. 17A).

Figure 17B:
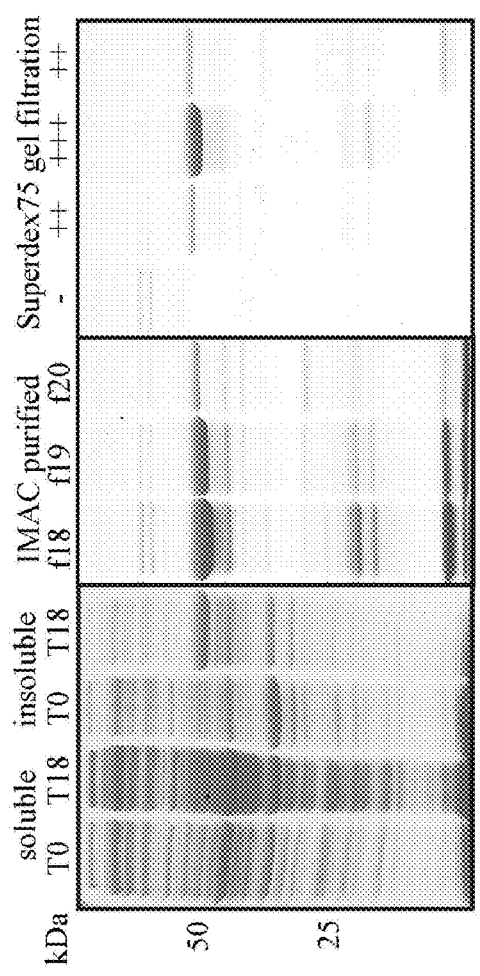

OsPMT protein expression and purification was monitored throughout this process by SDS-PAGE by following a protein near the expected molecular weight of 47 kDa (FIG. 17B). The identity of this protein was verified as OsPMT by LC-MS/MS on in-gel trypsin digested peptides. The additional bands present in the Superdex 75 fraction were identified as fragments of OsPMT by LC-MS/MS.

Figure 18A:
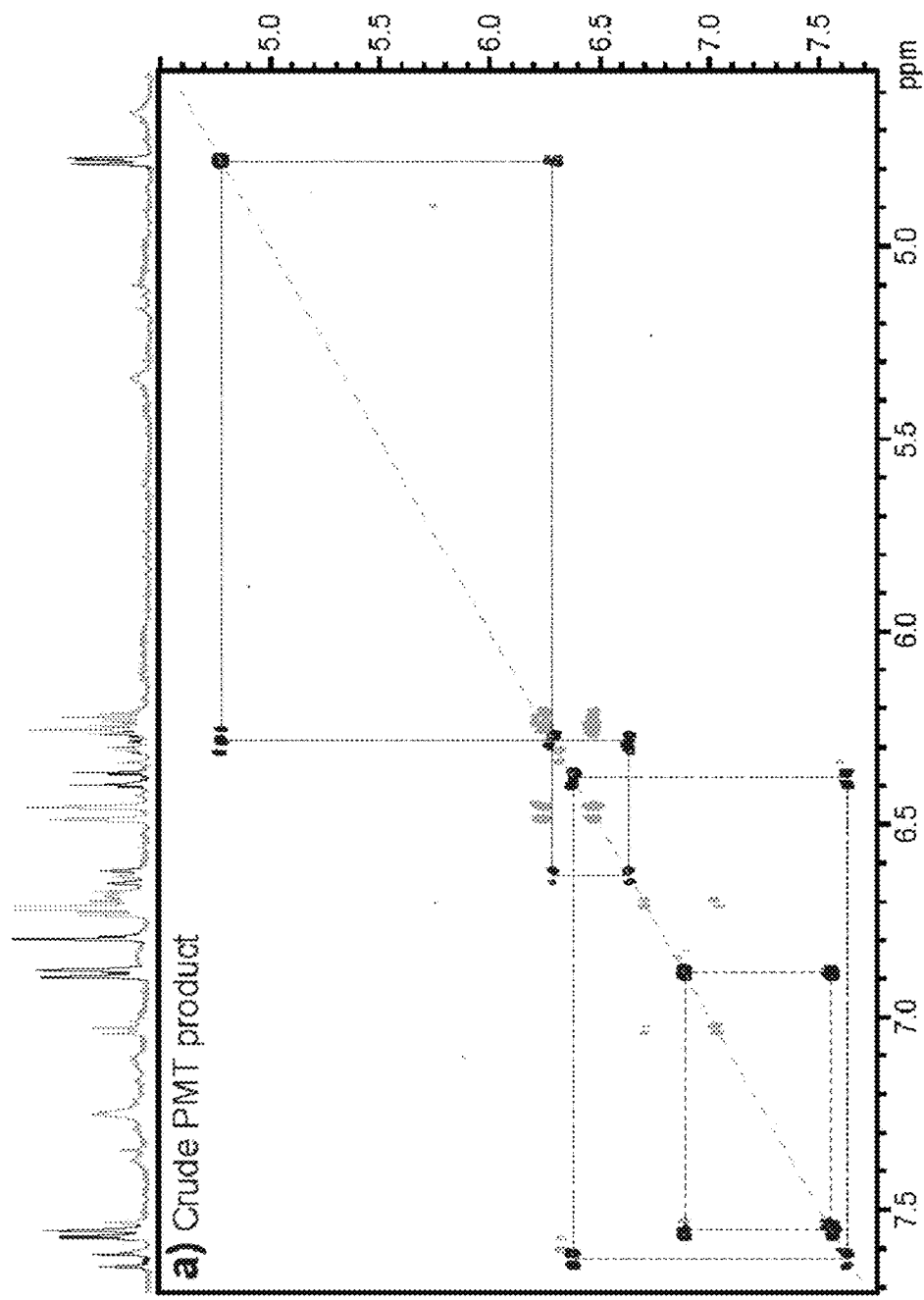
FIG. 18A-B illustrate that the PMT-catalyzed reaction between sinapyl alcohol 1S and p-coumaroyl-CoA 2a produced the sinapyl p-coumarate conjugate 3Sa as authenticated by 1D proton (horizontal projection) and 2D COSY NMR.
Figure 18B:
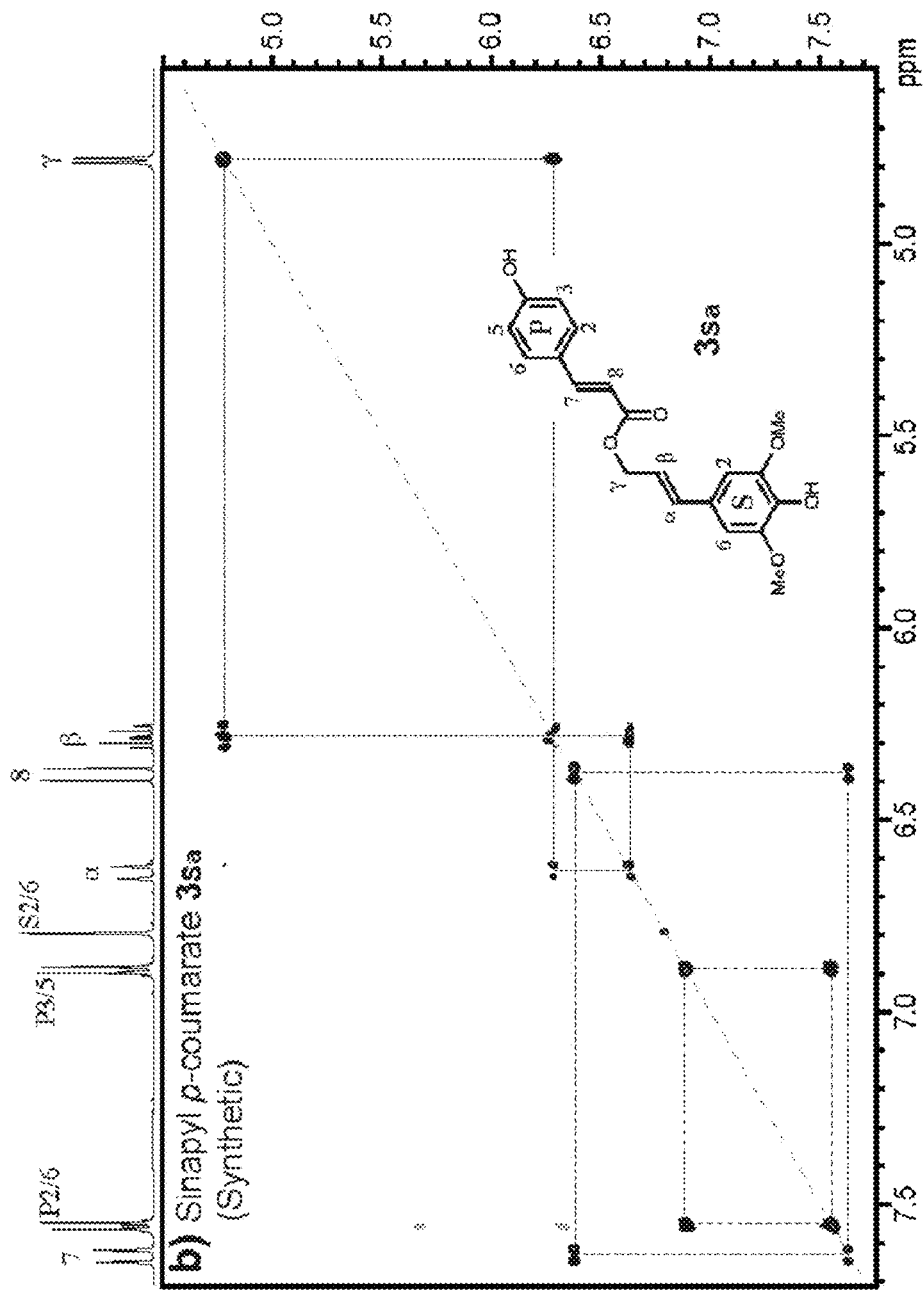

Determination of OsPMT Kinetic Parameters—Purified OsPMT produced a compound that eluted with authentic sinapyl p-coumarate 3Sa when incubated with sinapyl alcohol 1S and p-coumaroyl-CoA 2a. This activity followed the OsPMT protein during gel permeation chromatography as shown in FIG. 17A. The identity of the product was shown to be sinapyl p-coumarate 3Sa by NMR (FIG. 18). Enzyme substrate specificity was examined for the acyl donors: p-coumaroyl-CoA 2a, caffeoyl-CoA 2b, and feruloyl-CoA 2c, and the acyl acceptors p-coumaryl alcohol 1H, coniferyl alcohol 1G, and sinapyl alcohol 1S. Of the tested acyl donors p-coumaroyl-CoA 2a and caffeoyl-CoA 2b were good substrates while feruloyl-CoA 2c was a poor substrate (Table 1).

TABLE I

Kinetic data for OsPMT purified from *E. coli* extracts

| Varying Substrate | Saturating Substrate | $K_m \pm SE$ µM | $V_{max} \pm SE$ pkat mg$^{-1}$ | $K_{cat}$ sec$^{-1}$ |
|---|---|---|---|---|
| sinapyl alcohol 1S | p-coumaroyl-CoA 2a | 35 ± 5 | 10800 ± 351 | 0.51 |
| p-coumaroyl-CoA 2a | sinapyl alcohol 1S | 105 ± 12 | 12500 ± 417 | 0.60 |
| p-coumaryl alcohol 1H | p-coumaroyl-CoA 2a | 141 ± 14 | 54200 ± 2080 | 2.58 |
| p-coumaroyl-CoA 2a | p-coumaryl alcohol 1H | 281 ± 62 | 61500 ± 5300 | 2.93 |
| p-coumaroyl-CoA 2a | coniferyl alcohol 1G | NA | <2180 | NA |
| sinapyl alcohol 1S | caffeoyl-CoA 2b | 15 ± 2 | 8100 ± 244 | 0.39 |
| caffeoyl-CoA 2b | sinapyl alcohol 1S | 75 ± 5 | 7500 ± 150 | 0.36 |
| p-coumaryl alcohol 1H | caffeoyl-CoA 2b | 27 ± 6 | 5910 ± 399 | 0.28 |
| caffeoyl-CoA 2b | p-coumaryl alcohol 1H | 92 ± 11 | 8590 ± 309 | 0.41 |
| caffeoyl-CoA 2b | coniferyl alcohol 1G | NA | <2980 | NA |
| feruloyl-CoA 2c | sinapyl alcohol 1S | NA | <1230 | NA |
| feruloyl-CoA 2c | p-coumaryl alcohol 1H | NA | NA | NA |
| feruloyl-CoA 2c | coniferyl alcohol 1G | NA | NA | NA |

$K_m$ and $V_{max}$ data calculated from the mean of at least 3 replicates ± the standard error.
1 pkat = 1 pMol substrate sec$^{-1}$.
NA indicates parameters not calculated due to low activity The enzyme had the highest affinity for sinapyl alcohol 1S but the synthetic rate was 6 times higher with p-coumaryl alcohol 1H. Kinetic parameters for caffeyl alcohol 1C were not established due to its limited solubility. Caffeyl alcohol has never been found incorporated into monocot or dicot lignins, and has in fact only recently been identified in a softwood down-regulated in CCoAOMT (Wagner et al., *Plant J.* 67(1):119-29 (2011)). Too little activity was observed with feruloyl-CoA 2c or coniferyl alcohol 1G as the acceptors to obtain the Km for these compounds but an estimate was obtained of the maximum velocity. The activity measured with p-coumaroyl-CoA 2a or caffeoyl-CoA 2b as the acyl donor and coniferyl alcohol 1G as the receptor was also noticeably less than that of sinapyl alcohol 1S and p-coumaryl alcohol 1H. OsPMT was able to efficiently synthesize sinapyl p-coumarate 3Sa, p-coumaryl p-coumarate 3Ha, sinapyl caffeate 3Sb, and p-coumaryl caffeate 3Hb as measured by HPLC products from enzyme assay reactions (FIG. 19). Complete kinetic properties were determined for these substrates using a method modified from Santoro et al. (*Anal. Biochem.* 354: 70-77 (2006). Control reactions with no acyl donor substrate were run for each acyl acceptor and showed no OsPMT activity. These controls were repeated for each acyl donor substrate, containing no acyl acceptor, and also showed no activity. Reactions containing no enzyme produced no OsPMT activity (FIG. 19).

The kinetic properties indicate that OsPMT has similar affinity for sinapyl alcohol 1S and p-coumaryl alcohol 1H, shown by the very similar Km values; however, the reaction rates vary with the acyl donor. Although the Km for p-coumaroyl-CoA 2a and caffeoyl-CoA 2b are similar, the maximum reaction rate for p-coumaroyl-CoA 2a is at least 5-fold higher. OsPMT appears to synthesize primarily p-coumaryl p-coumarate 3Ha and sinapyl p-coumarate 3Sa. Based on the kinetic data, if p-coumaryl alcohol 1H is the more abundant monolignol, p-coumaryl p-coumarate 3Ha will be produced. If sinapyl alcohol 1S concentrations are greater or similar, the enzyme will produce sinapyl p-coumarate 3Sa. Therefore, the transferase enzyme OsPMT expressed in *E. coli* was shown to catalyze transesterification reactions between monolignols 1 and p-coumaroyl-CoA 2a, producing primarily monolignol p-coumarates where $R_1$ and $R_2$ are separately hydrogen, hydroxy, or alkoxy (e.g., O—$CH_3$), as illustrated below.

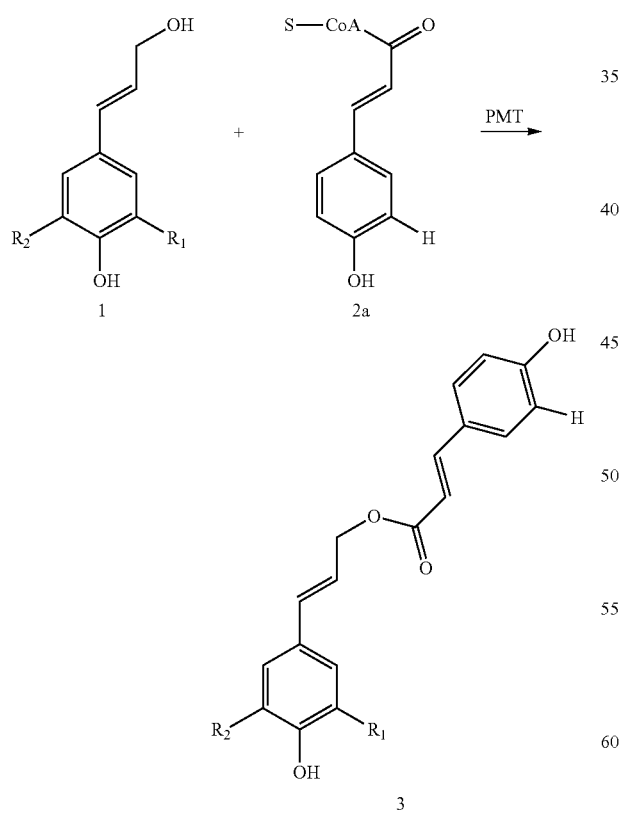

Figure 15:
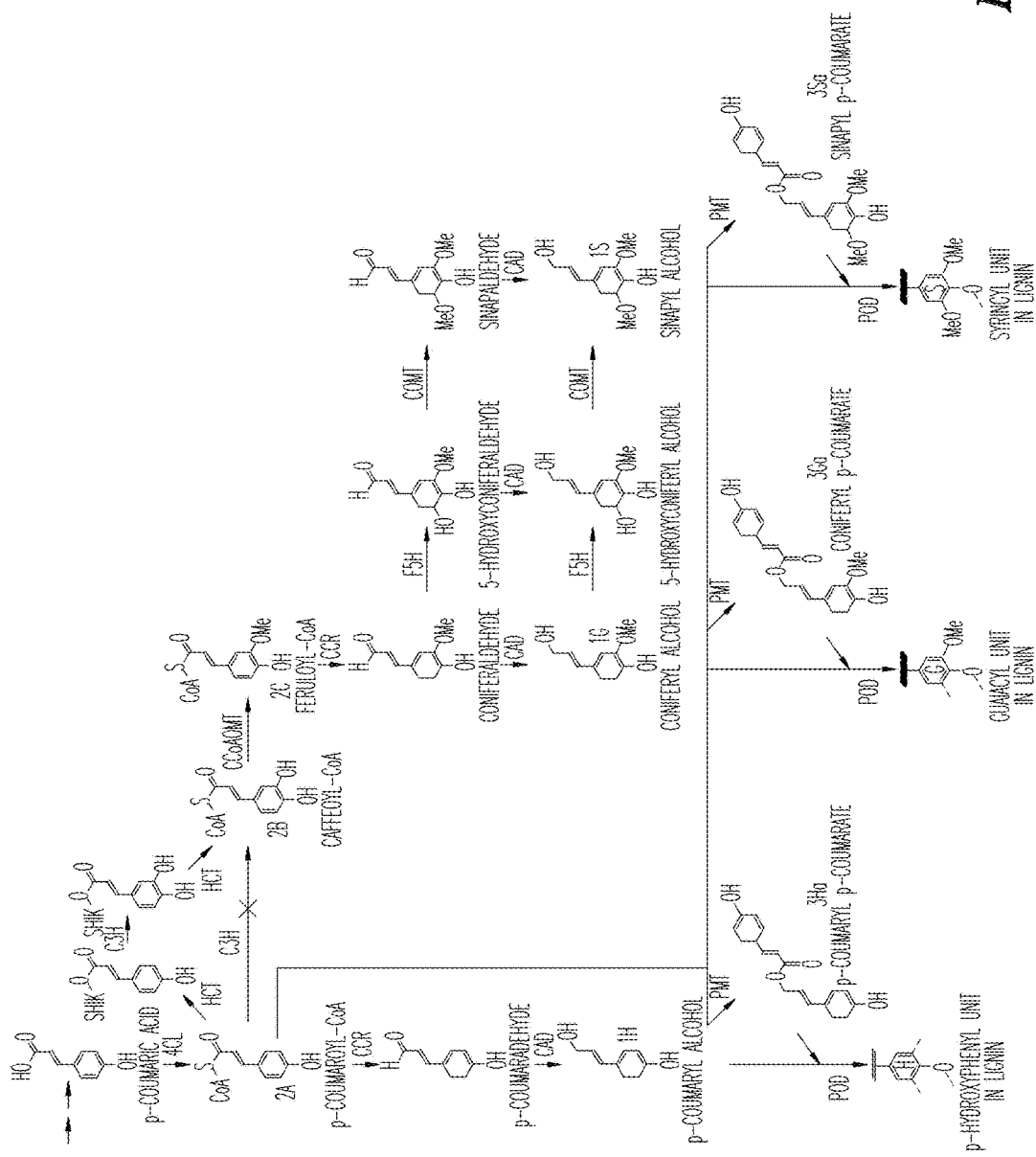
FIG. 15 illustrates standard lignin biosynthetic pathway in angiosperms, adapted from Vanholme et al. (*Lignin engineering*. in CURR OPIN PLANT BIOL (2008)). Currently understood pathways for synthesis of monolignol p-coumarate conjugates 3 are shown. The predominant route toward the three main monolignols 1 is shown, with some of the more minor pathways in gray. The various routes through the pathway have been reviewed by Boerjan et al. (*Lignin biosynthesis*. in ANNU REV PLANT BIOL (2003) and by Ralph et al. (Phytochemistry Reviews 3, 29-60 (2004)). Abbreviations used include: 4CL, 4-coumarate: CoA ligase; HCT, p-hydroxycinnamoyl-CoA: quinate shikimate p-hydroxycinnamoyl transferase; C3H, p-coumarate 3-hydroxylase; CCoAOMT, caffeoyl-CoA O-methyltransferase; CCR, cinnamoyl-CoA reductase; FSH, ferulate/coniferaldehyde 5-hydroxylase; COMT, caffeic acid/5-hydroxyconiferaldehyde O-methyltransferase; CAD, cinnamyl alcohol dehydrogenase; POD, a generic peroxidase (generating the radicals required for monomer polymerization to lignin); PMT, p-coumaroyl-CoA: monolignol transferase. Compound numbers are as explained in Example 6.

Although activity is measured using caffeoyl-CoA 2b as well, kinetic analysis indicates that the PMT enzyme has a higher affinity for p-coumaroyl-CoA 2a. Kinetic data also indicates that the affinity for sinapyl alcohol 1S is high; however the reaction rate for p-coumaryl alcohol 1H with saturating p-coumaroyl-CoA 2a, suggests that OsPMT will produce more p-coumaryl p-coumarate 3Ha if local concentrations of p-coumaryl alcohol are high enough. Thus, OsPMT could be the enzyme responsible for the p-coumaroylation seen in grasses. Because of the high p-coumaroylation, seen primarily on syringyl lignin units S and the low concentrations of p-hydroxyphenyl H units in grass lignins, the preferred substrates for the OsPMT reaction in the plant are likely sinapyl alcohol 1S and p-coumaroyl-CoA 2a. The enzyme favors the synthesis of sinapyl p-coumarate 3Sa over coniferyl p-coumarate 3Ga, which is consistent with the ratio (~90:10) of these conjugates observed incorporated into grass cell walls. The propensity of OsPMT to synthesize p-coumaryl p-coumarate 3Ha raises the possibility that grasses may use this compound in the synthesis of monolignols. The pathway includes the transesterification of p-coumaroyl-CoA 2a to a shikimic acid ester, which is the substrate for C3H (FIG. 15).

Plants such as *Brachypodium distachyon* have been tested using PMT gene knockdown constructs.

EXAMPLE 7

Knockdown of p-Coumarate Monolignol Transferase in *Brachypodium distachyon*

Figure 20A:
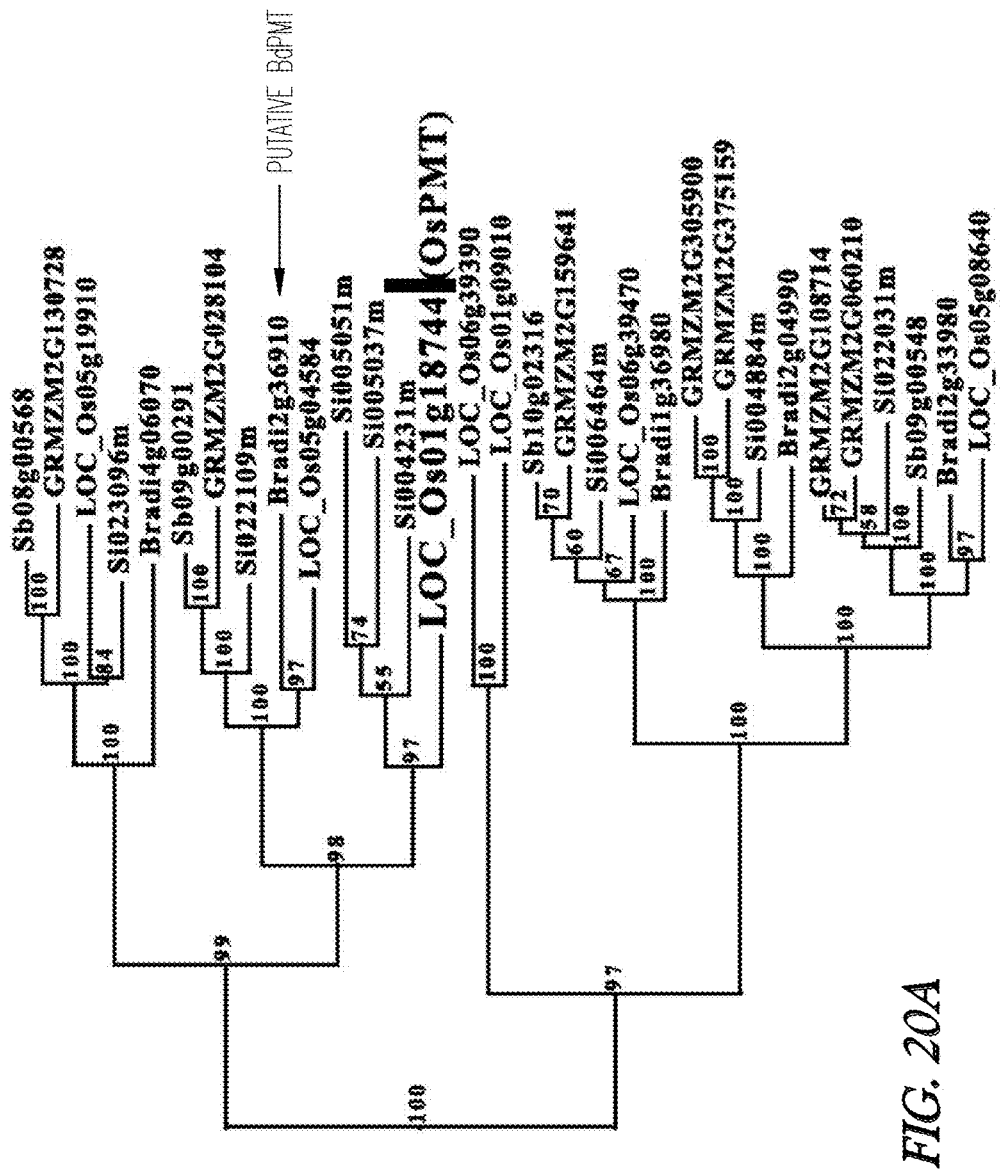
Figure 21:
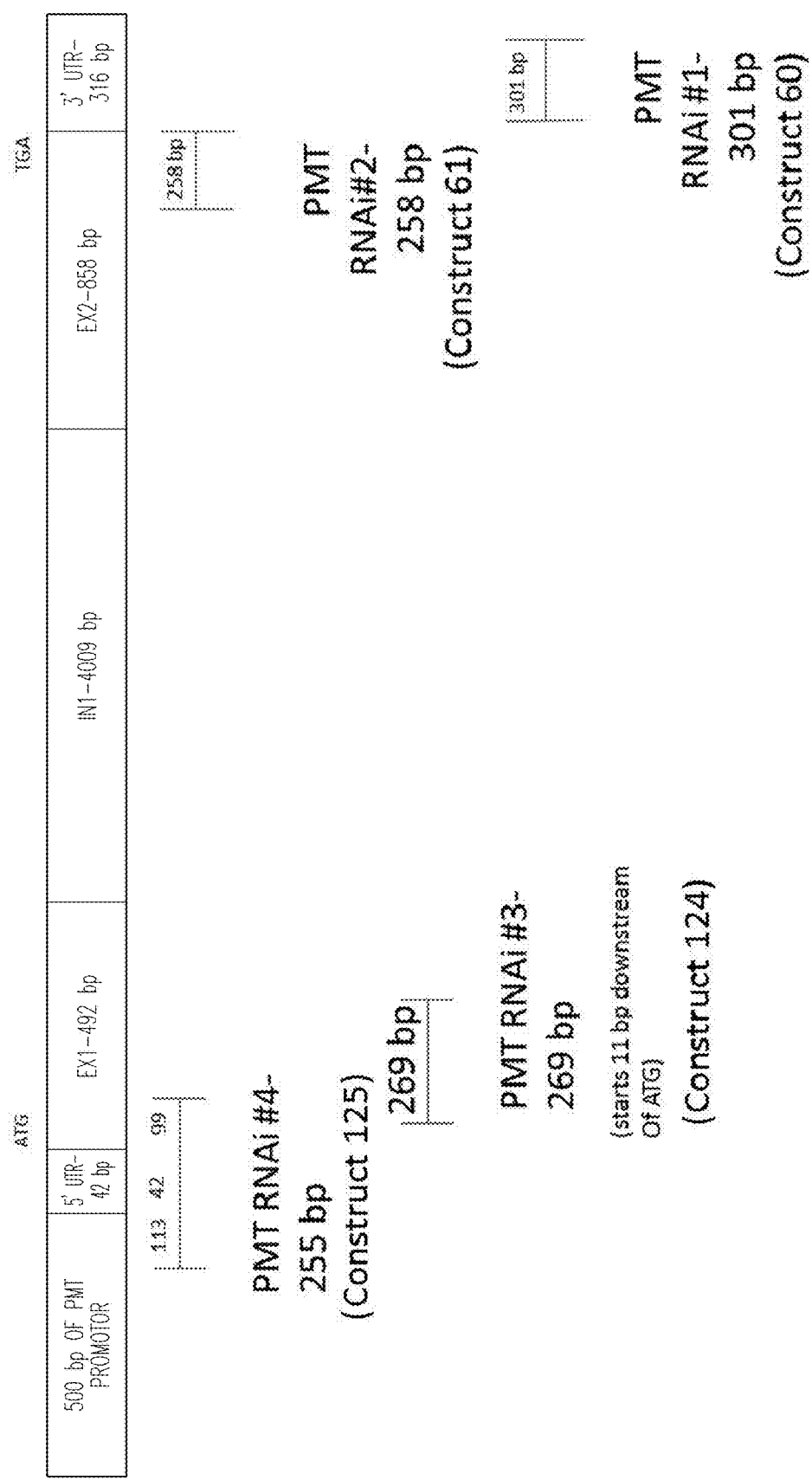
FIG. 21 is a schematic diagram of the *Brachypodium distachyon* p-coumaroyl-CoA: monolignol transferase gene, showing the regions selected for targeting by RNA interference by RNAi #1 (construct 60), RNAi #2 (construct 61), RNAi #3 (construct 124), and RNAi #4 (construct 125).

A putative PMT gene in *Brachypodium distachyon* was identified as the BRADI2G36910 gene (FIG. 20). The sequence of this gene was scrutinized and four regions were selected as targets for RNAi knockdown (FIG. 21).

RNAi constructs were made by polymerase chain (PCR) amplification of selected portion of the putative *Brachypodium distachyon* PMT gene coding sequences and cloning the amplicons into the pStarling vector (see website at pi.csiro.au/rnai/vectors.htm) to make RNAi hairpin loop cassettes. The *Brachypodium distachyon* target of the RNAi constructs had the following sequences.

Construct 60: RNAi #1 target at the 3' untranslated region (SEQ ID NO: 25).

```
  1 GTAAGCAACG ATCCATAATC GTCCATGTAT GAAACCCAAT
 41 TGAGCGTGCA AGCGCTTAAT TACTACACCT TTTTATAATC
 81 AGTAGCTCTT CTATGTCTGG TGTGTGTGCG TGCAATGTAT
121 GTAATTTGCT TGTTTGATCG AACTGGCGCA ATTAGGCGTT
161 GTGCTTAATT GTATCGTGGG TCCATCGAAT GAACGATGAT
201 GAAGCAATAA ATGACCATGA TTTGTACTGC TTCCAAATGT
241 ATACTGGTAG TATATAGTAC CATGTGTCAT GTGCGTGTGT
281 CATCTGGTAA AATTAAGACG G
```

Construct 61: RNAi #2 target at the 3' end of open reading frame (SEQ ID NO: 26).

```
  1 TACGAGCTGA CCTTCACCTA CGACTCCCTC TTCGTGTCGG
 41 ACTGGACCAG GCTGGGCTTT CTAGAGGCCG ACTACGGGTG
 81 GGGGCCCCCG GCCCACGTGG TGCCCTTCTC GTATCACCCC
121 TTCATGGCTG TTGCCGTCAT CGGCGCACCG CCCAAGCCCA
```

```
-continued
161  AGCTCGGCTC CCGCGTCATG ACCATGTGTG TGGAGGAAGA
201  CCACCTCCCG GAGTTCCGGG ACCAGATGAA CGCCTTCGCC
241  TTCACCGCCG GGAAGTGA
```

Construct 124: RNAi #3 target starting 11 bp downstream of the ATG translation start site (SEQ ID NO: 27).

```
  1  GTTCACGGTG ACTAGGACTA GCAAGTCCCT GGTGCCCCA
 41  TCTTCGTCTT CCCCAACACC GGCGGCGACA GAGGACGATG
 81  CACCAGTGCC GGTGATCATG CGCCTGTCGA CGATCGACCG
121  TGTTCCCGGG CTGCGCCACC TGGTGCTCTC CCTCCACGCC
161  TTCGACGGCC ATGGCGTCGT TGCCGGAGAA GACGACGAAG
201  AGCGAATTAG GTGGCCGGCG AGGGTGGTGA GGGAGGCGCT
241  GGGGAAGGCG CTCGTGGACT ACTACCCGT
```

Construct 125: RNAi #4 target spanning 156 bp of the promoter and 5' untranslated region plus 99 bp of the open reading frame (SEQ ID NO:28).

```
-156      CACTCC ACCTAGCTAG CTGAGCTCCG AAGTCCTGAA
-120  CTAATAACCC AGCCCGTCTA TATATACACA GAGCATATAT
 -80  ATCCATACAC TCATCGCAGC TAGAGCATGC AAGCTTAATT
 -40  AGCCTGCAGG CCGTGGATTT GATAGAGAGA GTGCTTTACA
   1  ATGGAGAAGA AGTTCACGGT GACTAGGACT AGCAAGTCCC
  41  TGGTGCCCCC ATCTTCGTCT TCCCCAACAC CGGCGGCGAC
  81  AGAGGACGAT GCACCAGTG
```

Construct 61 targeted a 258 bp stretch of DNA originating from the 3' end of the putative PMT gene Bradi2g36910. This stretch of DNA did not share sufficient sequence homology with other PMT-like genes to target expression knockdown of those genes.

Those RNAi expression cassettes were moved into the pWBvec8 binary vector backbone and introduced into *Brachypodium* tissue using a modified *Agrobacterium*-mediated plant transformation protocol developed by Vogel & Hill, Plant Cell Rep. 27:471-478 (2008).

Transgenic *Brachypodium* plants were regenerated from the transformed tissue, and plant lines with various levels of PMT gene expression knockdown were identified using quantitative Reverse Transcriptase-Polymerase Chain Reaction (qRT-PCR).

Two plant lines (4B and 7A) originating from independent transformation events were confirmed by PCR and drug marker selection to be harboring PMT RNAi Construct 61. These two plant lines were phenotypically characterized in detail because they were determined by qRT-PCR to have the most substantial knockdown of PMT expression (FIG. 22).

Figure 22A:
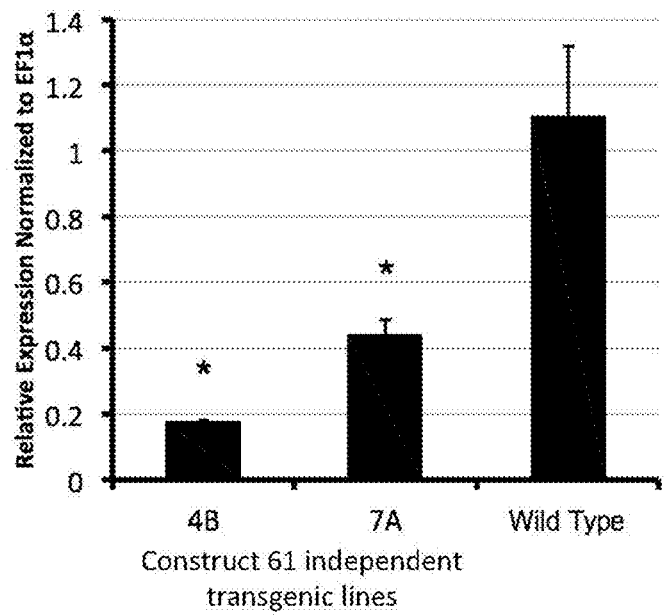
FIG. 22A-22B show that p-coumaroyl-CoA: monolignol transferase expression can be reduced by RNAi knockdown without adversely affecting *Brachypodium distachyon* plant growth.
Figure 22B:
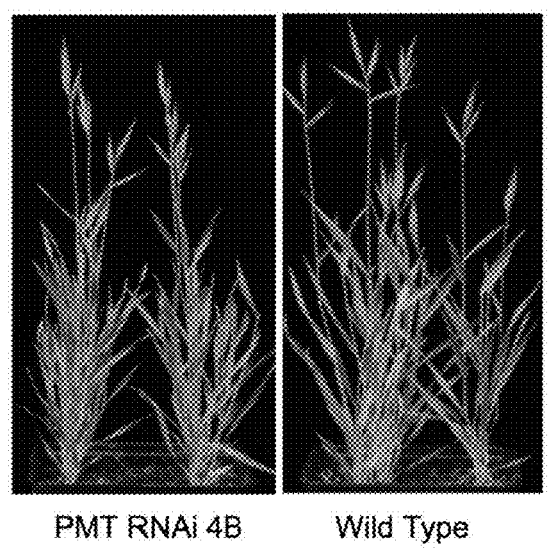

Lines 4B and 7A T0-generation plants were found to have 80% and 60% PMT gene expression knockdown, respectively (FIG. 22A). Line 4B T1-generation plants were found to have 95% PMT gene expression knockdown. All plants were found to grow normally under growth chamber conditions (FIG. 22B).

Figure 23A:
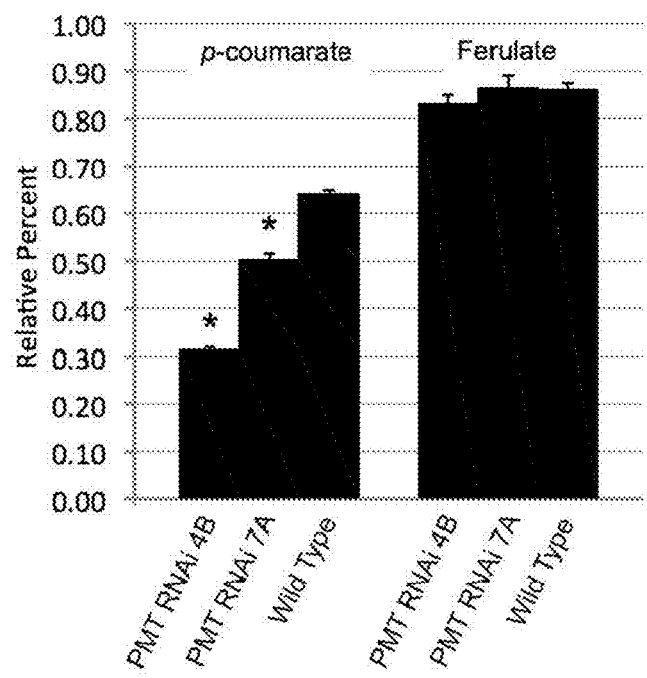
FIG. 23A-23B illustrate the levels of monolignols in that p-coumaroyl-CoA: monolignol transferase knockdown *Brachypodium distachyon* plant cell walls.
Figure 23B:
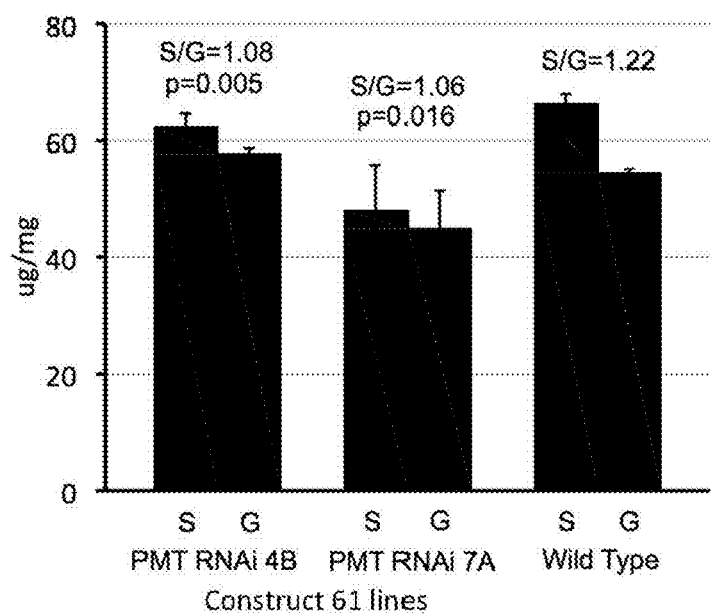
Figure 24:
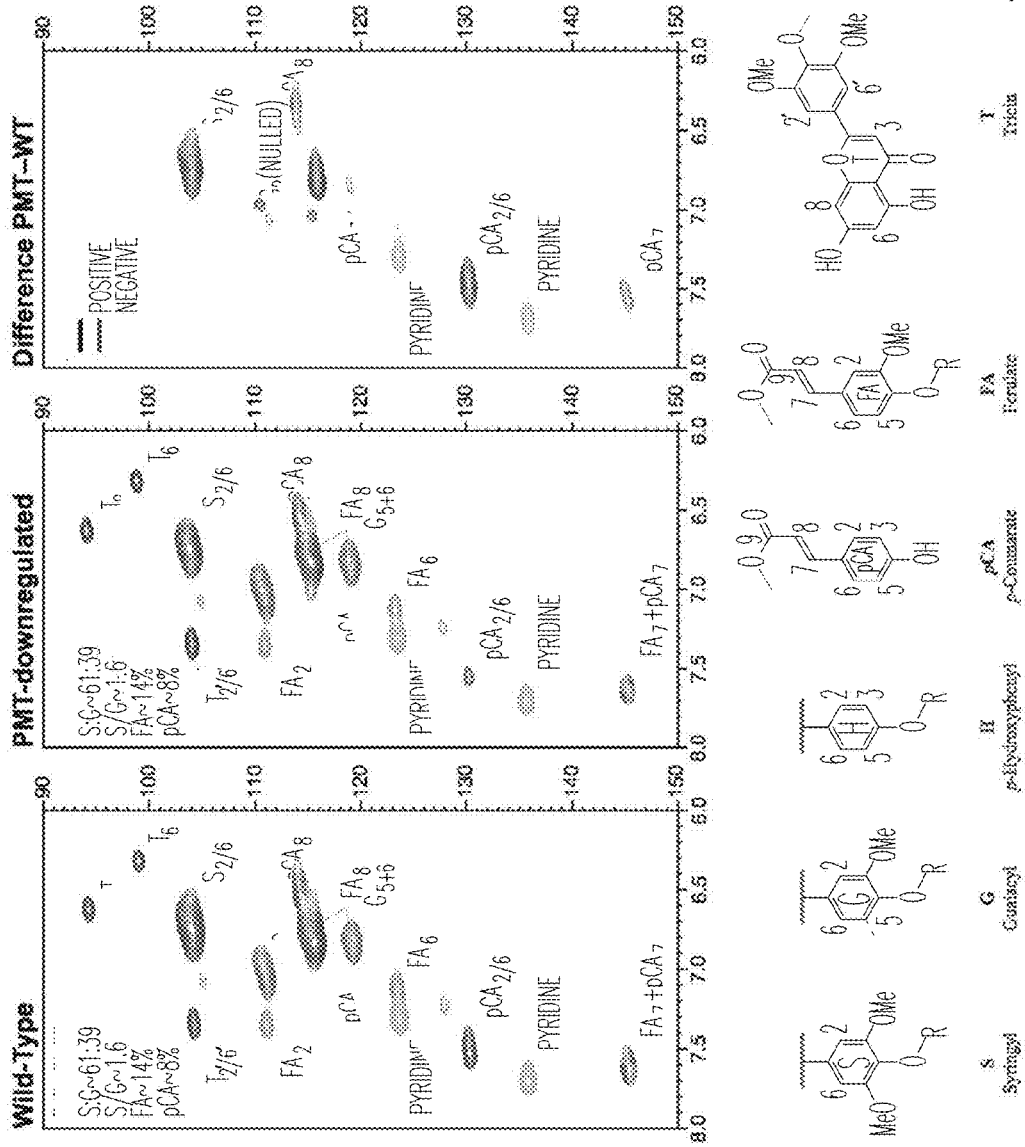
FIG. 24 shows 2D-NMR analysis of plant cell walls, illustrating that p-coumarate and syringyl levels are reduced in RNAi knockdown plant cell walls.

Senesced cell wall tissue from these plants were analyzed and determined to have substantially reduced levels of p-coumarate FIGS. 23-24). As shown in FIG. 23A greater than 60% reduction was observed for line 4B compared to wild type, with no significant changes in cell wall ferulate levels.

These results indicate that the identified *Brachypodium distachyon* PMT gene does play a role in decorating lignin with p-coumarate moieties. Therefore, PMT may compete with FMT in making ester conjugates that become incorporated into lignin and reduction of PMT activity in an FMT-expressing plant background can facilitate the generation of plants with increased ferulate content which can improve the deconstruction properties of grass species during biomass processing to biofuels.

EXAMPLE 8

PMT Sequences from Various Plant Species

Related PMT sequences were obtained from plant species having sequenced genomes using the Phytozome 7 locus keyword search feature (Ouyang et al., Nucleic Acids Research 35, D883-D887 (2007); see website at www.phytozome.net/search.php).

Sequences related to the PMT nucleic acids described herein include those in Table 2.

TABLE 2

| Species | Phytozome ID | Alignment | SEQ ID NO: |
|---|---|---|---|
| Citrus sinensis | orange1.1g014078m.g | ------FtrngeDPfapplaYtTLFiSeWgRLGFnqiDYGWGpPvHVVPiqgssiipVgi | 66 |
| Sorghum bicolor | Sb10g023160 | --------tGgvDPYriTsdYrTLlVSDWsRLGFaEvDYGWGcPvHVVPlTnldYlAtci | 67 |
| Zea mays | GRMZM2G060210 | ---------eDaDPYqiTsdYrTLlVSDWTRLGFaEvDYGWGpPaHVVPlTnldYiAtci | 68 |
| Bachypodium distachyon | Bradi4g06067 | agdkmkFv--QdDPYELrFehnvLFVSDWTRLGFLEvDYGWGvPsHVIPFnYadYMAVAV | 69 |
| Oryza sativa | LOC_Os05g19910 | -------v--KvDPYaLTFehnvLFVSDWTRLGFfEvDYGWGTPnHiIPFTYadYMAVAV | 70 |
| Panicum virgatum | Pavirv00015375m.g | -------v--svDPYqLTFehnvLFVSDWTRLGFsEvDYGWGaPdHiVPFTYadYMAVAV | 71 |

TABLE 2-continued

| Species | Phytozome ID | Alignment | SEQ ID NO: |
|---|---|---|---|
| Sorghum bicolor | Sb08g005680 | -------v--KvDPYqLTFkhnvLFVSDWTRLGFfEvDYGWGvPnHiIPFTYadYMAVAV | 72 |
| Zea mays | GRMZM2G130728 | -------v--KvDPYqLTFkhnvLFVSDWTRLGFfEvDYGWGvPnHilPFTYadYMAVAV | 73 |
| Bachypodium distachyon | Bradi2g36910 | -------F--EqDPYELTFTYDSLFVSDWTRLGFLEADYGWGpPaHVVPFsYHPFMAVAV | 74 |
| Oryza sativa | LOC_Os05g04584 | -------F--EeDPYELTFTYDSLFVSDWTRLGFLdADYGWGTPsHVVPFsYHPFMAVAV | 75 |
| Setaria italica | Si022109m.g | -------F--ErDPYELTFTYDSLFVSDWTRLGFLEADYGWGTPaHVlPFsYHPFMAVAV | 76 |
| Panicum virgatum | Pavirv00037046m.g | -------F--ErDPYELTFSYDSLFVSDWTRLGFLEADYGWGaPaHVVPFsYHPFMAVAV | 77 |
| Sorghum bicolor | Sb09g002910 | -------F--DrDPYELTFTYDSLFVSDWTRLGFLEADYGWGTPtHVVPFsYHPFMAVAV | 78 |
| Zea mays | GRMZM2G028104 | -------F--DrDPYELTFTYDSLFVSDWTRLGFLEADYGWGTPtHVlPFsYHPFMAVAV | 79 |
| Setaria italica | Si005037m.g | -------lvGveDPYELpFaYEALFVSDWTRLGFqEADYGWGgPsHVIPlaYHPhMpIAi | 80 |
| Oryza sativa | LOC_Os01g18744.1 | -------F--reDPYELsFTYDSLFVSDWTRLGFLEADYGWGpPsHVIPFaYYPFMAVAi | 81 |
| Setaria italica | Si004231m.g | ------lv--EkDPYELTFSYESLFVSDWTRLGFLdADYGWGTPlqVIPFTYHPaMpIAi | 82 |
| Panicum virgatum | Pavirv00066580m.g | ------lv--aqDPYELsFTYESLFVSDWTRLGFLEADYGWGTPeqVIPFaYHPcMpIAV | 83 |

Table 3 shows the nucleotide sequences for these peptide sequences. These nucleic acids can be used as isolated p-Coumarate Monolignol Transferase nucleic acids and as a source of inhibitory and mutating nucleic acids to target endogenous p-Coumarate Monolignol Transferase genes. See also, FIG. 25.

TABLE 3

Nucleotide Sequences for the Peptides shown in Table 2

| Species | Nucleotide Sequence |
|---|---|
| Citrus sinensis (orange1.1g014078m; peptide SEQ ID NO: 29) | gagctacctgttgaatttgctaagtacatgaatgg agattttaccaggaacggtgaggacccattcgccc cacctctggcttatacaacattgtttatatcagag tggggacgactgggattcaaccagattgactatgg gtggggccctcctgtccacgtggtaccaattcaa ggctcgagtattattccggttggcattgtgggtt cgatgccgttgcccaaa (SEQ ID NO: 47) |
| Sorghum bicolor (Sb10g023160.1; peptide SEQ ID NO: 30) | gcgcggtggagcgcggggggacaccggcggcgtgg acccgtaccggatcacgtcggactaccggacg ctgctggtgtcggactggtcgcggctcgggtt cgcggaggtggactacgggtggggctgccccgtgcac gtcgtcccgctcaccaacctcgactacatcgcgac gtgcatcctg (SEQ ID NO: 48) |
| Zea mays (GRMZM2G060210_T01; peptide SEQ ID NO: 31 | gaggacgccgaccccctaccagatcacctccga ctaccggacgctgctggtgtcggactggacgc ggctgggcttcgcggaggtggactac ggctggggcccgcccgcccacgtggtgcc gctgacgaacttggactacatcgccacgtgcatc (SEQ ID NO: 49) |
| Bachypodium distachyon (Bradi4g06067.1; peptide SEQ ID NO: 32) | ttaggaggaggaggggctggggataagatgaagtt tgtgcaggatgatcctatgagctgagtttgagcat aatgtgttgtttgtgtcggattggacgaggcttggg ttcttggaggtggactatggctggggcgtgcctag ccatgttataccttcaattatgcggactacatggcg gtcgcggtgctcggtgctccgccggcgccggtgaag gggactcgg (SEQ ID NO: 50) |

TABLE 3-continued

Nucleotide Sequences for the Peptides shown in Table 2

| Species | Nucleotide Sequence |
|---|---|
| *Oryzasathu* (LOC_Os05g19910.1; peptide SEQ ID NO: 33 | ggggatgtgaaagttgatccctacgcattgacattt gaacacaatgtgcttttgtgtctgattggacgagg ttaggattcttcgaggtagactatgggtggggtaca cctaatcacatcataccattcacttatgcagacta catggcagtcgcagtgcttggtgctccaccaatgcca (SEQ ID NO: 51) |
| *Panicum virgatum* (Pavirv00015375m; peptide SEQ ID NO: 34 | gggggattctatggcaactgcttctacccagtttc tgtgacggccactgctgaggatgttgt cactgcaggg ttgcttgatgtgatcaggatgataaggaatgggaag gccaggcttcccctggagttttccaagtgggcagca ggggatgtgagtgtggatccataccagttgacattt gagcacaacgtgttgtttgtgtctgattggacgaga cttgggttctccgaggttgactatgggtggggtgca ccggatcatatcgtgccattcacctatgcagactacat ggcggtggcggttcttggggctccg (SEQ ID NO: 52) |
| *Sorghum bicolor* (Sb08g005680.1; peptide SEQ ID NO: 35) | tttgccaaatggtccatgggtgatgtgaaggtagac ccatatcaactgacattcaagcacaatgttctgtttg tgtctgattggacgaggcttggattctttgaggttg actatgggtggggtgtaccaaaccatatcatacct ttcacttatgcagactacatggctgtagcagttctt (SEQ ID NO: 53) |
| *Zea mays* (GRMZM2G130728_T01; peptide SEQ ID NO: 36) | acgggcaatgtgaaagtagacccatatcaactaaca ttcaagcacaatgttctatttgtgtccgattggacac ggcttggattctttgaagttgactatgggtggggtgt accaaaccatatcctccctttcacttatgcagact acatggctgtagcagttcttggagctccaccgtct (SEQ ID NO: 54) |
| *Bachypodium distachyon* (Bradi2g36910.1; peptide SEQ ID NO: 37) | gccaggctggcggggacgtggcgaggtgggccgt gggcgggttcgagcaggaccccctacgagctgacctt cacctacgactccctcttcgtgtcggactggaccag gctgggcttctagaggccgactacgggtgggggc ccccggcccacgtggtgccttctcgtatcaccct tcatggctgttgccgtcatcggcgcaccgcccaagcc caagctcggc (SEQ ID NO: 55) |
| *Oryza sativa* (LOC_Os05g04584.1; peptide SEQ ID NO: 38) | gtgggcgggttcgaggaggaccccctacgagctgacc ttcacctacgactccctcttcgtctccgactggacg cggctcggcttcctagacgccgactatggctggggc acgccgtcgcacgtcgtgccgttctcctaccaccc gttcatggccgtcgccgtcatcggcgcgccgccggcg (SEQ ID NO: 56) |
| *Setaria italica* (Si022109m; peptide SEQ ID NO: 39) | cggctggccgcggacttcgcgcggtgggcgggcgga gggttcgagcgcgaccccctacgagctcaccttcacct acgactcgctcttcgtctccgactggacgcggctcg ggttcctggaggcggactacgggtggggcacgccgg cgcacgtcctgcccttctcgtaccacccttcatg gccgtcgccgtcatcggagcgccgccggcgcccaag cccggagcg (SEQ ID NO: 57) |
| *Panicum virgatum* (Pavirv00037046m; peptide SEQ ID NO: 40 | gcgcggtgggcggcgggcgggttcgagcgcgacccc tacgagctcaccttcagctacgactcgctcttcgtc tccgactggacgcggctggggttcctggaggcggac tacggtggggcgcgccggcgcacgtcgtgcccttt ctcctaccacccttcatggccgtcgccgtcatcggc (SEQ ID NO: 58) |
| *Sorghum bicolor* (Sb09g002910.1; peptide SEQ ID NO: 41) | tgggcggcgggcgggtttgatcgggacccctacga gctcaccttcacctacgactccctcttcgtctccg actggacgaggctagggttcctccgaggctgactat ggctgggcacgccgacgcacgtcgtgccgttctcg taccacccgttcatggccgtcgccgtcatcggggcg ccg (SEQ ID NO: 59) |
| *Zea mays* (GRMZM2G028104_T01; peptide SEQ ID | gcggcggcttcgaccgcgaccccctacgagctcac cttcacctacgactcgctcttcgtctccgactggac gcgcctcggcttcctcgaggcggactacggctgggg |

TABLE 3-continued

Nucleotide Sequences for the Peptides shown in Table 2

| Species | Nucleotide Sequence |
|---|---|
| NO: 42) | caccccgacacacgtcctgcccttctcctaccaccc<br>gttcatggccgtcgccgtcatcggcgcccgcctaag<br>(SEQ ID NO: 60) |
| *Setaria italica*<br>(Si005037m; peptide<br>SEQ ID NO: 43) | ccggcggagttcgcgcggtgggcggcggggagctc<br>gtcggggtcgaggacccctacgagctgccgttcgcg<br>tacgaggcgctattcgtgtcggactggacgcggctt<br>gggttccaggaagcggactacgggtggggtgggcc<br>ttcccacgtgatacctttggcttatcacccgcacat<br>gcccatcgccatcgtcggtgcaccgccggcgccacg<br>gatgggggtc<br>(SEQ ID NO: 61) |
| *Oryza sativa*<br>(LOC_Os01g18744.1;<br>peptide SEQ ID<br>NO: 44) | ttcgcgcggtgggcggtggccgacttcagggaggat<br>ccgtacgagctgagcttcacgtacgattccctgttc<br>gtctccgactggacgcggctggggttcctggaggcg<br>gactacgggtggggccgccgtcgcacgtcatacc<br>cttcgcgtactacccgttcatggccgtcgccatcatc<br>(SEQ ID NO: 62) |
| *Setaria italica*<br>(Si004231m; peptide<br>SEQ ID NO: 45) | ctcgtggagaaggaccctacgagctgacctttc<br>gtacgagtcgctgttcgtgtcggactggaccgc<br>tggggttcctggacgctgactacggctgggggacgc<br>cgttgcaggtgatacctttacgtaccacccggccat<br>gcccatcgccatcatcagcgcgccgccggcgcccaag<br>(SEQ ID NO: 63) |
| *Panicum virgatum*<br>(Pavirv00066580m;<br>peptide SEQ ID<br>NO: 46) | gcgcggctccccgccgagttcgcgcggtgggcggcg<br>ggcgagctcgtggcgcaggaccctacgagctgagc<br>ttcacgtacgagtcgctgttcgtgtcggactggacgc<br>ggctggggttcctggaggcggactacggctggggcac<br>gccggagcaggtgatacccttcgcgtaccacccg<br>tgcatgccatcgcggtcatcggccccgccgccgg<br>cgcccaagacg<br>(SEQ ID NO: 64) |

REFERENCES

Vanholme, R., Morreel, K., Ralph, J., and Boerjan, W. (2008) Lignin engineering. in Curr Opin Plant Biol.

Boerjan, W., Ralph, J., and Baucher, M. (2003) Lignin biosynthesis. in Annu Rev Plant Biol.

Ralph, J., Lundquist, K., Brunow, G., Lu, F., Kim, H., Schatz, P. F., Marita, J. M., Hatfield, R. D., Ralph, S. A., Christensen, J. H., and Boerjan, W. (2004) Lignins: Natural polymers from oxidative coupling of 4-hydroxyphenyl-propanoids Phytochemistry Reviews 3, 29-60.

Harkin, J. M. (1967) Lignin—a natural polymeric product of phenol oxidation. in Oxidative Coupling of Phenols (Taylor, W. I. a. B., A. R. ed.), Marcel Dekker, New York. pp 243-321.

Norman, A. G. (1969) Constitution and Biosynthesis of Lignin. K. Freudenberg and A. C. Neish. Springer-Verlag, N.Y., 1968. x+132 pp., illus. $7. Molecular Biology, Biochemistry and Biophysics, vol. 2 Science 165, 784.

Lu, F., and Ralph, J. (2008) Novel tetrahydrofuran structures derived from β-β-coupling reactions involving sinapyl acetate in Kenaf lignins Org. Biomol. Chem. 6, 3681-3694.

Lu, F., and Ralph, J. (2002) Preliminary evidence for sinapyl acetate as a lignin monomer in kenaf Chem. Commun, 90-91

Lu, F., and Ralph, J. (2005) Novel β-β-structures in natural lignins incorporating acylated monolignols. in Thirteenth International Symposium on Wood, Fiber, and Pulping Chemistry, APPITA, Australia, Auckland, New Zealand.

Ralph, J. (1996) An unusual lignin from Kenaf J. Nat. Prod. 59, 341-342.

del Rio, J. C., Marques, G., Rencoret, J., Martinez, A. T., and Gutierrez, A. (2007) Occurrence of naturally acetylated lignin units J. Agr. Food Chem. 55, 5461-5468.

Ralph, J., and Lu, F. (1998) The DFRC method for lignin analysis. Part 6. A modified method to determine acetate regiochemistry on native and isolated lignins J. Agr. Food Chem. 46, 4616-4619.

Smith, D. C. C. (1955) p-Hydroxybenzoates groups in the lignin of Aspen (*Populus tremula*) J. Chem. Soc., 2347.

Nakano, J., Ishizu, A., and Migita, N. (1961) Studies on lignin. XXXII. Ester groups of lignin Tappi 44, 30-32.

Landucci, L. L., Deka, G. C., and Roy, D. N. (1992) A 13C NMR study of milled wood lignins from hybrid Salix Clones Holzforschung 46, 505-511.

Sun, R. C., Fang, J. M., and Tomkinson, J. (1999) Fractional isolation and structural characterization of lignins from oil palm trunk and empty fruit bunch fibres J. Wood Chem. Technol. 19, 335-356.

Meyermans, H., Morreel, K., Lapierre, C., Pollet, B., De Bruyn, A., Busson, R., Herdewijn, P., Devreese, B., Van Beeumen, J., Marita, J. M., Ralph, J., Chen, C., Burggraeve, B., Van Montagu, M., Messens, E., and Boerjan, W. (2000) Modifications in lignin and accumulation of phenolic glucosides in poplar xylem upon down-regulation of caffeoyl-coenzyme A O-methyltransferase, an enzyme involved in lignin biosynthesis J. Biol. Chem. 275, 36899-36909.

Li, S., and Lundquist, K. (2001) Analysis of hydroxyl groups in lignins by 1H NMR spectrometry Nordic Pulp Paper Res. J. 16, 63-67.

Lu, F., and Ralph, J. (2003) Non-degradative dissolution and acetylation of ball-milled plant cell walls; high-resolution solution-state NMR Plant J. 35, 535-544.

Shimada, M., Fukuzuka, T., and Higuchi, T. (1971) Ester linkages of p-coumaric acid in bamboo and grass lignins Tappi 54, 72-78.

Ralph, J., Hatfield, R. D., Quideau, S., Helm, R. F., Grabber, J. H., and Jung, H.-J. G. (1994) Pathway of p-Coumaric Acid Incorporation into Maize Lignin As Revealed by NMR Journal of the American Chemical Society 116, 9448-9456.

Hartley, R. D. (1972) p-Coumaric and ferulic acid components of cell walls of ryegrass and their relations with lignin and digestibility J. Sci. Food Agr. 23, 1347-1354.

Harris, P. J., and Hartley, R. D. (1980) Phenolic constituents of the cell walls of monocotyledons, Biochem. Syst. Ecol. 8, 153-160.

Ralph, J. (2006) What makes a good monolignol substitute? in The Science and Lore of the Plant Cell Wall Biosynthesis, Structure and Function (Hayashi, T. ed.), Universal Publishers (BrownWalker Press), Boca Raton, Fla. pp 285-293.

Ralph, J. (2010) Hydroxycinnamates in lignification Phytochemistry Reviews 9, 65-83-83.

Martinez, A. T., Rencoret, J., Marques, G., Gutierrez, A., Ibarra, D., Jimenez-Barbero, J., and del Rio, J. C. (2008) Monolignol acylation and lignin structure in some non-woody plants: A 2D NMR study Phytochem. 69, 2831-2843.

del Rio, J. C., Rencoret, J., Marques, G., Gutierrez, A., Ibarra, D., Santos, J. I., Jimenez-Barbero, J., Zhang, L. M., and Martinez, A. T. (2008) Highly Acylated (Acetylated and/or p-Coumaroylated) Native Lignins from Diverse Herbaceous Plants J. Agr. Food Chem. 56, 9525-9534.

Lu, F., and Ralph, J. (1999) Detection and determination of p-coumaroylated units in lignins J. Agr. Food Chem. 47, 1988-1992.

Grabber, J. H., Quideau, S., and Ralph, J. (1996) p-Coumaroylated syringyl units in maize lignin; implications for β-ether cleavage by thioacidolysis Phytochem. 43, 1189-1194.

Hatfield, R. D., Wilson, J. R., and Mertens, D. R. (1999) Composition of cell walls isolated from cell types of grain sorghum stems J. Sci. Food Agr. 79, 891-899.

Ralph, J., Bunzel, M., Marita, J. M., Hatfield, R. D., Lu, F., Kim, H., Schatz, P. F., Grabber, J. H., and Steinhart, H. (2004) Peroxidase-dependent cross-linking reactions of p-hydroxycinnamates in plant cell walls Phytochem. Revs. 3, 79-96.

Hatfield, R. D., Ralph, J., and Grabber, J. H. (2008) A potential role of sinapyl p-coumarate as a radical transfer mechanism in grass lignin formation Planta 228, 919-928.

Grabber, J. H., Hatfield, R. D., Ralph, J., and Lu, F. (2008) Coniferyl ferulate incorporation into lignin dramatically enhances the delignification and enzymatic hydrolysis of maize cell walls. In 30th Symposium on Fuels and Chemicals, New Orleans.

D'Auria, J. (2006) Acyltransferases in plants: a good time to be BAHD Curr. Opin. Plant Biol. 9, 331-340.

Hatfield, R. D., Marita, J. M., Frost, K., Grabber, J. H., Lu, F., Kim, H., and Ralph, J. (2009) Grass lignin acylation: p-coumaroyl transferase activity and cell wall characteristics of C3 and C4 grasses Planta 229, 1253-1267.

Mitchell, R. A. C., Dupree, P., and Shewry, P. R. (2007) A novel bioinformatics approach identifies candidate genes for the synthesis and feruloylation of arabinoxylan Plant Physiol. 144, 43-53.

Bueuerle, T., and Pichersky, E. (2002) Enzymatic synthesis and purification of aromatic Coenzyme-A esters Anal. Biochem. 302, 305-312.

Stoeckigt, J., and Zenk, M. H. (1975) Chemical synthesis and properties of hydroxycinnamoyl coenzyme A derivatives Z. Naturforsch., C: Biosci. 30C, 352-358.

Lu, F., and Ralph, J. (1998) Facile synthesis of 4-hydroxycinnamyl p-coumarates J. Agr. Food Chem. 46, 2911-2913.

Santoro, N., Brtva, S., Vander Roest, K., Siegel, G., and Waldrop A. (2006) A high-throughput screening assay for the carboxyltransferase subunit of acetyl-CoA carboxylase Anal. Biochem. 354, 70-77.

Team, R. D. C. (2010) R: A language and environment for statistical computing,

Sato, Y., Antonio, B., Namiki, N., Motoyama, R., Sugimoto, K., Takehisa, H., Minami, H., Kamatsuki, K., Kusaba, M., Hirochika, H., and Nagamura, Y. (2011) Field transcriptome revealed critical developmental and physiological transitions involved in the expression of growth potential in japonica rice BMC Plant Biology 11, 10.

Sato, Y., Antonio, B. A., Namiki, N., Takehisa, H., Minami, H., Kamatsuki, K., Sugimoto, K., Shimizu, Y., Hirochika, H., and Nagamura, Y. (2010) RiceXPro: a platform for monitoring gene expression in japonica rice grown under natural field conditions Nucleic Acids Research.

Ouyang, S., Zhu, W., Hamilton, J., Lin, H., Campbell, M., Childs, K., Thibaud-Nissen, F. O., Malek, R. L., Lee, Y., Zheng, L., Orvis, J., Haas, B., Wortman, J., and Buell, C. R. (2007) The TIGR Rice Genome Annotation Resource: improvements and new features Nucleic Acids Research 35, D883-D887.

Edgar, R. C. (2004) MUSCLE: a multiple sequence alignment method with reduced time and space complexity. in BMC Bioinformatics.

Schmidt, H. A., Strimmer, K., Vingron, M., and von Haeseler, A. (2002) TREE-PUZZLE: maximum likelihood phylogenetic analysis using quartets and parallel computing. In Bioinformatics.

Huson, D. H., Richter, D. C., Rausch, C., Dezulian, T., Franz, M., and Rupp, R. (2007) Dendroscope: An interactive viewer for large phylogenetic trees. in BMC Bioinformatics.

Mitchell, R. A., Dupree, P., and Shewry, P. R. (2007) A novel bioinformatics approach identifies candidate genes for the synthesis and feruloylation of arabinoxylan. in Plant Physiol.

Wagner, A., Tobimatsu, Y., Phillips, L., Flint, H., Torr, K. M., Donaldson, L., Te Kiri, L., and Ralph, J. (2011) CCoAOMT suppression modifies lignin composition in Pinus radiata Plant J., in press, accepted Mar. 17, 2011

Brkljacic J, Grotewold E, Scholl R, Mockler T, Garvin D F, Vain P, Brutnell T, Sibout R, Bevan M, Budak H, Caicedo A L, Gao C, Gu Y, Hazen S P, Holt B F 3rd, Hong S Y, Jordan M, Manzaneda A J, Mitchell-Olds T, Mochida K, Mur L A, Park C M, Sedbrook J, Watt M, Zheng S J, Vogel J P. (2011) Brachypodium as a model for the grasses: today and the future. Plant Physiol. 157:3-13.

Cigan A M, Unger-Wallace E, Haug-Collet K. (2005) Transcriptional gene silencing as a tool for uncovering gene function in maize. Plant J. 43:929-940.

International Brachypodium Initiative (2010) Genome sequencing and analysis of the model grass Brachypodium distachyon. Nature 463:763-768.

Vogel J, Hill T. (2008) High-efficiency Agrobacterium-mediated transformation of Brachypodium distachyon inbred line Bd21-3. Plant Cell Rep. 27:471-478.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements are intended to describe and summarize features disclosed the foregoing description given in the specification.

Statements:

1. An isolated nucleic acid encoding at least a portion of a p-coumaroyl-CoA:monolignol transferase, and/or an isolated nucleic acid complementary to at least a portion of a p-coumaroyl-CoA:monolignol transferase nucleic acid, wherein the isolated nucleic acid can selectively hybridize to a DNA or RNA with a sequence homologous or complementary to a sequence selected from the group consisting of SEQ ID NO:16, SE ID NO:18, SEQ ID NO:19, SEQ ID NO:22, SEQ ID NO:23, SEQ ID NO:25, SEQ ID NO:26, SE ID NO:27, SEQ ID NO:28, and a combination thereof.
2. The isolated nucleic acid of statement 1, wherein the nucleic acid selectively hybridizes to a DNA or RNA comprising either strand of any of the SEQ ID NO:16, 18, 19, 22, 23, 25, 26, 27, 28, 47-63 and 64 sequences under physiological conditions within a live plant cell.
3. The isolated nucleic acid of statement 1, wherein the nucleic acid selectively hybridizes to a DNA or RNA comprising either strand of any of the SEQ ID NO:16, 18, 19, 22, 23, 25, 26, 27, 28, 47-63 and 64 sequences under stringent hybridization conditions.
4. The isolated nucleic acid of statement 3, wherein the stringent hybridization conditions comprise a wash in 0.1×SSC, 0.1% SDS at 65° C.
5. The isolated nucleic acid of any of statements 1-5, wherein the nucleic acid that selectively hybridizes to a DNA or RNA has at least about 40%, 50%, 60%, 70%, 80%, 90% sequence identity with either strand of any of the SEQ ID NO:16, 18, 19, 22, 23, 25, 26, 27, 28, 47-63 and 64 sequences.
6. The isolated nucleic acid of any of statements 1-5, wherein the nucleic acid encodes a p-coumaroyl-CoA: monolignol transferase that can catalyze the synthesis of monolignol p-coumarate(s) from monolignol(s) and p-coumaroyl-CoA.
7. The isolated nucleic acid of statement 6, wherein the monolignol is coniferyl alcohol, p-coumaryl alcohol, sinapyl alcohol or a combination thereof.
8. The isolated nucleic acid of any of statements 1-7, wherein the nucleic acid encodes a polypeptide with at least 50%, 60%, 70%, 80%, or 90% sequence identity to a polypeptide from *Oryza sativa* comprising a SEQ ID NO:17, 33, 38 or 44 sequence, *Brachypodium distachyon* comprising a SEQ ID NO:24, 32 or 37 sequence; *Citrus sinensis* comprising a SEQ ID NO:29 sequence, *Sorghum bicolor* comprising a SEQ ID NO:30, 35 or 41 sequence, *Zea mays* comprising a SEQ ID NO:31, 36 or 42 sequence, *Panicum virgatum* comprising a SEQ ID NO:34, 40 or 46 sequence, or *Setaria italica* comprising a SEQ ID NO:39, 43 or 45 sequence.
9. The isolated nucleic acid of any of statements 1-8, wherein the nucleic acid encodes p-coumaroyl-CoA: monolignol transferase that can catalyze the synthesis of monolignol p-coumarate(s) from a monolignol(s) and p-coumaroyl-CoA with at least about 50% of the activity of a p-coumaroyl-CoA:monolignol transferase with the SEQ ID NO:17 or SEQ ID NO:24.
10. The isolated nucleic acid of any of statements 1-9, where the isolated nucleic acid is an inhibitory nucleic acid adapted to inhibit the expression and/or translation of a p-coumaroyl-CoA:monolignol transferase mRNA.
11. The isolated nucleic acid of any of statements 1-9, where the isolated nucleic acid is mutating nucleic acid that binds to an endogenous p-coumaroyl-CoA:monolignol transferase gene in a cell of grass species.
12. The isolated nucleic acid of statement 11, wherein the mutating nucleic has two flanking segments and a central segment,
   wherein the central segment has a point mutation, a deletion, a missense mutation, or a nonsense mutation relative to a nucleic acid selected from the group consisting of SEQ ID NO:16, SE ID NO:18, SEQ ID NO:19, SEQ ID NO:22, SEQ ID NO:23, SEQ ID NO:25, SEQ ID NO:26, SE ID NO:27, SEQ ID NO:28; and wherein the two flanking segments are separately homologous or complementary to a different region of a nucleic acid selected from the group consisting of SEQ ID NO:16, SE ID NO:18, SEQ ID NO:19, SEQ ID NO:22, SEQ ID NO:23, SEQ ID NO:25, SEQ ID NO:26, SEQ ID NO:27, and SEQ ID NO:28.

13. A transgenic plant cell comprising the isolated nucleic acid of any of statements 1-12.
14. A transgenic plant comprising the plant cell of statement 12 or the isolated nucleic acid of any of statements 1-13.
15. An expression cassette comprising the p-coumaroyl-CoA:monolignol transferase nucleic acid of any of statements 1-14 operably linked to a promoter functional in a host cell.
16. The expression cassette of statement 15, further comprising a feruloyl-CoA:monolignol transferase nucleic acid operably linked to a promoter functional in a host cell.
17. The expression cassette of statement 15 or 16, which further comprises a selectable marker gene.
18. The expression cassette of any of statements 15-17, wherein the expression cassette is within an expression vector.
19. The expression cassette of any of statements 15-18, wherein at least one of the promoters is a promoter functional during plant development or growth.
20. The expression cassette of any of statements 15-19, wherein at least one of the promoters is a poplar xylem-specific secondary cell wall specific cellulose synthase 8 promoter, cauliflower mosaic virus promoter, Z10 promoter from a gene encoding a 10 kD zein protein, Z27 promoter from a gene encoding a 27 kD zein protein, pea rbcS gene or actin promoter from rice.
21. A plant cell comprising the expression cassette of any of statements 15-20.
22. The plant cell of statement 21, wherein the plant cell is a monocot cell, maize cell, grass cell or softwood cell.
23. The plant cell of statement 21 or 22, wherein the plant cell is a cell selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (sorghum), *Bachypodium distachyon* (purple false brome), a species recited in FIG. 20 and a species recited in Table 2.
24. The plant cell of statement 21, wherein the plant cell is a dicot cell or a hardwood cell.
25. A plant comprising the expression cassette of any of statements 15-20.
26. The plant of statement 25, wherein the plant is a monocot such as a grass species.
27. The plant of statement 25 or 26, wherein the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (sorghum), *Bachypodium distachyon* (purple false brome), a species recited in FIG. 20 and a species recited in Table 2.
28. The plant of statement 25, wherein the plant is a dicot or a hardwood.
29. A method for incorporating monolignol ferulates into lignin of a plant comprising:
    a) obtaining one or more plant cells having a knockout or knockdown mutation of the plant cells' endogenous p-coumaroyl-CoA:monolignol transferase gene;
    b) stably transforming the one or more plant cells with an expression cassette comprising a feruloyl-CoA:monolignol transferase nucleic acid to generate one or more transformed plant cells with the endogenous p-coumaroyl-CoA:monolignol transferase knockout or knockdown mutation;
    c) regenerating one or more of the transformed plant cells into at least one transgenic plant.
30. The method of statement 29, wherein the knockout or knockdown mutation increases incorporation of monolignol ferulates into the lignin of at least one of the transgenic plants compared to a control plant that (a) does not have the knockout or knockdown mutation but (b) is stably transformed with the expression cassette comprising feruloyl-CoA:monolignol transferase nucleic acid.
31. The method of statement 29 or 30, wherein the knockout or knockdown mutation increases incorporation of monolignol ferulates into the lignin of a plant by at least by 1%, or by at least 2%, or by at least 3%, or by at least 5% relative to a control plant plant that (a) does not have the knockout or knockdown mutation but (b) is stably transformed with the expression cassette comprising feruloyl-CoA:monolignol transferase nucleic acid.
32. The method of any of statements 29-31, wherein the endogenous p-coumaroyl-CoA:monolignol transferase gene can hybridize to a nucleic acid selected from the group consisting of SEQ ID NO:16, 18, 19, 22, 23, 25, 26, 27, 28, 47-63 and 64; or the endogenous p-coumaroyl-CoA:monolignol transferase gene has at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, or at least 97% sequence identity with a nucleic acid sequence selected from the group consisting of SEQ ID NO:16, 18, 19, 22, 23, 25, 26, 27, 28, 47-63 and 64.
33. A method for incorporating monolignol ferulates into lignin of a plant that includes:
    a) stably transforming one or more plant cells with a mutating nucleic acid adapted to hybridize to an endogenous p-coumaroyl-CoA:monolignol transferase gene within the plant cells and replace at least one nucleotide of the endogenous p-coumaroyl-CoA:monolignol transferase gene to generate at least one mutant plant cell with a p-coumaroyl-CoA:monolignol transferase gene knockdown or knockout mutation; or b) stably transforming one or plant cells with an expression cassette for expression of an inhibitory nucleic acid adapted to hybridize to an endogenous p-coumaroyl-CoA:monolignol transferase nucleic transcript to generate at least one transformed plant cell;

b) regenerating the mutant plant cell or the transformed plant cell into at least one transgenic plant.

34. The method of statement 33, wherein the transgenic plant(s) comprises a recombinant feruloyl-CoA:monolignol transferase nucleic acid operably linked to a promoter that expresses the feruloyl-CoA:monolignol transferase protein in the transgenic plant.

35. The method of statement 34, wherein the transgenic plant has increased incorporation of monolignol ferulates into its lignin compared to a control plant, wherein the control plant (a) does not have the knockout or knockdown mutation, (b) does not have the expression cassette comprising an inhibitory nucleic acid, but (c) is stably transformed with the recombinant feruloyl-CoA:monolignol transferase nucleic acid operably linked to a promoter that expresses the feruloyl-CoA:monolignol transferase protein.

36. The method of any of statements 33-35, wherein the knockout or knockdown mutation, or the expression cassette comprising an inhibitory nucleic acid, increases incorporation of monolignol ferulates into the lignin of a plant by at least by 1%, or by at least 2%, or by at least 3%, or by at least 5% relative to a control plant that (a) does not have the knockout or knockdown mutation (b) does not have the expression cassette comprising an inhibitory nucleic acid, but (c) is stably transformed with the recombinant feruloyl-CoA:monolignol transferase nucleic acid operably linked to a promoter that expresses the feruloyl-CoA:monolignol transferase protein.

37. The method of any of statements 33-36, wherein the endogenous p-coumaroyl-CoA:monolignol transferase gene can hybridize to a nucleic acid selected from the group consisting of SEQ ID NO:16, 18, 19, 22, 23, 25, 26, 27, 28, 47-63 and 64; or the endogenous p-coumaroyl-CoA:monolignol transferase gene has at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity, at least 95% sequence identity, or at least 97% sequence identity with a nucleic acid sequence selected from the group consisting of SEQ ID NO:16, 18, 19, 22, 23, 25, 26, 27, 28, 47-63 and 64.

38. The method of any of statements 33-37, wherein the mutating nucleic acid has two flanking segments and a central segment,
wherein the central segment has a point mutation, a deletion, a missense mutation, or a nonsense mutation relative to a nucleic acid selected from the group consisting of SEQ ID NO:16, SE ID NO:18, SEQ ID NO:19, SEQ ID NO:22, SEQ ID NO:23, SEQ ID NO:25, SEQ ID NO:26, SE ID NO:27, SEQ ID NO:28; and
wherein the two flanking segments can hybridize to different regions of one of the nucleic acids selected from the group consisting of SEQ ID NO:16, SE ID NO:18, SEQ ID NO:19, SEQ ID NO:22, SEQ ID NO:23, SEQ ID NO:25, SEQ ID NO:26, SEQ ID NO:27, and SEQ ID NO:28.

39. The method of any of statements 33-37, wherein the inhibitory nucleic acid can selectively hybridize to a nucleic acid with a sequence selected from the group consisting SEQ ID NO:16, 18, 19, 22, 23, 25, 26, 27, 28, and complementary sequences thereof 40. The method of any of statements 33-38, wherein an inhibitory nucleic acid inhibits expression and/or translation of an endogenous p-coumaroyl-CoA:monolignol transferase mRNA expressed in at least one transgenic plant.

41. The method of any of statements 29-40, wherein the transgenic plant is fertile.

42. The method of any of statements 29-41, further comprising recovering transgenic seeds from the transgenic plant.

43. The method of any of statements 29-42, wherein the plant is a monocot.

44. The method of any of statements 29-33, wherein the plant is a grass, maize or softwood plant.

45. The method of any of statements 29-44, the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (sorghum), *Bachypodium distachyon* (purple false brome), a species recited in FIG. 20 and a species recited in Table 2.

46. The method of any of statements 29-42, wherein the plant is a dicot, or hardwood.

47. The method of any of statements 29-46, wherein the lignin in the plant comprises at least 1% monolignol ferulate, at least 2% monolignol ferulate, at least 3% monolignol ferulate, at least 4% monolignol ferulate, at least 5% monolignol ferulate, at least 10% monolignol ferulate, at least 20% monolignol ferulate, or at least 25% monolignol ferulate.

48. The method of any of statements 29-47, wherein the lignin in the plant comprises about 1-30% monolignol ferulate, or about 2-30% monolignol ferulate.

49. The method of any of statements 29-48, further comprising breeding a fertile transgenic plant to yield a progeny plant.

50. The method of statement 49, wherein the progeny plant comprises lignin with at least 1% monolignol ferulate, at least 2% monolignol ferulate, at least 3% monolignol ferulate, at least 4% monolignol ferulate, at least 5% monolignol ferulate, at least 10% monolignol ferulate, at least 20% monolignol ferulate, or at least 25% monolignol ferulate.

51. The method of any of statements 29-50, further comprising breeding a fertile transgenic plant to yield a progeny plant that has an increase in the percentage of monolignol ferulates in the lignin of the progeny plant as a dominant trait while still maintaining functional agronomic characteristics relative to the corresponding untransformed plant.

52. The method of any of statements 29-51, further comprising stably transforming the plant cell with at least one selectable marker gene.

53. A fertile transgenic plant comprising a knockdown or knockout mutation in an endogenous p-coumaroyl-CoA:monolignol transferase gene, and a recombinant feruloyl-CoA:monolignol transferase nucleic acid operably linked to a promoter that expresses the feruloyl-CoA:monolignol transferase protein.

54. The fertile transgenic plant of statement 53, wherein the knockdown or knockout mutation and the feruloyl-CoA:monolignol transferase nucleic acid are transmitted through a complete normal sexual cycle of the transgenic plant to the next generation.

55. A fertile transgenic plant stably transformed by the nucleic acid of any of statements 1-11, wherein the nucleic acid is operably linked to a promoter functional in a host cell, wherein the nucleic acid expresses an inhibitory nucleic acid and the nucleic acid is transmitted through a complete normal sexual cycle of the transgenic plant to the next generation.

56. The fertile transgenic plant of statement 55, further comprising a feruloyl-CoA:monolignol transferase nucleic acid is transmitted through a complete normal sexual cycle of the transgenic plant to the next generation.

57. The fertile transgenic plant of any of statements 53-56, wherein the plant is a monocot, grass, maize, gymnosperm or softwood.

58. The fertile transgenic plant of any of statements 53-57, the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp. (e.g., *Sorghum bicolor*), *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass), *Sorghum bicolor* (*sorghum*), *Bachypodium distachyon* (purple false brome), a species recited in FIG. 20 and a species recited in Table 2.

59. The fertile transgenic plant of any of statements 53-56, wherein the plant is a dicot.

54. The fertile transgenic plant of any of statements 53-59, wherein the plant comprises lignin with at least 1% monolignol ferulate, at least 2% monolignol ferulate, at least 3% monolignol ferulate, at least 4% monolignol ferulate, at least 5% monolignol ferulate, at least 10% monolignol ferulate, at least 20% monolignol ferulate, or at least 25% monolignol ferulate.

55. A lignin isolated from a transgenic plant comprising the isolated nucleic of any of statements 1-12, or the plant cell of statement 13.

56. A method of making a product from a transgenic plant comprising:
(a) providing or obtaining a transgenic plant that comprises an isolated nucleic acid encoding a feruloyl-CoA:monolignol transferase and (i) a knockdown or knockout mutation in an endogenous p-coumaroyl-CoA:monolignol transferase gene, or (ii) an expression cassette for expression of an inhibitory nucleic acid adapted to hybridize to an endogenous p-coumaroyl-CoA:monolignol transferase nucleic transcript; and
(b) processing the transgenic plant's tissues under conditions sufficient to digest to the lignin to thereby generate the product from the transgenic plant;
wherein the transgenic plant's tissues comprise lignin having an increased percent of monolignol ferulates relative to a corresponding untransformed plant.

57. The method of statement 56, wherein the conditions sufficient to digest to the lignin comprise conditions sufficient to cleave ester bonds within monolignol ferulate-containing lignin.

58. The method of statement 56 or 57, wherein the conditions sufficient to digest to the lignin comprise mildly alkaline conditions.

59. The method of any of statements 56-58, wherein the conditions sufficient to digest to the lignin comprise contacting the transgenic plant's tissues with ammonia for a time and a temperature sufficient to cleave ester bonds within monolignol ferulate-containing lignin.

60. The method of any of statements 56-59, wherein the conditions sufficient to digest to the lignin would substantially not cleave ether and carbon-carbon bonds in lignin from a corresponding plant that does not contain the isolated nucleic acid encoding the feruloyl-CoA:monolignol transferase.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

Other embodiments are within the following claims.

SEQUENCE LISTING

```
<160> NUMBER OF SEQ ID NOS: 83

<210> SEQ ID NO 1
<211> LENGTH: 1326
<212> TYPE: DNA
<213> ORGANISM: Angelica sinensis

<400> SEQUENCE: 1
atgacgatca tggaggttca agttgtatct aagaagatgg taaagccatc agttccgact      60
cctgaccacc acaagacttg caaattgacg gcattcgatc agattgctcc tccggatcaa     120
gttcccatta tttacttcta caacagcagc aacatccaca atattcgcga gcaattggta     180
```

-continued

```
aaatccttgt ccgaaactct aaccaagttt tatccattag ctggaagatt tgttcaagat    240
ggtttctatg tcgattgtaa tgatgaaggg gtcttgtacg tagaagctga agttaacatt    300
ccgctaaacg aattcatcgg acaagcaaag aaaaatatac aacttatcaa tgatcttgtt    360
ccgaaaaaaa acttcaagga tattcattca tatgaaaatc caatagtggg attacagatg    420
agttatttca agtgtggtgg acttgctatt tgcatgtatc tttcgcatgt tgtagctgat    480
ggatatacag cagcagcatt cactaaagag tggtctaaca caaccaatgg catcatcaat    540
ggcgatcaac tagtttcttc ttctccgatt aacttcgaat tggcaactct agtcccagct    600
agagatttat cgacggtgat caagccagcc gtgatgccac catcaaagat caaggaaacc    660
aaggttgtca aaggaggtt tctgttcgat gaaaatgcga tatcagcttt caaagaccat    720
gtcatcaaat ccgaaagcgt taaccggcct acacgggtgg aagttgtgac atctgtgtta    780
tggaaggctc tgatcaacca gtctaagctt ccaagttcta cactatattt tcacctcaac    840
tttagaggga aaacaggcat caacacccca ccgctagata atcattttc gctttgcgga    900 aacttttaca ctcaggttcc tacaaggttc aggggggaa atcaaacaaa acaggatttg    960
gaattgcatg aattggtcaa gttgttgaga ggaaagttgc gtaacactct gaagaattgc   1020
tccgaaatta acactgccga tgggctgttc ctggaagcag ctagtaattt caatattata   1080
caggaagatt tggaggacga acaagtggat gttcggattt ttacaacgtt gtgtaggatg   1140
cctttgtatg aaactgagtt tgggtgggga aaaccagaat gggttaccat tccagagatg   1200
catttggaga tagtgtttct tttggacact aaatgtggga ctggtattga ggcattagtg   1260
agcatggatg aagcagatat gcttcagttt gaacttgatc ccaccatctc tgctttcgct   1320
tcctag                                                              1326
```

<210> SEQ ID NO 2
<211> LENGTH: 441
<212> TYPE: PRT
<213> ORGANISM: Angelica sinensis

<400> SEQUENCE: 2

```
Met Thr Ile Met Glu Val Gln Val Val Ser Lys Lys Met Val Lys Pro
 1               5                  10                  15

Ser Val Pro Thr Pro Asp His His Lys Thr Cys Lys Leu Thr Ala Phe
             20                  25                  30

Asp Gln Ile Ala Pro Pro Asp Gln Val Pro Ile Ile Tyr Phe Tyr Asn
         35                  40                  45

Ser Ser Asn Ile His Asn Ile Arg Glu Gln Leu Val Lys Ser Leu Ser
     50                  55                  60

Glu Thr Leu Thr Lys Phe Tyr Pro Leu Ala Gly Arg Phe Val Gln Asp
 65                  70                  75                  80

Gly Phe Tyr Val Asp Cys Asn Asp Glu Gly Val Leu Tyr Val Glu Ala
                 85                  90                  95

Glu Val Asn Ile Pro Leu Asn Glu Phe Ile Gly Gln Ala Lys Lys Asn
            100                 105                 110

Ile Gln Leu Ile Asn Asp Leu Val Pro Lys Lys Asn Phe Lys Asp Ile
        115                 120                 125

His Ser Tyr Glu Asn Pro Ile Val Gly Leu Gln Met Ser Tyr Phe Lys
    130                 135                 140

Cys Gly Gly Leu Ala Ile Cys Met Tyr Leu Ser His Val Val Ala Asp
145                 150                 155                 160

Gly Tyr Thr Ala Ala Ala Phe Thr Lys Glu Trp Ser Asn Thr Thr Asn
```

-continued

```
                     165                 170                 175
Gly Ile Ile Asn Gly Asp Gln Leu Val Ser Ser Pro Ile Asn Phe
            180                 185                 190

Glu Leu Ala Thr Leu Val Pro Ala Arg Asp Leu Ser Thr Val Ile Lys
        195                 200                 205

Pro Ala Val Met Pro Pro Ser Lys Ile Lys Glu Thr Lys Val Val Thr
    210                 215                 220

Arg Arg Phe Leu Phe Asp Glu Asn Ala Ile Ser Ala Phe Lys Asp His
225                 230                 235                 240

Val Ile Lys Ser Glu Ser Val Asn Arg Pro Thr Arg Val Glu Val Val
                245                 250                 255

Thr Ser Val Leu Trp Lys Ala Leu Ile Asn Gln Ser Lys Leu Pro Ser
            260                 265                 270

Ser Thr Leu Tyr Phe His Leu Asn Phe Arg Gly Lys Thr Gly Ile Asn
        275                 280                 285

Thr Pro Pro Leu Asp Asn His Phe Ser Leu Cys Gly Asn Phe Tyr Thr
    290                 295                 300

Gln Val Pro Thr Arg Phe Arg Gly Gly Asn Gln Thr Lys Gln Asp Leu
305                 310                 315                 320

Glu Leu His Glu Leu Val Lys Leu Leu Arg Gly Lys Leu Arg Asn Thr
                325                 330                 335

Leu Lys Asn Cys Ser Glu Ile Asn Thr Ala Asp Gly Leu Phe Leu Glu
            340                 345                 350

Ala Ala Ser Asn Phe Asn Ile Ile Gln Glu Asp Leu Glu Asp Glu Gln
        355                 360                 365

Val Asp Val Arg Ile Phe Thr Thr Leu Cys Arg Met Pro Leu Tyr Glu
    370                 375                 380

Thr Glu Phe Gly Trp Gly Lys Pro Glu Trp Val Thr Ile Pro Glu Met
385                 390                 395                 400

His Leu Glu Ile Val Phe Leu Leu Asp Thr Lys Cys Gly Thr Gly Ile
                405                 410                 415

Glu Ala Leu Val Ser Met Asp Glu Ala Asp Met Leu Gln Phe Glu Leu
            420                 425                 430

Asp Pro Thr Ile Ser Ala Phe Ala Ser
        435                 440

<210> SEQ ID NO 3
<211> LENGTH: 50
<212> TYPE: DNA
<213> ORGANISM: Artificial Sequence
<220> FEATURE:
<223> OTHER INFORMATION: A synthetic primer
<220> FEATURE:
<221> NAME/KEY: misc_feature
<222> LOCATION: (1)...(50)
<223> OTHER INFORMATION: N = any nucleic acid

<400> SEQUENCE: 3
tagaggccga ggcggccgac atgttttgtt ttttttttctt ttttttttvn                50

<210> SEQ ID NO 4
<211> LENGTH: 39
<212> TYPE: DNA
<213> ORGANISM: Artificial Sequence
<220> FEATURE:
<223> OTHER INFORMATION: A synthetic primer

<400> SEQUENCE: 4
```

```
aaaaaagcag gcttcatgac gatcatggag gttcaagtt                              39

<210> SEQ ID NO 5
<211> LENGTH: 39
<212> TYPE: DNA
<213> ORGANISM: Artificial Sequence
<220> FEATURE:
<223> OTHER INFORMATION: A synthetic primer

<400> SEQUENCE: 5
gtacaagaaa gctgggttct aggaagcgaa agcagagat                              39

<210> SEQ ID NO 6
<211> LENGTH: 29
<212> TYPE: DNA
<213> ORGANISM: Artificial Sequence
<220> FEATURE:
<223> OTHER INFORMATION: A synthetic primer

<400> SEQUENCE: 6
ggggacaagt ttgtacaaaa aagcaggct                                        29

<210> SEQ ID NO 7
<211> LENGTH: 28
<212> TYPE: DNA
<213> ORGANISM: Artificial Sequence
<220> FEATURE:
<223> OTHER INFORMATION: A synthetic primer

<400> SEQUENCE: 7
gggaccactt tgtacaagaa agctgggt                                         28

<210> SEQ ID NO 8
<211> LENGTH: 1389
<212> TYPE: DNA
<213> ORGANISM: Hibiscus cannabinus

<400> SEQUENCE: 8
atggcaaccc acagcactat catgttctca gtcgatagaa acgatgtcgt gtttgtcaaa      60
cccttcaaac ctacaccctc acaggttcta tctctctcca ccatcgacaa tgatcccaac     120
cttgagatca tgtgccatac tgtttttgtg tatcaagcca atgccgattt cgatgttaag     180
cccaaggatc cagcttccat aatccaggaa gcactctcca agctcttggt ttattactat     240
cccttagcgg ggaagatgaa gagggagacc gatggaaaac ttcgaatcgc ttgcactgcc     300
gacgatagcg tgcccttctt agtagccacc gccgattgca agctctcgtc gttgaaccac     360
ttggatggca tagatgttca taccgggaaa gaattcgcct tggattttgc atccgaatcc     420
gacggtggct attatcaccc tctggtcatg caggtgacga agttcatatg cggagggttc     480
accatcgctt tgagtttatc gcactcggtt tgtgatggct tcggtgcagc tcagatcttt     540
caagcattga ccgagctcgc aagtggcagg aacgagccct cggttaaacc cgtgtgggag     600
aggcaactat tagtggcgaa accggccgag gaaatccctc ggtcgattgt cgataaggac     660
ttgtcggcag cttcaccgta tctgccgaca accgacatag tccatgcctg cttttatgta     720
accgaggaga gtataaaaac actgaaaatg aatctgatca agaaagcaa agatgagagt     780 ataaccagtc tcgaggtcct ttcagcctat atatggagag caaggtttag agcattgaaa     840
ttgagtccag ataaaaccac aatgctcggc atggccgtag gcatacgacg caccgtgaaa     900
ccacggtttg ccgaaggata ctacgggaat gctttcacct cggcaaatac ggccatgacc     960
gggaaggaac tcgaccaagg accgctctcg aaagctgtga acaaaatcaa ggagagcaaa    1020
```

```
aagcttgctt cggagaatga ctatatctgg aacttgatga gcattaacga gaagctgaga    1080
gaactgaatt cgaagttcga agcggccgcc ggttcaacca tggtcataac agattggagg    1140
cggttgggac tattggaaga tgtggatttt ggatggaaag gtagcgtaaa catgatacca    1200
ctgccgtgga acatgttcgg gtacgtggat ttggttcttt tattgcctcc ttgtaaactg    1260
gaccaatcga tgaaaggcgg tgctagagtg ttggtttcct ttcccacggc tgctattgcc    1320
aaattcaagg aagaaatgga tgctctcaaa catgataaca aggttgccgg cgatgctcta    1380
gtgatctag                                                            1389
```

<210> SEQ ID NO 9
<211> LENGTH: 462
<212> TYPE: PRT
<213> ORGANISM: Hibiscus cannabinus

<400> SEQUENCE: 9

Met Ala Thr His Ser Thr Ile Met Phe Ser Val Asp Arg Asn Asp Val
1               5                   10                  15

Val Phe Val Lys Pro Phe Lys Pro Thr Pro Ser Gln Val Leu Ser Leu
            20                  25                  30

Ser Thr Ile Asp Asn Asp Pro Asn Leu Glu Ile Met Cys His Thr Val
        35                  40                  45

Phe Val Tyr Gln Ala Asn Ala Asp Phe Asp Val Lys Pro Lys Asp Pro
    50                  55                  60

Ala Ser Ile Ile Gln Glu Ala Leu Ser Lys Leu Val Tyr Tyr Tyr
65                  70                  75                  80

Pro Leu Ala Gly Lys Met Lys Arg Glu Thr Asp Gly Lys Leu Arg Ile
                85                  90                  95

Ala Cys Thr Ala Asp Asp Ser Val Pro Phe Leu Val Ala Thr Ala Asp
            100                 105                 110

Cys Lys Leu Ser Ser Leu Asn His Leu Asp Gly Ile Asp Val His Thr
        115                 120                 125

Gly Lys Glu Phe Ala Leu Asp Phe Ala Ser Glu Ser Asp Gly Gly Tyr
    130                 135                 140

Tyr His Pro Leu Val Met Gln Val Thr Lys Phe Ile Cys Gly Gly Phe
145                 150                 155                 160

Thr Ile Ala Leu Ser Leu Ser His Ser Val Cys Asp Gly Phe Gly Ala
                165                 170                 175

Ala Gln Ile Phe Gln Ala Leu Thr Glu Leu Ala Ser Gly Arg Asn Glu
            180                 185                 190

Pro Ser Val Lys Pro Val Trp Glu Arg Gln Leu Leu Val Ala Lys Pro
        195                 200                 205

Ala Glu Glu Ile Pro Arg Ser Ile Val Asp Lys Asp Leu Ser Ala Ala
    210                 215                 220

Ser Pro Tyr Leu Pro Thr Thr Asp Ile Val His Ala Cys Phe Tyr Val
225                 230                 235                 240

Thr Glu Glu Ser Ile Lys Thr Leu Lys Met Asn Leu Ile Lys Glu Ser
                245                 250                 255

Lys Asp Glu Ser Ile Thr Ser Leu Glu Val Leu Ser Ala Tyr Ile Trp
            260                 265                 270

Arg Ala Arg Phe Arg Ala Leu Lys Leu Ser Pro Asp Lys Thr Thr Met
        275                 280                 285

Leu Gly Met Ala Val Gly Ile Arg Thr Val Lys Pro Arg Leu Pro
    290                 295                 300

-continued

Glu Gly Tyr Tyr Gly Asn Ala Phe Thr Ser Ala Asn Thr Ala Met Thr
305                 310                 315                 320

Gly Lys Glu Leu Asp Gln Gly Pro Leu Ser Lys Ala Val Lys Gln Ile
            325                 330                 335

Lys Glu Ser Lys Lys Leu Ala Ser Glu Asn Asp Tyr Ile Trp Asn Leu
        340                 345                 350

Met Ser Ile Asn Glu Lys Leu Arg Glu Leu Asn Ser Lys Phe Glu Ala
            355                 360                 365

Ala Ala Gly Ser Thr Met Val Ile Thr Asp Trp Arg Arg Leu Gly Leu
    370                 375                 380

Leu Glu Asp Val Asp Phe Gly Trp Lys Gly Ser Val Asn Met Ile Pro
385                 390                 395                 400

Leu Pro Trp Asn Met Phe Gly Tyr Val Asp Leu Val Leu Leu Leu Pro
                405                 410                 415

Pro Cys Lys Leu Asp Gln Ser Met Lys Gly Gly Ala Arg Val Leu Val
            420                 425                 430

Ser Phe Pro Thr Ala Ala Ile Ala Lys Phe Lys Glu Met Asp Ala
        435                 440                 445

Leu Lys His Asp Asn Lys Val Ala Gly Asp Ala Leu Val Ile
    450                 455                 460

<210> SEQ ID NO 10
<211> LENGTH: 38
<212> TYPE: DNA
<213> ORGANISM: Artificial Sequence
<220> FEATURE:
<223> OTHER INFORMATION: A synthetic primer

<400> SEQUENCE: 10
aaaaaagcag gcttcatggc aacccacagc actatcat                           38

<210> SEQ ID NO 11
<211> LENGTH: 41
<212> TYPE: DNA
<213> ORGANISM: Artificial Sequence
<220> FEATURE:
<223> OTHER INFORMATION: A synthetic primer

<400> SEQUENCE: 11
gtacaagaaa gctgggttct agatcactag agcatcgccg g                       41

<210> SEQ ID NO 12
<211> LENGTH: 29
<212> TYPE: DNA
<213> ORGANISM: Artificial Sequence
<220> FEATURE:
<223> OTHER INFORMATION: A synthetic primer

<400> SEQUENCE: 12
ggggacaagt ttgtacaaaa aagcaggct                                     29

<210> SEQ ID NO 13
<211> LENGTH: 28
<212> TYPE: DNA
<213> ORGANISM: Artificial Sequence
<220> FEATURE:
<223> OTHER INFORMATION: A synthetic primer

<400> SEQUENCE: 13
gggaccactt tgtacaagaa agctgggt                                      28

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
cgcactcggt ttgtgatggc                                                   20

<210> SEQ ID NO 15
<211> LENGTH: 22
<212> TYPE: DNA
<213> ORGANISM: Artificial Sequence
<220> FEATURE:
<223> OTHER INFORMATION: A synthetic primer

<400> SEQUENCE: 15
ttcacagctt tcgagagcgg tc                                                22

<210> SEQ ID NO 16
<211> LENGTH: 1320
<212> TYPE: DNA
<213> ORGANISM: Oryza sativa

<400> SEQUENCE: 16
atggggttcg cggtggtgag gacgaaccgg gagttcgtgc ggccgagcgc ggcgacgccg        60
ccgtcgtccg gcgagctgct ggagctgtcc atcatcgacc gcgtggtggg gctccgccac       120
ctggtgcggt cgctgcacat cttctccgcc gccgccccga gcggcggcga cgccaagccg       180
tcgccggcgc gggtgatcaa ggaggcgctg ggaaggcgc tggtggacta ctacccgttc        240
gcggggaggt tcgtggacgg cggcggcggg ccggggagcg cccgcgtgga gtgcaccggc       300
gagggcgcct ggttcgtgga ggccgccgcc ggctgcagcc tcgacgacgt gaacggcctc       360
gaccacccgc tcatgatccc cgaggacgac ctcctccccg acgccgcccc cggtgtccac       420
cccctcgacc tccccctcat gatgcaggtg acggagttca gttgcggagg gttcgtggtg       480
ggcctgatct cggtgcacac gatggcggac gggctagggg ccgggcagtt catcaacgcg       540
gtgggcgact acgcccgcgg gctggacagg ccgagggtga gcccggtctg ggcccgcgag       600
gccatcccga gccgccgaa gctgcccccg ggccgccgc cggagctgaa gatgttccag        660
ctccgccacg tcaccgccga cctgagcctg gacagcatca acaaggccaa gtccgcctac       720
ttcgccgcca ccggccaccg ctgctccacc ttcgacgtcg ccatcgccaa gacgtggcag       780
gcgcgcaccc gcgcgctccg cctcccggaa cccacctccc gcgtcaacct ctgcttcttc       840
gccaacaccc gccacctcat ggccggcgcc gccgcctggc ccgcacccgc cgccggcggc       900
aatggcggca atgggttcta cggcaactgc ttctacccgg tgtcggtggt ggcggagagc       960
ggggcggtgg aggcggcgga cgtggccggg gtggtgggga tgatacggga ggcgaaggcg      1020
aggctgccgg cggacttcgc gcggtgggcg gtggccgact tcagggagga tccgtacgag      1080
ctgagcttca cgtacgattc cctgttcgtc tccgactgga cgcggctggg gttcctggag      1140
gcggactacg ggtgggggcc gccgtcgcac gtcataccct tcgcgtacta cccgttcatg      1200
gccgtcgcca tcatcggcgc gccgccggtg cccaagaccg gcgcccggat catgacgcag      1260
tgcgtcgagg acgaccacct gccggcgttc aaggaggaga tcaaggcctt cgacaagtaa      1320

<210> SEQ ID NO 17
<211> LENGTH: 439

```
<212> TYPE: PRT
<213> ORGANISM: Oryza sativa

<400> SEQUENCE: 17

Met Gly Phe Ala Val Val Arg Thr Asn Arg Glu Phe Val Arg Pro Ser
1               5                   10                  15

Ala Ala Thr Pro Pro Ser Ser Gly Glu Leu Leu Glu Leu Ser Ile Ile
            20                  25                  30

Asp Arg Val Val Gly Leu Arg His Leu Val Arg Ser Leu His Ile Phe
        35                  40                  45

Ser Ala Ala Ala Pro Ser Gly Gly Asp Ala Lys Pro Ser Pro Ala Arg
    50                  55                  60

Val Ile Lys Glu Ala Leu Gly Lys Ala Leu Val Asp Tyr Tyr Pro Phe
65                  70                  75                  80

Ala Gly Arg Phe Val Asp Gly Gly Gly Pro Gly Ser Ala Arg Val
                85                  90                  95

Glu Cys Thr Gly Glu Gly Ala Trp Phe Val Glu Ala Ala Gly Cys
                100                 105                 110

Ser Leu Asp Asp Val Asn Gly Leu Asp His Pro Leu Met Ile Pro Glu
            115                 120                 125

Asp Asp Leu Leu Pro Asp Ala Ala Pro Gly Val His Pro Leu Asp Leu
    130                 135                 140

Pro Leu Met Met Gln Val Thr Glu Phe Ser Cys Gly Gly Phe Val Val
145                 150                 155                 160

Gly Leu Ile Ser Val His Thr Met Ala Asp Gly Leu Gly Ala Gly Gln
                165                 170                 175

Phe Ile Asn Ala Val Gly Asp Tyr Ala Arg Gly Leu Asp Arg Pro Arg
            180                 185                 190

Val Ser Pro Val Trp Ala Arg Glu Ala Ile Pro Ser Pro Pro Lys Leu
        195                 200                 205

Pro Pro Gly Pro Pro Glu Leu Lys Met Phe Gln Leu Arg His Val
210                 215                 220

Thr Ala Asp Leu Ser Leu Asp Ser Ile Asn Lys Ala Lys Ser Ala Tyr
225                 230                 235                 240

Phe Ala Ala Thr Gly His Arg Cys Ser Thr Phe Asp Val Ala Ile Ala
                245                 250                 255

Lys Thr Trp Gln Ala Arg Thr Arg Ala Leu Arg Leu Pro Glu Pro Thr
            260                 265                 270

Ser Arg Val Asn Leu Cys Phe Phe Ala Asn Thr Arg His Leu Met Ala
        275                 280                 285

Gly Ala Ala Ala Trp Pro Ala Pro Ala Ala Gly Gly Asn Gly Gly Asn
290                 295                 300

Gly Phe Tyr Gly Asn Cys Phe Tyr Pro Val Ser Val Ala Glu Ser
305                 310                 315                 320

Gly Ala Val Glu Ala Ala Asp Val Ala Gly Val Val Gly Met Ile Arg
                325                 330                 335

Glu Ala Lys Ala Arg Leu Pro Ala Asp Phe Ala Arg Trp Ala Val Ala
            340                 345                 350

Asp Phe Arg Glu Asp Pro Tyr Glu Leu Ser Phe Thr Tyr Asp Ser Leu
        355                 360                 365

Phe Val Ser Asp Trp Thr Arg Leu Gly Phe Leu Glu Ala Asp Tyr Gly
    370                 375                 380

Trp Gly Pro Pro Ser His Val Ile Pro Phe Ala Tyr Tyr Pro Phe Met
385                 390                 395                 400
```

Ala Val Ala Ile Ile Gly Ala Pro Pro Val Pro Lys Thr Gly Ala Arg
         405                 410                 415

Ile Met Thr Gln Cys Val Glu Asp Asp His Leu Pro Ala Phe Lys Glu
         420                 425                 430

Glu Ile Lys Ala Phe Asp Lys
     435

<210> SEQ ID NO 18
<211> LENGTH: 3998
<212> TYPE: DNA
<213> ORGANISM: Oryza sativa

<400> SEQUENCE: 18

| | | | | | |
|---|---|---|---|---|---|
| accaccatca | ccaccacctc | gaaggtcttg | agctccatct | ccggcgacgg | cggcgacgac | 60 |
| gacgacgacg | gcgaggagga | gctagtagct | agctgagcca | gacagcatgg | ggttcgcggt | 120 |
| ggtgaggacg | aaccgggagt | tcgtgcggcc | gagcgcggcg | acgccgccgt | cgtccggcga | 180 |
| gctgctggag | ctgtccatca | tcgaccgcgt | ggtggggctc | cgccacctgg | tgcggtcgct | 240 |
| gcacatcttc | tccgccgccg | ccccgagcgg | cggcgacgcc | aagccgtcgc | cggcgcgggt | 300 |
| gatcaaggag | gcgctgggga | aggcgctggt | ggactactac | ccgttcgcgg | ggaggttcgt | 360 |
| ggacggcggc | ggcgggccgg | ggagcgcccg | cgtggagtgc | accggcgagg | gcgcctggtt | 420 |
| cgtggaggcc | gccgccggct | gcagcctcga | cgacgtgaac | ggcctcgacc | acccgctcat | 480 |
| gatccccgag | gacgacctcc | tccccgacgc | cgccccggt | gtccaccccc | tcgacctccc | 540 |
| cctcatgatg | caggtataat | actacccgta | tacgtacgtt | tctacgtacg | taagtacgtg | 600 |
| ctatacttgc | gagcagacaa | aaacaaataa | aatcggtaac | aacaattaac | catccagtta | 660 |
| tgcttacaac | taattcaaat | tatcttaatt | aattaaaact | gtccggctaa | ttaagtgatt | 720 |
| attaagggtg | tgtttttatc | acatcttccc | gactggtact | ccctcatttt | ccacacggat | 780 |
| gttttacaac | tgctaaacgg | tacgtattat | cagaaaaaag | ttatatatat | aaattgtttt | 840 |
| aaaatcatat | taatctattt | ttaagtttat | tttagctaat | agttaaataa | acacgcgcta | 900 |
| acggatcatt | atgttttgtg | tgtggggaga | tatagtttct | aacctccacc | tctaaacaca | 960 |
| gcataattgt | tggtacgtag | ggcctattca | ctttaacgca | aaaaagaac | cttaccaagt | 1020 |
| tgccaaaatt | ttggtaggat | ttcttatata | gttactaaaa | tttgatagca | aactaaatat | 1080 |
| aaccactttt | ttataacttt | accaaaattt | gctaagattg | aaaatggcat | caaagtgaac | 1140 |
| aggcccgtat | acgtacggag | aatgctgacc | tctccggatg | ataccttta | ttttcactt | 1200 |
| gtgtggatgt | gcacacatgt | acgaggacga | acacattcaa | acccgtgaag | attttaatat | 1260 |
| gtggacgaac | tcgatctatg | gtattgttgc | tgacgaatta | attacaaaag | tgctcaagga | 1320 |
| gttatgtaac | tataagaaca | aaactatata | tgtttgccca | agtagaaata | tatacgaaca | 1380 |
| aaaacacaga | catgaataga | acctacgcgt | acgtacatat | gtgccattac | atgcatgtac | 1440 |
| acaatcatta | gctagtgtcc | tggattatat | tctagtcaat | tataactttc | tagaaattag | 1500 |
| gtactaatat | atgtatgact | ctcaaactgt | agtcatgctt | gtgtcaagtt | ataattaagt | 1560 |
| acaataatca | caccgattta | ttttacataa | agtacagtag | gattcaagat | aagactgagc | 1620 |
| tatatagtac | taggcaggat | gatgagctag | ctagagctta | gtgctcaaca | taaactagtt | 1680 |
| ggagcgtgca | ctgcaatttt | caaagtaaaa | ttagttaatt | tgcactaggt | gaagttgatc | 1740 |
| ctgtcaggta | ggtaagctca | ccaactccaa | agattggaca | gaatgaagca | tctgtggaag | 1800 |
| tgaaagcagt | tgcgttggcg | taagaccaca | ctaaccagag | aactcataat | acaaaataca | 1860 |

```
tatacagcac acaatttata ttgtgtatat atatatatat atatatatat atatgtatgt    1920
atgtatgtat gtatgtattc taactgtgtt atccaatttt taagaaattt catcttttca    1980
aaagtagtag tatttgagtg atgcatgtgc acgttttag atatgtacat ataectcatc     2040
tatctttaaa aataaaataa attttataca tgagtcggaa cactaagctt taacactgat    2100
atctgacgat agcatgacgg gatgagcttg tcatcaattg cagcagggca attaggcatg    2160
taaactgggg ccattgattt ctgtcgagca cactatgctt tccctgtctt attctgccta    2220
acttaacact aatatttgac acactatcaa ttgttagcta ttgatatggc agtttgacat    2280
cgaccctgct ccatcattat tactgcatgc ccgcccattc gatgattgac ttgaccaaac    2340
ccacaagtgc aaattggaaa attaattaat taattaatta gcaagataaa tatatccatc    2400
agggattcag gatcaggtca tgatgtaat cactctcaaa catagctaat cattgtgctt     2460
atggtccaag tgatcattcc ccctaatcaa caactcgctt gctagcaaga cgtcccttcg    2520
aatggattat ttgatagcta gagcatatca ccttgcactt caccactccc cttatgcaga   2580
gtgtacgtat gtctaaccag aatctagtgg tgagcgtaaa agatcaaagt gcccttatca    2640
ataacaaaat actccgtaat acatttggtg gatatatagg tatataagta ttaaaggaat    2700
aaaactttca aatttgtgga ttctaataaa aactaatatt aattttgata aacctgaatt    2760
gtagatactc taacttaggg tagtagttga agcatgcaaa gctctaaaaa tatatatgaa    2820
tttcggcgtg tttatatata tttctccgtg gatataaaag cttaaaattt ataatcattt    2880
tatgatgatc aggtgacgga gttcagttgc ggagggttcg tggtgggcct gatctcggtg    2940
cacacgatgg cggacgggct aggggccggg cagttcatca acgcggtggg cgactacgcc    3000
cgcgggctgg acaggccgag ggtgagcccg gtctgggccc gcgaggccat cccgagcccg    3060
ccgaagctgc ccccgggccc gccgccggag ctgaagatgt tccagctccg ccacgtcacc    3120
gccgacctga gctggacag catcaacaag gccaagtccg cctacttcgc cgccaccggc     3180
caccgctgct ccaccttcga cgtcgccatc gccaagacgg ggcaggcgcg cacccgcgcg    3240
ctccgcctcc cggaacccac ctcccgcgtc aacctctgct tcttcgccaa cacccgccac    3300
ctcatggccg gcgccgccgc ctggcccgca cccgccgccg cgcgcaatgg cggcaatggg    3360
ttctacggca actgcttcta cccggtgtcg gtggtggcgg agagcggggc ggtggaggcg    3420
gcggacgtgg ccggggtggt ggggatgata cgggaggcga aggcgaggct gccggcggac    3480
ttcgcgcggt gggcggtggc cgacttcagg gaggatccgt acgagctgag cttcacgtac    3540
gattccctgt tcgtctccga ctggacgcgc ctggggttcc tggagcgga ctacgggtgg     3600
gggccgccgt cgcacgtcat acccttcgcg tactacccgt tcatggccgt cgccatcatc    3660
ggcgcgccgc cggtgcccaa gaccggcgcc cggatcatga cgcagtgcgt cgaggacgac    3720
cacctgccgg cgttcaagga ggagatcaag gccttcgaca agtaaaatgc ttgtgaaatg    3780
tgaactttgt tattgttact acttctatgg gctcgttgct caatgggctt ttttttgctt    3840
ttgttttgtg tgtgtgggcc gacacgattg gtcaaaaggg atttggtgga ggcccagttg    3900
taataagatg gtccacgcat catggattaa tcgttaattg taaggtagta ctacacggat    3960
ttgttaacaa ggaataagtt cacttggtga cccagtga                            3998
```

<210> SEQ ID NO 19
<211> LENGTH: 1320
<212> TYPE: DNA
<213> ORGANISM: Oryza sativa

<400> SEQUENCE: 19

```
atgggatttg ctgttgtccg cacaaaccgt gaatttgttc gcccctcggc agctacccca    60
ccatcatccg gcgaattatt ggaattatca atcattgatc gtgtagttgg tctccgtcat   120
ctggttcgtt ctttacatat tttttctgca gctgcaccat ctggcggtga tgcaaaaccc   180
tccccggctc gcgttattaa agaagcattg gcaaagcac ttgtagacta ctatcctttc    240
gcaggtcgtt tcgttgacgg cggcggcggt ccgggcagtg cgcgtgtaga atgtaccggt   300
gaaggtgctt ggtttgtaga agcagctgct ggatgttcat tagacgatgt caatggctta   360
gatcatccat taatgattcc tgaagacgat ctcttacccg atgcagcccc tggcgttcac   420
ccactggatt taccgttaat gatgcaagtt actgaatttt catgcggcgg ttttgttgtt   480
ggcttgatta gcgtccacac aatggctgac ggtttaggcg caggccaatt tatcaatgca   540
gtaggcgatt atgctcgtgg cctcgaccgt ccgcgtgtta gcccggtatg ggcacgcgaa   600
gccattccta gccctccgaa gttaccaccc ggtccacctc ccgaattaaa aatgttccaa   660
cttcgtcatg tgacagccga tttgtctctc gattctatca acaaggcgaa atcagcgtat   720
tttgcagcca ccgtcatcg ttgctccaca ttcgacgtcg ctattgcaaa acatggcaa    780
gcccgcactc gtgcccttcg tctcccagaa ccaacgtcac gtgttaacct gtgttttttt   840
gctaatacccc gccatttaat ggcaggcgca gcggcctggc ccgctccagc agccggaggt   900
aatggtggca acggcttcta tggcaattgt ttctacccgg tgtctgttgt ggccgaatca   960
ggtgcagttg aagcggcaga tgtggcaggt gttgttggta tgatccgtga ggccaaagcc  1020
cgtctcccag ccgatttgc acgttgggca gttgccgatt tcgcgaaga cccttatgaa    1080
ctttcattta catatgattc cttgtttgtc tcagattgga ctcgtttagg atttctcgaa  1140
gctgattatg ttggggccc accctctcat gtaattcctt tcgcatatta cccgtttatg  1200
gcggtagcta tcatcggcgc tcctccagtt ccaaaaaccg gcgcacgtat tatgactcag  1260
tgtgtagaag atgatcattt accagcgttt aaagaagaaa ttaaagcctt cgataagtga  1320
```

<210> SEQ ID NO 20
<211> LENGTH: 374
<212> TYPE: PRT
<213> ORGANISM: Hibiscus cannabinus

<400> SEQUENCE: 20

```
Glu Ala Leu Ser Lys Leu Leu Val Tyr Tyr Pro Leu Ala Gly Lys
1               5                   10                  15

Met Lys Arg Glu Thr Asp Gly Lys Leu Arg Ile Ala Cys Thr Ala Asp
            20                  25                  30

Asp Ser Val Pro Phe Leu Val Ala Thr Ala Asp Cys Lys Leu Ser Ser
        35                  40                  45

Leu Asn His Leu Asp Gly Ile Asp Val His Thr Gly Lys Glu Phe Ala
    50                  55                  60

Leu Asp Phe Ala Ser Glu Ser Asp Gly Gly Tyr Tyr His Pro Leu Val
65                  70                  75                  80

Met Gln Val Thr Lys Phe Ile Cys Gly Gly Phe Thr Ile Ala Leu Ser
                85                  90                  95

Leu Ser His Ser Val Cys Asp Gly Phe Gly Ala Ala Gln Ile Phe Gln
            100                 105                 110

Ala Leu Thr Glu Leu Ala Ser Gly Arg Asn Glu Pro Ser Val Lys Pro
        115                 120                 125

Val Trp Glu Arg Gln Leu Leu Val Ala Lys Pro Ala Glu Glu Ile Pro
```

```
                    130                 135                 140
Arg Ser Ile Val Asp Lys Asp Leu Ser Ala Ala Ser Pro Tyr Leu Pro
145                 150                 155                 160

Thr Thr Asp Ile Val His Ala Cys Phe Tyr Val Thr Glu Glu Ser Ile
                165                 170                 175

Lys Thr Leu Lys Met Asn Leu Ile Lys Glu Ser Lys Asp Glu Ser Ile
            180                 185                 190

Thr Ser Leu Glu Val Leu Ser Ala Tyr Ile Trp Arg Ala Arg Phe Arg
        195                 200                 205

Ala Leu Lys Leu Ser Pro Asp Lys Thr Thr Met Leu Gly Met Ala Val
    210                 215                 220

Gly Ile Arg Arg Thr Val Lys Pro Arg Leu Pro Gly Tyr Tyr Gly
225                 230                 235                 240

Asn Ala Phe Thr Ser Ala Asn Thr Ala Met Thr Gly Lys Glu Leu Asp
                245                 250                 255

Gln Gly Pro Leu Ser Lys Ala Val Lys Gln Ile Lys Glu Ser Lys Lys
            260                 265                 270

Leu Ala Ser Glu Asn Asp Tyr Ile Trp Asn Leu Met Ser Ile Asn Glu
        275                 280                 285

Lys Leu Arg Glu Leu Asn Ser Lys Phe Glu Ala Ala Ala Gly Ser Thr
    290                 295                 300

Met Val Ile Thr Asp Trp Arg Arg Leu Gly Leu Leu Glu Asp Val Asp
305                 310                 315                 320

Phe Gly Trp Lys Gly Ser Val Asn Met Ile Pro Leu Pro Trp Asn Met
                325                 330                 335

Phe Gly Tyr Val Asp Leu Val Leu Leu Pro Pro Cys Lys Leu Asp
            340                 345                 350

Gln Ser Met Lys Gly Gly Ala Arg Val Leu Val Ser Phe Pro Thr Ala
        355                 360                 365

Ala Ile Ala Lys Phe Lys
    370

<210> SEQ ID NO 21
<211> LENGTH: 371
<212> TYPE: PRT
<213> ORGANISM: Angelica sinensis

<400> SEQUENCE: 21

Lys Ser Leu Ser Glu Thr Leu Thr Lys Phe Tyr Pro Leu Ala Gly Arg
1               5                   10                  15

Phe Val Gln Asp Gly Phe Tyr Val Asp Cys Asn Asp Glu Gly Val Leu
            20                  25                  30

Tyr Val Glu Ala Glu Val Asn Ile Pro Leu Asn Glu Phe Ile Gly Gln
        35                  40                  45

Glu Lys Lys Asn Ile Gln Leu Ile Asn Asp Leu Val Pro Lys Lys Asn
    50                  55                  60

Phe Lys Asp Ile His Ser Tyr Glu Asn Pro Ile Val Gly Leu Gln Met
65                  70                  75                  80

Ser Tyr Phe Lys Cys Gly Gly Leu Ala Ile Cys Met Tyr Leu Ser His
                85                  90                  95

Val Val Ala Asp Gly Tyr Thr Ala Ala Ala Phe Thr Lys Glu Trp Ser
            100                 105                 110

Asn Thr Thr Asn Gly Ile Ile Asn Gly Asp His Leu Val Ser Ser Ser
        115                 120                 125
```

```
Pro Ile Asn Phe Asp Leu Ala Thr Leu Val Pro Thr Arg Asp Leu Ser
            130                 135                 140

Thr Val Ile Lys Pro Ala Val Met Pro Pro Ser Lys Ile Lys Glu Thr
145                 150                 155                 160

Lys Val Val Thr Arg Arg Phe Leu Phe Asp Glu Asn Ala Ile Ser Ala
                165                 170                 175

Phe Lys Asp His Val Ile Lys Ser Glu Ser Val Asn Arg Pro Thr Arg
            180                 185                 190

Val Glu Val Val Thr Ser Val Leu Trp Lys Ala Leu Ile Asn Gln Ser
        195                 200                 205

Lys Leu Pro Ser Ser Thr Leu Tyr Phe His Leu Asn Phe Arg Gly Lys
    210                 215                 220

Thr Gly Ile Asn Thr Pro Pro Leu Asp Asn His Phe Ser Leu Cys Gly
225                 230                 235                 240

Asn Phe Tyr Thr Gln Val Pro Thr Arg Phe Arg Gly Glu Asn Gln Thr
                245                 250                 255

Lys Gln Asp Leu Glu Leu His Glu Leu Val Lys Leu Leu Arg Gly Lys
            260                 265                 270

Leu Arg Asn Thr Leu Lys Asn Cys Ser Glu Ile Asn Thr Ala Asp Gly
        275                 280                 285

Leu Phe Leu Glu Ala Ala Ser Asn Phe Asn Ile Ile Gln Glu Asp Leu
    290                 295                 300

Glu Asp Glu Gln Val Asp Val Arg Ile Phe Thr Thr Leu Cys Arg Met
305                 310                 315                 320

Pro Leu Tyr Glu Thr Glu Leu Gly Trp Gly Lys Pro Glu Trp Val Thr
                325                 330                 335

Ile Pro Glu Met His Leu Glu Ile Val Phe Leu Leu Asp Thr Lys Cys
            340                 345                 350

Gly Thr Gly Ile Glu Ala Leu Val Ser Met Asp Glu Ala Asp Met Leu
        355                 360                 365

Gln Phe Glu
    370

<210> SEQ ID NO 22
<211> LENGTH: 1708
<212> TYPE: DNA
<213> ORGANISM: Brachypodium distachyon

<400> SEQUENCE: 22
ttagcctgca ggccgtggat ttgatagaga gagtgcttta caatggagaa gaagttcacg    60
gtgactagga ctagcaagtc cctggtgccc ccatcttcgt cttccccaac accggcggcg   120
acagaggacg atgcaccagt gccggtgatc atgcgcctgt cgacgatcga ccgtgttccc   180
gggctgcgcc acctggtgct ctccctccac gccttcgacg ccatggcgt cgttgccgga   240 gaagacgacg aagagcgaat taggtggccg gcgagggtgg tgaggaggc gctggggaag   300 gcgctcgtgg actactaccc gtttgccggg aggttcgtgg tggacgagga aggggaggtg   360
ggcgtgaagt gcagcggcga gggggcgtgg ttcgtggagg ccaaggcgga gtgctcgttg   420
gaggaggcga ggcaccttga tgggaacccc atggagatgg tgatcccaa ggaggacctt   480 ctcccggagc ccattccgg ggtcgacccc ctcgacatcc ccctcatcat gcaggtgaca   540
gaattcacat gcggcggctt cgtggtgggc ctgatctcgg tgcacaccat cgccgacggg   600
ctaggcgccg ccagttcat caacgcggtg gcggactacg cgcgggggcct cccgaagcct   660 cgtgtgtctc cggtgtgggc ccgggacctc gtcccggacc ctccgaagat gccggcgcca   720
```

```
ccgccgaagc tggagctcct ggacctccgc cacttcaccg tggacctgag cccggaccac    780
atcgccaagg tcaagtccca gtacttcgcc tccacgggcc accgctgctc cgccttcgac    840
gtcgtcgtcg ccgtcacctg gcagtcccgc acccgtgccc tccgcctcgc cggtgccggc    900
tacgacgacg tccacgtctg cttcttcgcc aacacccgcc acctcatgct ccacggtggc    960
gccggcgcgg cggggttcta cggcaactgc ttctacccgg tgagagccac gtgcgggagc   1020
gctgaggtgg cgtcggctga cgtggcgggg gtggtgaagg tggtgaggga cgccaaggcc   1080
aggctggcgg gggacgtggc gaggtgggcc gtgggcgggt cgagcagga cccctacgag    1140 ctgaccttca cctacgactc cctcttcgtg tcggactgga ccaggctggg ctttctagag   1200
gccgactacg ggtgggggcc cccggcccac gtggtgccct tctcgtatca ccccttcatg   1260
gctgttgccg tcatcggcgc accgcccaag cccaagctcg gctcccgcgt catgaccatg   1320
tgtgtggagg aagaccacct cccggagttc cgggaccaga tgaacgcctt cgccttcacc   1380
gccgggaagt gagtaagcaa cgatccataa tcgtccatgt atgaaaccca attgagcgtg   1440
caagcgctta attactacac cttttttataa tcagtagctc ttctatgtct ggtgtgtgtg   1500
cgtgcaatgt atgtaatttg cttgtttgat cgaactggcg caattaggcg ttgtgcttaa   1560
ttgtatcgtg ggtccatcga atgaacgatg atgaagcaat aaatgaccat gatttgtact   1620
gcttccaaat gtatactggt agtatatagt accatgtgtc atgtgcgtgt gtcatctggt   1680
aaaattaaga cggattttct tctggcct                                     1708

<210> SEQ ID NO 23
<211> LENGTH: 1350
<212> TYPE: DNA
<213> ORGANISM: Brachypodium distachyon

<400> SEQUENCE: 23
atggagaaga agttcacggt gactaggact agcaagtccc tggtgccccc atcttcgtct     60
tccccaacac cggcggcgac agaggacgat gcaccagtgc cggtgatcat cgcgcctgtcg    120 acgatcgacc gtgttcccgg gctgcgccac ctggtgctct ccctccacgc cttcgacggc    180 catgcgtcg ttgccggaga agacgacgaa gagcgaatta ggtggccggc gagggtggtg     240
agggaggcgc tggggaaggc gctcgtggac tactacccgt ttgccgggag gttcgtggtg    300
gacgaggaag gggaggtggg cgtgaagtgc agcggcgagg gggcgtggtt cgtggaggcc    360
aaggcggagt gctcgttgga ggaggcgagg caccttgatg ggaacccat ggagatggtg     420 atccccaagg aggaccttct cccggagccc attcccgggg tcgacccct cgacatcccc    480 ctcatcatgc aggtgacaga attcacatgc ggcggcttcg tggtgggcct gatctcggtg    540
cacaccatcg ccgacgggct aggcgccggc cagttcatca acgcggtggc ggactacgcg    600
cggggcctcc cgaagcctcg tgtgtctccg gtgtgggccc gggacctcgt cccggaccct    660
ccgaagatgc cggcgccacc ggccgaagctg gagctcctgg acctccgcca cttcaccgtg    720
gacctgagcc cggaccacat cgccaaggtc aagtcccagt acttcgcctc cacgggccac    780
cgctgctccg ccttcgacgt cgtcgtcgcc gtcacctggc agtcccgcac ccgtgccctc    840
cgcctcgccg gtgccggcta cgacgacgtc cacgtctgct tcttcgccaa cacccgccac    900
ctcatgctcc acggtggcgc cggcgcggcg gggttctacg gcaactgctt ctacccggtg    960
agagccacgt gcgggagcgc tgaggtgcg tcggctgacg tggcggggt ggtgaaggtg     1020 gtgagggacg ccaaggccag gctggcgggg gacgtggcga ggtgggccgt gggcgggttc   1080
```

```
gagcaggacc cctacgagct gaccttcacc tacgactccc tcttcgtgtc ggactggacc   1140
aggctgggct ttctagaggc cgactacggg tgggggcccc cggcccacgt ggtgcccttc   1200
tcgtatcacc ccttcatggc tgttgccgtc atcggcgcac cgcccaagcc caagctcggc   1260
tcccgcgtca tgaccatgtg tgtggaggaa gaccacctcc cggagttccg ggaccagatg   1320
aacgccttcg ccttcaccgc cgggaagtga                                    1350
```

<210> SEQ ID NO 24
<211> LENGTH: 449
<212> TYPE: PRT
<213> ORGANISM: Brachypodium distachyon

<400> SEQUENCE: 24

```
Met Glu Lys Lys Phe Thr Val Thr Arg Thr Ser Lys Ser Leu Val Pro
1               5                   10                  15

Pro Ser Ser Ser Pro Thr Pro Ala Ala Thr Glu Asp Asp Ala Pro
            20                  25                  30

Val Pro Val Ile Met Arg Leu Ser Thr Ile Asp Arg Val Pro Gly Leu
        35                  40                  45

Arg His Leu Val Leu Ser Leu His Ala Phe Asp Gly His Gly Val Val
    50                  55                  60

Ala Gly Glu Asp Asp Glu Arg Ile Arg Trp Pro Ala Arg Val Val
65                  70                  75                  80

Arg Glu Ala Leu Gly Lys Ala Leu Val Asp Tyr Tyr Pro Phe Ala Gly
                85                  90                  95

Arg Phe Val Val Asp Glu Glu Gly Val Gly Val Lys Cys Ser Gly
            100                 105                 110

Glu Gly Ala Trp Phe Val Glu Ala Lys Ala Glu Cys Ser Leu Glu Glu
        115                 120                 125

Ala Arg His Leu Asp Gly Asn Pro Met Glu Met Val Ile Pro Lys Glu
    130                 135                 140

Asp Leu Leu Pro Glu Pro Ile Pro Gly Val Asp Pro Leu Asp Ile Pro
145                 150                 155                 160

Leu Ile Met Gln Val Thr Glu Phe Thr Cys Gly Gly Phe Val Val Gly
                165                 170                 175

Leu Ile Ser Val His Thr Ile Ala Asp Gly Leu Gly Ala Gly Gln Phe
            180                 185                 190

Ile Asn Ala Val Ala Asp Tyr Ala Arg Gly Leu Pro Lys Pro Arg Val
        195                 200                 205

Ser Pro Val Trp Ala Arg Asp Leu Val Pro Pro Pro Lys Met Pro
    210                 215                 220

Ala Pro Pro Lys Leu Glu Leu Leu Asp Leu Arg His Phe Thr Val
225                 230                 235                 240

Asp Leu Ser Pro Asp His Ile Ala Lys Val Lys Ser Gln Tyr Phe Ala
                245                 250                 255

Ser Thr Gly His Arg Cys Ser Ala Phe Asp Val Val Ala Val Thr
            260                 265                 270

Trp Gln Ser Arg Thr Arg Ala Leu Arg Leu Ala Gly Ala Gly Tyr Asp
        275                 280                 285

Asp Val His Val Cys Phe Phe Ala Asn Thr Arg His Leu Met Leu His
    290                 295                 300

Gly Gly Ala Gly Ala Ala Gly Phe Tyr Gly Asn Cys Phe Tyr Pro Val
305                 310                 315                 320

Arg Ala Thr Cys Gly Ser Ala Glu Val Ala Ser Ala Asp Val Ala Gly
```

```
                 325                 330                 335
Val Val Lys Val Val Arg Asp Ala Lys Ala Arg Leu Ala Gly Asp Val
            340                 345                 350

Ala Arg Trp Ala Val Gly Gly Phe Glu Gln Asp Pro Tyr Glu Leu Thr
            355                 360                 365

Phe Thr Tyr Asp Ser Leu Phe Val Ser Asp Trp Thr Arg Leu Gly Phe
        370                 375                 380

Leu Glu Ala Asp Tyr Gly Trp Gly Pro Pro Ala His Val Val Pro Phe
385                 390                 395                 400

Ser Tyr His Pro Phe Met Ala Val Ala Val Ile Gly Ala Pro Pro Lys
                405                 410                 415

Pro Lys Leu Gly Ser Arg Val Met Thr Met Cys Val Glu Glu Asp His
            420                 425                 430

Leu Pro Glu Phe Arg Asp Gln Met Asn Ala Phe Ala Phe Thr Ala Gly
            435                 440                 445

Lys

<210> SEQ ID NO 25
<211> LENGTH: 301
<212> TYPE: DNA
<213> ORGANISM: Brachypodium distachyon

<400> SEQUENCE: 25
gtaagcaacg atccataatc gtccatgtat gaaacccaat tgagcgtgca agcgcttaat      60
tactacacct ttttataatc agtagctctt ctatgtctgg tgtgtgtgcg tgcaatgtat     120
gtaatttgct tgtttgatcg aactggcgca attaggcgtt gtgcttaatt gtatcgtggg     180
tccatcgaat gaacgatgat gaagcaataa atgaccatga tttgtactgc ttccaaatgt     240
atactggtag tatatagtac catgtgtcat gtgcgtgtgt catctggtaa aattaagacg     300
g                                                                    301

<210> SEQ ID NO 26
<211> LENGTH: 258
<212> TYPE: DNA
<213> ORGANISM: Brachypodium distachyon

<400> SEQUENCE: 26
tacgagctga ccttcaccta cgactccctc ttcgtgtcgg actggaccag gctgggcttt      60
ctagaggccg actacgggtg ggggcccccg gcccacgtgg tgcccttctc gtatcacccc     120
ttcatggctg ttgccgtcat cggcgcaccg cccaagccca agctcggctc ccgcgtcatg     180
accatgtgtg tggaggaaga ccacctcccg gagttccggg accagatgaa cgccttcgcc     240
ttcaccgccg ggaagtga                                                   258

<210> SEQ ID NO 27
<211> LENGTH: 269
<212> TYPE: DNA
<213> ORGANISM: Brachypodium distachyon

<400> SEQUENCE: 27
gttcacggtg actaggacta gcaagtccct ggtgccccca tcttcgtctt ccccaacacc      60
ggcggcgaca gaggacgatg caccagtgcc ggtgatcatg cgcctgtcga cgatcgaccg     120
tgttcccggg ctgcgccacc tggtgctctc cctccacgcc ttcgacgcc atggcgtcgt      180 tgccggagaa gacgacgaag agcgaattag gtggccggcg agggtggtga gggaggcgct     240
```

```
ggggaaggcg ctcgtggact actacccgt                                     269
```

<210> SEQ ID NO 28
<211> LENGTH: 255
<212> TYPE: DNA
<213> ORGANISM: Brachypodium distachyon

<400> SEQUENCE: 28

```
cactccacct agctagctga gctccgaagt cctgaactaa taacccagcc cgtctatata   60
tacacagagc atatatatcc atacactcat cgcagctaga gcatgcaagc ttaattagcc  120
tgcaggccgt ggatttgata gagagagtgc tttacaatgg agaagaagtt cacggtgact  180
aggactagca agtccctggt gcccccatct tcgtcttccc caacaccggc ggcgacagag  240
gacgatgcac cagtg                                                   255
```

<210> SEQ ID NO 29
<211> LENGTH: 67
<212> TYPE: PRT
<213> ORGANISM: Citrus sinensis

<400> SEQUENCE: 29

Glu Leu Pro Val Glu Phe Ala Lys Tyr Met Asn Gly Asp Phe Thr Arg
1               5                   10                  15

Asn Gly Glu Asp Pro Phe Ala Pro Pro Leu Ala Tyr Thr Thr Leu Phe
            20                  25                  30

Ile Ser Glu Trp Gly Arg Leu Gly Phe Asn Gln Ile Asp Tyr Gly Trp
        35                  40                  45

Gly Pro Pro Val His Val Val Pro Ile Gln Gly Ser Ser Ile Ile Pro
    50                  55                  60

Val Gly Ile
65

<210> SEQ ID NO 30
<211> LENGTH: 59
<212> TYPE: PRT
<213> ORGANISM: Sorghum bicolor

<400> SEQUENCE: 30

Ala Arg Trp Ser Ala Gly Asp Thr Gly Gly Val Asp Pro Tyr Arg Ile
1               5                   10                  15

Thr Ser Asp Tyr Arg Thr Leu Leu Val Ser Asp Trp Ser Arg Leu Gly
            20                  25                  30

Phe Ala Glu Val Asp Tyr Gly Trp Gly Cys Pro Val His Val Val Pro
        35                  40                  45

Leu Thr Asn Leu Asp Tyr Ile Ala Thr Cys Ile
    50                  55

<210> SEQ ID NO 31
<211> LENGTH: 45
<212> TYPE: PRT
<213> ORGANISM: Zea mays

<400> SEQUENCE: 31

Glu Asp Ala Asp Pro Tyr Gln Ile Thr Ser Asp Tyr Arg Thr Leu Leu
1               5                   10                  15

Val Ser Asp Trp Thr Arg Leu Gly Phe Ala Glu Val Asp Tyr Gly Trp
            20                  25                  30

Gly Pro Pro Ala His Val Val Pro Leu Thr Asn Leu Asp
        35                  40                  45

<210> SEQ ID NO 32
<211> LENGTH: 63
<212> TYPE: PRT
<213> ORGANISM: Bachypodium distachyon

<400> SEQUENCE: 32

Leu Gly Gly Gly Ala Gly Asp Lys Met Lys Phe Val Gln Asp Asp
1               5                   10                  15

Pro Tyr Glu Leu Arg Phe Glu His Asn Val Leu Phe Val Ser Asp Trp
            20                  25                  30

Thr Arg Leu Gly Phe Leu Glu Val Asp Tyr Gly Trp Gly Val Pro Ser
        35                  40                  45

His Val Ile Pro Phe Asn Tyr Ala Asp Tyr Met Ala Val Ala Val
    50                  55                  60

<210> SEQ ID NO 33
<211> LENGTH: 53
<212> TYPE: PRT
<213> ORGANISM: Oryza sativa

<400> SEQUENCE: 33

Gly Asp Val Lys Val Asp Pro Tyr Ala Leu Thr Phe Glu His Asn Val
1               5                   10                  15

Leu Phe Val Ser Asp Trp Thr Arg Leu Gly Phe Glu Val Asp Tyr
            20                  25                  30

Gly Trp Gly Thr Pro Asn His Ile Ile Pro Phe Thr Tyr Ala Asp Tyr
        35                  40                  45

Met Ala Val Ala Val
    50

<210> SEQ ID NO 34
<211> LENGTH: 101
<212> TYPE: PRT
<213> ORGANISM: Panicum virgatum

<400> SEQUENCE: 34

Gly Gly Phe Tyr Gly Asn Cys Phe Tyr Pro Val Ser Val Thr Ala Thr
1               5                   10                  15

Ala Glu Asp Val Val Thr Ala Gly Leu Leu Asp Val Ile Arg Met Ile
            20                  25                  30

Arg Asn Gly Lys Ala Arg Leu Pro Leu Glu Phe Ser Lys Trp Ala Ala
        35                  40                  45

Gly Asp Val Ser Val Asp Pro Tyr Gln Leu Thr Phe Glu His Asn Val
    50                  55                  60

Leu Phe Val Ser Asp Trp Thr Arg Leu Gly Phe Ser Glu Val Asp Tyr
65                  70                  75                  80

Gly Trp Gly Ala Pro Asp His Ile Val Pro Phe Thr Tyr Ala Asp Tyr
            85                  90                  95

Met Ala Val Ala Val
            100

<210> SEQ ID NO 35
<211> LENGTH: 59
<212> TYPE: PRT
<213> ORGANISM: Sorghum bicolor

<400> SEQUENCE: 35

Phe Ala Lys Trp Ser Met Gly Asp Val Lys Val Asp Pro Tyr Gln Leu

-continued

```
                1               5                   10                  15
         Thr Phe Lys His Asn Val Leu Phe Val Ser Asp Trp Thr Arg Leu Gly
                        20                  25                  30
         Phe Phe Glu Val Asp Tyr Gly Trp Gly Val Pro Asn His Ile Ile Pro
                        35                  40                  45
         Phe Thr Tyr Ala Asp Tyr Met Ala Val Ala Val
                        50                  55

<210> SEQ ID NO 36
<211> LENGTH: 54
<212> TYPE: PRT
<213> ORGANISM: Zea mays

<400> SEQUENCE: 36

Thr Gly Asn Val Lys Val Asp Pro Tyr Gln Leu Thr Phe Lys His Asn
1               5                   10                  15
Val Leu Phe Val Ser Asp Trp Thr Arg Leu Gly Phe Glu Val Asp
                20                  25                  30
Tyr Gly Trp Gly Val Pro Asn His Ile Leu Pro Phe Thr Tyr Ala Asp
                35                  40                  45
Tyr Met Ala Val Ala Val
                50

<210> SEQ ID NO 37
<211> LENGTH: 65
<212> TYPE: PRT
<213> ORGANISM: Bachypodium distachyon

<400> SEQUENCE: 37

Ala Arg Leu Ala Gly Asp Val Ala Arg Trp Ala Val Gly Gly Phe Glu
1               5                   10                  15
Gln Asp Pro Tyr Glu Leu Thr Phe Thr Tyr Asp Ser Leu Phe Val Ser
                20                  25                  30
Asp Trp Thr Arg Leu Gly Phe Leu Glu Ala Asp Tyr Gly Trp Gly Pro
                35                  40                  45
Pro Ala His Val Val Pro Phe Ser Tyr His Pro Phe Met Ala Val Ala
                50                  55                  60
Val
65

<210> SEQ ID NO 38
<211> LENGTH: 54
<212> TYPE: PRT
<213> ORGANISM: Oryza sativa

<400> SEQUENCE: 38

Val Gly Gly Phe Glu Glu Asp Pro Tyr Glu Leu Thr Phe Thr Tyr Asp
1               5                   10                  15
Ser Leu Phe Val Ser Asp Trp Thr Arg Leu Gly Phe Leu Asp Ala Asp
                20                  25                  30
Tyr Gly Trp Gly Thr Pro Ser His Val Val Pro Phe Ser Tyr His Pro
                35                  40                  45
Phe Met Ala Val Ala Val
                50

<210> SEQ ID NO 39
<211> LENGTH: 64
<212> TYPE: PRT
<213> ORGANISM: Setaria italica
```

<400> SEQUENCE: 39

Arg Leu Ala Ala Asp Phe Ala Arg Trp Ala Gly Gly Gly Phe Glu Arg
1               5                   10                  15

Asp Pro Tyr Glu Leu Thr Phe Thr Tyr Asp Ser Leu Phe Val Ser Asp
            20                  25                  30

Trp Thr Arg Leu Gly Phe Leu Glu Ala Asp Tyr Gly Trp Gly Thr Pro
        35                  40                  45

Ala His Val Leu Pro Phe Ser Tyr His Pro Phe Met Ala Val Ala Val
    50                  55                  60

<210> SEQ ID NO 40
<211> LENGTH: 58
<212> TYPE: PRT
<213> ORGANISM: Panicum virgatum

<400> SEQUENCE: 40

Ala Arg Trp Ala Ala Gly Gly Phe Glu Arg Asp Pro Tyr Glu Leu Thr
1               5                   10                  15

Phe Ser Tyr Asp Ser Leu Phe Val Ser Asp Trp Thr Arg Leu Gly Phe
            20                  25                  30

Leu Glu Ala Asp Tyr Gly Trp Gly Ala Pro Ala His Val Val Pro Phe
        35                  40                  45

Ser Tyr His Pro Phe Met Ala Val Ala Val
    50                  55

<210> SEQ ID NO 41
<211> LENGTH: 56
<212> TYPE: PRT
<213> ORGANISM: Sorghum bicolor

<400> SEQUENCE: 41

Trp Ala Ala Gly Gly Phe Asp Arg Asp Pro Tyr Glu Leu Thr Phe Thr
1               5                   10                  15

Tyr Asp Ser Leu Phe Val Ser Asp Trp Thr Arg Leu Gly Phe Leu Glu
            20                  25                  30

Ala Asp Tyr Gly Trp Gly Thr Pro Thr His Val Val Pro Phe Ser Tyr
        35                  40                  45

His Pro Phe Met Ala Val Ala Val
    50                  55

<210> SEQ ID NO 42
<211> LENGTH: 54
<212> TYPE: PRT
<213> ORGANISM: Zea mays

<400> SEQUENCE: 42

Ala Gly Gly Phe Asp Arg Asp Pro Tyr Glu Leu Thr Phe Thr Tyr Asp
1               5                   10                  15

Ser Leu Phe Val Ser Asp Trp Thr Arg Leu Gly Phe Leu Glu Ala Asp
            20                  25                  30

Tyr Gly Trp Gly Thr Pro Thr His Val Leu Pro Phe Ser Tyr His Pro
        35                  40                  45

Phe Met Ala Val Ala Val
    50

<210> SEQ ID NO 43
<211> LENGTH: 64
<212> TYPE: PRT

```
<213> ORGANISM: Setaria italica

<400> SEQUENCE: 43

Pro Ala Glu Phe Ala Arg Trp Ala Ala Gly Glu Leu Val Gly Val Glu
 1               5                  10                  15

Asp Pro Tyr Glu Leu Pro Phe Ala Tyr Glu Ala Leu Phe Val Ser Asp
            20                  25                  30

Trp Thr Arg Leu Gly Phe Gln Glu Ala Asp Tyr Gly Trp Gly Gly Pro
        35                  40                  45

Ser His Val Ile Pro Leu Ala Tyr His Pro His Met Pro Ile Ala Ile
    50                  55                  60

<210> SEQ ID NO 44
<211> LENGTH: 59
<212> TYPE: PRT
<213> ORGANISM: Oryza sativa

<400> SEQUENCE: 44

Phe Ala Arg Trp Ala Val Ala Asp Phe Arg Glu Asp Pro Tyr Glu Leu
 1               5                  10                  15

Ser Phe Thr Tyr Asp Ser Leu Phe Val Ser Asp Trp Thr Arg Leu Gly
            20                  25                  30

Phe Leu Glu Ala Asp Tyr Gly Trp Gly Pro Pro Ser His Val Ile Pro
        35                  40                  45

Phe Ala Tyr Tyr Pro Phe Met Ala Val Ala Ile
    50                  55

<210> SEQ ID NO 45
<211> LENGTH: 52
<212> TYPE: PRT
<213> ORGANISM: Setaria italica

<400> SEQUENCE: 45

Leu Val Glu Lys Asp Pro Tyr Glu Leu Thr Phe Ser Tyr Glu Ser Leu
 1               5                  10                  15

Phe Val Ser Asp Trp Thr Arg Leu Gly Phe Leu Asp Ala Asp Tyr Gly
            20                  25                  30

Trp Gly Thr Pro Leu Gln Val Ile Pro Phe Thr Tyr His Pro Ala Met
        35                  40                  45

Pro Ile Ala Ile
    50

<210> SEQ ID NO 46
<211> LENGTH: 67
<212> TYPE: PRT
<213> ORGANISM: Panicum virgatum

<400> SEQUENCE: 46

Ala Arg Leu Pro Ala Glu Phe Ala Arg Trp Ala Ala Gly Glu Leu Val
 1               5                  10                  15

Ala Gln Asp Pro Tyr Glu Leu Ser Phe Thr Tyr Glu Ser Leu Phe Val
            20                  25                  30

Ser Asp Trp Thr Arg Leu Gly Phe Leu Glu Ala Asp Tyr Gly Trp Gly
        35                  40                  45

Thr Pro Glu Gln Val Ile Pro Phe Ala Tyr His Pro Cys Met Pro Ile
    50                  55                  60

Ala Val Ile
65
```

<210> SEQ ID NO 47
<211> LENGTH: 225
<212> TYPE: DNA
<213> ORGANISM: Citrus sinensis

<400> SEQUENCE: 47

| gagctacctg | ttgaatttgc | taagtacatg | aatggagatt | ttaccaggaa | cggtgaggac | 60 |
| ccattcgccc | cacctctggc | ttatacaaca | ttgtttatat | cagagtgggg | acgactggga | 120 |
| ttcaaccaga | ttgactatgg | gtggggccct | cctgtccacg | tggtaccaat | tcaaggctcg | 180 |
| agtattattc | cggttggcat | tgtgggttcg | atgccgttgc | ccaaa | | 225 |

<210> SEQ ID NO 48
<211> LENGTH: 180
<212> TYPE: DNA
<213> ORGANISM: Sorghum bicolor

<400> SEQUENCE: 48

| gcgcggtgga | gcgcggggga | caccggcggc | gtggacccgt | accggatcac | gtcggactac | 60 |
| cggacgctgc | tggtgtcgga | ctggtcgcgg | ctcgggttcg | cggaggtgga | ctacgggtgg | 120 |
| ggctgccccg | tgcacgtcgt | cccgctcacc | aacctcgact | acatcgcgac | gtgcatcctg | 180 |

<210> SEQ ID NO 49
<211> LENGTH: 153
<212> TYPE: DNA
<213> ORGANISM: Zea mays

<400> SEQUENCE: 49

| gaggacgccg | acccctacca | gatcacctcc | gactaccgga | cgctgctggt | gtcggactgg | 60 |
| acgcggctgg | gcttcgcgga | ggtggactac | ggctggggcc | cgcccgccca | cgtggtgccg | 120 |
| ctgacgaact | tggactacat | cgccacgtgc | atc | | | 153 |

<210> SEQ ID NO 50
<211> LENGTH: 225
<212> TYPE: DNA
<213> ORGANISM: Bachypodium distachyon

<400> SEQUENCE: 50

| ttaggaggag | gaggggctgg | ggataagatg | aagtttgtgc | aggatgatcc | ttatgagctg | 60 |
| aggtttgagc | ataatgtgtt | gtttgtgtcg | gattggacga | ggcttgggtt | cttggaggtg | 120 |
| gactatggct | ggggcgtgcc | tagccatgtt | ataccttca | attatgcgga | ctacatggcg | 180 |
| gtcgcggtgc | tcggtgctcc | gccggcgccg | gtgaagggga | ctcgg | | 225 |

<210> SEQ ID NO 51
<211> LENGTH: 180
<212> TYPE: DNA
<213> ORGANISM: Oryza sativa

<400> SEQUENCE: 51

| ggggatgtga | agttgatcc | ctacgcattg | acatttgaac | acaatgtgct | ttttgtgtct | 60 |
| gattggacga | ggttaggatt | cttcgaggta | gactatgggt | ggggtacacc | taatcacatc | 120 |
| ataccattca | cttatgcaga | ctacatggca | gtcgcagtgc | ttggtgctcc | accaatgcca | 180 |

<210> SEQ ID NO 52
<211> LENGTH: 315
<212> TYPE: DNA
<213> ORGANISM: Panicum virgatum

<400> SEQUENCE: 52

```
gggggattct atggcaactg cttctaccca gtttctgtga cggccactgc tgaggatgtt      60
gtcactgcag ggttgcttga tgtgatcagg atgataagga atgggaaggc caggcttccc     120
ctggagtttt ccaagtgggc agcaggggat gtgagtgtgg atccatacca gttgacattt     180
gagcacaacg tgttgtttgt gtctgattgg acgagacttg gttctccga ggttgactat      240
gggtggggtg caccggatca tatcgtgcca ttcacctatg cagactacat ggcggtggcg     300
gttcttgggg ctccg                                                      315
```

<210> SEQ ID NO 53
<211> LENGTH: 180
<212> TYPE: DNA
<213> ORGANISM: Sorghum bicolor

<400> SEQUENCE: 53

```
tttgccaaat ggtccatggg tgatgtgaag gtagacccat atcaactgac attcaagcac      60
aatgttctgt ttgtgtctga ttggacgagg cttggattct ttgaggttga ctatgggtgg     120
ggtgtaccaa accatatcat acctttcact tatgcagact acatggctgt agcagttctt     180
```

<210> SEQ ID NO 54
<211> LENGTH: 180
<212> TYPE: DNA
<213> ORGANISM: Zea mays

<400> SEQUENCE: 54

```
acgggcaatg tgaaagtaga cccatatcaa ctaacattca agcacaatgt tctatttgtg      60
tccgattgga cacggcttgg attctttgaa gttgactatg ggtggggtgt accaaaccat     120
atcctccctt tcacttatgc agactacatg gctgtagcag ttcttggagc tccaccgtct     180
```

<210> SEQ ID NO 55
<211> LENGTH: 225
<212> TYPE: DNA
<213> ORGANISM: Bachypodium distachyon

<400> SEQUENCE: 55

```
gccaggctgg cggggacgt ggcgaggtgg ccgtgggcg ggttcgagca ggacccctac        60
gagctgacct tcacctacga ctccctcttc gtgtcggact ggaccaggct gggctttcta     120
gaggccgact acgggtgggg gccccggcc cacgtggtgc ccttctcgta tcaccccttc      180
atggctgttg ccgtcatcgg cgcaccgccc aagcccaagc tcggc                     225
```

<210> SEQ ID NO 56
<211> LENGTH: 180
<212> TYPE: DNA
<213> ORGANISM: Oryza sativa

<400> SEQUENCE: 56

```
gtgggcgggt tcgaggagga cccctacgag ctgaccttca cctacgactc cctcttcgtc      60
tccgactgga cgcggctcgg cttcctagac gccgactatg gctggggcac gccgtcgcac     120
gtcgtgccgt tctcctacca cccgttcatg gccgtcgccg tcatcggcgc gccgccggcg     180
```

<210> SEQ ID NO 57
<211> LENGTH: 225
<212> TYPE: DNA
<213> ORGANISM: Setaria italica

```
<400> SEQUENCE: 57
cggctggccg cggacttcgc gcggtgggcg ggcggagggt tcgagcgcga cccctacgag    60
ctcaccttca cctacgactc gctcttcgtc tccgactgga cgcggctcgg gttcctggag   120
gcggactacg ggtggggcac gccggcgcac gtcctgccct tctcgtacca ccccttcatg   180
gccgtcgccg tcatcggagc gccgccggcg cccaagcccg gagcg                   225

<210> SEQ ID NO 58
<211> LENGTH: 180
<212> TYPE: DNA
<213> ORGANISM: Panicum virgatum

<400> SEQUENCE: 58
gcgcggtggg cggcgggcgg gttcgagcgc gaccccctacg agctcaccttt cagctacgac    60 tcgctcttcg tctccgactg gacgcggctg gggttcctgg aggcggacta cgggtggggc   120
gcgccggcgc acgtcgtgcc cttctcctac cacccccttca tggccgtcgc cgtcatcggc   180

<210> SEQ ID NO 59
<211> LENGTH: 180
<212> TYPE: DNA
<213> ORGANISM: Sorghum bicolor

<400> SEQUENCE: 59
tgggcggcgg gcgggtttga tcgggacccc tacgagctca ccttcaccta cgactccctc    60
ttcgtctccg actggacgag gctagggttc ctcgaggctg actatggctg gggcacgccg   120
acgcacgtcg tgccgttctc gtaccacccg ttcatggccg tcgccgtcat cggggcgccg   180

<210> SEQ ID NO 60
<211> LENGTH: 180
<212> TYPE: DNA
<213> ORGANISM: Zea mays

<400> SEQUENCE: 60
gcgggcggct tcgaccgcga cccctacgag ctcaccttca cctacgactc gctcttcgtc    60
tccgactgga cgcgcctcgg cttcctcgag gcggactacg gctggggcac cccgacacac   120
gtcctgccct tctcctacca cccgttcatg gccgtcgccg tcatcggcgc cccgcctaag   180

<210> SEQ ID NO 61
<211> LENGTH: 225
<212> TYPE: DNA
<213> ORGANISM: Setaria italica

<400> SEQUENCE: 61
ccggcggagt tcgcgcggtg ggcggcgggg gagctcgtcg gggtcgagga cccctacgag    60
ctgccgttcg cgtacgaggc gctattcgtg tcggactgga cgcggcttgg gttccaggaa   120
gcggactacg ggtggggtgg gccttccac gtgatacctt tggcttatca cccgcacatg   180
cccatcgcca tcgtcggtgc accgccggcg ccacggatgg gggtc                   225

<210> SEQ ID NO 62
<211> LENGTH: 180
<212> TYPE: DNA
<213> ORGANISM: Oryza sativa

<400> SEQUENCE: 62
ttcgcgcggt gggcggtggc cgacttcagg gaggatccgt acgagctgag cttcacgtac    60
gattccctgt tcgtctccga ctggacgcgg ctggggttcc tggaggcgga ctacgggtgg   120
```

```
gggccgccgt cgcacgtcat acccttcgcg tactacccgt tcatggccgt cgccatcatc    180
```

<210> SEQ ID NO 63
<211> LENGTH: 180
<212> TYPE: DNA
<213> ORGANISM: Setaria italica

<400> SEQUENCE: 63

```
ctcgtggaga aggacccctc cgagctgacc ttttcgtacg agtcgctgtt cgtgtcggac    60
tggacccggc tggggttcct ggacgctgac tacggctggg ggacgccgtt gcaggtgata   120
ccctttacgt accacccggc catgcccatc gccatcatca gcgcgccgcc ggcgcccaag   180
```

<210> SEQ ID NO 64
<211> LENGTH: 225
<212> TYPE: DNA
<213> ORGANISM: Panicum virgatum

<400> SEQUENCE: 64

```
gcgcggctcc ccgccgagtt cgcgcggtgg gcggcgggcg agctcgtggc gcaggacccc    60
tacgagctga gcttcacgta cgagtcgctg ttcgtgtcgg actggacgcg gctggggttc   120
ctggaggcgg actacggctg gggcacgccg gagcaggtga tacccttcgc gtaccacccg   180
tgcatgccca tcgcggtcat cggcccgccg ccggcgccca agacg                    225
```

<210> SEQ ID NO 65
<211> LENGTH: 9
<212> TYPE: RNA
<213> ORGANISM: Artificial Sequence
<220> FEATURE:
<223> OTHER INFORMATION: Synthetic Oligonucleoside

<400> SEQUENCE: 65

```
uucaagaga                                                              9
```

<210> SEQ ID NO 66
<211> LENGTH: 54
<212> TYPE: PRT
<213> ORGANISM: Citrus sinensis

<400> SEQUENCE: 66

Phe Thr Arg Asn Gly Glu Asp Pro Phe Ala Pro Pro Leu Ala Tyr Thr
1               5                   10                  15

Thr Leu Phe Ile Ser Glu Trp Gly Arg Leu Gly Phe Asn Gln Ile Asp
            20                  25                  30

Tyr Gly Trp Gly Pro Pro Val His Val Val Pro Ile Gln Gly Ser Ser
        35                  40                  45

Ile Ile Pro Val Gly Ile
    50

<210> SEQ ID NO 67
<211> LENGTH: 52
<212> TYPE: PRT
<213> ORGANISM: Sorghum bicolor

<400> SEQUENCE: 67

Thr Gly Gly Val Asp Pro Tyr Arg Ile Thr Ser Asp Tyr Arg Thr Leu
1               5                   10                  15

Leu Val Ser Asp Trp Ser Arg Leu Gly Phe Ala Glu Val Asp Tyr Gly
            20                  25                  30

```
Trp Gly Cys Pro Val His Val Pro Leu Thr Asn Leu Asp Tyr Ile
         35                  40                  45

Ala Thr Cys Ile
         50

<210> SEQ ID NO 68
<211> LENGTH: 51
<212> TYPE: PRT
<213> ORGANISM: Zea mays

<400> SEQUENCE: 68

Glu Asp Ala Asp Pro Tyr Gln Ile Thr Ser Asp Tyr Arg Thr Leu Leu
1               5                   10                  15

Val Ser Asp Trp Thr Arg Leu Gly Phe Ala Glu Val Asp Tyr Gly Trp
            20                  25                  30

Gly Pro Pro Ala His Val Val Pro Leu Thr Asn Leu Asp Tyr Ile Ala
         35                  40                  45

Thr Cys Ile
         50

<210> SEQ ID NO 69
<211> LENGTH: 58
<212> TYPE: PRT
<213> ORGANISM: Bachypodium distachyon

<400> SEQUENCE: 69

Ala Gly Asp Lys Met Lys Phe Val Gln Asp Asp Pro Tyr Glu Leu Arg
1               5                   10                  15

Phe Glu His Asn Val Leu Phe Val Ser Asp Trp Thr Arg Leu Gly Phe
            20                  25                  30

Leu Glu Val Asp Tyr Gly Trp Gly Val Pro Ser His Val Ile Pro Phe
         35                  40                  45

Asn Tyr Ala Asp Tyr Met Ala Val Ala Val
         50                  55

<210> SEQ ID NO 70
<211> LENGTH: 51
<212> TYPE: PRT
<213> ORGANISM: Oryza sativa

<400> SEQUENCE: 70

Val Lys Val Asp Pro Tyr Ala Leu Thr Phe Glu His Asn Val Leu Phe
1               5                   10                  15

Val Ser Asp Trp Thr Arg Leu Gly Phe Phe Glu Val Asp Tyr Gly Trp
            20                  25                  30

Gly Thr Pro Asn His Ile Ile Pro Phe Thr Tyr Ala Asp Tyr Met Ala
         35                  40                  45

Val Ala Val
         50

<210> SEQ ID NO 71
<211> LENGTH: 51
<212> TYPE: PRT
<213> ORGANISM: Panicum virgatum

<400> SEQUENCE: 71

Val Ser Val Asp Pro Tyr Gln Leu Thr Phe Glu His Asn Val Leu Phe
1               5                   10                  15

Val Ser Asp Trp Thr Arg Leu Gly Phe Ser Glu Val Asp Tyr Gly Trp
            20                  25                  30
```

Gly Ala Pro Asp His Ile Val Pro Phe Thr Tyr Ala Asp Tyr Met Ala
            35                  40                  45

Val Ala Val
    50

<210> SEQ ID NO 72
<211> LENGTH: 51
<212> TYPE: PRT
<213> ORGANISM: Sorghum bicolor

<400> SEQUENCE: 72

Val Lys Val Asp Pro Tyr Gln Leu Thr Phe Lys His Asn Val Leu Phe
1               5                   10                  15

Val Ser Asp Trp Thr Arg Leu Gly Phe Phe Glu Val Asp Tyr Gly Trp
            20                  25                  30

Gly Val Pro Asn His Ile Ile Pro Phe Thr Tyr Ala Asp Tyr Met Ala
            35                  40                  45

Val Ala Val
    50

<210> SEQ ID NO 73
<211> LENGTH: 51
<212> TYPE: PRT
<213> ORGANISM: Zea mays

<400> SEQUENCE: 73

Val Lys Val Asp Pro Tyr Gln Leu Thr Phe Lys His Asn Val Leu Phe
1               5                   10                  15

Val Ser Asp Trp Thr Arg Leu Gly Phe Phe Glu Val Asp Tyr Gly Trp
            20                  25                  30

Gly Val Pro Asn His Ile Leu Pro Phe Thr Tyr Ala Asp Tyr Met Ala
            35                  40                  45

Val Ala Val
    50

<210> SEQ ID NO 74
<211> LENGTH: 51
<212> TYPE: PRT
<213> ORGANISM: Bachypodium distachyon

<400> SEQUENCE: 74

Phe Glu Gln Asp Pro Tyr Glu Leu Thr Phe Thr Tyr Asp Ser Leu Phe
1               5                   10                  15

Val Ser Asp Trp Thr Arg Leu Gly Phe Leu Glu Ala Asp Tyr Gly Trp
            20                  25                  30

Gly Pro Pro Ala His Val Val Pro Phe Ser Tyr His Pro Phe Met Ala
            35                  40                  45

Val Ala Val
    50

<210> SEQ ID NO 75
<211> LENGTH: 51
<212> TYPE: PRT
<213> ORGANISM: Oryza sativa

<400> SEQUENCE: 75

Phe Glu Glu Asp Pro Tyr Glu Leu Thr Phe Thr Tyr Asp Ser Leu Phe
1               5                   10                  15

Val Ser Asp Trp Thr Arg Leu Gly Phe Leu Asp Ala Asp Tyr Gly Trp

```
                    20                  25                  30

Gly Thr Pro Ser His Val Val Pro Phe Ser Tyr His Pro Phe Met Ala
        35                  40                  45

Val Ala Val
    50

<210> SEQ ID NO 76
<211> LENGTH: 51
<212> TYPE: PRT
<213> ORGANISM: Setaria italica

<400> SEQUENCE: 76

Phe Glu Arg Asp Pro Tyr Glu Leu Thr Phe Thr Tyr Asp Ser Leu Phe
1               5                   10                  15

Val Ser Asp Trp Thr Arg Leu Gly Phe Leu Glu Ala Asp Tyr Gly Trp
            20                  25                  30

Gly Thr Pro Ala His Val Leu Pro Phe Ser Tyr His Pro Phe Met Ala
        35                  40                  45

Val Ala Val
    50

<210> SEQ ID NO 77
<211> LENGTH: 51
<212> TYPE: PRT
<213> ORGANISM: Panicum virgatum

<400> SEQUENCE: 77

Phe Glu Arg Asp Pro Tyr Glu Leu Thr Phe Ser Tyr Asp Ser Leu Phe
1               5                   10                  15

Val Ser Asp Trp Thr Arg Leu Gly Phe Leu Glu Ala Asp Tyr Gly Trp
            20                  25                  30

Gly Ala Pro Ala His Val Val Pro Phe Ser Tyr His Pro Phe Met Ala
        35                  40                  45

Val Ala Val
    50

<210> SEQ ID NO 78
<211> LENGTH: 51
<212> TYPE: PRT
<213> ORGANISM: Sorghum bicolor

<400> SEQUENCE: 78

Phe Asp Arg Asp Pro Tyr Glu Leu Thr Phe Thr Tyr Asp Ser Leu Phe
1               5                   10                  15

Val Ser Asp Trp Thr Arg Leu Gly Phe Leu Glu Ala Asp Tyr Gly Trp
            20                  25                  30

Gly Thr Pro Thr His Val Val Pro Phe Ser Tyr His Pro Phe Met Ala
        35                  40                  45

Val Ala Val
    50

<210> SEQ ID NO 79
<211> LENGTH: 51
<212> TYPE: PRT
<213> ORGANISM: Zea mays

<400> SEQUENCE: 79

Phe Asp Arg Asp Pro Tyr Glu Leu Thr Phe Thr Tyr Asp Ser Leu Phe
1               5                   10                  15
```

```
Val Ser Asp Trp Thr Arg Leu Gly Phe Leu Glu Ala Asp Tyr Gly Trp
            20                  25                  30

Gly Thr Pro Thr His Val Leu Pro Phe Ser Tyr His Pro Phe Met Ala
            35                  40                  45

Val Ala Val
    50

<210> SEQ ID NO 80
<211> LENGTH: 53
<212> TYPE: PRT
<213> ORGANISM: Setaria italica

<400> SEQUENCE: 80

Leu Val Gly Val Glu Asp Pro Tyr Glu Leu Pro Phe Ala Tyr Glu Ala
1               5                   10                  15

Leu Phe Val Ser Asp Trp Thr Arg Leu Gly Phe Gln Glu Ala Asp Tyr
            20                  25                  30

Gly Trp Gly Gly Pro Ser His Val Ile Pro Leu Ala Tyr His Pro His
            35                  40                  45

Met Pro Ile Ala Ile
    50

<210> SEQ ID NO 81
<211> LENGTH: 51
<212> TYPE: PRT
<213> ORGANISM: Oryza sativa

<400> SEQUENCE: 81

Phe Arg Glu Asp Pro Tyr Glu Leu Ser Phe Thr Tyr Asp Ser Leu Phe
1               5                   10                  15

Val Ser Asp Trp Thr Arg Leu Gly Phe Leu Glu Ala Asp Tyr Gly Trp
            20                  25                  30

Gly Pro Pro Ser His Val Ile Pro Phe Ala Tyr Tyr Pro Phe Met Ala
            35                  40                  45

Val Ala Ile
    50

<210> SEQ ID NO 82
<211> LENGTH: 52
<212> TYPE: PRT
<213> ORGANISM: Setaria italica

<400> SEQUENCE: 82

Leu Val Glu Lys Asp Pro Tyr Glu Leu Thr Phe Ser Tyr Glu Ser Leu
1               5                   10                  15

Phe Val Ser Asp Trp Thr Arg Leu Gly Phe Leu Asp Ala Asp Tyr Gly
            20                  25                  30

Trp Gly Thr Pro Leu Gln Val Ile Pro Phe Thr Tyr His Pro Ala Met
            35                  40                  45

Pro Ile Ala Ile
    50

<210> SEQ ID NO 83
<211> LENGTH: 52
<212> TYPE: PRT
<213> ORGANISM: Panicum virgatum

<400> SEQUENCE: 83

Leu Val Ala Gln Asp Pro Tyr Glu Leu Ser Phe Thr Tyr Glu Ser Leu
1               5                   10                  15
```

```
Phe Val Ser Asp Trp Thr Arg Leu Gly Phe Leu Glu Ala Asp Tyr Gly
            20                  25                  30

Trp Gly Thr Pro Glu Gln Val Ile Pro Phe Ala Tyr His Pro Cys Met
        35                  40                  45

Pro Ile Ala Val
    50
```

What is claimed:

1. A genetically modified grass plant comprising a feruloyl-CoA: monolignol transferase nucleic acid that encodes a polypeptide with at least 95% sequence identity to an amino acid sequence selected from the group consisting of SEQ ID NO: 2, 9, 20 and 21 operably linked to a heterologous promoter functional in cells of the plant, which plant has a knockdown or knockout of the grass plant's endogenous p-coumaroyl-CoA: monolignol transferase gene comprising a sequence with at least 95% sequence identity to SEQ ID NO:16 or 18.

2. The genetically modified plant of claim 1, wherein the knockdown or knockout is a mutation selected from the group consisting of a point mutation, a deletion, a missense mutation, insertion or a nonsense mutation in the endogenous p-coumaroyl-CoA:monolignol transferase gene.

3. The genetically modified plant of claim 1, wherein the knockdown or knockout comprises a point mutation, a deletion, a missense mutation, insertion or a nonsense mutation in the endogenous p-coumaroyl-CoA: monolignol transferase gene encoding a polypeptide with at least 95% sequence identity to an amino acid sequence selected from the group consisting of SEQ ID NO: 17 or 24.

4. The genetically modified plant of claim 1, wherein the knockdown or knockout comprises expression of at least one inhibitory nucleic acid comprising 20 nucleotides with at least 95% sequence identity to either strand of SEQ ID NO:16 or 18 nucleic acid sequence.

5. The genetically modified plant of claim 1, wherein the knockdown or knockout reduces acylation of monolignols with p-coumarate.

6. The genetically modified plant of claim 1, wherein the knockdown or knockout reduces acylation of monolignols with p-coumarate, where the monolignols are selected from the group consisting of p-coumaryl alcohol, coniferyl alcohol and sinapyl alcohol.

7. The genetically modified plant of claim 1, wherein the knockdown or knockout reduces acylation of monolignols with p-coumarate by at least 30%.

8. The genetically modified plant of claim 1, wherein the a feruloyl-CoA:monolignol transferase nucleic acid is operably linked to a promoter selected from the group consisting of a poplar xylem-specific secondary cell wall specific cellulose synthase 8 promoter, a cauliflower mosaic virus promoter, a Z10 promoter from a gene encoding a 10 kD zein protein, a Z27 promoter from a gene encoding a 27 kD zein protein, a pea rbcS gene promoter, or an actin promoter from rice.

9. The genetically modified plant of claim 1, wherein the plant is selected from the species consisting of *Miscanthus giganteus, Panicum virgatum* (switchgrass), *Zea mays* (corn), *Oryza sativa* (rice), *Saccharum* sp. (sugar cane), *Triticum* sp. (wheat), *Avena sativa* (oats), *Pennisetum glaucum* (pearl millet), *Setaria italica* (foxtail millet), *Sorghum* sp., *Bambuseae* species (bamboo), *Sorghastrum nutans* (indiangrass), *Tripsacum dactyloides* (eastern gamagrass), *Andropogon gerardii* (big bluestem), *Schizachyrium scoparium* (little bluestem), *Bouteloua curtipendula* (sideoats grama), *Silphium terebinthinaceum* (prairie rosinweed), *Pseudoroegneria spicata* (bluebunch wheatgrass) *Sorghum bicolor* (sorghum) and *Bachypodium distachyon* (purple false brome).

10. The genetically modified plant of claim 1, wherein the plant is fertile.

11. A seed from the genetically modified plant of claim 1, wherein the seed comprises an expression cassette encoding an inhibitory nucleic acid that reduces expression of the plant's endogenous p-coumaroyl-CoA:monolignol transferase gene; or the seed comprises a mutation in the plant's endogenous p-coumaroyl-CoA:monolignoltransferase gene.

* * * * *